(12) United States Patent
Dahlman et al.

(10) Patent No.: US 12,201,696 B2
(45) Date of Patent: Jan. 21, 2025

(54) MULTIPLEXED ANALYSIS OF MATERIALS FOR TISSUE DELIVERY

(71) Applicant: Georgia Tech Research Corporation, Atlanta, GA (US)

(72) Inventors: James Dahlman, Atlanta, GA (US); Cory Sago, Boston, MA (US); Melissa Lokugamage, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 1302 days.

(21) Appl. No.: 16/753,241

(22) PCT Filed: Oct. 30, 2018

(86) PCT No.: PCT/US2018/058171
§ 371 (c)(1),
(2) Date: Apr. 2, 2020

(87) PCT Pub. No.: WO2019/089561
PCT Pub. Date: May 9, 2019

(65) Prior Publication Data
US 2020/0330607 A1     Oct. 22, 2020

Related U.S. Application Data

(60) Provisional application No. 62/690,240, filed on Jun. 26, 2018, provisional application No. 62/578,594, filed on Oct. 30, 2017.

(51) Int. Cl.
| | |
|---|---|
| *A61K 47/69* | (2017.01) |
| *A61K 48/00* | (2006.01) |
| *A61K 49/00* | (2006.01) |
| *C12N 15/11* | (2006.01) |
| *C12N 15/63* | (2006.01) |
| *C12N 15/85* | (2006.01) |
| *C12Q 1/6869* | (2018.01) |
| *G01N 15/14* | (2024.01) |

(52) U.S. Cl.
CPC ........ *A61K 47/6935* (2017.08); *A61K 48/005* (2013.01); *A61K 49/0017* (2013.01); *C12N 15/11* (2013.01); *C12N 15/63* (2013.01); *C12N 15/85* (2013.01); *C12Q 1/6869* (2013.01); *G01N 15/14* (2013.01); *A01K 2267/03* (2013.01); *C12N 2310/315* (2013.01)

(58) Field of Classification Search
None
See application file for complete search history.

(56) References Cited

U.S. PATENT DOCUMENTS

| | | |
|---|---|---|
| 5,579,250 A | 11/1996 | Balaji et al. |
| 5,612,895 A | 3/1997 | Balaji et al. |
| 5,631,280 A | 5/1997 | Ciccarone et al. |
| 2015/0322494 A1 | 11/2015 | Navarro et al. |
| 2020/0330607 A1 | 10/2020 | Dahlman et al. |

FOREIGN PATENT DOCUMENTS

| | | |
|---|---|---|
| CA | 3081414 A1 | 5/2019 |
| EP | 3704262 A1 | 9/2020 |
| JP | 2021-500925 A | 1/2021 |
| WO | 2015/089419 A2 | 6/2015 |
| WO | 2016/024281 A1 | 2/2016 |
| WO | 2019/089561 A1 | 5/2019 |

OTHER PUBLICATIONS

Akinc et al., "Targeted Delivery of RNAi Therapeutics With Endogenous and Exogenous Ligand-Based Mechanisms," Mol. Ther., 18(7):1357¬1364 (2010).
Alabi et al., "Multiparametric approach for the evaluation of lipid nanoparticles for siRNA delivery," Proc. Natl. Acad. Sci. U S A., 110(32):12881-6 (2013).
Bertrand et al., "Mechanistic understanding of in vivo protein corona formation on polymeric nanoparticles and impact on pharmacokinetics," Nat. Commun., 8(1):777 (2017).
Chahal et al., "Dendrimer-RNA nanoparticles generate protective immunity against lethal Ebola, H1N1 influenza, and Toxoplasma gondii challenges with a single dose," Proc. Natl. Acad. Sci. U S A., 113(29):E4133-42 (2016).
Chen et al., "Rapid discovery of potent siRNA-containing lipid nanoparticles enabled by controlled microfluidic formulation," J. Am. Chem. Soc., 134:6948-6951 (2012).
Coelho et al., "Safety and Efficacy of RNAi Therapy for Transthyretin Amyloidosis," N. Engl. J. Med., 369(9):819-829 (2013).
Cory D. Sago et al: "High-throughput in vivo screen of functional Mrna delivery identifies nanoparticles for endothelial cell gene editing", Proceedings of the National Academy of Sciences of the United States of America, vol. 115, No. 42, Oct. 1, 2018, pp. E9944-E9952.
Dahlman et al., "In vivo endothelial siRNA delivery using polymeric nanoparticles with low molecular weight," Nat. Nanotechnol., 9(8):648-655 (2014).
Davis, "Design and development of IT-101, a cyclodextrin-containing polymer conjugate of camptothecin," Adv. Drug. Deliv. Rev., 61(13):1189-92 (2009).
Dong et al., "Lipopeptide nanoparticles for potent and selective siRNA delivery in rodents and nonhuman primates," Proc. Natl. Acad. Sci. U S A., 111(11):3955-60 (2014).
Dong et al., "Poly(glycoamidoamine) Brushes Formulated Nanomaterials for Systemic siRNA and mRNA Delivery in Vivo," Nano Lett., 16(2):842-8 (2016).

(Continued)

*Primary Examiner* — Nancy J Leith
*Assistant Examiner* — Jessica D Parisi
(74) *Attorney, Agent, or Firm* — Proskauer Rose LLP

(57) ABSTRACT

Disclosed herein are compositions and methods for identifying materials suitable for functional delivery of a bioactive agent to a target tissue. These compositions and methods have the advantage of simultaneously screening a library of materials for the ability to deliver a bioactive agent to a cell, tissue, or organ. The compositions and methods can also be used to confirm that the agent is delivered in a manner sufficient for function of the agent.

18 Claims, 74 Drawing Sheets
Specification includes a Sequence Listing.

(56) References Cited

OTHER PUBLICATIONS

Eltoukhy et al., "Nucleic acid-mediated intracellular protein delivery by lipid-like nanoparticles," Biomaterials., 35(24):6454-6461 (2014).
Gaudreault et al., "Increased caveolin-1 expression in Alzheimer's disease brain," Neurobiology of Aging, 25(6):753-759 (2004).
Gaur et al., "Preclinical study of the cyclodextrin-polymer conjugate of camptothecin CRLX101 for the treatment of gastric cancer," Nanomedicine., 8(5):721-730 (2012).
Green et al., "A Combinatorial Polymer Library Approach Yields Insight into Nonviral Gene Delivery," Acc. Chem. Res., 41(6):749-759 (2008).
Gvaramia et al., "Role of caveolin-1 in fibrotic diseases," Matrix Biol., 32(6):307-315 (2013).
Hao et al., "Rapid Synthesis of a Lipocationic Polyester Library via Ring-Opening Polymerization of Functional Valerolactones for Efficacious siRNA Delivery," J. Am. Chem. Soc., 137(29):9206-9209 (2015).
Hindson et al., "Absolute quantification by droplet digital PCRCR versus analog real-time PCRCR," Nat. Methods, 10(10):1003-1005 (2013).
International Preliminary Report on Patentability received for International Application PCT/US2018/058171, mailed on May 5, 2020. (9 pages).
International Preliminary Report on Patentability received for PCT Patent Application No. PCT/US18/058171, mailed on May 14, 2020, 10 pages.
International Search Report and Written Opinion received for International Application PCT/US2018/058171, mailed on Jan. 1, 2019. (14 pages).
International Search Report and Written Opinion received for PCT Patent Application No. PCT/US18/058171, mailed on Jan. 15, 2019, 13 pages.
James E. Dahlman et al.: "Barcoded nanoparticles for high througput in vivo discovery of targeted therapeutics", Proceedings of the National Academ of Sciences of the United States of America, vol. 114, No. 8, Feb. 6, 2017, pp. 2060-2065.
Kaczmarek et al., "Polymer-Lipid Nanoparticles for Systemic Delivery of mRNA to the Lungs," Angew Chem. Int. Ed. Engl., 55(44):13808-13812 (2016).
Kathryn A. Whitehead et al: "Degradable lipid nanoparticles with predictable in vivo siRNA delivery activity", Nature Communications, vol. 5, Jun. 27, 2014.
Ming Want et al: "Efficient delivery of genome-editing proteins using bioreducible lipid nanoparticles", Proceedings of the National Academy of Sciences of the United States of America, vol. 113, No. 11, Feb. 29, 2016.
Nair et al., "Impact of enhanced metabolic stability on pharmacokinetics and pharmacodynamics of GalNAc-siRNA conjugates," Nucleic Acids Res., 45(19): 10969-10977 (2017).
Paunescu et al., "Detecting and Number Counting of Single Engineered Nanoparticles by Digital Particle Polymerase Chain Reaction," ACS nano., 9(10):9564-9572 (2015).
Paunovska et al., "A Direct Comparison of in Vitro and in Vivo Nucleic Acid Delivery Mediated by Hundreds of Nanoparticles Reveals a Weak Correlation," Nano. Lett., 18(3):2148-2157 (2018).
Porel et al., "Sequence-defined bioactive macrocycles via an acid-catalysed cascade reaction," Nat. Chem., Jun.;8(6):590-596 (2016).
Ronan et al., "Avoiding common pitfalls when clustering biological data," Sci. Signal., 9(432):re6 (2016).
Sager et al., "Proliferation and recruitment contribute to myocardial macrophage expansion in chronic heart failure," Circ. Res., 119(7):853-864 (2016).
Sager et al., "RNAi targeting multiple cell adhesion molecules reduces immune cell recruitment and vascular inflammation after myocardial infarction," Sci. Transl. Med., 8(342): 342ra80 (2016).
Sahay et al., "Endocytosis of Nanomedicines," J. Control Release., 145(3):182-195 (2010).
Semple et al., "Rational design of cationic lipids for siRNA delivery," Nat. Biotechnol., 28(2):172-176 (2010).
Siegwart et al., "Combinatorial synthesis of chemically diverse core-shell nanoparticles for intracellular delivery," Proc. Natl. Acad Sci. U S A., 108(32):12996-13001 (2011).
Sorkin et al., "Versatile Platform for the Synthesis of Orthogonally Cleavable Heteromultifunctional Cross-Linkers," Bioconjug. Chem., 28(4):907-912 (2017).
Sotgia et al., "Understanding the Warburg effect and the prognostic value of stromal caveolin-1 as a marker of a lethal tumor microenvironment," Breast Cancer Res., 13(4):213 (2011).
Tanowitz et al., "Asialoglycoprotein receptor 1 mediates productive uptake of N-acetylgalactosamine-conjugated and unconjugated phosphorothioate antisense oligonucleotides into liver hepatocytes," Nucleic Acids Res., 45(21):12388-12400. (2017).
Turnbull et al., "Lipidoid mRNA Nanoparticles for Myocardial Delivery in Rodents," Methods Mol. Biol., 1521:153-166 (2017).
Witkiewicz et al., "An Absence of Stromal Caveolin-1 Expression Predicts Early Tumor Recurrence and Poor Clinical Outcome in Human Breast Cancers," Am. J. Pathol., 174(6):2023-2034 (2009).
Yan et al., "Functional polyesters enable selective siRNA delivery to lung cancer over matched normal cells," Proc. Natl. Acad. Sci. U S A., 113(39):E5702-E5710 (2016).
Yang et al., "Caveolin-1 Expression in Clinically Confined Human Prostate Cancer: A Novel Prognostic Marker1," Cancer Res., 59(22):5719-5723 (1999).
Yang, "Nucleases: Diversity of Structure, Function and Mechanism," Quarterly reviews of biophysics, 44(1):1-93 (2011).
Zamboni et al., "Polymeric Nanoparticles as Cancer-specific DNA Delivery Vectors to Human Hepatocellular Carcinoma," J. Control Release, 263:18-28 (2017).
Zhang et al., "Biodegradable Amino-Ester Nanomaterials for Cas9 mRNA Delivery in Vitro and in Vivo," ACS Appl. Mater Interfaces, 9(30):25481-25487 (2017).
Zhang et al., "Lipid-Modified Aminoglycoside Derivatives for in vivo siRNA Delivery," Adv Mater, 25(33):4641-4645 (2013).
Zhou et al., "Modular degradable dendrimers enable small RNAs to extend survival in an aggressive liver cancer model," Proc. Natl. Acad. Sci. U S A., 113(3):520-525 (2016).
Zimmermann et al., "Clinical Proof of Concept for a Novel Hepatocyte-Targeting GalNAc-siRNA Conjugate," Mol. Ther., Jan. 4;25(1):71-78 (2017).
Zuckerman et al., "siRNA Delivery to the Glomerular Mesangium Using Polycationic Cyclodextrin Nanoparticles Containing siRNA," Nucleic Acid Ther., 25(2):53-64 (2015).

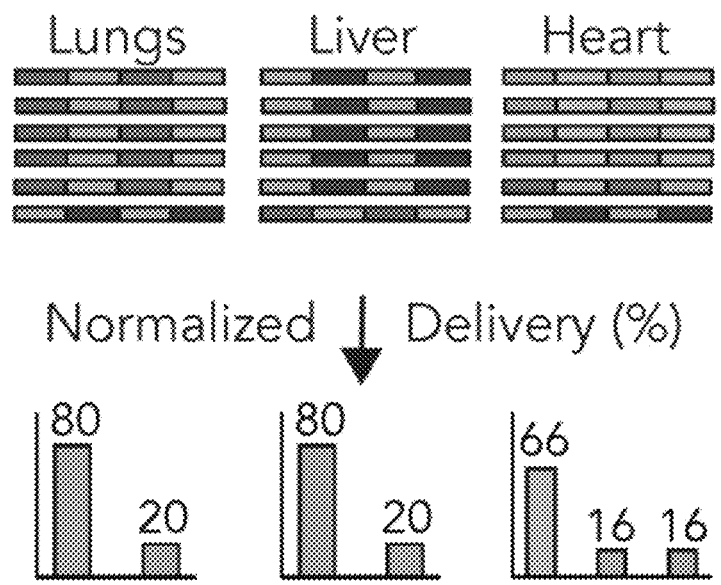
FIG. 1C
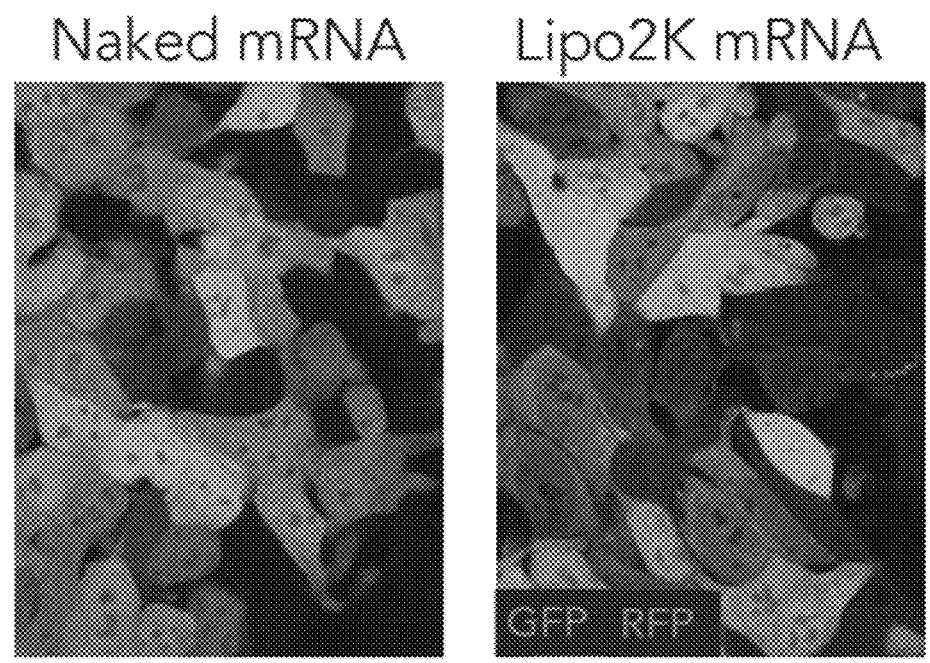
FIG. 1D   FIG. 1E

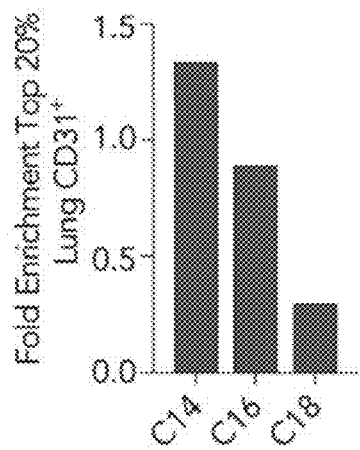
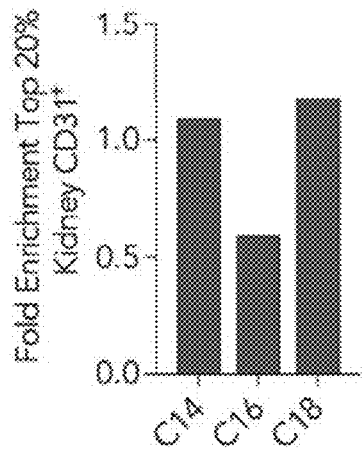
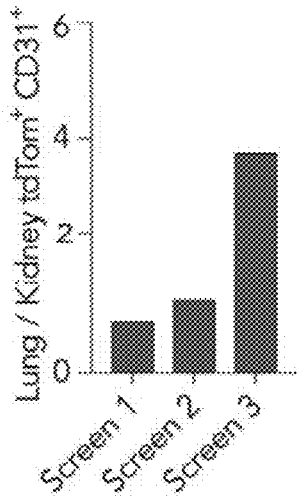
FIG. 2F　　　FIG. 2G　　　FIG. 2H
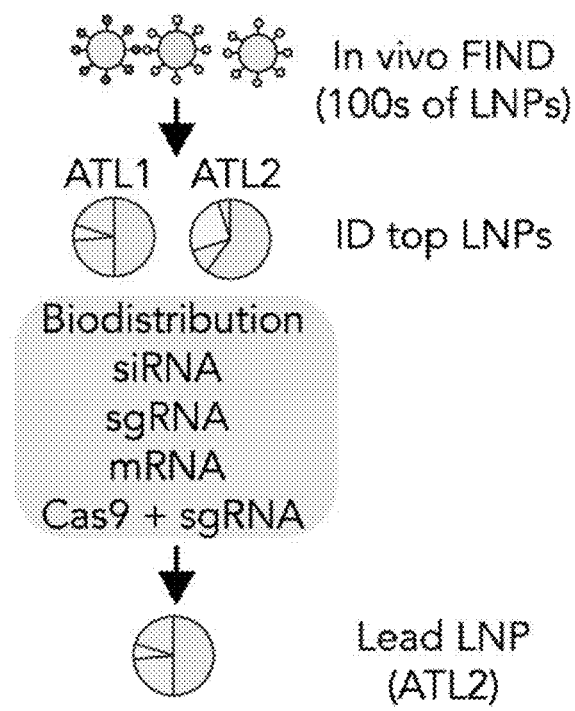
FIG. 3A

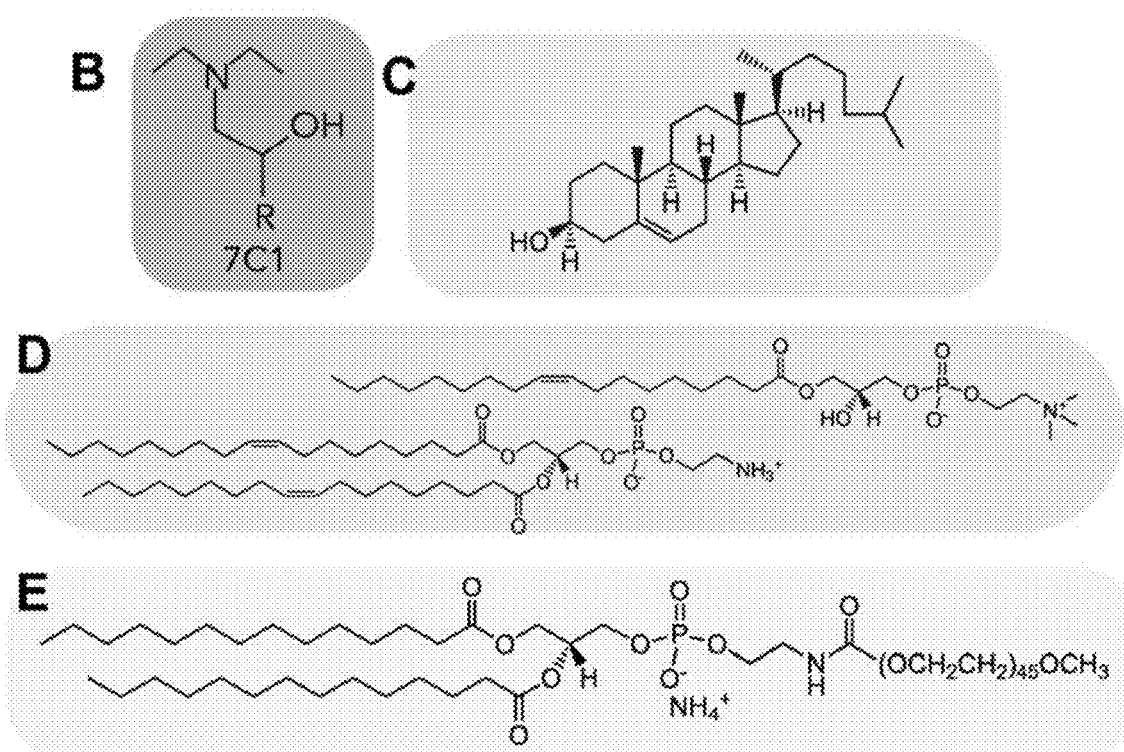
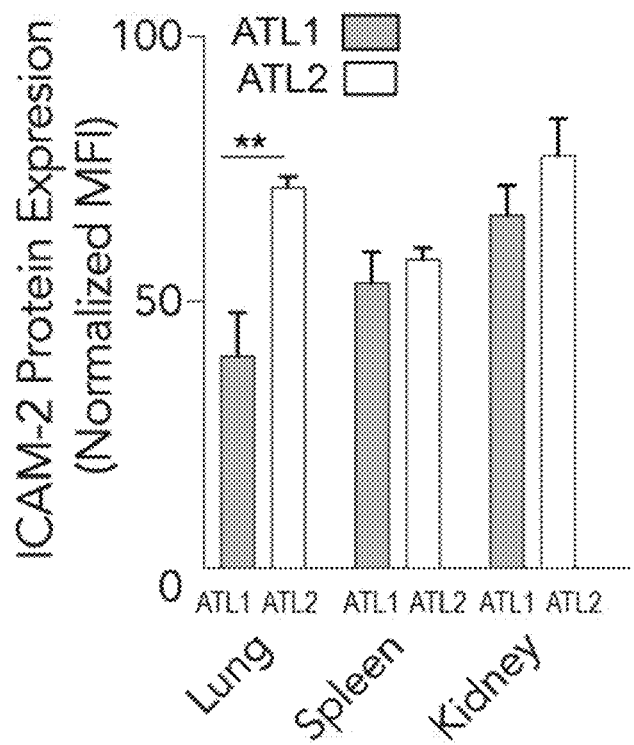
FIG.3B-3E
FIG.3F

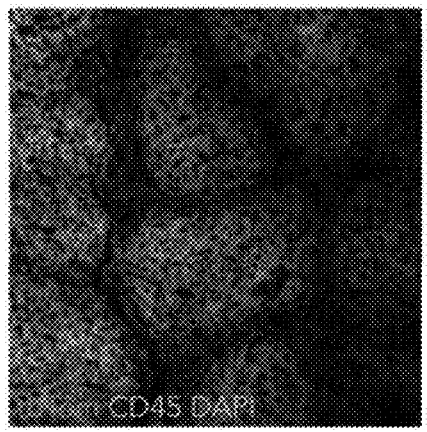 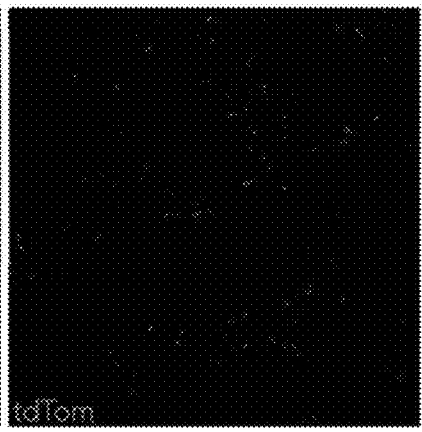 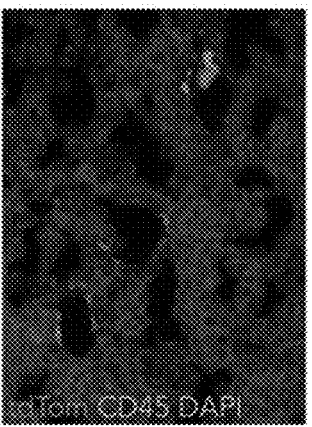
FIG. 3K  FIG. 3L  FIG. 3M
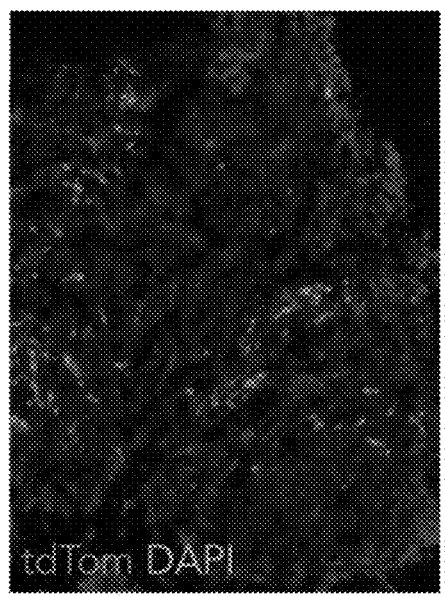
FIG. 3N

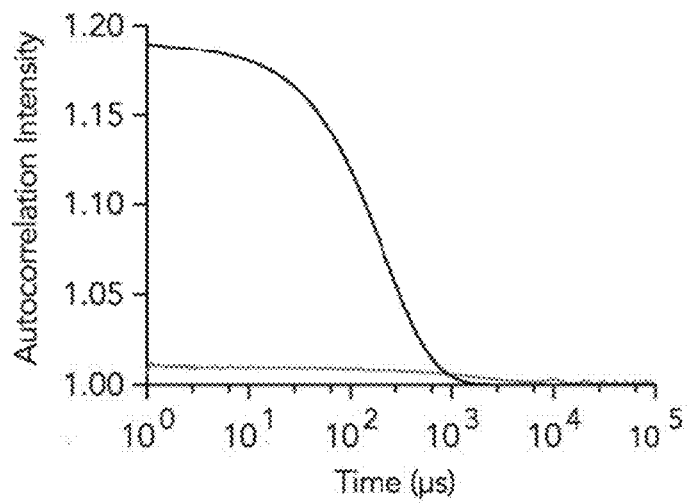
FIG. 4B
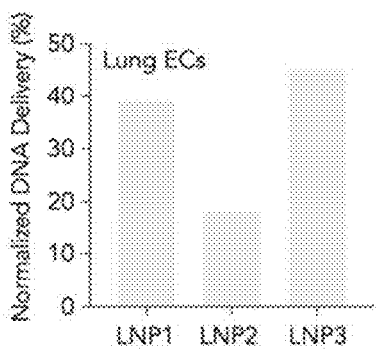
FIG. 4C
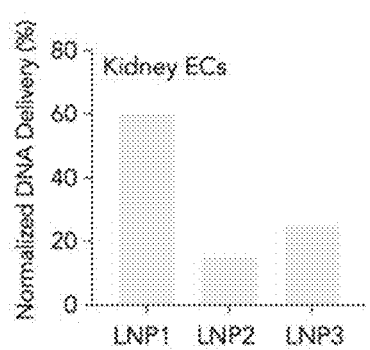
FIG. 4D
AGACGTGTGCTCTTCCGATCTGAGGGTACTTNNNNNNNAGATCGGAAGAGCGTCGTGT
Universal primer site    8 nt barcode    N₇    Universal primer site
Phosphorothioate modification
FIG. 4E

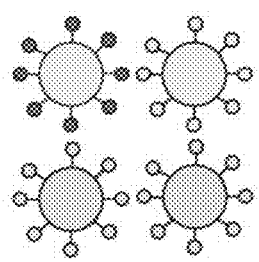 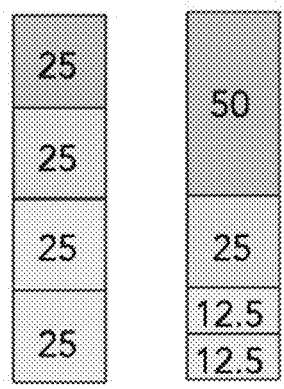 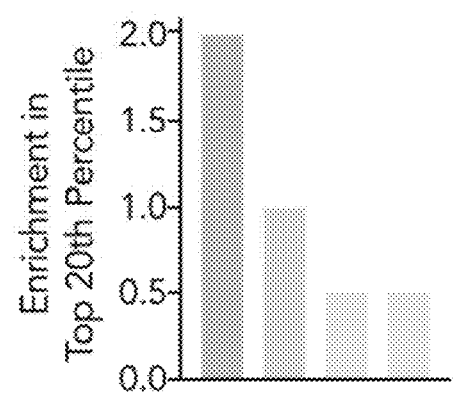
FIG. 5L     FIG. 5M     FIG. 5N     FIG. 5O silCAM-2 sense: 5' - AGGAcGGucucAAcuuuuc dT sdT - 3'
silCAM-2 antisense: 5' - GAAAAGUuGAGACCGUCCU dT sdT -3' silGFP sense: 5' - AcAuGAAGcAGcACGACuU dT sdT - 3'
silGFP antisense: 5' - AAGUCGUGCUGCUUCAUGU dT sdT -3'

A, G, U, C: RNA nucleotide
dT: deoxy-T
a, g, u, c: 2'-O-Methyl nucleotide
s: phosphorothioate sg-ICAM2a  5' gscsusUACCUGGGCUGUAGAACGUUUUAGAGCUAGAA
AUAGCAAGUUAAAAUAAGGCUAGUCCGUUAUCAACUUG
AAAAAGUGGCACCGAGUCGGUGCusususU 3'
sg-ICAM2b  5' asasgsACGGACAGGCACCUACGGUUUUAGAGCUAGAA
AUAGCAAGUUAAAAUAAGGCUAGUCCGUUAUCAACUUG
AAAAAGUGGCACCGAGUCGGUGCusususU 3'
FIG.6M
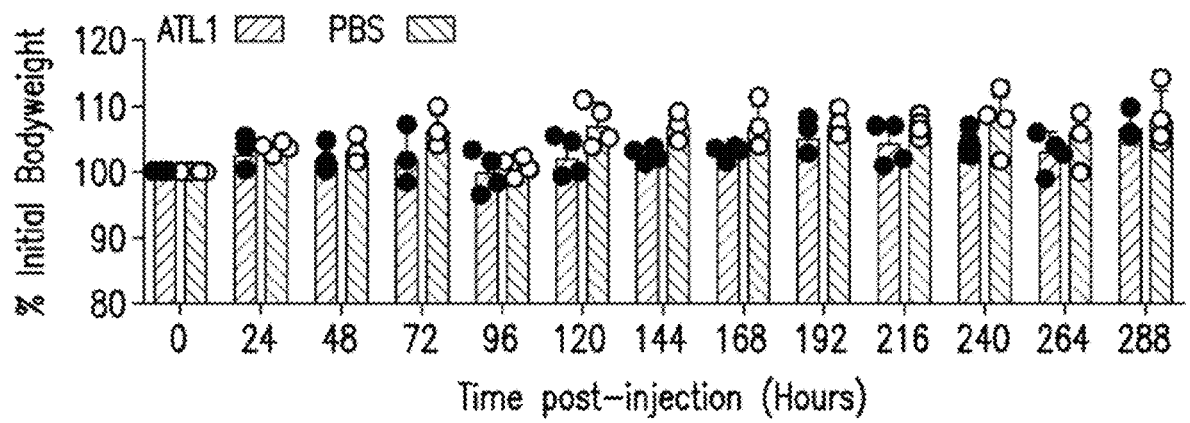
FIG.6N
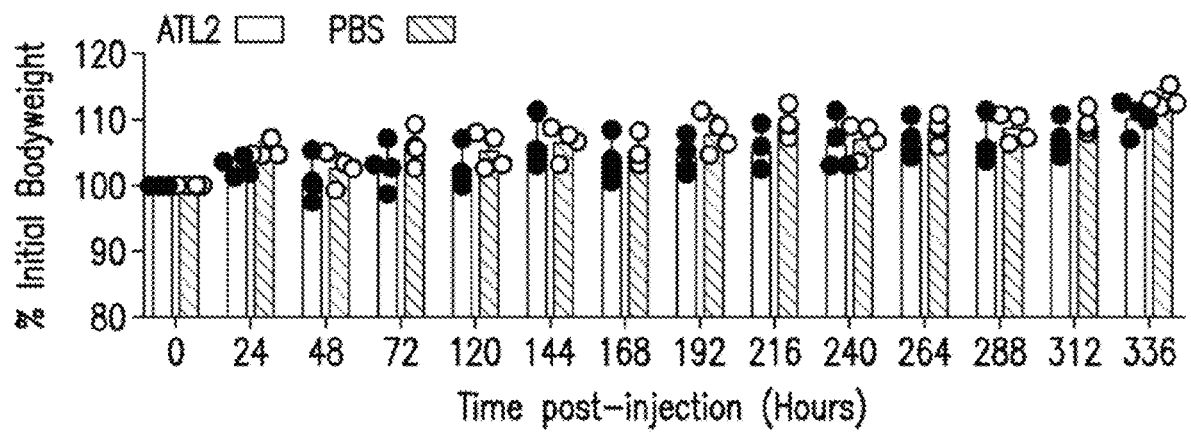
FIG.6O Universal Forward  NHNW  Probe  NWNH 8 nt Barcode NWH  Universal Reverse

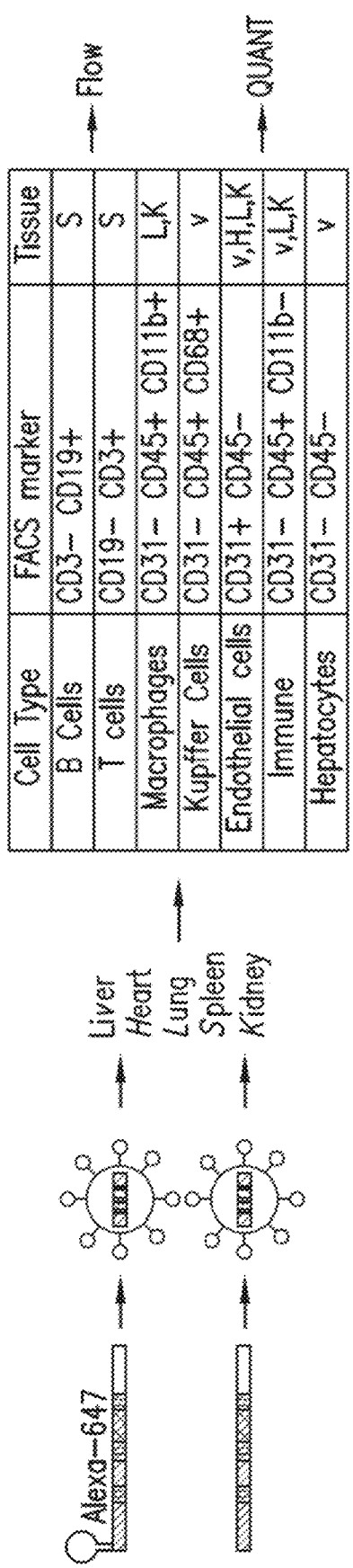

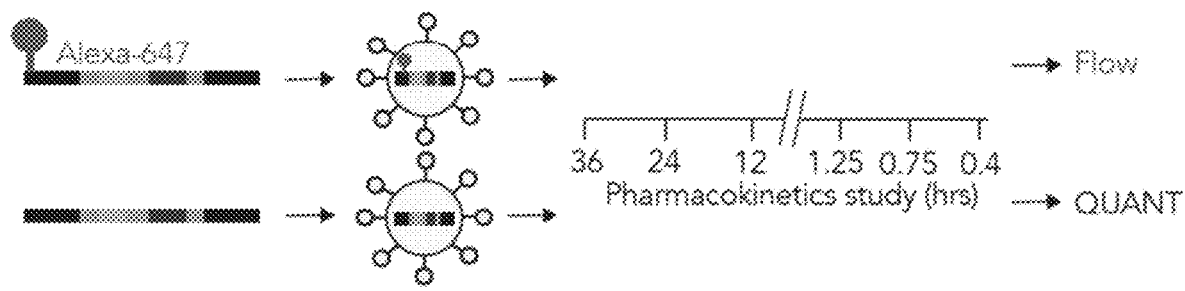
FIG. 16A
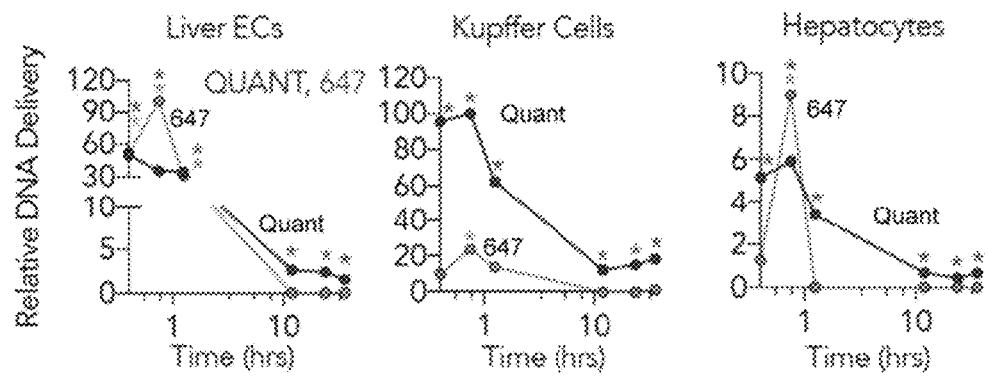
FIG. 16B    FIG. 16C    FIG. 16D
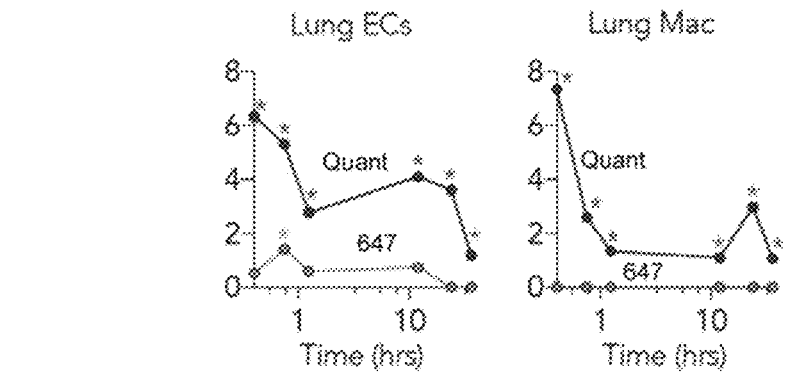
FIG. 16E    FIG. 16F

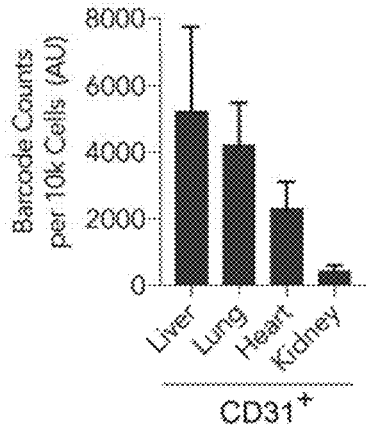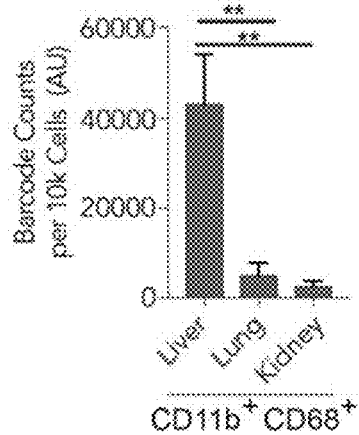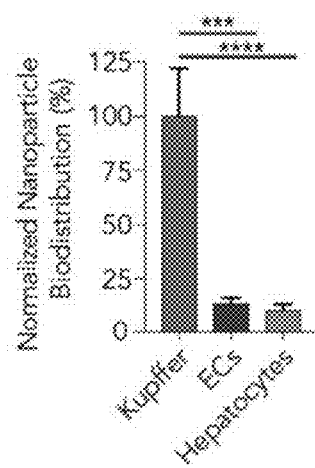
FIG. 18H  FIG. 18I  FIG. 18J
FIG. 19A

FIG.19B

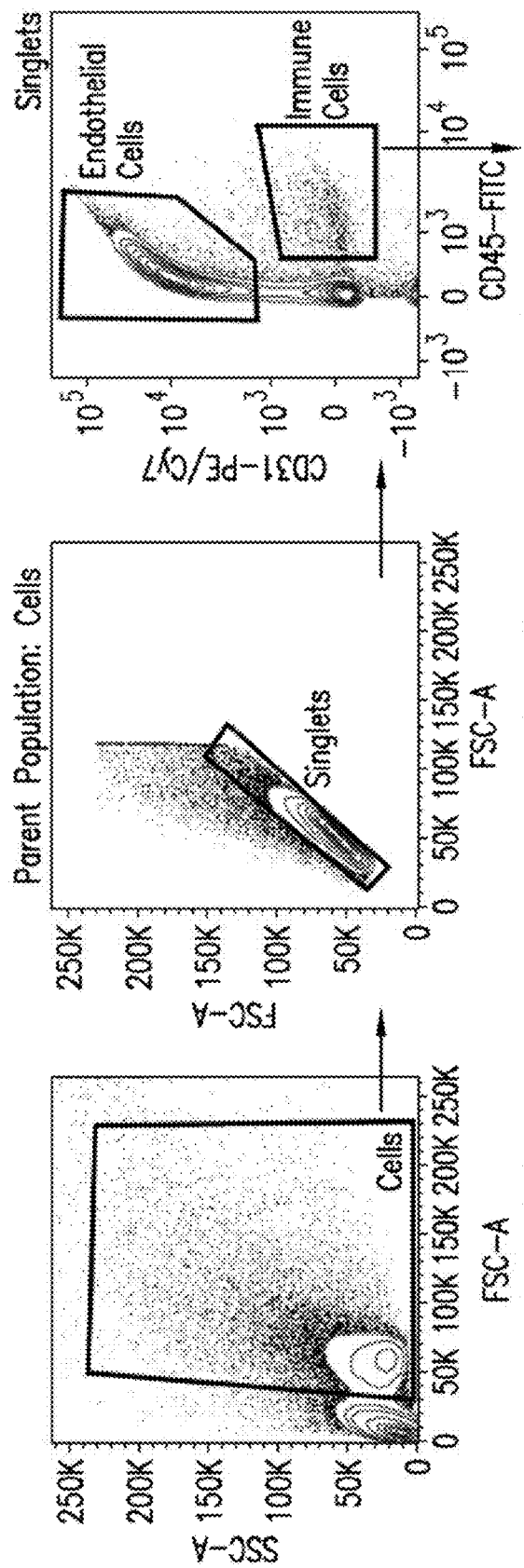

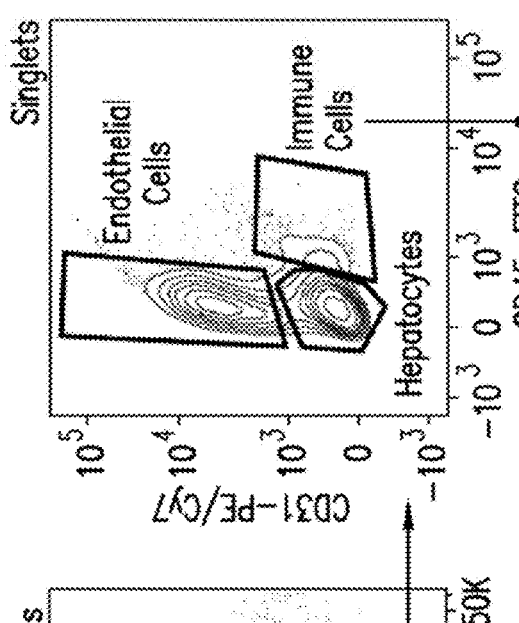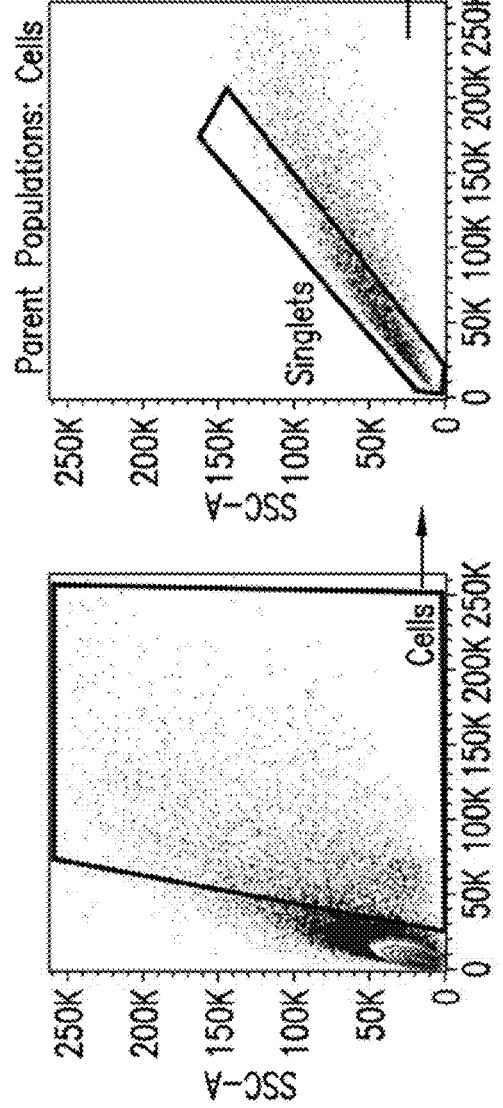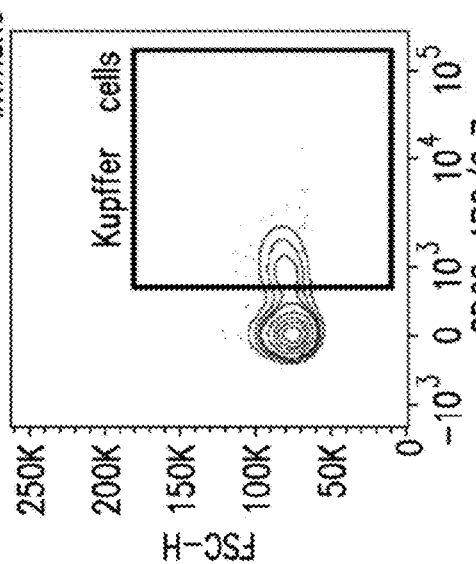

MULTIPLEXED ANALYSIS OF MATERIALS FOR TISSUE DELIVERY

CROSS REFERENCE TO RELATED APPLICATIONS

This application is a national stage application, filed under 35 U.S.C. § 371, of International Patent Application No. PCT/US2018/058171 filed on Oct. 30, 2018, which claims benefit of and priority to U.S. Provisional Patent Application No. 62/578,594 filed on Oct. 30, 2017 and U.S. Provisional Patent Application No. 62/690,240 filed on Jun. 26, 2018, which are incorporated herein by reference in their entirety.

REFERENCE TO SEQUENCE LISTING

The Sequence Listing submitted on Jul. 7, 2020, as a text file named "064489.036_replacement_seq.txt" created on Jul. 7, 2020, and having a size of 7,314 bytes is hereby incorporated by reference pursuant to 37 C.F.R. § 1.52(e)(5).

TECHNICAL FIELD

The invention is generally directed to methods and compositions for characterizing delivery vehicles including but not limited to nanoparticle delivery vehicles.

BACKGROUND

The development of targeted particles for the treatment and detection of human diseases is expected to result in an explosion of the market for this class of biomaterials. Nanoparticles carrying mRNA encounter dynamic hurdles evolved to prevent foreign nucleic acid delivery. To overcome these challenges, LNPs are imparted with chemical diversity two ways. First, thousands of compounds with variable ionizability, pKa, and hydrophobicity can be synthesized. Second, each compound can be formulated into hundreds of chemically distinct LNPs by adding poly(ethylene glycol) (PEG), cholesterol, 1,2-dioleoyl-sn-glycero-3-phosphoethanolamine (DOPE), or other constituents.

Nanoparticle libraries, consisting of hundreds to thousands of LNPs, can be screened in vitro. This process is only efficient if it predicts in vivo (in a living animal) delivery. In vivo mRNA delivery is affected by pulsatile blood flow, heterogenous vasculature, and clearance by the kidney, spleen, liver, lymphatics, and immune system. Barcoding technologies have quantified LNP biodistribution, which is necessary, but not sufficient, for cytoplasmic nucleic acid delivery. More specifically, less than 3% of a drug that reaches a target cell can escape into the cytoplasm, and the genes that alter whether the nanoparticle escapes into the endosome are likely to vary with each cell type. As a result, it is not possible to predict functional delivery of drug into the cytoplasm or nucleus by measuring biodistribution.

To overcome these obstacles, there is a need for a method for characterizing and screening delivery vehicles that exhibit a desired tropism and deliver functional cargo to a specific cell or tissue.

SUMMARY

Compositions and methods for characterizing delivery vehicles that deliver functional cargo are provided. Many delivery vehicles are able to deliver cargo to cells, but the cargo may be trapped in an endosome or lysosome and is effectively rendered non-functional. The disclosed compositions and methods advantageously have the ability to assay multiple delivery vehicle formulations in a single run that not only deliver the agent to a desired cell or tissue, but are also able to identify delivery vehicle formulations that deliver cargo in its functional form. For example, if the cargo is a nucleic acid, expression of the nucleic acid in the cell shows that the nucleic acid is functional when delivered to the cytoplasm or nucleus of the cell.

In one embodiment, the method includes a delivery vehicle that contains a reporter and a chemical composition identifier. The method includes the step of formulating multiple delivery vehicles having different chemical compositions. In one embodiment >100 or even greater than >250 different delivery vehicle formulations are assayed in one run. The delivery vehicles are formulated to be taken up by cells. The delivery vehicles contain a reporter that can generate a detectable signal when it is functionally delivered into the cytoplasm or nucleus of cells of a non-human animal, and a composition identifier that identifies the chemical composition of the delivery vehicle. The reporter can be a nucleic acid such as mRNA that encodes a protein that when expressed in a cell is able to generate a detectable signal. For example, the protein can be a fluorescent protein or an enzyme the produces a detectable substance in the cell.

The method also includes the steps of pooling and administering the multiple delivery vehicles to a non-human mammal, for example a laboratory animal such as a mouse, rat, or non-human primate. After administration of the multiple delivery vehicles, cells from multiple tissues of the non-human mammal that generate the detectable signal are sorted from cells that do not generate the detectable signal. In one embodiment, the cells are sorted using fluorescence activated cell sorting (FACS). In some embodiments, the cells that generate the detectable signal are also sorted based on the presence or absence of a cell surface protein that is indicative of tissue type or cell type. Representative cell surface proteins include, but are not limited to, cluster of differentiation proteins. Fluorophore-conjugated antibodies to the cell surface proteins are used to detect the cell surface proteins on the cells and sort the cells.

The method also includes the step of identifying the chemical composition identifier in the sorted cells that generate the detectable signal to determine the chemical composition of the delivery vehicles in the sorted cells and to correlate the chemical composition of the delivery vehicles to the tissue or cell type containing the particles based on the cell surface markers on the sorted cells. In one embodiment the chemical composition identifier is a nucleic acid barcode, and the sequence is determined for example using deep sequencing techniques (also referred to as high-throughput sequencing or next generation sequencing).

Once the delivery vehicles are characterized, they can be used to deliver cargo to the cells of a subject in need thereof. The cargo can be a biologically active agent including, but not limited to nucleic acids and proteins. Exemplary agents include, but are not limited to mRNA, siRNA, nucleases, recombinases, and combinations thereof.

In some embodiments, the delivery vehicles are particles, for example nanoparticles. Nanoparticles typically have a diameter of less than 1 micron. In one embodiment, the nanoparticles have a diameter of 20 to 200 nm. In one embodiment, the particles are lipid nanoparticles.

In some embodiments, the delivery vehicle is a conjugate containing three components: (1) a reporter; (2) a chemical composition identifier; and (3) one of the group consisting of a peptide, a lipid, ssRNA, dsRNA, ssDNA, dsDNA, or a polymer. The three components can be in any arrangement in the conjugate. Exemplary reporters include, but are not limited to siRNA, mRNA, nuclease mRNA, small molecules, epigenetic modifiers, and phenotypic modifiers. An epigenetic modifier is a molecule that can cause a detectable change in the structure of DNA inside the cell when the molecule is delivered to the cell. An exemplary epigenetic modifier includes a protein that alters the chromatin structure of DNA inside a cell in a way that can be analyzed using DNA sequencing (e.g., ATAC-seq). A phenotypic modifier is a molecule that can cause a detectable change in the structure or behavior of a cell when the molecule is delivered to the cell. An exemplary phenotypic modifier includes a molecule that induces a change in the cell, for example cell morphology. The chemical composition identifier can be a nucleic acid barcode as discuss above.

Another embodiment provides a composition containing a delivery vehicle, a nucleic acid bar code, and a reporter that is biologically active when delivered to the cytoplasm or nucleus of a cell. In some embodiments, the delivery vehicle is a lipid nanoparticle. In other embodiments, the delivery vehicle is a conjugate.

Still another embodiment provides a nucleic acid barcode composition according to the following formula

R1-R2-R3-R4-R5-R6-R7-R8-R1 wherein R1 represents 1, 2, 3, 4, 5, 6, 7, 8, 9, or 10 nucleotides with phosphorothioate linkages,
R2 represents a first universal primer binding site,
R3 represents a spacer,
R4 represents a digital droplet PCR probe binding site,
R5 represents a random nucleotide sequence;
R6 represents a nucleic acid barcode sequence,
R7 represents a random nucleic acid sequence; and
R8 represents a second universal primer binding site.

Another embodiment provides a nucleic acid barcode comprising 80, 85, 90, 95, 99, or 100% sequence identity to SEQ ID NO:8.

Another embodiment provides pharmaceutically acceptable composition containing the nucleic acid barcodes disclosed herein.

The details of one or more embodiments are set forth in the accompanying drawings and the description below. Other features, objects, and advantages of the invention will be apparent from the description and drawings, and from the claims.

DESCRIPTION OF DRAWINGS

FIGS. 1A to 1H show high throughput analysis of cytoplasmic mRNA delivery. FIGS. 1A and 1B show nanoparticles formulated to carry Cre mRNA and a DNA barcode, before they were administered to Cre reporter cell lines or mice. In these reporter cell lines, the cells only become fluorescent if Cre mRNA has been functionally delivered into the cytoplasm and translated into functional protein. In these reporter mice, cells within the mouse only become fluorescent if Cre mRNA has been functionally delivered into the cytoplasm and translated into functional protein. Cells that underwent Cre-mediated genetic changes were isolated using FACS, and the DNA barcode was sequenced to identify the LNP that delivered the mRNA. FIG. 1C shows LNP barcodes ranked by 'normalized delivery'; each sample (e.g., Lung 1 vs. Heart 1) was analyzed individually on a single run, using dual indexing. FIG. 1D-1E show GFP and RFP expression in HEK cells that express RFP after exposure to Cre protein. Cells were treated with naked Cre mRNA (FIG. 1D) or Cre mRNA carried by Lipofectamine® 2000 (L2K) (FIG. 1E). FIG. 1F shows Alexa 647 and RFP intensities after treatment with LNPs carrying Cre mRNA and Alexa-647 labeled DNA barcode. FIG. 1G shows RFP+ HEK cells as a function of the administered Cre mRNA, which was carried by using L2K. FIG. 1H shows normalized DNA barcode delivery for 54 LNPs sequenced from RFP+ HEK cells after the administration of 10 ng total mRNA, or 100 ng total mRNA.

FIGS. 2A to 2H show high throughput analysis of cytoplasmic mRNA delivery in vivo. FIG. 2A shows LNPs formulated to carry Cre mRNA and a DNA barcode, before they were injected in LoxP-Stop-LoxP-tdTomato reporter mice. FIG. 2B shows 112 LNPs formulated with varied the structure of the lipid-amine compound, as well as the molar ratio of the compound, PEG, cholesterol, and DOPE. FIG. 2C shows dynamic light scattering analysis of 112 LNPs from this library; 71 formed stable LNPs and were included. FIG. 2D shows normalized DNA delivery in kidney and lung endothelial cells (CD31+CD45−) after LNPs were intravenously injected, as well as CD45+ and CD45− cells isolated following intramuscular injection. FIG. 2E shows in vivo LNP targeting heatmap generated by unbiased, Euclidean grouping. FIG. 2F-2G show enrichment analysis for lung (FIG. 2F) and kidney (FIG. 2G) endothelial cells in an iterative, second LNP screen. FIG. 2H shows the ratio of Lung/Kidney endothelial cell delivery for all 3 LNP screens.

FIGS. 3A to 3I show characterization of lead nanoparticles discovered by FIND. FIG. 3A shows top 2 particles, ATL1 and ATL2, discovered following three rounds of FIND are thoroughly characterized for biodistribution, delivery of siRNA, sgRNA, mRNA, and combinations thereof. FIG. 3B-3E shows ATL1 and ATL2 are comprised of 7C1 compound, cholesterol, C14-PEG2000 and differing helper lipids, 18:1 Lyso PC and DOPE, respectively. FIG. 3F shows ATL1 and ATL2 induced ICAM2 protein silencing in endothelial cells of various organs following a 1 mg/kg siICAM2 administration. FIG. 3G to 3I show ICAM2 protein (FIG. 3D) and indels (FIGS. 3E, 3F) measured in endothelial cells from multiple organs following repeat administration of 1.5 mg/kg sgICAM2a and sgICAM2b delivered by ATL1 and ATL2. FIG. 3K-3M show representative images of tdTomato+ cells in LSL-Tom spleen following 1.5 mg/kg ATL1-Cre injection. FIG. 3N shows a representative image of tdTomato+ cells in LSL-Tom spleen following three 1.5 mg/kg ATL2-Cre injections.

FIG. 4A-4B show LNP inclusion criteria. FIG. 4E shows DNA barcode design (SEQ ID NO:1); DNA barcodes were designed to reduce exonuclease activity and PCR bias.

FIGS. 5L-5O show enrichment criteria. Material properties from the top 20% of LNPs in a tissue are divided by the materials properties present in the initial library formulation. This enrichment criteria encompasses both formulation stability as well as in vivo performance. FIGS. 5W-5CC shows the composition of the compounds in the LNP library used for the second in vivo experiment LNP library used for third in vivo experiment. Helper lipid type was varied. FIGS. 5DD-5LL show the correlation between LNP diameter and normalized counts in select cell types in screens 1, 2, and 3.

FIG. 6M shows sequences of sgICAM2a (SEQ ID NO:6) and sgICAM2b (SEQ ID NO:7) used. FIGS. 6N and 6O show body weight over time after multiple injections of ATL1- and ATL2-sgICAM2ab or PBS.

In FIG. 13, the reporter molecule corrects a splicing mutation in an RNA, which then leads to the change described in FIGS. 12A to 12E.

FIGS. 14A to 14H show QUANT barcodes rationally designed to provide highly sensitive readouts of nanoparticle delivery. FIG. 14A shows QUANT barcodes contain universal primer sites, an 8 nucleotide barcode region, a probe binding site, and split semi-randomized regions. These designs reduce DNA secondary structure and increase DNA polymerase access. FIG. 14B shows barcodes can be formulated into chemically distinct lipid nanoparticles using high throughput microfluidics. FIG. 14C shows many chemically distinct barcoded lipid nanoparticles can be pooled together and administered simultaneously. DNA barcodes can be extracted and quantified for absolute (ddPCR) and relative (deep sequencing) delivery. FIG. 14D shows standard curve of QUANT barcodes diluted in TE buffer. FIG. 14E shows barcodes can be identified above background at 300 fM concentrations. **$p<0.01$, 2 tailed t-test. FIG. 14F shows an in vitro standard curve; barcodes were quantified 24 hours after being delivered to cell using Lipofectamine2000. FIG. 14G shows QUANT barcode readouts immediately after DNA was isolated from cells following in vivo nanoparticle delivery, or after the samples were stored at $-20°$ C. for 20 or 31 days. Each experiment was performed using different stock reagents, demonstrating the repeatability of the assay.

FIGS. 15A to 15E show a direct comparison of fluorescent- and ddPCR-based biodistribution in vivo reveals differences. FIG. 15A shows a schematic workflow in which QUANT barcodes with (or without) a fluorophore were formulated into LNPs and injected intravenously. Five tissues were isolated and barcode delivery to 13 cell types isolated by FACS was measured by QUANT or fluorescence. FIG. 15B shows cumulative biodistribution measured by QUANT or fluorescence in liver and non-liver cell types. **$p<0.01$, 2 tailed t-test. FIGS. 15C-15E show cumulative biodistribution within the 5 tissues examined by QUANT (FIG. 15D) and fluorescence (FIG. 15E). Fluorescence readouts overestimate liver delivery.

FIGS. 16A to 16D show QUANT biodistribution is more sensitive in an in vivo pharmacokinetic study. FIG. 16A shows a schematic workflow in which QUANT barcodes with (or without) a fluorophore were formulated into LNPs, injected intravenously, and isolated at different timepoints. Nanoparticle distribution was measured using QUANT or fluorescence. FIGS. 16B-16F show relative nanoparticle biodistribution in various cell types (normalized to maximal signal in any cell type) over time (hours) after administration of an LNP carrying 647-QUANT barcode or QUANT barcodes at a dose of 0.5 mg/kg. Asterisk denotes a signal that was significantly different than PBS-treated mice; QUANT measured statistical delivery to all cell types at all time points, unlike fluorescence.

FIGS. 18A to 18J show high throughput QUANT studies reveal Caveolin1 affects delivery in a cell type-specific manner in vivo. FIG. 18A is a schematic workflow showing QUANT ddPCR readouts can be coupled to DNA sequencing to measure absolute delivery mediated by >100 LNPs at once in vivo. FIG. 18B shows nanoparticle formulation ratios and diameters from screen 1 which included 128 different LNPs. FIG. 18C shows average normalized delivery for all cell types for all LNPs and the naked barcode (negative control). FIG. 18D shows LNP targeting heatmap to endothelial cells in wild-type and Cav1−/− mice in screen 1. Euclidean clustering was performed on cell-types to generate the dendrogram. FIG. 18E shows heatmap of relative nanoparticle delivery to macrophages in wild-type and Cav1−/− mice in screen 1. Euclidean clustering was performed on cell-types to generate the dendrogram. FIG. 18F shows normalized nanoparticle biodistribution across two screens (>220 LNPs) for endothelial cells from Cav1−/− or wild-type mice. *p<0.05, *p<0.001 1 tailed t-test. FIG. 18G shows normalized nanoparticle biodistribution across two screens (>220 LNPs) for Kupffer cells from Cav1−/− or wild-type mice. Lung and kidney macrophages were less impacted by the loss of caveolin. p<0.01 1 tailed t-test. FIG. 18H shows nanoparticle biodistribution in endothelial cells isolated from multiple tissues from wild-type mice in screen 1. FIG. 18I shows nanoparticle biodistribution in macrophages isolated from multiple tissues from wild-type mice in screen 1. FIG. 18J shows comparison of normalized nanoparticle biodistribution across two screens (>220 LNPs) in three cell types in the liver. *p<0.001, **p<0.0001 One-way ANOVA.

FIGS. 19A to 19I shows QUANT barcodes rationally designed for high sensitivity. FIG. 19A shows QUANT Barcode Design (SEQ ID NO:8). FIG. 19B shows primer combinations tested to avoid non-specific amplification by genomic DNA (gDNA). Different primer pairs were added to mouse and human gDNA without any barcode template. FIGS. 19C and 19D show a two-step PCR adds Illumina nextera chemistry regions, indices, and Illumina adapters for Illumina sequencing (FIG. 19C) and produces a clear product (FIG. 19D). FIG. 19E shows ddPCR was optimized using an annealing temperature of 60° C. and probe concentration 2× more than the ddPCR standard protocol concentration. FIG. 19F shows a scrabbled probe site tested to verify the specificity of the probe-based signal. FIG. 19G shows Alexa-647 fluorescence 24 hours after fluorescently labeled QUANT barcodes were administered in vitro to iMAECs with Lipofectamine 2000 and analyzed with flow cytometry.

FIG. 23A shows representative FACS gating for lung tissue. Endothelial cells (CD31+CD45−) and macrophages (CD31−CD45+CD11b+) were isolated. FIG. 23B shows representative FACS gating for liver tissue. Endothelial cells (CD31+CD45−), Kupffer cells (CD31−CD45+CD68+), and Hepatocytes (CD31−CD45−CD68−) were isolated.

DETAILED DESCRIPTION

Figure 1A:
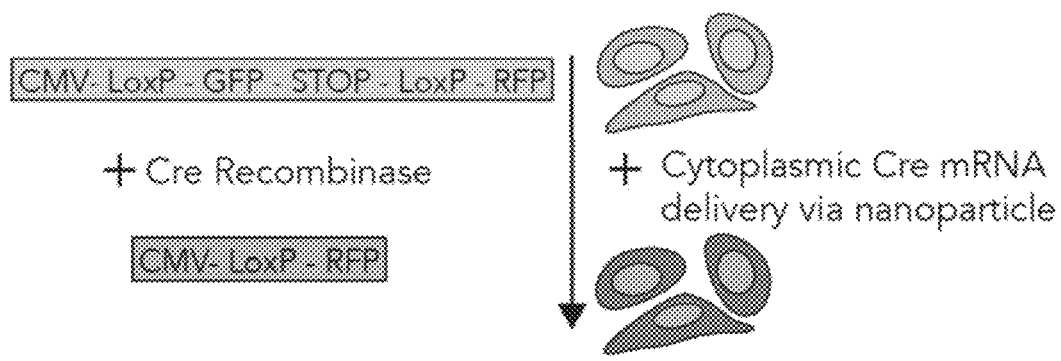

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed to in different sequence where this is logically possible.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be separated from or combined with the features of any of the other several embodiments without departing from the scope or spirit of the present disclosure. Any recited method can be carried out in the order of events recited or in any other order that is logically possible.

The following examples are put forth so as to provide those of ordinary skill in the art with a complete disclosure and description of how to perform the methods and use the probes disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

It must be noted that, as used in the specification and the appended claims, the singular forms "a," "an," and "the" include plural referents unless the context clearly dictates otherwise.

I. Definitions

As used herein, "bioactive agent" is used to refer to compounds or entities that alter, inhibit, activate, or otherwise affect biological or chemical events. For example, bioactive agents may be chemical entities or biological products that have therapeutic or diagnostic activity when delivered to a cell in a subject. The chemical entity or biological product can be an organic or inorganic molecule. In some embodiments, the bioactive agent is a modified or unmodified polynucleotide. In some embodiments, the bioactive agent is a peptide or peptidomimetics. In some cases, the bioactive agent is a protein. In some embodiments, the bioactive agent is an antisense nucleic acid, RNAi (e.g. siRNA, miRNA or shRNA), receptor, ligand, antibody, aptamer, or a fragment, analogue, or variant thereof. In some embodiments, the bioactive agent is a vector comprising a nucleic acid encoding a therapeutic or diagnostic gene. Bioactive agents may include, but are not limited to, anti-AIDS substances, anti-cancer substances, antibiotics, immunosuppressants, anti-viral substances, enzyme inhibitors, including but not limited to protease and reverse transcriptase inhibitors, fusion inhibitors, neurotoxins, opioids, hypnotics, anti-histamines, lubricants, tranquilizers, anti-convulsants, muscle relaxants and anti-Parkinson substances, anti-spasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and anti-adhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, anti-secretory factors, anticoagulants and/or antithrombotic agents, local anesthetics, ophthalmics, prostaglandins, anti-depressants, anti-psychotic substances, anti-emetics, and imaging agents. In a certain embodiments, the bioactive agent is a drug. A more complete listing of bioactive agents and specific drugs suitable for use in the present invention may be found in "Pharmaceutical Substances: Syntheses, Patents, Applications" by Axel Kleemann and Jurgen Engel, Thieme Medical Publishing, 1999; the "Merck Index: An Encyclopedia of Chemicals, Drugs, and Biologicals", Edited by Susan Budavari et al., CRC Press, 1996, and the United States Pharmacopeia-25/National Formulary-20, published by the United States Pharmcopeial Convention, Inc., Rockville Md., 2001, all of which are incorporated herein by reference.

The term "biomolecules", as used herein, refers to molecules (e.g., proteins, amino acids, peptides, polynucleotides, nucleotides, carbohydrates, sugars, lipids, nucleoproteins, glycoproteins, lipoproteins, steroids, etc.) whether naturally-occurring or artificially created (e.g., by synthetic or recombinant techniques) that are commonly found in nature (e.g., organisms, tissues, cells, or viruses). Specific classes of biomolecules include, but are not limited to, enzymes, receptors, neurotransmitters, hormones, cytokines, cell response modifiers such as growth factors and chemotactic factors, antibodies, vaccines, haptens, toxins, interferons, ribozymes, anti-sense agents, plasmids, siRNA, mRNA, miRNA, DNA, and RNA.

As used herein, "biodegradable" polymers are polymers that degrade (i.e., down to monomeric species or oligomers that can be eliminated or processed by the body) under physiological conditions. In some embodiments, the polymers and polymer biodegradation byproducts are biocompatible. Biodegradable polymers are not necessarily hydrolytically degradable and may require enzymatic action to fully degrade. In certain embodiments, the biodegradable polymer is degraded by the endosome As used herein, the term "functionally expressed" refers to a coding sequence which is transcribed, translated, post-translationally modified (if relevant), and positioned in a cell such that the protein functions.

The terms "polynucleotide", "nucleic acid", or "oligonucleotide" refer to a polymer of nucleotides. The terms "polynucleotide", "nucleic acid", and "oligonucleotide", may be used interchangeably. Typically, a polynucleotide comprises at least two nucleotides. DNAs and RNAs are polynucleotides. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, C5-propynylcytidine, C5-propynyluridine, C5-bromouridine, C5-fluorouridine, C5-iodouridine, C5-methylcytidine, 7-deazaadenosine, 7-deazaguanosine, 8-oxoadenosine, 8-oxoguanosine, O(6)-methylguanine, and 2-thiocytidine), chemically modified bases, biologically modified bases (e.g., methylated bases), intercalated bases, modified sugars (e.g., 2'-fluororibose, 2'-methoxyribose, 2'-aminoribose, ribose, 2'-deoxyribose, arabinose, and hexose), unnatural base pairs (UBPs), or modified phosphate groups (e.g., phosphorothioates and 5'-N phosphoramidite linkages). Enantiomers of natural or modified nucleosides may also be used. Nucleic acids also include nucleic acid-based therapeutic agents, for example, nucleic acid ligands, siRNA, short hairpin RNA, antisense oligonucleotides, ribozymes, aptamers, and SPIEGELMERS™, oligonucleotide ligands described in Wlotzka, et al., Proc. Natl. Acad. Sci. USA, 2002, 99(13):8898, the entire contents of which are incorporated herein by reference. Nucleic acids can also include nucleotide analogs (e.g., BrdU), and non-phosphodiester internucleoside linkages (e.g., peptide nucleic acid (PNA) or thiodiester linkages). In particular, nucleic acids can include, without limitation, DNA, RNA, cDNA, gDNA, ssDNA, dsDNA or any combination thereof.

The terms "polypeptide", "peptide", and "protein", may be used interchangeably to refer a string of at least three amino acids linked together by peptide bonds. Peptide may refer to an individual peptide or a collection of peptides. Peptides can contain natural amino acids, non-natural amino acids (i.e., compounds that do not occur in nature but that can be incorporated into a polypeptide chain), and/or amino acid analogs. Also, one or more of the amino acids in a peptide may be modified, for example, by the addition of a chemical entity such as a carbohydrate group, a phosphate group, a farnesyl group, an isofarnesyl group, a fatty acid group, a linker for conjugation, functionalization, or other modification, etc. Modifications may include cyclization of the peptide, the incorporation of D-amino acids, etc.

As used herein, "peptidomimetic" refers to a mimetic of a peptide which includes some alteration of the normal peptide chemistry. Peptidomimetics typically enhance some property of the original peptide, such as increase stability, increased efficacy, enhanced delivery, increased half-life, etc. Methods of making peptidomimetics based upon a known polypeptide sequence is described, for example, in U.S. Pat. Nos. 5,631,280; 5,612,895; and 5,579,250. Use of peptidomimetics can involve the incorporation of a non-amino acid residue with non-amide linkages at a given position. One embodiment of the present invention is a peptidomimetic wherein the compound has a bond, a peptide backbone or an amino acid component replaced with a suitable mimic. Some non-limiting examples of unnatural amino acids which may be suitable amino acid mimics include β-alanine, L-α-amino butyric acid, L-γ-amino butyric acid, L-α-amino isobutyric acid, L-ε-amino caproic acid, 7-amino heptanoic acid, L-aspartic acid, L-glutamic acid, N-ε-Boc-N-α-CBZ-L-lysine, N-ε-Boc-N-α-Fmoc-L-lysine, L-methionine sulfone, L-norleucine, L-norvaline, N-α-Boc-N-δCBZ-L-ornithine, N-δ-Boc-N-α-CBZ-L-ornithine, Boc-p-nitro-L-phenylalanine, Boc-hydroxyproline, and Boc-L-thioproline.

The terms "polysaccharide", "carbohydrate", or "oligosaccharide" may be used interchangeably to refer to a polymer of sugars. Typically, a polysaccharide comprises at least two sugars. The polymer may include natural sugars (e.g., glucose, fructose, galactose, mannose, arabinose, ribose, and xylose) and/or modified sugars (e.g., 2'-fluororibose, 2'-deoxyribose, and hexose).

As used herein, the term "small molecule" is used to refer to molecules, whether naturally-occurring or artificially created (e.g., via chemical synthesis) that have a relatively low molecular weight. Typically, a small molecule is an organic compound (i.e., it contains carbon). The small molecule may contain multiple carbon-carbon bonds, stereocenters, and other functional groups (e.g., amines, hydroxyl, carbonyls, heterocyclic rings, etc.). In some embodiments, small molecules are monomeric and have a molecular weight of less than about 1500 g/mol. In certain embodiments, the molecular weight of the small molecule is less than about 1000 g/mol or less than about 500 g/mol. Preferred small molecules are biologically active in that they produce a biological effect in animals, preferably mammals, more preferably humans. Small molecules include, but are not limited to, radionuclides and imaging agents. In certain embodiments, the small molecule is a drug. Preferably, though not necessarily, the drug is one that has already been deemed safe and effective for use in humans or animals by the appropriate governmental agency or regulatory body. For example, drugs approved for human use are listed by the FDA under 21 C.F.R. §§ 330.5, 331 through 361, and 440 through 460, incorporated herein by reference; drugs for veterinary use are listed by the FDA under 21 C.F.R. §§ 500 through 589, incorporated herein by reference. All listed drugs are considered acceptable for use in accordance with the present invention.

The term "subject" refers to any individual who is the target of administration or treatment. The subject can be a vertebrate, for example, a mammal and particularly a human. Thus, the subject can be a human or veterinary patient. The term "patient" refers to a subject under the treatment of a clinician, e.g., physician.

The term "therapeutically effective" refers to the amount of the composition used is of sufficient quantity to ameliorate one or more causes or symptoms of a disease or disorder. Such amelioration only requires a reduction or alteration, not necessarily elimination.

II. Methods for Characterizing Particle Delivery Vehicles

Methods and compositions for characterizing vehicle delivery formulations to identify formulations with a desired tropism and that deliver functional cargo to the cytoplasm of specific cells are provided. The disclosed methods and compositions use a reporter that has a functionality that can be detected when delivered to the cell. Detecting the function of the reporter in the cell indicates that the formulation of the delivery vehicle will deliver functional cargo to the cell. A chemical composition identifier is included in each different delivery vehicle formulation to keep track of the chemical composition specific for each different delivery vehicle formulation. In one embodiment, the chemical composition identifier is a nucleic acid barcode. The sequence of the nucleic acid bar code is paired to the chemical components used to formulate the delivery vehicle in which it is loaded so that when the nucleic acid bar code is sequenced, the chemical composition of the delivery vehicle that delivered the barcode is identified. Representative reporters include, but are not limited to siRNA, mRNA, nuclease protein, nuclease mRNA, small molecules, epigenetic modifiers, and phenotypic modifiers.

Figure 12A:
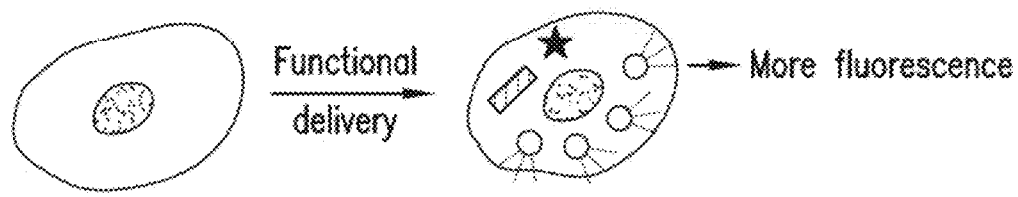
FIGS. 12A to 12E illustrate how a reporter system can generate an interpretable change in a cell, including an increase in fluorescence (FIG. 12A), decrease in fluorescence (FIG. 12B), a change in physical state of the cell (FIG. 12C), change in downstream signaling in the cell (FIG. 12D), or insertion of the barcode in the genome of the cell (FIG. 12E).
Figure 12B:
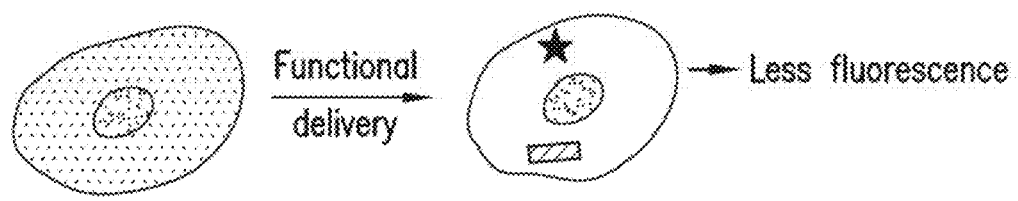
Figure 12C:
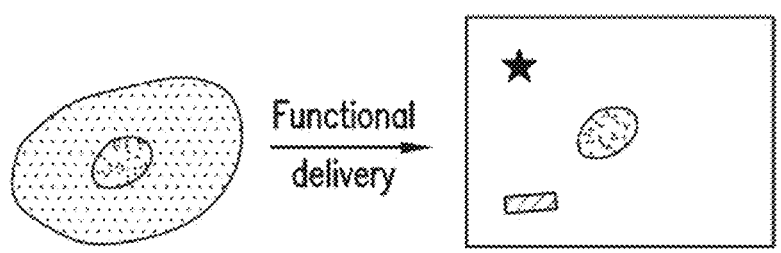
Figure 12D:
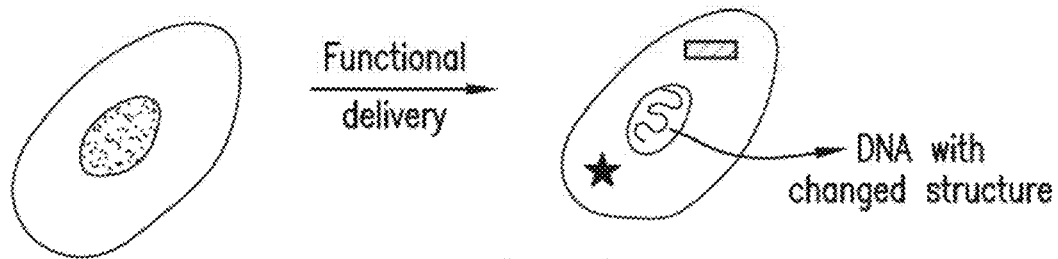
Figure 12E:
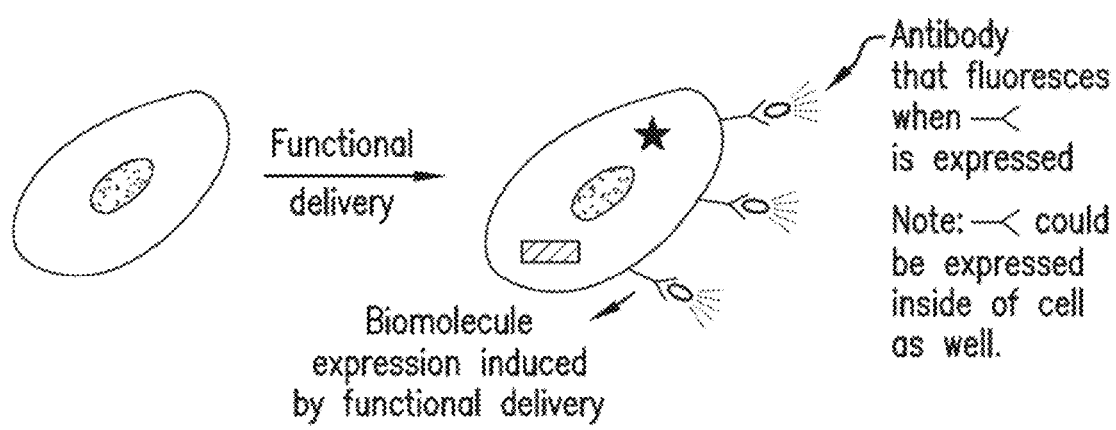
Figure 12F:
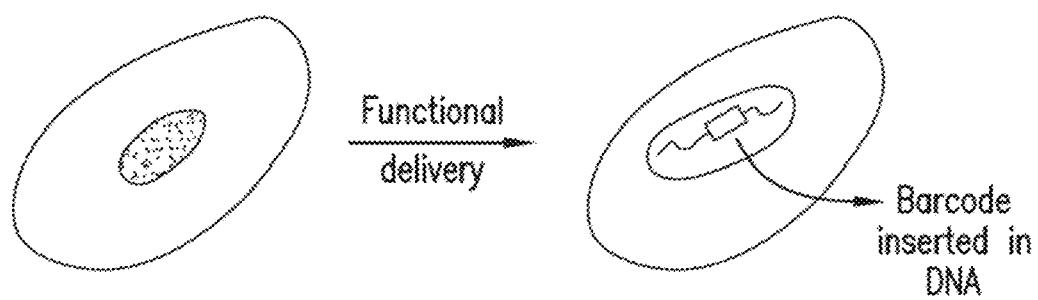
Figure 13:
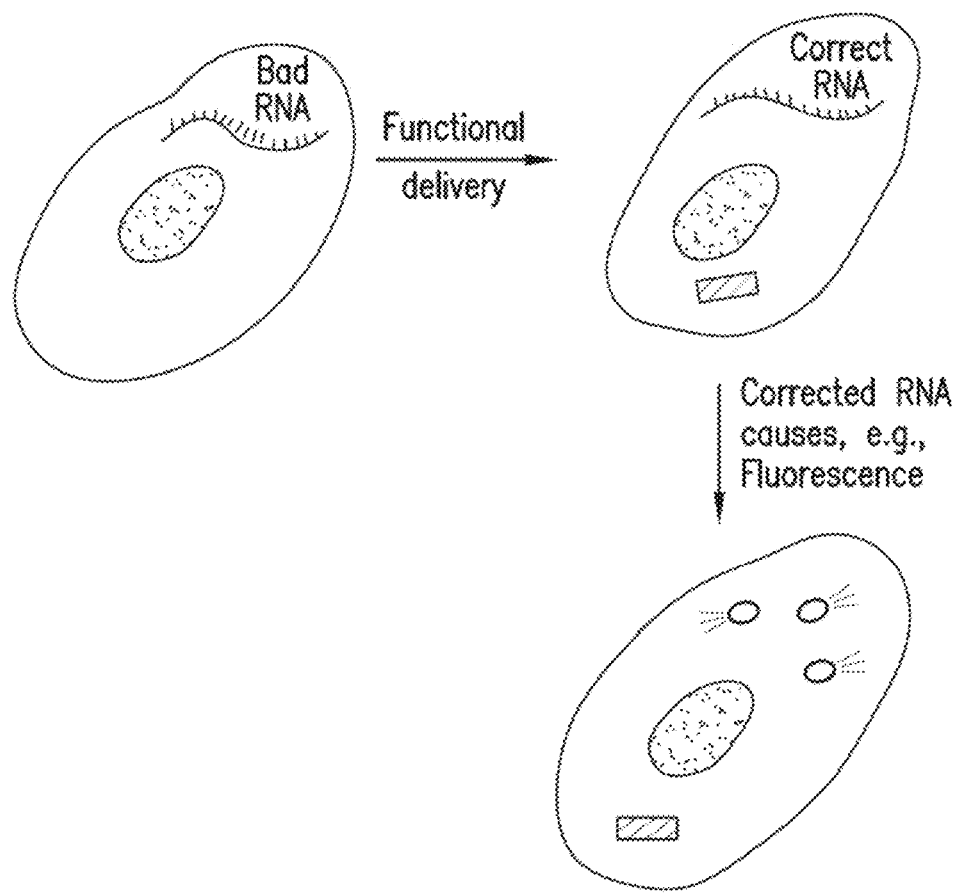
FIG. 13 is an illustration of how in all cases of FIGS. 12A to 12F, the interpretable change can also be caused by a change in a different molecule.

FIGS. 12A-12E illustrate how the disclosed methods and compositions can identify delivery vehicle compositions that deliver functional cargo to cells. In FIG. 12A, the reporter, when delivered to the cell by the delivery vehicle, causes increased fluorescence in the cell. The reporter can be a nucleic acid encoding a fluorescent protein that when expressed and exposed to the proper wavelength of light can fluoresce. In FIG. 12B, the reporter, when expressed or activated in the cell, causes a decrease in fluorescence. In FIG. 12C, the reporter causes the cell to change morphology. In FIG. 12D the reporter causes the expression of a biomolecule, for example an antibody that binds to a detectable label, for example a fluorescent label. FIG. 12E shows that the reporter causes the insertion of the chemical composition identifier into the genome of the cell. FIG. 13 shows that the reporter causes the correction of a nucleic acid, for example a nucleic acid with a mutation that inhibits expression of the nucleic acid. The reporter in this case can be a nuclease or recombinase such as CRISPR/Cas.

A. In Vivo Methods

One embodiment provides an in vivo method for characterizing delivery vehicle formulations for in vivo delivery of an agent including the steps of formulating multiple delivery vehicles having different chemical compositions, wherein each delivery vehicle contains a reporter that can generate a detectable signal when delivered to the cytoplasm of cells of a non-human mammal, and a composition identifier that identifies the chemical composition of the vehicle. The method also includes the steps of pooling and administering the multiple delivery vehicles to a non-human mammal. The method also includes the step of sorting cells from to multiple tissues of the non-human mammal that generate the detectable signal from cells that do not generate the detectable signal, wherein the cells that generate the detectable signal are also sorted based on the presence or absence of a cell surface protein that is indicative of tissue type or cell type. After the cells are sorted, the method includes the step of identifying the chemical composition identifier in the sorted cells that generate the detectable signal to determine the chemical composition of the delivery vehicle in the sorted cells and correlate the chemical composition of the delivery vehicle with the tissue or cell type containing the delivery vehicle. In some embodiments, the delivery vehicle is a particulate delivery vehicle, and in other embodiments the delivery vehicle is a conjugate. In some embodiments, the method is a high-throughput screening assay.

The pool of multiple delivery vehicle formulations is typically administered parenterally, for example by intravenous injection or intramuscular injection. Alternatively, the composition may be administered by other routes, e.g., intra-arterial, inhalational, intradermal, subcutaneous, oral, nasal, bronchial, ophthalmic, transdermal (topical), transmucosal, peritoneal, rectal, and vaginal routes. In some embodiments, the materials are not only optimized to reach a particular tissue site but for a particular delivery route.

After a defined period of time post-administration, the tissues or cells are harvested and processed for sorting. In some cases, targeted cells positive for the reporter or label are isolated. In other cases, targeted cells negative for the reporter or label are isolated, e.g., wherein the materials contain an inhibitor of a constitutive reporter transgene. The materials that are present in those cells can then be isolated for identification. In some embodiments, the materials are processed to release the associated barcodes, which are used to identify the materials that were present in the tissue. The amount of total materials present per cell may also be quantified. Alternatively or in addition, samples from non-targeted cells or organs can be collected, and the materials identified by the same process. This way, those materials with undesirable biophysiochemical properties, such as non-specific tissue targeting, may be identified and eliminated from subsequent rounds of enrichment.

In some embodiments, target cells are assayed to identify the nucleic acid barcodes present in the cells, thereby identifying the corresponding materials. In some cases, this involves sequencing the barcodes, e.g. using PCR amplification, followed by next generation sequencing (NGS or deep sequencing).

The protocols used for reporter positive cell isolation will vary based on the reporter system used, as well the cell source (e.g. in vivo tissue/blood and in vitro cell culture). Tissues and cells may be isolated with the animal alive or post-mortem. Whole or partial tissue and organs may be extracted from the animal. Biopsies may be the source of cells. Cells may be isolated from blood from various routes including cardiac puncture or retro orbital blood draw. Isolation may occur via enzymatic (e.g. trypsin, various collagenases, and combinations) and/or mechanical methods (e.g.-centrifugation, mortar and pestle, chopping, and grinding). The resulting cell suspensions may be either heterogeneous or homogenous cell types depending on source. These suspensions can then be separated based on a multitude of criteria (e.g., cell type, cell markers, cell cycle, reporter status) simultaneously or in sequential manner. This may be done by fluorescent assisted cell sorting, magnetic assisted cell sorting, centrifugation, and affinity based cell isolation (e.g., antibody-DNA conjugates, antibody-biotin). Cells can be isolated into single-cell or bulk populations. Barcodes are then isolated from the cell. This can be done via chromatography or solution-based methods. Barcodes may be first separated from genomic DNA via size differences or other characteristics, or genomic DNA can be degraded; alternatively, genomic DNA may be left unperturbed. Extracted barcodes can be left concentrated or diluted for further analysis. This barcode extract can be sequenced directly or amplified by PCR to make more copies. Barcodes can be sequenced by Sanger sequencing, Next-Generation Sequencing (e.g.—Illumina, Roche 454, Ion torrent), or Nanopore-based sequencing methods.

Those formulations that demonstrate functional targeting of the desired tissue, while optionally demonstrating a low level of uptake by non-targeted organs may be enriched. The screening may be repeated several times, for example, to improve the resolution of the assay. In addition, the strength of the screen may be modified by requiring higher or lower levels of signal from a particular label in order to select the corresponding material for enrichment.

In some embodiments, the method further involves creating or producing a new library of delivery vehicles based on those shown to demonstrate functional targeting. The disclosed method in this way can be used to optimize the biophysical characteristics of the materials. Parameters for optimization may include but are not limited to any of size, polymer composition, surface hydrophilicity, surface charge, and the presence, composition and density of targeting agents on the material surface. The new library can be assayed as above and used to determine which optimizations were effective.

In one embodiment, the delivery vehicles are nanoparticles formulated using a microfluidic device. Nanoparticle 1, with chemical composition 1, is formulated to carry reporter mRNA and barcode 1. Nanoparticle 2, with chemical composition 2, is formulated to carry reporter mRNA and barcode 2. This process is repeated N times, such that Nanoparticle N, with chemical composition N, is formulated to carry reporter mRNA and barcode N. The chemical components making up nanoparticle 1 are loaded into one glass syringe. The barcode 1 and reporter mRNA are loaded into a separate syringe. The contents of the syringes are mixed together at flow rates of 200 µL/min for the nanoparticle syringe and 600 µL/min for the barcode and reporter mRNA syringe. Nanoparticles are then characterized by diluting them into sterile 1×PBS at a concentration of 0.00001 to 0.01 mg/mL. At this point, the hydrodynamic diameter of the nanoparticles as well as their autocorrelation curves are analyzed using DLS. The nanoparticles are then dialyzed into a regenerated cellulose membrane, and then dialyzed into a large molecular weight (>100 kDa) cellulose membrane. The nanoparticles are then sterile filtered through a 0.22 µm filter, and loaded into a sterilized plastic tube.

The nanoparticles are then administered to mice, and a timepoint between 2 hours and 168 hours later, the mice are sacrificed.

In one embodiment, the reporter mRNA encodes GFP; in this case, GFP$^+$ cells would be isolated and the timepoint would range between 2 and 48 hours.

In another embodiment, the reporter mRNA encodes tdTomato. In this case, tdTomato cells are isolated and the timepoint would range between 2 and 120 hours.

In another embodiment, the reporter is RFP. RFP$^+$ cells are isolated and the timepoint would range between 2 and 48 hours.

In another embodiment, the reporter is BFP. In this case, BFP$^+$ cells are isolated and the timepoint would range between 2 and 48 hours.

In another embodiment, the reporter is ICAM-2, which is a gene that is expressed on the cell surface. In this case, ICAM-2$^+$ cells are isolated using an ICAM-2 antibody (BioLegend clone 3C4) and the timepoint would range between 2 and 48 hours.

In another embodiment, the reporter is MHC1, which is a gene that can be expressed on the cell surface. In this case, MHC1$^+$ cells are isolated from a MHC2$^+$ mouse strain (i.e., 002087) using a MHC1 antibody (Clone ERMP42) and the timepoint would range between 2 and 48 hours.

In another embodiment, the reporter is MHC2, which is a gene that can be expressed on the cell surface. In this case, MHC2$^+$ cells are isolated from a MHC1$^+$ mouse strain (i.e., 003584) using a MHC2 antibody (Clone IBL-5/22) and the timepoint would range between 2 and 48 hours.

In another embodiment, the reporter is Firefly Luciferase, which is a protein that is expressed in the cytoplasm. In this case, Luciferase$^+$ cells are isolated using a Luciferase antibody (Clone C12 or polyclonal) and the timepoint would range between 2 and 48 hours.

In another embodiment, the reporter is Renilla Luciferase, which is a protein that is expressed in the cytoplasm. In this case, Luciferase$^+$ cells are isolated using a Luciferase antibody (Clone EPR17792 or polyclonal) and the timepoint would range between 2 and 48 hours.

In yet another embodiment, the reporter is Cre. In this case, the nanoparticles are injected into a Cre reporter mouse (for example, the Lox-Stop-Lox-tdTomato Ai14 mouse strain) and tdTomato$^+$ cells are isolated, and the timepoint would range between 2 and 120 hours.

In one embodiment, the reporter siRNA is siGFP. In this case, the nanoparticles are administered to a GFP-positive mouse (e.g. JAX 003291). GFP$^{low}$ cells are isolated and the timepoint would range between 2 and 96 hours.

In another embodiment, the reporter is siRFP; in this case, the nanoparticles are administered to a RFP-positive mouse (e.g. JAX 005884). RFP$^{low}$ cells are isolated and the timepoint would range between 2 and 96 hours.

In another embodiment, the reporter is siICAM-2, which is a gene that is expressed on the cell surface. In this case, ICAM-2$^{low}$ cells are isolated using an ICAM-2 antibody (BioLegend clone 3C4) and the timepoint would range between 2 and 96 hours.

In another embodiment, the reporter is siCD45, which is a gene that is expressed on the cell surface. In this case, CD45$^{low}$ cells are isolated using a CD45 antibody (BioLegend clone 102) and the timepoint would range between 2 and 96 hours.

In another embodiment, the reporter is siCD47, which is a gene that is expressed on the cell surface. In this case, CD47$^{low}$ cells are isolated using a CD47 antibody (BioLegend clone miap301) and the timepoint would range between 2 and 96 hours.

In another embodiment, the reporter is siTie2, which is a gene that is expressed on the cell surface. In this case, Tie2$^{low}$ cells are isolated using a Tie2 antibody (BioLegend clone TEK4 and the timepoint would range between 2 and 96 hours. In other embodiments, the reporter siRNA is a microRNA.

In one embodiment, the reporter sgRNA is sgGFP. In this case, the nanoparticles are administered to a Cas9-GFP expressing mouse (e.g. JAX 026179). GFP$^{low}$ cells are isolated and the timepoint would range between 2 and 120 hours.

In another embodiment, the reporter is sgICAM-2 and is injected into Cas9 expressing mice, which is a gene that is expressed on the cell surface. In this case, ICAM-2$^{low}$ cells are isolated using an ICAM-2 antibody (BioLegend clone 3C4) and the timepoint would range between 2 and 120 hours.

In another embodiment, the reporter is sgCD45 and is injected into Cas9 expressing mice, which is a gene that is expressed on the cell surface. In this case, iCD45$^{low}$ cells are isolated using a CD45 antibody (BioLegend clone 102) and the timepoint would range between 2 and 120 hours.

In another embodiment, the reporter is sgCD47 and is injected into Cas9 expressing mice, which is a gene that is expressed on the cell surface. In this case, CD47$^{low}$ cells are isolated using a CD47 antibody (BioLegend clone miap301) and the timepoint would range between 2 and 96 hours.

In another embodiment, the reporter is sgTie2 and is injected into Cas9 expressing mice, which is a gene that is expressed on the cell surface. In this case, Tie2$^{low}$ cells are isolated using a Tie2 antibody (BioLegend clone TEK4) and the timepoint would range between 2 and 120 hours.

In another embodiment, the reporter is sgLoxP and is injected into Cas9-Lox-Stop-Lox-tdTomato expressing mice. tdTomato$^+$ cells are isolated and the timepoint would range between 2 and 120 hours.

At the appropriate timepoint, the tissues from the mice are digested, and cells that are positive for the functional reporter molecule are isolated. In some embodiments, the cells are isolated by sacrificing the animal, dissecting the tissues, and adding enzymes to digest the tissues including but not limited to the following: Collagenase Type I, IV, XI, and Hyaluronidase. The tissues are then shaken at a temperature of 37° C. for 15-60 minutes, and strained through a 40, 70, or 100 µm strainer to isolate individual cell types. In some embodiments the cells are sorted by cell type or tissue type using a fluorescence activated cell sorter.

The cells are then lysed to isolate the barcodes inside. In some embodiments, cells are exposed to DNA-extraction protocols, for example QuickExtract™. In this embodiment, the cells are then prepared for DNA sequencing using PCR that adds indices that indicate the sample, purified using magnetic beads, added to PhiX control sequences (if using an Illumina machine) diluted to 4 nM concentrations, and sequenced using a MiniSeq®, MiSeq®, NextSeq®, or other next generation sequencing machine.

In other embodiments, cells are exposed to RNA-extraction protocols, for example OligoTex® kits. In this embodiment, reverse transcriptase is applied to the cells to convert any RNA to cDNA. At this point, the cDNA is prepared for sequencing using PCR that adds indices that indicate the sample, purified using magnetic beads, added to PhiX® control sequences (if using an Illumina machine) diluted to 4 nM concentrations, and sequenced using a MiniSeq®, MiSeq®, NextSeq®, or other next generation sequencing machine.

B. In Vitro Methods

Another embodiment provides an in vitro method of characterizing the delivery vehicle formulations. In this embodiment cells or a cell line can be used that contain a gene that has been modified to prevent expression of the gene, for example a gene that encodes a fluorescent protein. The reporter in the delivery vehicle can be a recombinase or nuclease or nucleic acids that encode the recombinase or nuclease. When the delivery vehicle delivers the reporter to the cells, the recombinase or nuclease repairs the modified gene so that the fluorescent protein is expressed. The cells can be a heterogeneous pool of cells from several different tissues. After administration of the delivery vehicles the cells can be sorted to identify the cells that fluoresce and for tissue or cell type. Nucleic acid bar codes can be isolated form the different types of cells, sequenced to identify the chemical composition of the delivery vehicles that delivered them.

III. Delivery Vehicles

A. Representative Delivery Vehicles

Another embodiment provides a composition containing a delivery vehicle, a chemical composition identifier, for example a nucleic acid bar code, and a reporter that is biologically active when delivered to the cytoplasm of a cell. The composition optionally contains a targeting agent. In some embodiments, the delivery vehicle is a lipid nanoparticle. In other embodiments, the delivery vehicle is a conjugate. The reporter can be siRNA, mRNA, a nuclease, a recombinase, a small molecule, an epigenetic modifier, or a combination thereof.

In one embodiment, the delivery vehicle contains a pegylated C6 to C18 alkyl, cholesterol, DOPE, a chemical composition identifier and reporter. In still other embodiments, the delivery vehicle is a conjugate.

1. Nanoparticle Delivery Vehicles

The following exemplary delivery vehicles can be used in the disclosed compositions and methods and contain a reporter and a chemical composition identifier. In some embodiments, the delivery vehicle is a lipidoid nanoparticle as described in Turnbull I C, et al. Methods Mol Biol. 2017 1521:153-166, which is incorporated by reference for this teaching. In some embodiments, the delivery vehicles is a polymer-lipid nanoparticle as described in Kaczmarek J C, et al. Angew Chem Int Ed Engl. 2016 55(44):13808-13812, which is incorporated by reference for this teaching. In some embodiments, the delivery vehicle is a dendrimer-RNA nanoparticle as described in Chahal J S, et al. Proc Natl Acad Sci USA. 2016 113(29):E4133-42, which is incorporated by reference for this teaching. In some embodiments, the delivery vehicle is a poly(glycoamidoamine) brush as described in Dong Y, et al. Nano Lett. 2016 16(2):842-8, which is incorporated by reference for this teaching. In some embodiments, the delivery vehicle is a lipid-like nanoparticle as described in Eltoukhy A A, et al. Biomaterials. 2014 35(24): 6454-61, which is incorporated by reference for this teaching. In some embodiments, the delivery vehicle is a low-molecular-weight polyamines and lipid nanoparticle as described in Dahlman J E, et al. Nat Nanotechnol. 2014 9(8):648-655, which is incorporated by reference for this teaching. In some embodiments, the delivery vehicle is a lipopeptide nanoparticle as described in Dong Y, et al. Proc Natl Acad Sci USA. 2014 111(11):3955-60, which is incorporated by reference for this teaching. In some embodiments, the delivery vehicle is a lipid-modified aminoglycoside derivative as described in Zhang Y, et al. Adv Mater. 2013 25(33):4641-5, which is incorporated by reference for this teaching. In some embodiments, the delivery vehicle is a functional polyester as described in Yan Y, et al. Proc Natl Acad Sci USA. 2016 113(39):E5702-10, which is incorporated by reference for this teaching. In some embodiments, the delivery vehicle is a degradable dendrimers as described in Zhou K, et al. Proc Natl Acad Sci USA. 2016 113(3): 520-5, which is incorporated by reference for this teaching. In some embodiments, the delivery vehicle is a lipocationic polyester as described in Hao J, et al. J Am Chem Soc. 2015 137(29):9206-9, which is incorporated by reference for this teaching. In some embodiments, the delivery vehicle is a nanoparticle with a cationic cores and variable shell as described in Siegwart D J, et al. Proc Natl Acad Sci USA. 2011 108(32):12996-3001, which is incorporated by reference for this teaching. In some embodiments, the delivery vehicle is an amino-ester nanomaterial as described in Zhang X, et al. ACS Appl Mater Interfaces. 2017 9(30): 25481-25487, which is incorporated by reference for this teaching. In some embodiments, the delivery vehicle is a polycationic cyclodextrin nanoparticle as described in Zuckerman J E, et al. Nucleic Acid Ther. 2015 25(2):53-64, which is incorporated by reference for this teaching. In some embodiments, the delivery vehicle is a cyclodextrin-containing polymer conjugate of camptothecin as described in Davis M E. Adv Drug Deliv Rev. 2009 61(13):1189-92, or Gaur S, et al. Nanomedicine. 2012 8(5):721-30, which are incorporated by reference for these teachings. In some embodiments, the delivery vehicle is an oligothioetheramide as described in Sorkin M R, et al. Bioconjug Chem. 2017 28(4):907-912, which is incorporated by reference for this teaching. In some embodiments, the delivery vehicle is a macrocycles as described in Porel M, et al. Nat Chem. 2016 June; 8(6):590-6, which is incorporated by reference for this teaching. In some embodiments, the delivery vehicle is a lipid nanoparticle as described in Alabi C A, et al. Proc Natl Acad Sci USA. 2013 110(32):12881-6, which is incorporated by reference for this teaching. In some embodiments, the delivery vehicle is a poly(beta-amino ester) (PBAE) nanoparticle as described in Zamboni C G, et al. J Control Release. 2017 263:18-28, which is incorporated by reference for this teaching. In some embodiments, the delivery vehicle is a poly(β-amino ester) (PBAE) as described in Green J J, et al. Acc Chem Res. 2008 41(6):749-59, which is incorporated by reference for this teaching. In some embodiments, the delivery vehicle is a stable nucleic acid lipid particles (SNALP) as described in Semple S C, et al. Nat Biotechnol. 2010 28(2):172-6, which is incorporated by reference for this teaching. In some embodiments, the material is an amino sugar. In one embodiment the material is GalNAc as described in Tanowitz M, et al. Nucleic Acids Res. 2017 Oct. 23; Nair J K, et al. Nucleic Acids Res. 2017 Sep. 15; and Zimmermann T S, et al. Mol Ther. 2017 Jan. 4; 25(1):71-78, which are incorporated by reference for these teaching.

2. Conjugate Delivery Vehicles

Figure 8A:
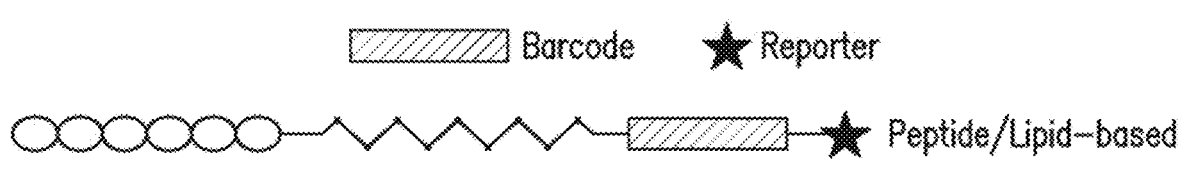
FIGS. 8A and 8B are illustrations of combined peptide-based and lipid-based systems.
Figure 8B:
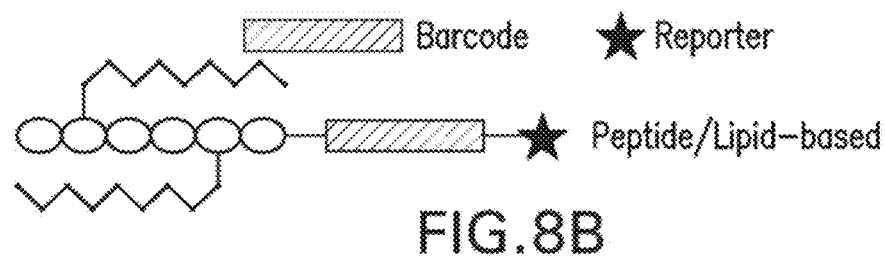
Figure 9A:
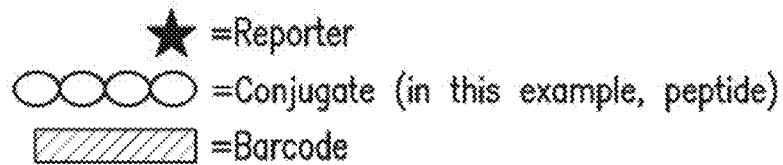
FIG. 9 is an illustration of systems where the reporter is connected to the conjugate (FIG. 9A), connected to the barcode (FIG. 9B), embedded in the conjugate (FIG. 9C), or embedded in the barcode (FIG. 9D). In each case, the reporter can be connected or embedded via covalent interactions or non-covalent interactions.
Figure 9B:
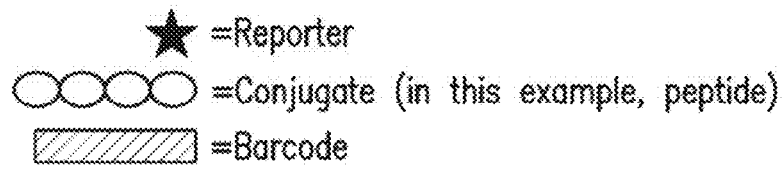
Figure 9C:
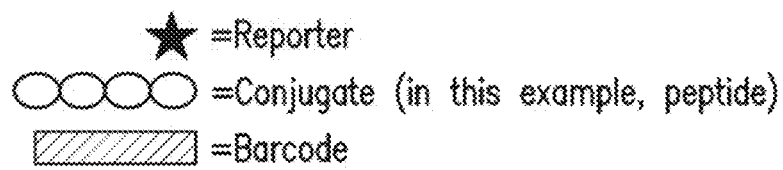
Figure 9D:
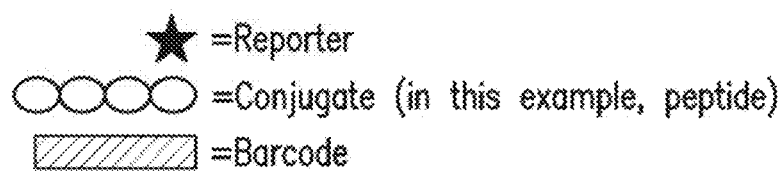

In some embodiments, the delivery vehicle is a conjugate system. FIGS. 7A-7G, 8A-8B, and 9A-9D are schematic representations of several representative conjugate delivery vehicles containing a core material, a chemical composition identifier, and a reporter. The core material can be a peptide, lipid, ssRNA, dsRNA, ssDNA, dsDNA, a polymer, a polymer/lipid combination, a peptide/lipid combination, or combinations thereof. As shown in FIGS. 9A-9D, the components of the conjugate delivery vehicle can be in any order. As shown in FIG. 8B, the components of the conjugate delivery vehicle can be modified with a sugar, lipid, peptide, or other modifier.

Figure 10:
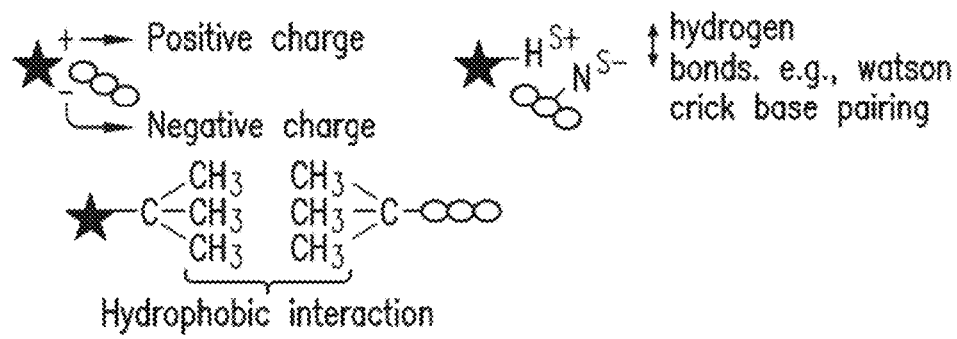
FIG. 10 is an illustration of example interactions connecting reporter to the conjugate or the barcode.

In one embodiment the reporter is ionically bonded to the conjugate delivery vehicle (FIG. 10). The reporter can be bonded to the conjugate delivery system by hydrogen bonding, Watson-Crick base pairing, or hydrophobic interaction.

Figure 11:
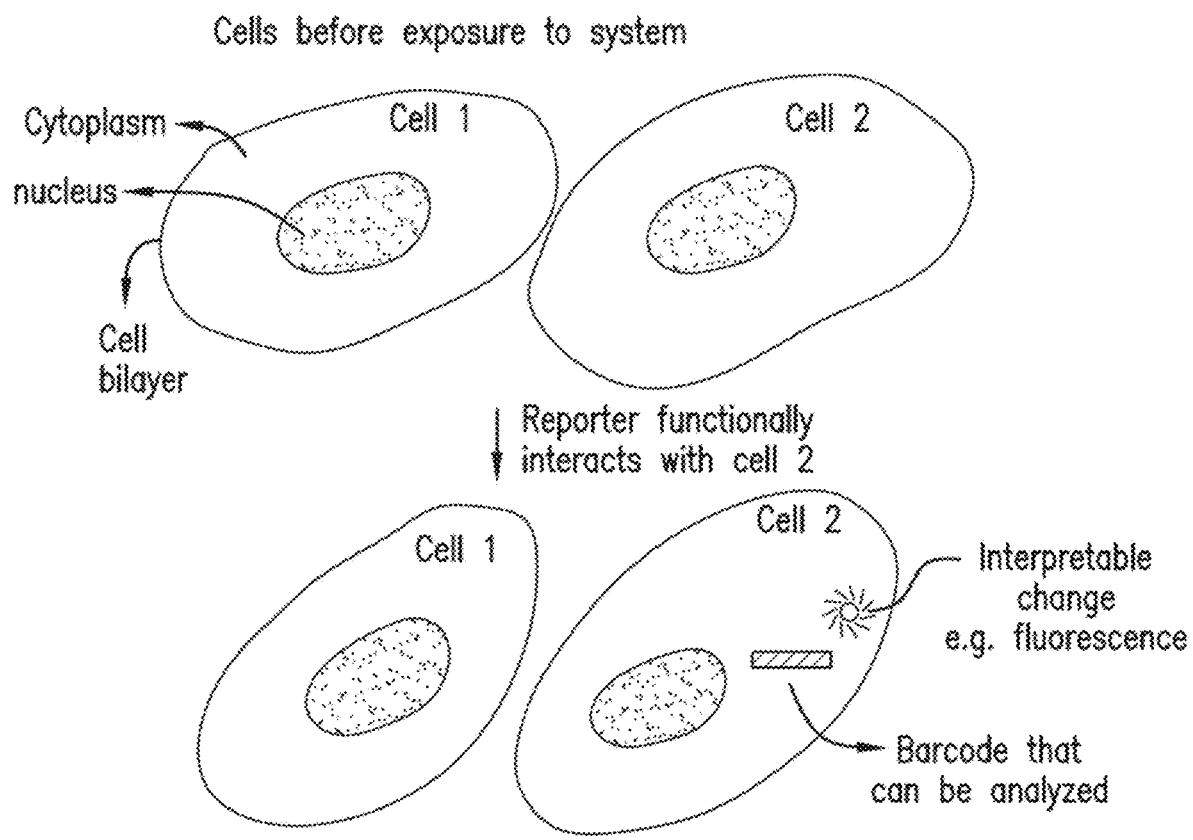
FIG. 11 is an illustration of how a reporter system can generate an interpretable change in a cell.

Exemplary reporters include, but are not limited to siRNA, nuclease protein, mRNA, nuclease mRNA, small molecules, and epigenetic modifiers (FIG. 11). In one embodiment the reporter causes a detectable, phenotypic change in the cell. For example, the reporter can cause the cell to change morphology, metabolic activity, increase or decrease in gene expression, etc.

B. Formulating Delivery Vehicles

In one embodiment, the delivery vehicle used in the disclosed methods is a particulate delivery vehicle. For example the delivery vehicle can be nanoparticle including but not limited to a lipid nanoparticle. In one embodiment, the particulate delivery vehicle encapsulates the reporter and the chemical composition identifier. In other embodiments, the reporter, the chemical composition identifier, or both are conjugated to the delivery vehicle.

In one embodiment nanoparticles are formulated by combining a biomaterial with a synthetic or commercial lipid in a tube with an organic solvent such as 100% ethanol and mixing them. In a second tube, the reporter and the chemical composition identifier are combined and mixed, typically in a buffered solution. Next the content of the two tubes are mixed together to produce the nanoparticles. The biomaterial in tube one can be an ionizable lipid, a polymer, a peptide, nucleic acid, carbohydrate, etc. A variety of different formulations can be quickly produced using a microfluidic device as disclosed in Chen D, et al. (2012) Rapid discovery of potent siRNA-containing lipid nanoparticles enabled by controlled microfluidic formulation. J Am Chem Soc 134:6948-6951, which is incorporated by reference in its entirety.

In another embodiment, nucleic acids (mRNA, DNA barcodes, siRNA, and sgRNA) are diluted in a buffer, for example 10 mM citrate buffer, while lipid-amine compounds, alkyl-tailed PEG, cholesterol, and helper lipids were diluted in ethanol. For nanoparticle screens, the reporter and chemical composition identifier, for example DNA barcodes, are mixed at a 10:1 mass ratio. It will be appreciated that the mass ratio can be optimized for each run. Citrate and ethanol phases were combined in a microfluidic device by syringes (Hamilton Company) at a flow rate of 600 µL/min and 200 µL/min, respectively. All PEGs, cholesterol, and helper lipids were purchased from Avanti Lipids.

The biophysical and chemical characteristics of materials use to formulate the delivery vehicles. Parameters for optimization may include but are not limited to any of size, polymer composition, surface hydrophilicity, surface charge, and the presence, composition and density of targeting agents on the material surface. A library of delivery vehicles in which these or other parameters are varied may be produced using combinatorial techniques. Combinatorial techniques may also be used to provide a unique label for each material or population of materials. A large number of different formulations for the delivery vehicles can be achieved by varying lipid-amine compound, the molar amount of PEG, the structure of PEG, and the molar amount of cholesterol in the particles is varied among the particles.

1. Representative Polymers

The delivery vehicles can be formulated from a variety of materials. In some embodiments, the delivery vehicles contain helper lipids. Helper lipids contribute to the stability and delivery efficiency of the delivery vehicles. Helper lipids with cone-shape geometry favoring the formation hexagonal II phase can be used. An example is dioleoylphosphatidylethanolamine (DOPE) which can promote endosomal release of cargo. Cylindrical-shaped lipid phosphatidylcholine can be used to provide greater bilayer stability, which is important for in vivo application of LNPs. Cholesterol can be included as a helper that improves intracellular delivery as well as LNP stability in vivo. Inclusion of a PEGylating lipid can be used to enhance LNP colloidal stability in vitro and circulation time in vivo. In some embodiments, the PEGylation is reversible in that the PEG moiety is gradually released in blood circulation. pH-sensitive anionic helper lipids, such as fatty acids and cholesteryl hemisuccinate (CHEMS), can trigger low-pH-induced changes in LNP surface charge and destabilization that can facilitate endosomal release.

Representative materials that can be used to produce the disclosed delivery vehicles include, but are not limited to poly(ethylene glycol), cholesterol, 1,2-dioleoyl-sn-glycero-3-phosphoethanolamine (DOPE), 1-(1Z-hexadecenyl)-sn-glycero-3-phosphocholine, 1-O-1'-(Z)-octadecenyl-2-hydroxy-sn-glycero-3-phosphocholine, 1-(1Z-octadecenyl)-2-oleoyl-sn-glycero-3-phosphocholine, 1-(1Z-octadecenyl)-2-arachidonoyl-sn-glycero-3-phosphocholine, 1-O-1'-(Z)-octadecenyl-2-hydroxy-sn-glycero-3-phosphoethanolamine, 1-(1Z-octadecenyl)-2-docosahexaenoyl-sn-glycero-3-phosphocholine, 1-(1Z-octadecenyl)-2-oleoyl-sn-glycero-3-phosphoethanolamine, 1-(1Z-octadecenyl)-2-arachidonoyl-sn-glycero-3-phosphoethanolamine, 1-(1Z-octadecenyl)-2-docosahexaenoyl-sn-glycero-3-phosphoethanolamine, 1-palmitoyl-2-(5'-oxo-valeroyl)-sn-glycero-3-phosphocholine, 1-palmitoyl-2-(9'-oxo-nonanoyl)-sn-glycero-3-phosphocholine, 1-palmitoyl-2-glutaryl-sn-glycero-3-phosphocholine, 1-hexadecyl-2-azelaoyl-sn-glycero-3-phosphocholine, 1-palmitoyl-2-azelaoyl-sn-glycero-3-phosphocholine, 1-(10-pyrenedecanoyl)-2-glutaroyl-sn-glycero-3-phosphocholine, 1-(10-pyrenedecanoyl)-2-(5,5-dimethoxyvaleroyl)-sn-glycero-3-phosphocholine, 1-palmitoyl-2-glutaroyl-sn-glycero-3-phosphoethanolamine-N-[4-(dipyrrometheneboron difluoride)butanoyl] (ammonium salt), 1-palmitoyl-2-(5,5-dimethoxyvaleroyl)-sn-glycero-3-phosphoethanolamine-N-[4-(dipyrrometheneboron difluoride)butanoyl] (ammonium salt), 2-((2,3-bis(oleoyloxy)propyl)dimethylammonio)ethyl hydrogen phosphate, 2-((2,3-bis(oleoyloxy)propyl)dimethylammonio)ethyl ethyl phosphate, 1-oleoyl-2-cholesterylhemisuccinoyl-sn-glycero-3-phosphocholine, 1,2-dicholesterylhemisuccinoyl-sn-glycero-3-phosphocholine, 1-palmitoyl-2-cholesterylcarbonoyl-sn-glycero-3-phosphocholine, 1-palmitoyl-2-cholesterylhemisuccinoyl-sn-glycero-3-phosphocholine, 1-O-hexadecanyl-2-O-(9Z-octadecenyl)-sn-glycero-3-phosphocholine, 1-O-hexadecanyl-2-O-(9Z-octadecenyl)-sn-glycero-3-phospho-(1'-rac-glycerol (ammonium salt), 1-O-hexadecanyl-2-O-(9Z-octadecenyl)-sn-glycero-3-phosphoethanolamine, 1-O-hexadecyl-sn-glycerol (HG), 1,2-di-O-phytanyl-sn-glycerol, 1,2-di-O-phytanyl-sn-glycero-3-phosphoethanolamine, 1,2-di-O-tetradecyl-sn-glycero-3-phospho-(1'-rac-glycerol), 1,2-di-O-hexyl-sn-glycero-3-phosphocholine, 1,2-di-0-dodecyl-sn-glycero-3-phosphocholine, 1,2-di-O-tridecyl-sn-glycero-3-phosphocholine, 1,2-di-O-hexadecyl-sn-glycero-3-phosphocholine, 1,2-di-O-octadecyl-sn-glycero-3-phosphocholine, 1,2-di-O-(9Z-octadecenyl)-sn-glycero-3-phosphocholine, 1,2-di-O-phytanyl-sn-glycero-3-phosphocholine, 1-O-octadecyl-2-O-methyl-sn-glycero-3-phosphocholine, 1',3'-bis[1,2-dimyristoyl-sn-glycero-3-phospho]-sn-glycerol, 1',3'-bis[1,2-dimyristoleoyl-sn-glycero-3-phospho]-sn-glycerol, 1',3'-bis[1,2-dipalmitoleoyl-sn-glycero-3-phospho]-sn-glycerol, 1,3'-bis[1,2-distearoyl-sn-glycero-3-phospho]-sn-glycerol, 1',3'-bis[1,2-dioleoyl-sn-glycero-3-phospho]-sn-glycerol, 1',3'-bis[1,2-dipalmitoyl-sn-glycero-3-phospho]-sn-glycerol, 1',3'- bis[1-palmitoyl-2-oleoyl-sn-glycero-3-phospho]-sn-glycerol, 1-palmitoyl-2-oleoyl-sn-glycero-3-phospho-(1'-myo-inositol-4'-phosphate), 1-stearoyl-2-arachidonoyl-sn-glycero-3-phospho-(1'''-myo-inositol-4'-phosphate), 1,2-dioctanoyl-sn-glycero-3-(phosphoinositol-3-phosphate), 1,2-dioctanoyl-sn-glycero-3-phospho-(1'-myo-inositol-3',4',5'-trisphosphate), 1,2-dioctanoyl-sn-glycero-3-phospho-(1'-myo-inositol-4',5'-bisphosphate), 1,2-dioctanoyl-sn-glycero-3-phospho-(1'-myo-inositol-3',4'-bisphosphate), 1,2dioctanoyl-sn-glycero-3-phospho-(1'-myo-inositol-4'-phosphate), 1,2-dioctanoyl-sn-glycero-3-phospho-(1'-myo-inositol), 1,2-dihexanoyl-sn-glycero-3-phospho-(1'-myo-inositol-3',4',5'-trisphosphate), 1,2-dihexanoyl-sn-glycero-3-phospho-(1'-myo-inositol-3',5'-bisphosphate), 1-stearoyl-2-arachidonoyl-sn-glycero-3-phospho-(1-myo-inositol-3',4',5'-trisphosphate), 1-stearoyl-2-arachidonoyl-sn-glycero-3-phospho-(1'-myo-inositol-4',5'-bisphosphate), 1-stearoyl-2-arachidonoyl-sn-glycero-3-phospho-(1'-myo-inositol-3',5-bisphosphate), 1,2-dioleoyl-sn-glycero-3-phospho-(1'-myo-inositol-3',4',5'-trisphosphate), 1,2-dioleoyl-sn-glycero-3-phospho-(1'-myo-inositol-4',5'-bisphosphate), 1,2-dioleoyl-sn-glycero-3-phospho-(1'-myo-inositol-3',5'-bisphosphate), 1,2-dioleoyl-sn-glycero-3-phospho-(1'-myo-inositol-3',4'-bisphosphate), 1,2-dioleoyl-sn-glycero-3-phospho-(1'-myo-inositol-5'-phosphate), 1,2-dioleoyl-sn-glycero-3-phospho-(1'-myo-inositol-4'-phosphate), 1,2-dioleoyl-sn-glycero-3-phospho-(1'-myo-inositol-3'-phosphate), 1,2-dioleoyl-sn-glycero-3-phospho-(1'-myo-inositol), 1-stearoyl-2-arachidonoyl-sn-glycero-3-phosphoinositol, 1,2-distearoyl-sn-glycero-3-phosphoinositol, 1-palmitoyl-2-oleoyl-sn-glycero-3-phosphoinositol, 1,2-dipalmitoyl-sn-glycero-3-phospho-(1'-myo-inositol), 1-oleoyl-2-(6-((4,4-difluoro-1,3-dimethyl-5-(4-methoxyphenyl)-4-bora-3a,4a-diaza-s-indacene-2-propionyl)amino)hexanoyl)-sn-glycero-3-phosphoinositol-4.5-bisphosphate, 1-oleoyl-2-hydroxy-sn-glycero-3-phospho-(1'-myo-inositol), 1-tridecanoyl-2-hydroxy-sn-glycero-3-phospho-(1'-myo-inositol), 1-palmitoyl-2-hydroxy-sn-glycero-3-phosphoinositol, 1-(10Z-heptadecenoyl)-2-hydroxy-sn-glycero-3-phospho-(1'-myo-inositol), 1-stearoyl-2-hydroxy-sn-glycero-3-phosphoinositol, 1-arachidonoyl-2-hydroxy-sn-glycero-3-phosphoinositol, D-myo-inositol-1,3,4-trisphosphate, D-myo-inositol-1,3,5-triphosphate, D-myo-inositol-1,4,5-triphosphate, D-myo-inositol-1,3,4,5-tetraphosphate, 1-(10Z-heptadecenoyl)-2-hydroxy-sn-glycero-3-[phospho-L-serine], or any combination thereof.

2. Biocompatible Polymers

In certain embodiments, the delivery vehicles are fabricated from or contain biocompatible polymers. A variety of biodegradable and/or biocompatible polymers are well known to those skilled in the art. Exemplary synthetic polymers suitable for use with the disclosed compositions and methods include but are not limited to poly(lactide), poly(glycolide), poly(lactic co-glycolic acid), poly(arylates), poly(anhydrides), poly(hydroxy acids), polyesters, poly(ortho esters), polycarbonates, poly(propylene fumerates), poly(caprolactones), polyamides, polyphosphazenes, polyamino acids, polyethers, polyacetals, polylactides, polyhydroxyalkanoates, polyglycolides, polyketals, polyesteramides, poly(dioxanones), polyhydroxybutyrates, polyhydroxyvalyrates, polycarbonates, polyorthocarbonates, poly(vinyl pyrrolidone), biodegradable polycyanoacrylates, polyalkylene oxalates, polyalkylene succinates, poly(malic acid), poly(methyl vinyl ether), poly(ethylene imine), poly(acrylic acid), poly(maleic anhydride), biodegradable polyurethanes and polysaccharides. In certain embodiments, the materials include polyethylene glycol (PEG). In certain embodiments, the polymer used to make the materials is PEGylated (i.e., conjugated to a polyethylene glycol moiety).

In some embodiments, the delivery vehicle is formed from material identified to as Generally Recognized as Safe (GRAS) by the FDA.

3. Naturally-Occurring Polymers

Naturally-occurring polymers, such as polysaccharides and proteins, may also be employed to produce the disclosed delivery vehicles. Exemplary polysaccharides include alginate, starches, dextrans, celluloses, chitin, chitosan, hyaluronic acid and its derivatives; exemplary proteins include collagen, albumin, and gelatin. Polysaccharides such as starches, dextrans, and celluloses may be unmodified or may be modified physically or chemically to affect one or more of their properties such as their characteristics in the hydrated state, their solubility, or their half-life in vivo. In certain embodiments, the materials do not include protein.

In other embodiments, the polymer includes polyhydroxy acids such as polylactic acid (PLA), polyglycolic acid (PGA), their copolymers poly(lactic-co-glycolic acid) (PLGA), and mixtures of any of these. In certain embodiments, the materials include poly(lactic-co-glycolic acid) (PLGA). In certain embodiments, the materials include poly(lactic acid). In certain other embodiments, the materials include poly(glycolic acid). These polymers are among the synthetic polymers approved for human clinical use as surgical suture materials and in controlled release devices. They are degraded by hydrolysis to products that can be metabolized and excreted. Furthermore, copolymerization of PLA and PGA offers the advantage of a large spectrum of degradation rates from a few days to several years by simply varying the copolymer ratio of glycolic acid to lactic acid, which is more hydrophobic and less crystalline than PGA and degrades at a slower rate.

Non-biodegradable polymers may also be used to produce materials. Exemplary non-biodegradable, yet biocompatible polymers include polystyrene, polyesters, non-biodegradable polyurethanes, polyureas, poly(vinyl alcohol), polyamides, poly(tetrafluoroethylene), poly(ethylene vinyl acetate), polypropylene, polyacrylate, non-biodegradable polycyanoacrylates, non-biodegradable polyurethanes, polymethacrylate, poly(methyl methacrylate), polyethylene, polypyrrole, polyanilines, polythiophene, and poly(ethylene oxide).

4. Functionalized Polymers

Any of the above polymers may be functionalized with a poly(alkylene glycol), for example, poly(ethylene glycol) (PEG) or poly(propyleneglycol) (PPG), or any other hydrophilic polymer system. Alternatively or in addition, they may have a particular terminal functional group, e.g., poly(lactic acid) modified to have a terminal carboxyl group so that a poly(alkylene glycol) or other material may be attached. Exemplary PEG-functionalized polymers include but are not limited to PEG-functionalized poly(lactic acid), PEG-functionalized poly(lactic-co-glycolic acid), PEG-functionalized poly(caprolactone), PEG-functionalized poly(ortho esters), PEG-functionalized polylysine, and PEG-functionalized poly(ethylene imine). When used in formulations for oral delivery, poly(alkylene glycols) are known to increase the bioavailability of many pharmacologically useful compounds, partly by increasing the gastrointestinal stability of derivatized compounds. For parenterally administered pharmacologically useful compounds, including particle delivery systems, poly(alkylene glycols) are known to increase stability, partly by decreasing opsinization of these compounds, thereby reducing immunogenic clearance, and partly by decreasing non-specific clearance of these compounds by immune cells whose function is to remove foreign material from the body. Poly(alkylene glycols) are chains may be as short as a few hundred Daltons or have a molecular weight of several thousand or more.

Co-polymers, mixtures, and adducts of any of the above modified and unmodified polymers may also be employed. For example, amphiphilic block co-polymers having hydrophobic regions and anionic or otherwise hydrophilic regions may be employed. Block co-polymers having regions that engage in different types of non-covalent or covalent interactions may also be employed. Alternatively or in addition, polymers may be chemically modified to have particular functional groups. For example, polymers may be functionalized with hydroxyl, amine, carboxy, maleimide, thiol, N-hydroxy-succinimide (NHS) esters, or azide groups. These groups may be used to render the polymer hydrophilic or to achieve particular interactions with materials that are used to modify the surface as described below.

One skilled in the art will recognize that the molecular weight and the degree of cross-linking may be adjusted to control the decomposition rate of the polymer. Methods of controlling molecular weight and cross-linking to adjust release rates are well known to those skilled in the art.

5. Non-Polymer Materials

Delivery vehicles may also be produced from non-polymer materials, e.g., metals, and semiconductors. For example, where it is desired to provide a contrast or imaging agent to a particular tissue, it may not be necessary to combine a particulate agent with a polymer carrier.

The surface chemistry of the delivery vehicles may be varied using any technique known to the skilled artisan. Both the surface hydrophilicity and the surface charge may be modified. Some methods for modifying the surface chemistry of polymer materials are discussed above. Silane or thiol molecules may be employed to tether particular functional groups to the surface of polymer or non-polymer materials. For example, hydrophilic (e.g., thiol, hydroxyl, or amine) or hydrophobic (e.g., perfluoro, alkyl, cycloalkyl, aryl, cycloaryl) groups may be tethered to the surface. Acidic or basic groups may be tethered to the surface of the materials to modify their surface charge. Exemplary acidic groups include carboxylic acids, nitrogen-based acids, phosphorus based acids, and sulfur based acids. Exemplary basic groups include amines and other nitrogen containing groups. The pKa of these groups may be controlled by adjusting the environment of the acidic or basic group, for example, by including electron donating or electron withdrawing groups adjacent to the acidic or basic group, or by including the acidic or basic group in a conjugated or non-conjugated ring. Alternatively, materials may be oxidized, for example, using peroxides, permanganates, oxidizing acids, plasma etching, or other oxidizing agents, to increase the density of hydroxyl and other oxygenated groups at their surfaces. Alternatively or in addition, borohydrides, thiosulfates, or other reducing agents may be used to decrease the hydrophilicity of the surface.

6. Size Range

The delivery vehicles may be any size that permits cells to uptake the particles. For example, the particles can have a diameter of about 1 nm to about 1000 µm, or about 1 and about 50 nm, or 50 to 100 nm, or about 100 to about 500 nm, or about 500 to about 1000 nm, or about 1 µm to about 10 µm.

In some embodiments, the screening method is used to screen microparticles (having a diameter between 1 and 10 microns) or nanoparticles (having a diameter between 1 and 1000 nm) for characteristics suitable for delivering a functional bioactive agent to a cell, tissue, or organ of interest.

The number of delivery vehicles characterized per run of the assay can be at least 50, 100, 150, 200, 250, 300, 350, 400, 450, 500 or more depending on the size of the non-human mammal used in the assay.

7. Targeting Agents

In some embodiments, targeting agents may be employed to more precisely direct the delivery vehicles to a tissue or cell of interest. Therefore, the disclosed delivery vehicles can contain a tissue-targeting moiety, a cell-targeting moiety, a receptor-targeting moiety, or any combination thereof One skilled in the art will recognize that the tissue of interest need not be healthy tissue but may be a tumor or particular form of damaged or diseased tissue, such as areas of arteriosclerosis or unstable antheroma plaque in the vasculature. Targeting agents may target any part or component of a tissue. For example, to targeting agents may exhibit an affinity for an epitope or antigen on a tumor or other tissue cell, an integrin or other cell-attachment agent, an enzyme receptor, an extracellular matrix material, or a peptide sequence in a particular tissue. Targeting agents may include but are not limited to antibodies and antibody fragments (e.g. the Fab, Fab', or F(ab')2 fragments, or single chain antibodies), nucleic acid ligands (e.g., aptamers), oligonucleotides, oligopeptides, polysaccharides, low-density lipoproteins (LDLs), folate, transferrin, asialycoproteins, carbohydrates, polysaccharides, sialic acid, glycoprotein, or lipid. Targeting agents may include any small molecule, bioactive agent, or biomolecule, natural or synthetic, which binds specifically to a cell surface receptor, protein or glycoprotein found at the surface of cells. In some embodiments, the targeting agent is an oligonucleotide sequence. In certain embodiments, the targeting agent is an aptamer. In some embodiments, the targeting agent is a naturally occurring carbohydrate molecule or one selected from a library of carbohydrates. Libraries of peptides, carbohydrates, or polynucleotides for use as potential targeting agents may be synthesized using techniques known to those skilled in the art. Various macromolecule libraries may also be purchased from companies such as Invitrogen and Cambridge Peptide.

The targeting agent may be conjugated to the material by covalent interactions. For example, a polymeric material may be modified with a carboxylate group, following which an aminated targeting agent, or one that is modified to be aminated, is coupled to the polymer using a coupling reagent such as EDC or DCC. Alternatively, polymers may be modified to have an activated NHS ester which can then be reacted with an amine group on the targeting agent. Other reactive groups that may be employed to couple targeting agents to materials include but are not limited to hydroxyl, amine, carboxyl, maleimide, thiol, NHS ester, azide, and alkyne. Standard coupling reactions may then be used to couple the modified material to a second material having a complementary group (e.g., a carboxyl modified targeting agent coupled to an aminated polymer). Materials fabricated from inorganic materials may be modified to carry any of these groups using self-assembled monolayer forming materials to tether the desired functional group to the surface.

Alternatively, the targeting agents can be attached to the materials directly or indirectly via non-covalent interactions. Non-covalent interactions include but are not limited to electrostatic Interactions, affinity Interactions, metal coordination, physical adsorption, host-guest interactions, and hydrogen bonding interactions.

8. Nucleic Acid Bar Codes

Figure 19B:
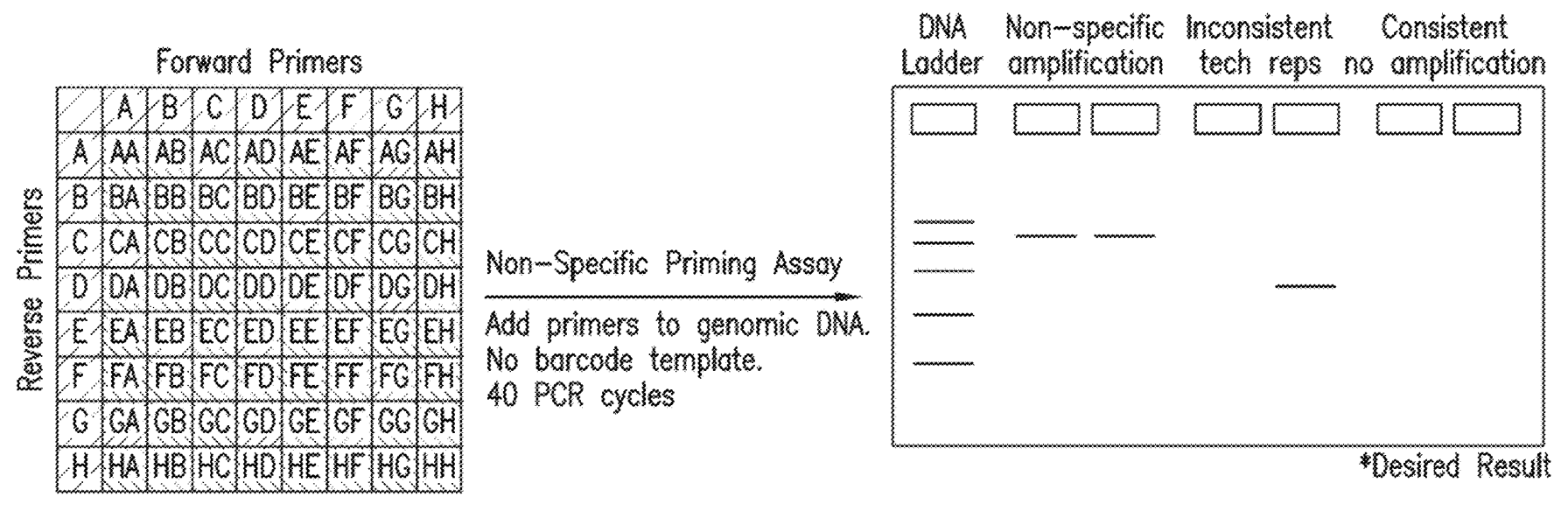
Figure 19C:
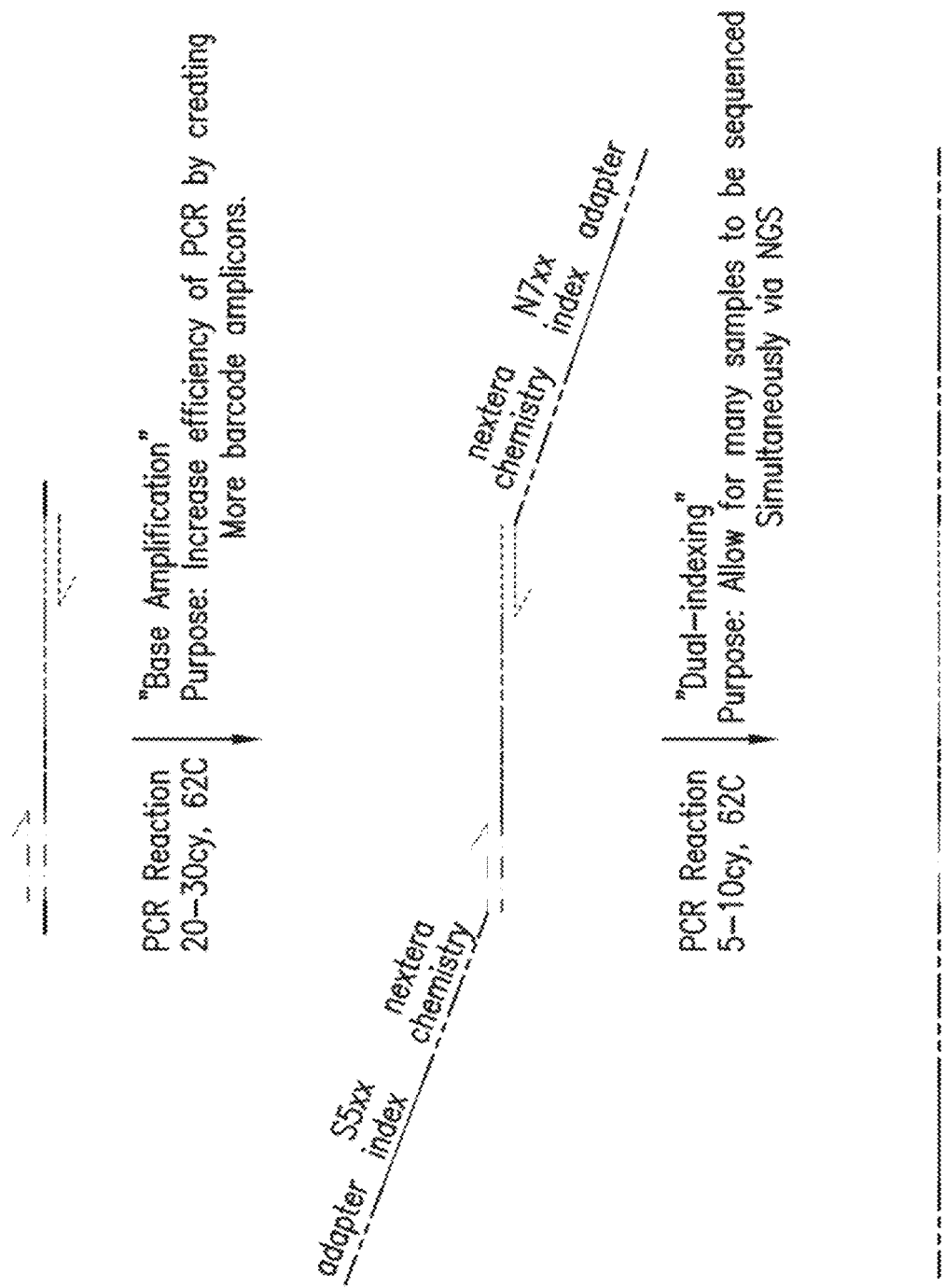

One embodiment provides a nucleic acid bar code. FIG. 19A shows an exemplary nucleic acid bar code. The nucleic acid barcodes can be rationally designed to increase DNA polymerase access and so that DNA secondary structure on the forward and reverse primer sites are minimized and G-quadruplex formation is minimized by separating the fully randomized nucleotide region.

One embodiment provides a nucleic acid barcode according to the following formula

R1-R2-R3-R4-R5-R6-R7-R8-R1 wherein R1 represents 1, 2, 3, 4, 5, 6, 7, 8, 9, or 10 nucleotides with phosphorothioate linkages,
R2 represents a forward universal primer binding site,
R3 represents a spacer,
R4 represents a digital droplet PCR probe binding site,
R5 represents a random nucleotide sequence;
R6 represents a nucleic acid barcode sequence;
R7 represents a random nucleic acid sequence;
R8 represents a reverse universal primer binding site.

In one embodiment, the nucleic acid barcode does not contain phosphorothioate linkages.

In another embodiment, R3 has the following sequence NHNW, wherein N is A, T, G, or C; W is A or T; and H is A, T, or C. In one embodiment R5 has the following sequence NWNH and R7 has the following sequence NWH, wherein N is A, T, G, or C; W is A or T; and H is A, T, or C.

In still another embodiment, the nucleic acid probe has 85, 90, 95, 99, or 100% sequence identity to SEQ ID NO:8.

As used herein, the term "nucleic acid barcode" refers to an oligonucleotide having a nucleic acid sequence that contains a series of nucleotides ("barcode sequence") unique to the barcode and optionally a series of nucleotides common to other barcodes. The common nucleotides can be used, for example, to isolate and sequence the barcode. Therefore, in some cases, the barcode sequence is flanked by upstream and downstream primer sites, such as, for example, universal primer sites. The polynucleotide can include a DNA nucleotide, an RNA nucleotide, or a combination thereof. Each delivery vehicle formulation is paired with its own unique nucleic acid barcode. The unique nucleic acid barcode is paired to the chemical composition of the delivery vehicle formulation and by sequencing the nucleic acid barcode, one can identify the specific chemical composition used to produce that specific vehicle delivery formulation.

The barcode can contain 5 to 100 nucleotides in length, about 5 to about 90 nucleotides in length, about 5 to about 80 nucleotides in length, about 5 to about 70 nucleotides in length, about 5 to about 60 nucleotides in length, about 5 to about 50 nucleotides in length, about 5 to about 45 nucleotides in length, about 5 to about 40 nucleotides. The nucleic acid barcodes can be covalently or non-covalently attached to the disclosed delivery vehicle. In some embodiments, the nucleic acid barcode is encapsulated by the delivery vehicle.

Another embodiment provides a pharmaceutically acceptable composition containing the nucleic acid barcodes described herein.

A number of embodiments of the invention have been described. Nevertheless, it will be understood that various modifications may be made without departing from the spirit and scope of the invention. Accordingly, other embodiments are within the scope of the following claims.

EXAMPLES

Example 1: Multiplexed In Vivo Analysis of Nanoparticle-Mediated mRNA Delivery Materials and Methods Nanoparticle Formulation.

Nanoparticles were formulated using a microfluidic device as previously described. Briefly, nucleic acids (mRNA, DNA barcodes, siRNA, sgRNA) were diluted in 10 mM citrate buffer (Teknova) while lipid-amine compounds, alkyl tailed PEG, cholesterol, and helper lipids were diluted in ethanol. For nanoparticle screens, Cre mRNA and DNA barcodes were mixed at a 10:1 mass ratio. Citrate and ethanol phases were combined in a microfluidic device by syringes (Hamilton Company) at a flow rate of 600 μL/min and 200 μL/min, respectively. All PEGs, cholesterol, and helper lipids were purchased from Avanti Lipids.

DNA Barcoding.

Each LNP was formulated to carry its own unique DNA barcode (FIG. 1) that corresponded to the unique chemical composition of the LNP. For example, LNP1 carried DNA barcode 1, while the chemically distinct LNP2 carried DNA barcode 2. DNA barcodes were designed rationally with several characteristics, as previously described (Dahlman, Kauffman et al. 2017). 56 nucleotide long single stranded DNA sequences were purchased from Integrated DNA Technologies. The 2 nucleotides on the 5' and 3' end of the 56-nucleotide ssDNA were modified with phosphorothioates to reduce exonuclease degradation and improve DNA barcode stability. To ensure equal amplification of each sequence, 2 universal forward and reverse primer regions were included on all barcodes. To monitor for PCR bias, each barcode was also designed with 7 random nucleotides. Each barcode was distinguished using a unique 8 bp sequence. An 8 bp sequence can generate 65,536 ($4^8$) distinct barcodes. 250 distinct 8 bp sequences were designed to prevent sequence bleaching on the Illumine MiniSeq™ sequencing machine. Specifically, the barcodes were designed such that in the 8 nucleotide region, every barcode sequence was distinct from every other barcode at 3 (or more) of the 8 positions.

Nanoparticle Characterization.

LNP hydrodynamic diameter was measured using high throughput dynamic light scattering (DLS) (DynaPro plate reader II, Wyatt). LNPs were diluted in sterile 1×PBS to a concentration of ~0.06 ug/mL, and analyzed. To avoid using unstable LNPs, and to enable sterile purification using a 0.22 μm filter, LNPs were included only if they met 3 criteria: diameter >20 nm, diameter <200 nm, and correlation function with 1 inflection point. Over the course of the experiments, ~65% of the LNPs formulated met all 3 criteria. Particles that met these criteria were dialyzed with 1× phosphate buffered saline (PBS, Invitrogen), and were sterile filtered with a 0.22 μm filter.

Cell Culture.

In vitro experiments were performed using HEK293 cells (GenTarget) stably transduced with a CMV-lox-GFP-stop-lox-RFP construct cultured in DMEM/F-12 50/50 media (Corning) supplemented by 10% (v/v) FBS (VWR) and 1% (v/v) penicillin-streptomycin (ThermoFisher Scientific). Cells were seeded in a 6-well plate at a density of 300 k cells/well. 24 hours later, LNPs were added with a total mRNA dose of 100 ng. 6 hours after transfection, media was refreshed. DNA was isolated using 50 μL of QuickExtract (EpiCentre).

Endocytosis Inhibition.

For experiments shown in FIG. 1, cells were incubated with endocytosis inhibitors 1 hour prior to incubation with pooled LNPs against clathrin-mediated endocytosis (chlorpromazine, 100 µM, Alfa Aesar), caveolae-mediated endocytosis (genistein, 100 µM, TCI America), and macropinocytosis (5-(N-Ethyl-N-isopropyl) Amiloride, EIPA, 50 µM, Toronto Research Chemicals).

Animal Experiments.

All animal experiments were performed in accordance with the Georgia Institute of Technology's Physiological Research Laboratory (PRL) animal care and services policy. LSL-Tomato (#007914), C57BL/6J (#000664) and constitutive SpCas9 (#026179) mice were purchased from The Jackson Laboratory and used between 5-12 weeks of age. In all experiments, N=3-5 mice/group were used. Mice were injected intravenously via the lateral tail vein or intramuscularly into the quadriceps, tibialis anterior and gastrocnemius. The nanoparticle concentration was determined using NanoDrop (Thermo Scientific). For in vivo nanoparticle screens, mice were administered 1.5 mg/kg for intravascular and 1 mg/kg for intramuscular administration.

Cell Isolation & Staining.

Cells were isolated 72 hours after injection with LNPs unless otherwise noted. Mice were perfused with 20 mL of 1×PBS through the right atrium. Tissues were finely cut, and then placed in a digestive enzyme solution with Collagenase Type I (Sigma Aldrich), Collagenase XI (Sigma Aldrich) and Hyaluronidase (Sigma Aldrich) at 37° C. at 550 rpm for 45 minutes. The digestive enzyme for heart and spleen included Collagenase IV (Dahlman, Barnes et al. 2014, Sager, Dutta et al. 2016, Sager, Hulsmans et al. 3016. Cell suspension was filtered through 70 µm mesh and red blood cells were lysed. Cells were stained to identify specific cell populations and sorted using the BD FacsFusion and BD Facs Aria Illu cell sorters in the Georgia Institute of Technology Cellular Analysis Core. For in vitro experiments, BD Accuri C6 and BD FacsFusion were used. The antibody clones were used: anti-CD31 (390. BioLegend), anti-CD45.2 (104 BioLegend), anti-CD3 (17A2, BioLegend), anti-CD102 (3C4, BioLegend). PE anti-CD47 (miap301, BioLegend) was used for tdTomato compensation. Cell populations were defined hi the following manner: endothelial cells (CD31+CD45−), immune cells (CD31−CD45+), and other cells (CD31−CD45−). PBS injected Ai14 mice were used to gate tdTomato populations for intravenous administration, while contralateral limbs were used to gate for intramuscular experiments.

Biodistribution.

LNPs encapsulating Cy5.5-tagged DNA Barcode were administered at 0.75 mg/kg. After 3 hours, tissues were isolated without perfusion, weighed individually, and imaged using the Licor Odyssey CLx imaging system. Signal intensity was normalized to tissue weight.

Cre mRNA Administration.

Cre mRNA (TriLink Biotechnology, L-7211) was administered either naked or encapsulated into ATL1 or ATL2, and administered either once or three times into LSL-Tom mice as specified. 72 hrs after final injection, the percent of tdTomato+ cells was quantified using flow cytometry.

Endothelial RNAi.

C57BL/6J Mice were injected with ATL1 and 7C4 with PBS, 2 mg/kg siCTRL (siGFP-647), or 1 mg/kg siICAM2. In all cases, siRNAs were chemically modified at the 2' position to increase stability and negate immunostimulation. Both siGFP and siICAM-2 sequences have been previously reported several times (Dahlman, Barnes et al. 2014, Sager, Dutta et al. 2016, Sager, Hulsmans et al. 2016. 72 hours after injection, tissues were isolated and protein expression was determined via flow cytometry. ICAM-2 MFI expression in PBS-treated mice was normalized to 100 percent, and all treated groups were compared to this control group MFI.

Endothelial Gene Editing.

Mice constitutively expressing SpCas9 were injected three times with ATL1 or ATL2 carrying 1.5 mg/kg of two chemically-modified sgRNAs (TriLink Biotechnologies) targeting ICAM2 (sgICAM2-combo) (1:1 mass ratio). 5 days after the last injection, tissues were isolated, and ICAM2 protein expression was measured concurrently while ~20,000 CD31+ endothelial cells were sorted into QuickExtract. Indel formation was measured by TIDE.

PCR Amplification.

All samples were amplified and prepared for sequencing using a 1 step PCR protocol as previously described Dahlman, Kauffman et al. 2016. More specifically, 1 µL of primers (5 µM for Final Reverse/Forward, 0.5 uM for Base Forward) were added to 5 µL of Kapa HiFi 2× master mix, and 4 µL template DNA/water. The reaction was run for 30 cycles. When the PCR reaction did not produce clear bands, the primer concentrations, DNA template input, PCR temperature, and number of cycles was optimized for individual samples.

Deep Sequencing.

Illumina deep sequencing was conducted in Georgia Tech's Molecular Evolution core. Runs were performed on an Illumina Miniseg™. Primers were designed based on Nextera XT adapter sequences.

Data Normalization.

Counts for each particle, per tissue, were normalized. The barcoded LNP mixture injected into the mouse was also sequenced. This 'input' DNA provided the DNA counts, and was used to normalize DNA counts from the cells and tissues (Table 1).

Data Analysis.

Sequencing results were processed using a custom python-based tool to extract raw barcode counts for each tissue. These raw counts were then normalized with an R script prior to further analysis. Statistical analysis was done using GraphPad Prism 7.

Results

Figure 1B:
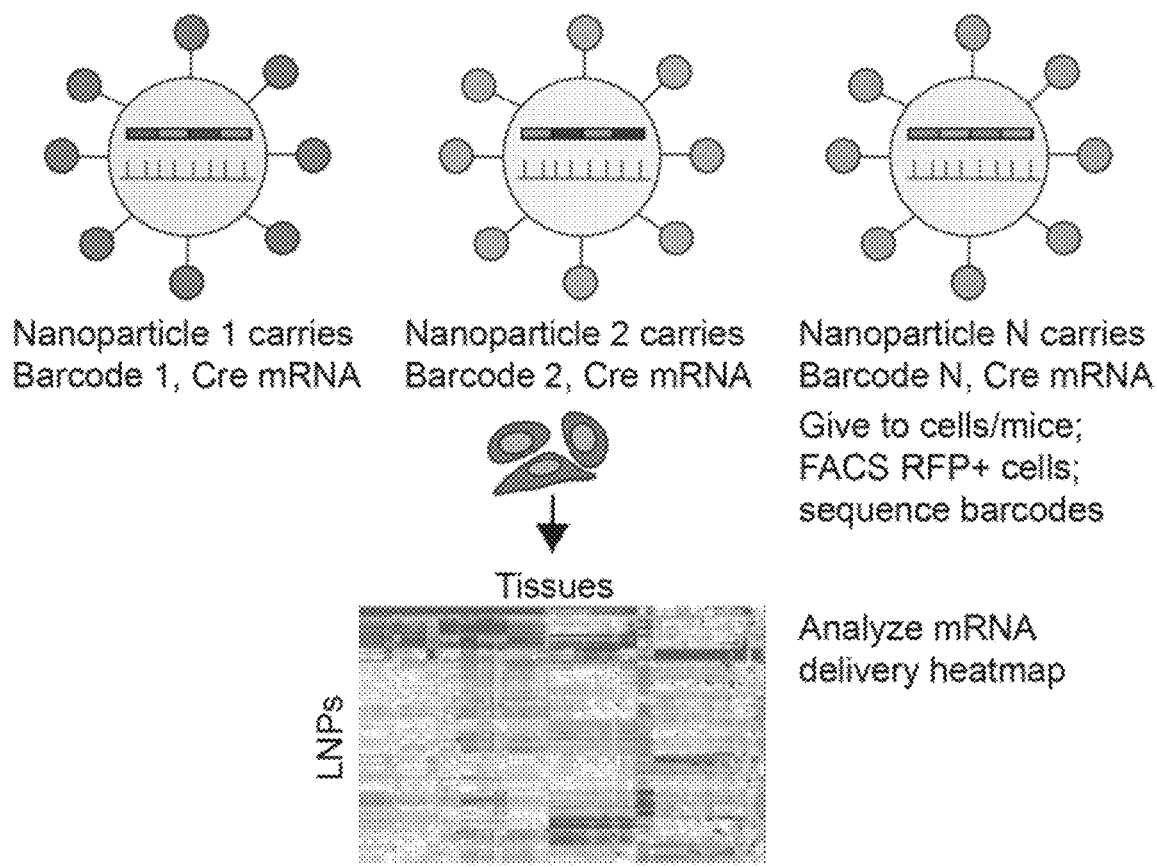

An ideal in vivo drug delivery screen would be sensitive, use common animal models, enable scientists to test many LNPs simultaneously, and measure intracellular delivery to any combination of on- and off-target cell types. FIND was designed to meet these criteria. In this example, FIND uses Cre-lox reporter systems to identify LNPs that deliver Cre mRNA (FIG. 1A). Using microfluidics, LNP-1, with chemical structure 1, was formulated to carry DNA barcode 1 and Cre mRNA. This was repeated N times, so that LNP-N, with chemical structure N, DNA barcode N and Cre mRNA (FIG. 1B). It was reasoned that the co-delivery of mRNA and 56 nt single stranded DNA (ssDNA) barcode would approximate the delivery of a mRNA encoding a nuclease (e.g., Cas9, Cpf1, or Cas13) and single guide RNA (sgRNA) (Doudna and Charpentier 2014, Hsu, Lander et al. 2014, Zetsche, Gootenberg et al. 2015, Abudayyeh, Gootenberg et al. 2016, Abudayyeh, Gootenberg et al. 2017.

After barcoding up to 158 LNPs in a single day, the size and stability of each LNP was characterized using high throughput dynamic light scattering (DLS). Unstable or large (>220 nm) LNPs were discarded (FIGS. 4a-4b), and the stable nanoparticles were pooled, before being administered to cells or mice engineered to fluoresce if Cre protein is translocated to the nucleus. Reporter positive cells were isolated using fluorescence activated cell sorting (FACS) and the identified barcodes were enriched in reporter-positive cells with Illumina deep sequencing (FIG. 1B-C, FIGS. 4C-4D, Table 1).

Rationally designed DNA barcodes were used. The barcodes included universal primer sites, 7 random nucleotides to identify PCR bias, and were chemically modified at the 5' and 3' ends with phosphorothioate linkages to reduce exonuclease degradation (Dahlman, Kauffman et al. 2017, Paunovska 2018) (FIG. 4e). Eight nucleotides in the middle of the 56-mer ssDNA constituted the barcode sequence; of the $4^8$ DNA barcode combinations, 240 optimized for multiplexing on Illumina machines were selected (Table 2). Individual samples were labeled with dual indices that were also optimized for Illumina sequencing (Table 3). These barcodes were previously characterized in vitro and in vivo, showing that the DNA barcode readouts are linear, can be sequenced from FACS-isolated cells, can be read at doses as low as 0.0001 mg/kg DNA per barcode, and do not change delivery, Additionally, LNPs can be made so that hybrid particles are not formed in solution (Dahlman, Kauffman et al. 2017, Paunovska 2018).

Figure 1F:
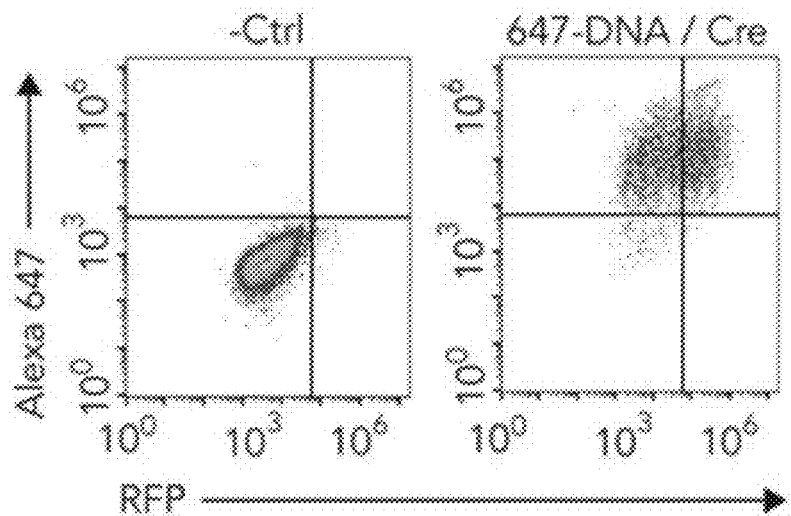
Figure 4A:
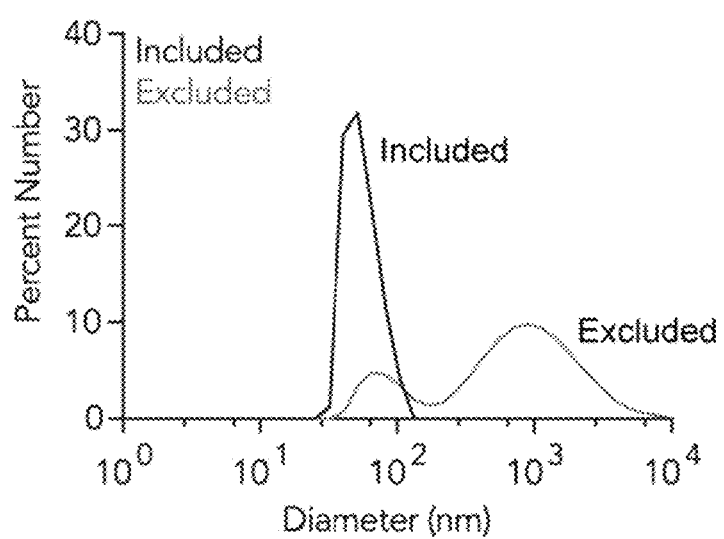
Figure 4F:
FIG. 4F-4G show GFP and RFP expression 72 hours after LoxP-GFP-Stop-LoxP-RFP HEK cells transfected with naked Cre mRNA (− ctrl) (FIG. 4F) or Cre mRNA carried by L2K (FIG. 4G).
Figure 4G:
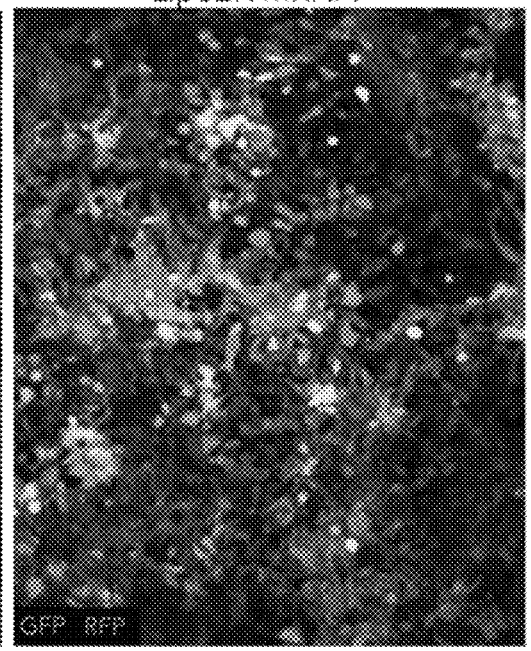
Figure 4H:
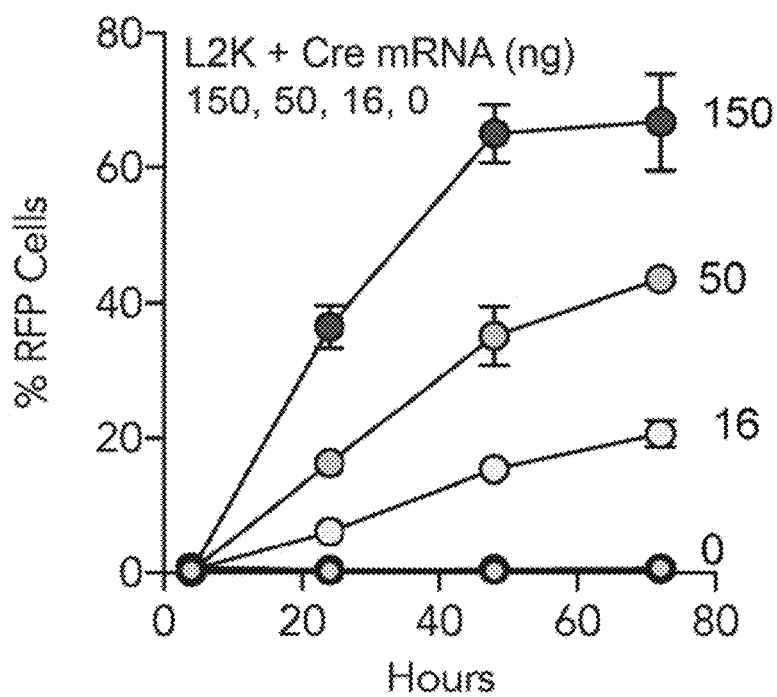
FIG. 4H-4I show RFP positive cells as a function of time and dose for cells transfected with naked Cre mRNA (− ctrl) (FIG. 4I) or Cre mRNA carried by L2K (FIG. 4H).
Figure 4I:
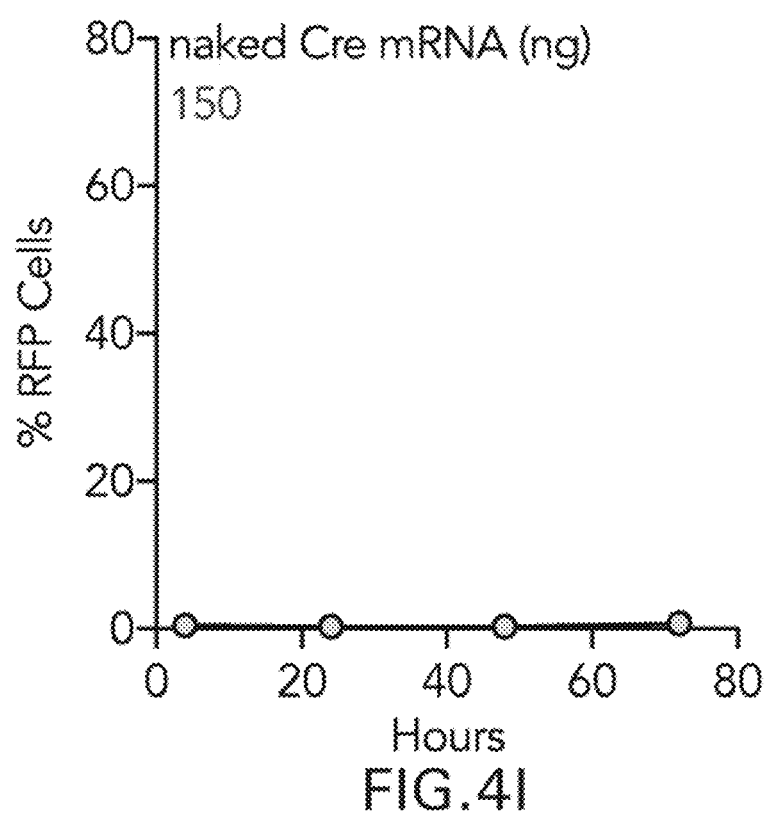
Figures 4J, 4K, 4L, 4M, 4N, 4O:
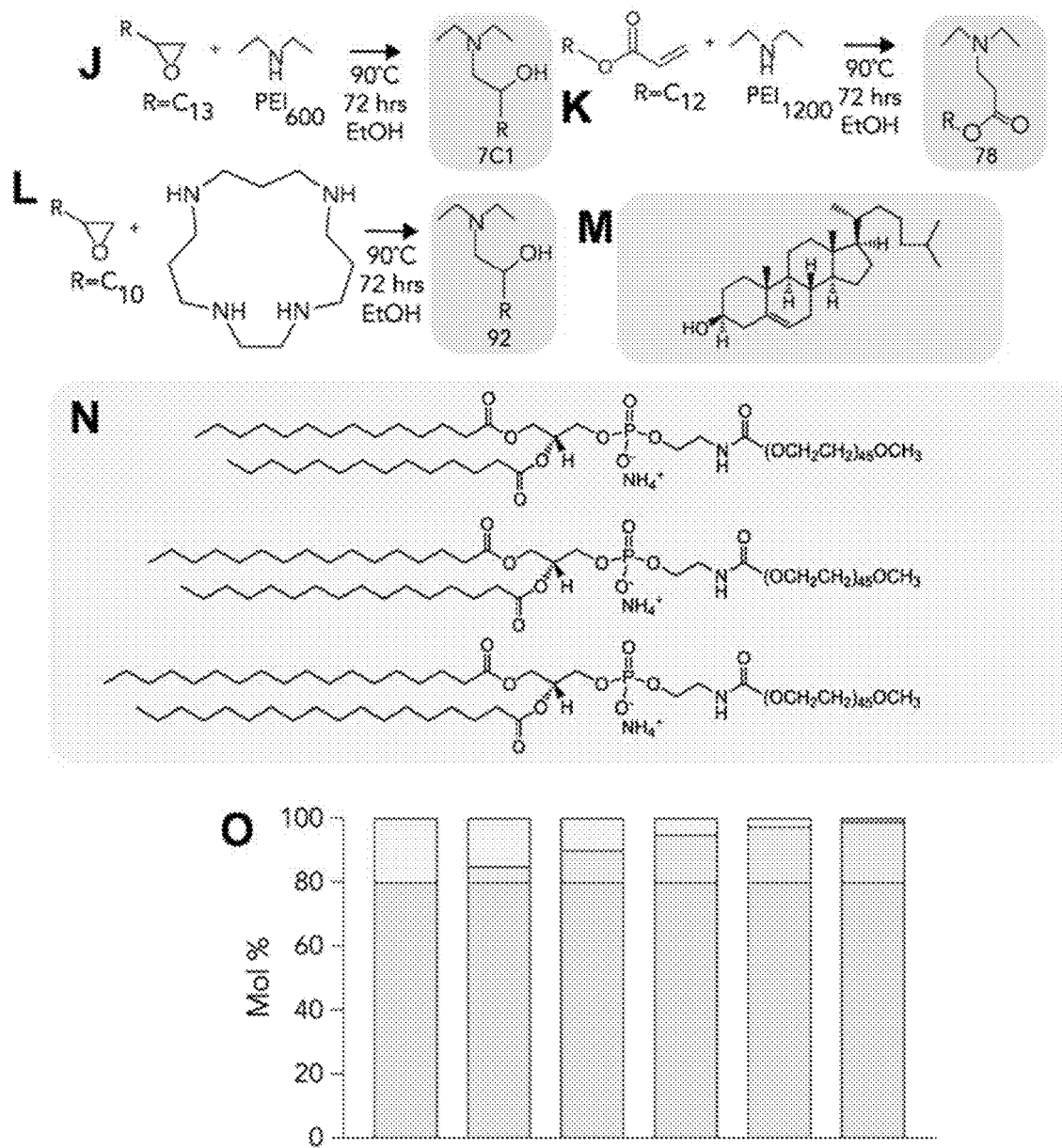
FIG. 4J-4L shows synthesis used to the compounds 7C1, 78, and 92. epoxide-, acrylate-, and methacrylate-based chemistries were selected.

FIND was characterized using a series of in vitro and in vivo experiments. HEK cells that expressed LoxP-GFP-Stop-LoxP-RFP (LGSL-RFP) were cultured under a CMV promoter (FIG. 1A). As expected, these cells became $RFP^+$ 72 hours after treatment with Cre mRNA carried by Lipofectamine 2000 (L2K), but not with naked Cre mRNA (FIG. 1D-1E, FIG. 4F-4G). The number of $RFP^+$ cells after L2K treatment increased with dose and time, up to 3 days (FIG. 4H-4I). L2K was then co-formulated with Cre mRNA and an Alexa647-labeled DNA barcode. After 24 hours, 53, 45, 2, and 0% of the cells were $647^+RFP^-$, $647^+RFP^+$, $647^-RFP^-$, and $647^-RFP^+$ positive. No cells were reporter positive and barcode negative, indicating that biodistribution was required, but not sufficient, for functional mRNA delivery (FIG. 1F).

Figure 1G:
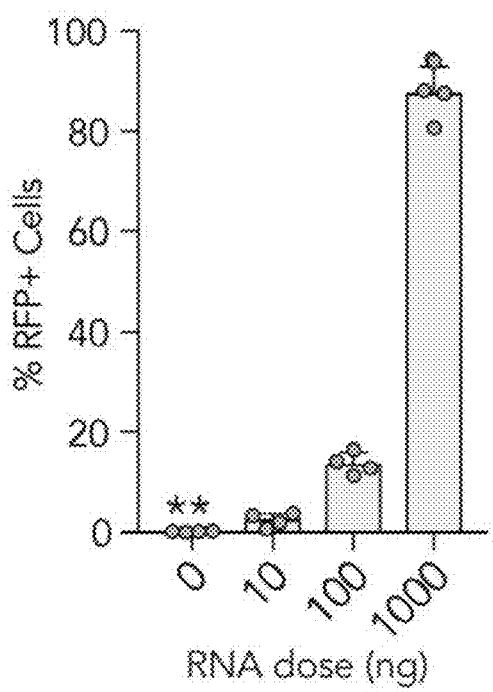
Figure 1H:
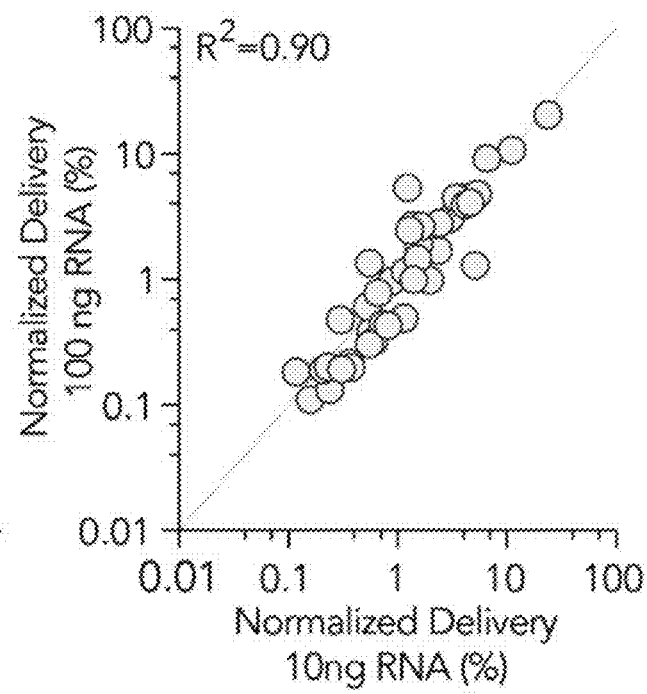
Figure 1I:
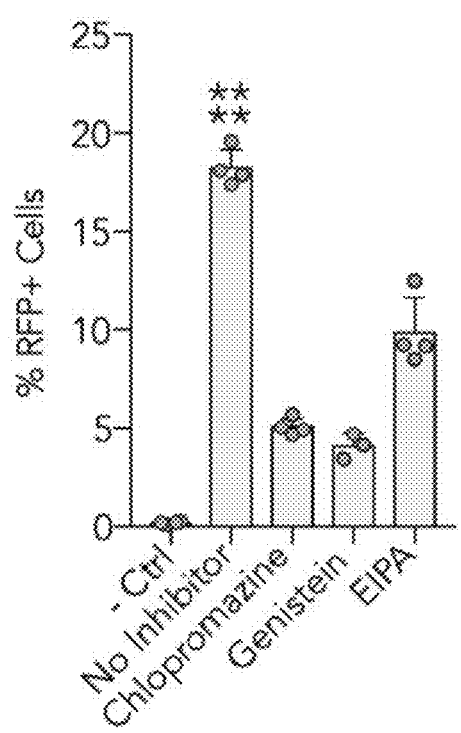
FIG. 1I shows RFP+ HEK cells following the administration of 54 LNPs (100 ng total mRNA), after cells were treated with endocytosis inhibitors. N=3-4 wells/group. $p<0.001$, **$p<0.0001$, 2 tailed t-test.
Figures 4P, 4Q:
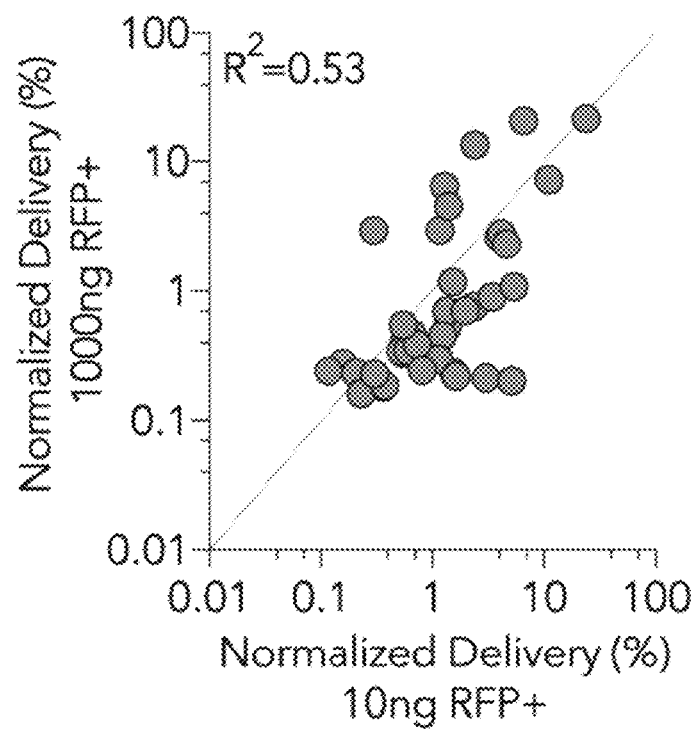
FIG. 4P-4Q show LNP size distribution for the in vitro screen; LNPs between 20 and 200 nm were included. Normalized DNA barcode readouts from RFP+ cells after cells were treated with 10, 100, or 1000 ng mRNA led to 4, 20, and 80% RFP+ cells.

To determine whether FIND could simultaneously measure delivery mediated by many nanoparticles, 54 chemically distinct LNPs were formulated (Table 5, FIGS. 4J-4O); each carried Cre mRNA and a unique DNA barcode. The LNPs were administered to HEK cells in a 6 well plate using an mRNA dose of 10, 100, or 1000 ng/well, and a mRNA: DNA barcode mass ratio of 10:1. A dose-dependent increase in $RFP^+$ cells was observed, with over 80% of the cells $RFP^+$ at 1000 ng 72 hours after transfection (FIG. 1G). Barcodes were deep sequenced at all 3 doses, reasoning that LNPs which delivered barcodes at the lowest dose (4% $RFP^+$ cells) would also deliver LNPs at the middle dose (20% $RFP^+$ cells). There was a strong relationship between normalized delivery at these 2 doses (FIG. 1H). Cells treated with 1000 ng mRNA were also sequenced. As expected, the relationship between 1000 ng and either 10 or 100 ng weakened, since at this dose, nearly all the cells (>80% were $RFP^+$), leading to system saturation (FIG. 4P-4Q). Finally, it was evaluated whether the number of $RFP^+$ cells decreased when cells were pre-treated with Chlorpromazine, Genistein, or Ethylisopropyl amiloride (EIPA), which inhibit clathrin-, caveolin-, and macropinocytosis-mediated endocytosis, respectively. Compared to cells that were not treated with inhibitors, the number of $RFP^+$ cells decreased by 40-60%, recapitulating previous LNP results (Sahay, Querbes et al. 2013, Dahlman, Barnes et al. 2014, Wittrup, Ai et al. 2015) (FIG. 1I).

Figure 2A:
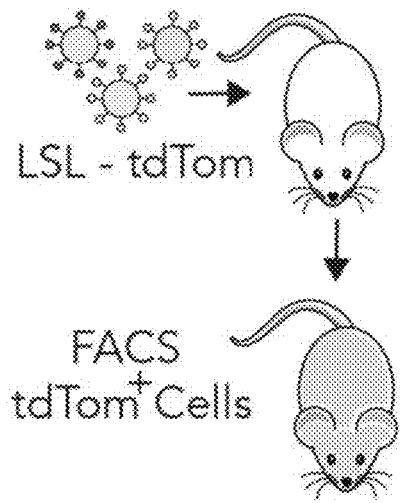
Figure 2B:
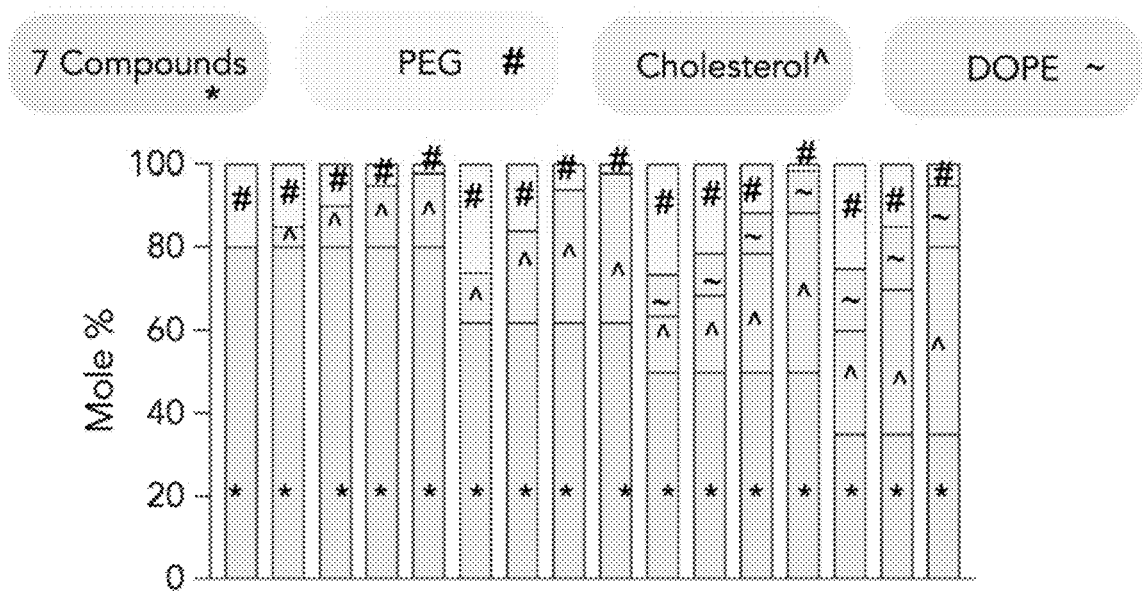
Figure 2C:
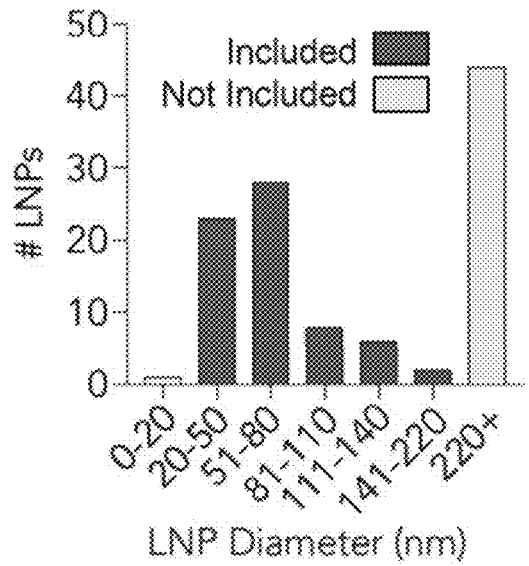
Figure 2D:
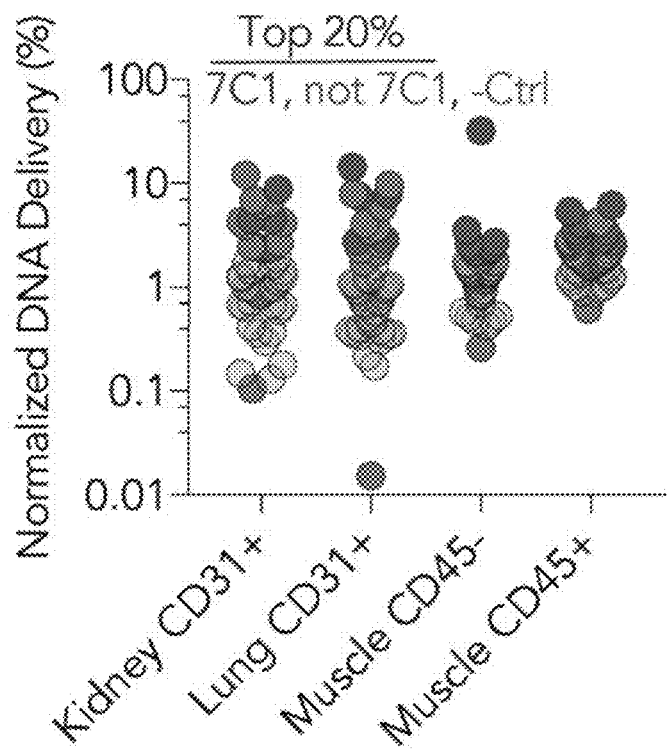
Figure 2E:
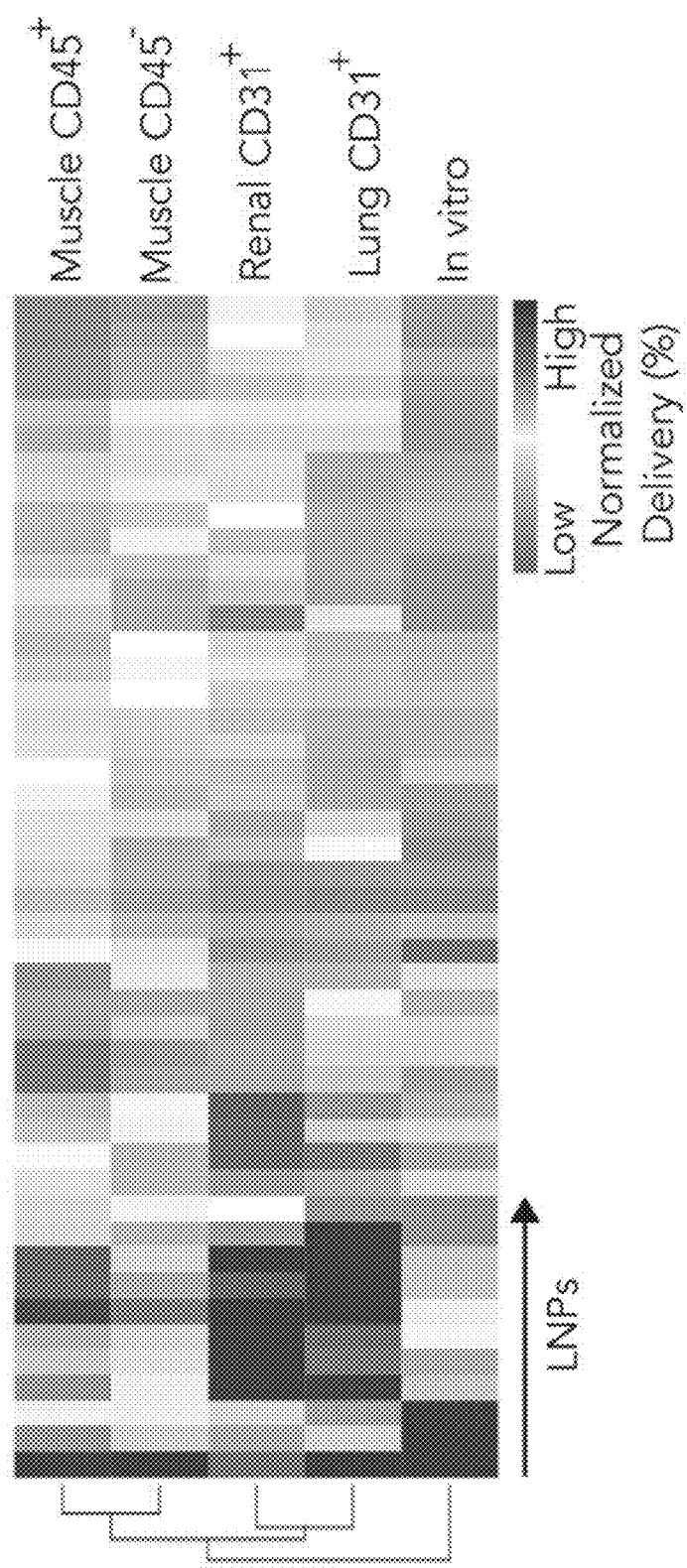

To determine whether FIND quantified LNP delivery in vivo, mice expressing LoxP-Stop-LoxP-tdTomato (LSL-tdTom) under the control of a CAG reporter were used (Madisen, Zwingman et al. 2010) (FIG. 2A). 112 LNPs were formulated, varying 4 factors known to influence LNP delivery: the structure of the lipid-amine compound, the molar amount of PEG, the structure of PEG, and the molar amount of cholesterol (FIG. 2B, FIGS. 5A-5K and Table 6B). Seventy-one formulations were determined to be stable and were pooled together (FIG. 2C). Naked DNA barcode was included as a negative control. 1.5 mg/kg total RNA was injected intravenously, and lung and kidney endothelial cells were isolated ($tdTomato^+CD45^-CD31^+$) 72 hours later (Dahlman, Barnes et al. 2014, Platt, Chen et al. 2014, Sager, Dutta et al. 2016, Sager, Hulsmans et al. 2016). Separately, 1.0 mg/kg total RNA was injected intramuscularly, and immune ($tdTomato^+CD45^+$) and non-immune ($tdTomato^+CD45^-$) cells were isolated. 100 ng of mRNA was also administered to LGSL-RFP expressing HEK cells. It was reasoned that different LNPs would deliver mRNA in intravenous, intramuscular, and in vitro conditions. To minimize false positives, gates were placed on PBS-injected LSL-tdTom mice for intravenously injected mice and the contralateral limb for intramuscular administration. Several lines of evidence suggested these data were robust. First, the naked barcode was delivered less efficiently than every LNP (FIG. 2D). Second, 7C1-based LNPs, which were previously optimized for in vivo RNA delivery, were enriched in the top 20% LNPs by 2.3 to 4.7 fold (FIG. 2d, FIG. 5l-5o) (Dahlman, Barnes et al. 2014). Finally, unbiased Euclidean clustering separated intravenous, intramuscular, and in vitro delivery into 3 distinct clusters (FIG. 2E). Other unbiased algorithms did not change the clustering (Ronan, Qi et al. 2016).

Figures 5A, 5B, 5C, 5D, 5E, 5F, 5G, 5H, 5I, 5J, 5K:
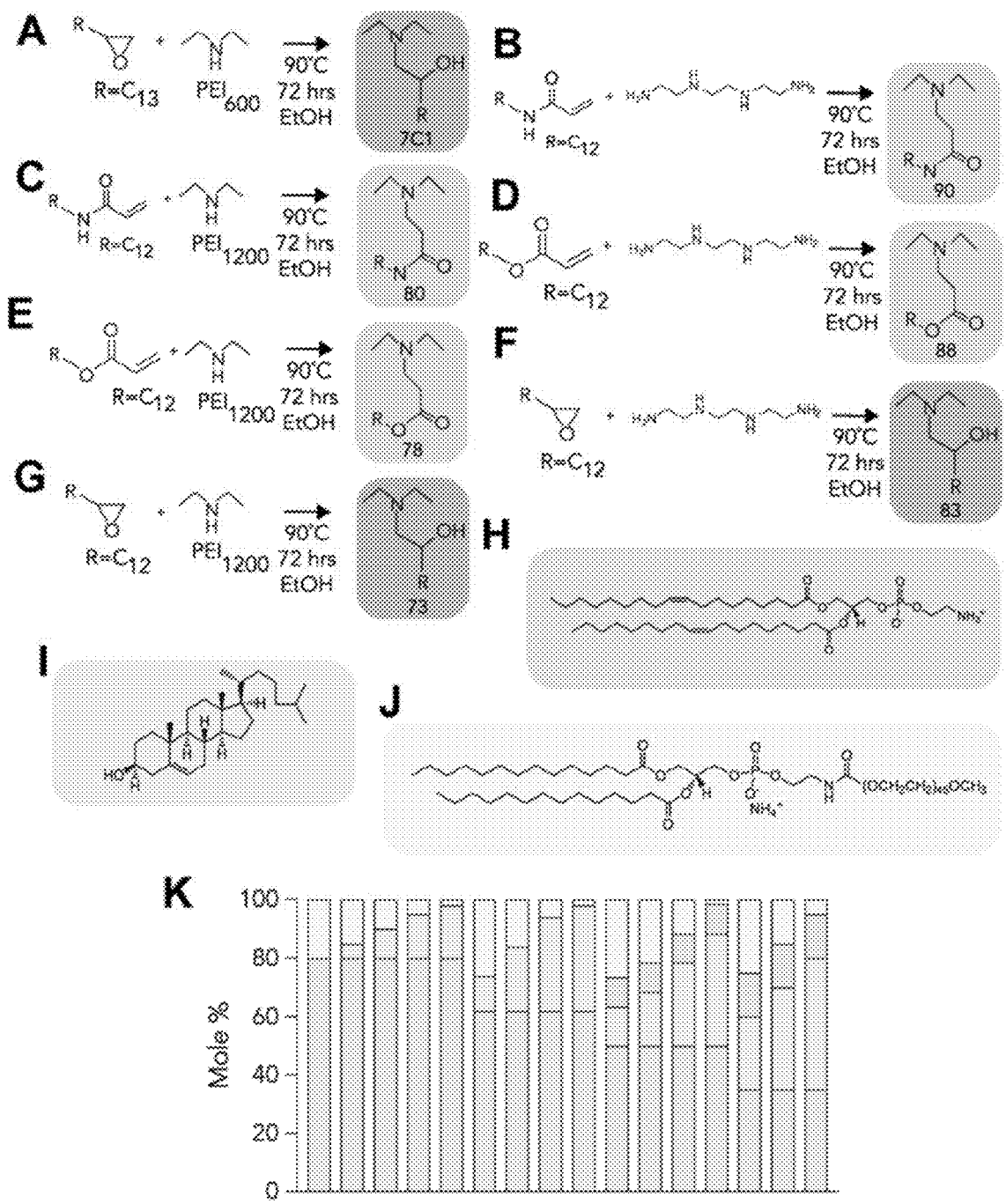
FIGS. 5A-5K show the composition of compounds 7C1, 78, and 92. Epoxide- and acrylate-based chemistries reacting various alkyl lengths and PEI600, PEI1200, and triethyltetramine were selected.
Figures 5P, 5Q, 5R, 5S, 5T, 5U, 5V:
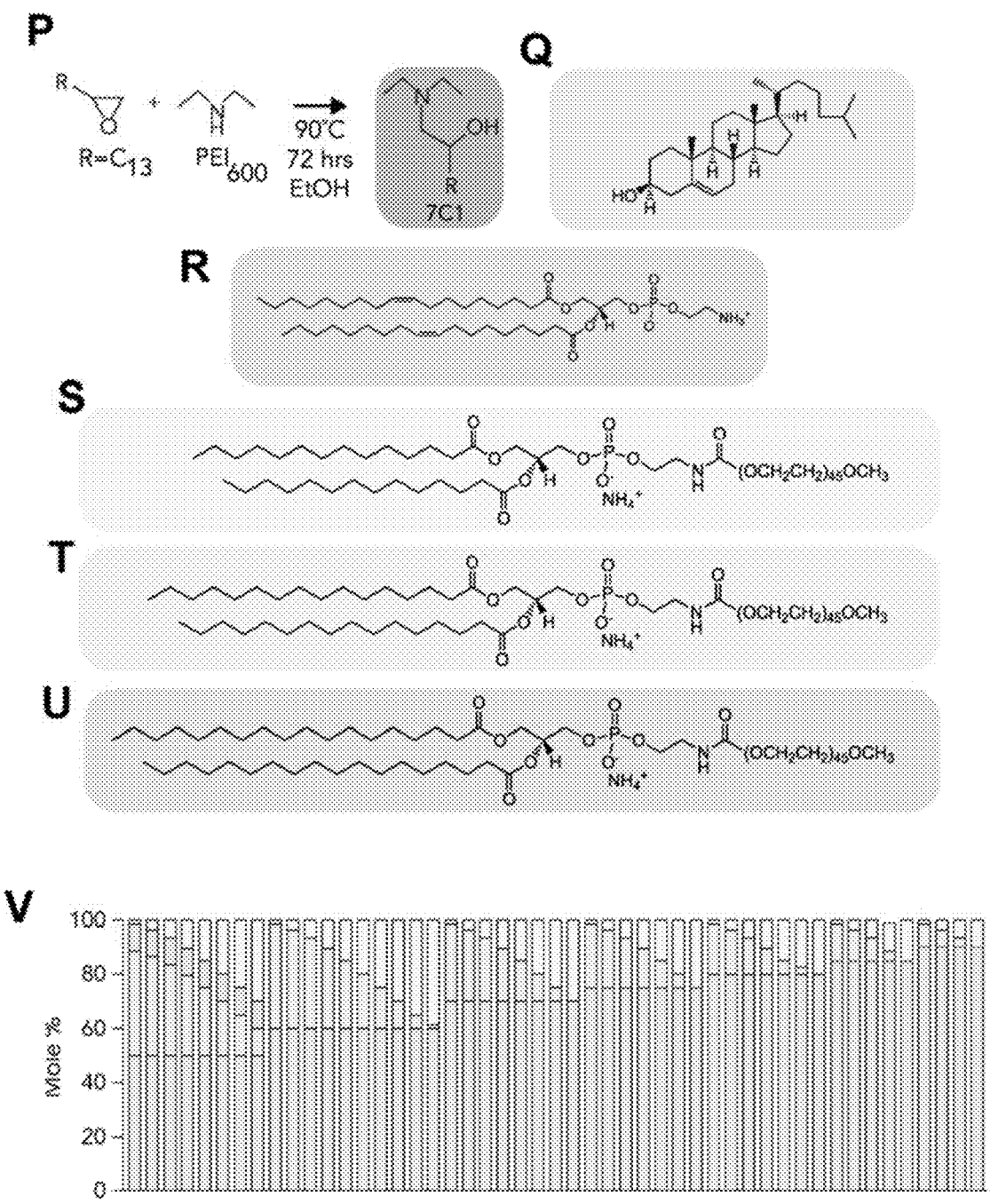
FIGS. 5P-5V show the composition of the compounds in the LNP library used for the second in vivo experiment. PEG alkyl length was varied.
Figures 5C, 5W:
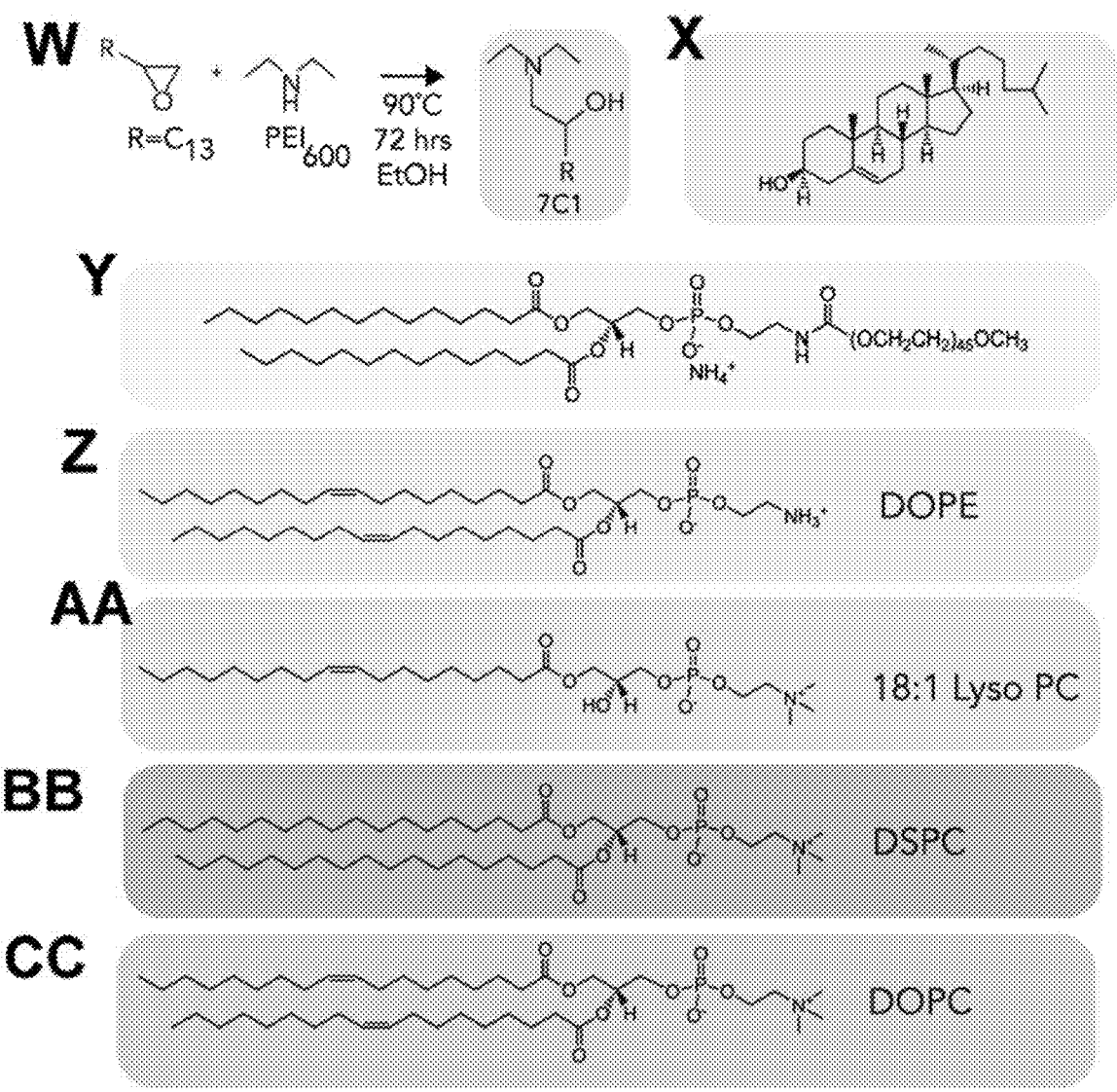
Figure 5D:
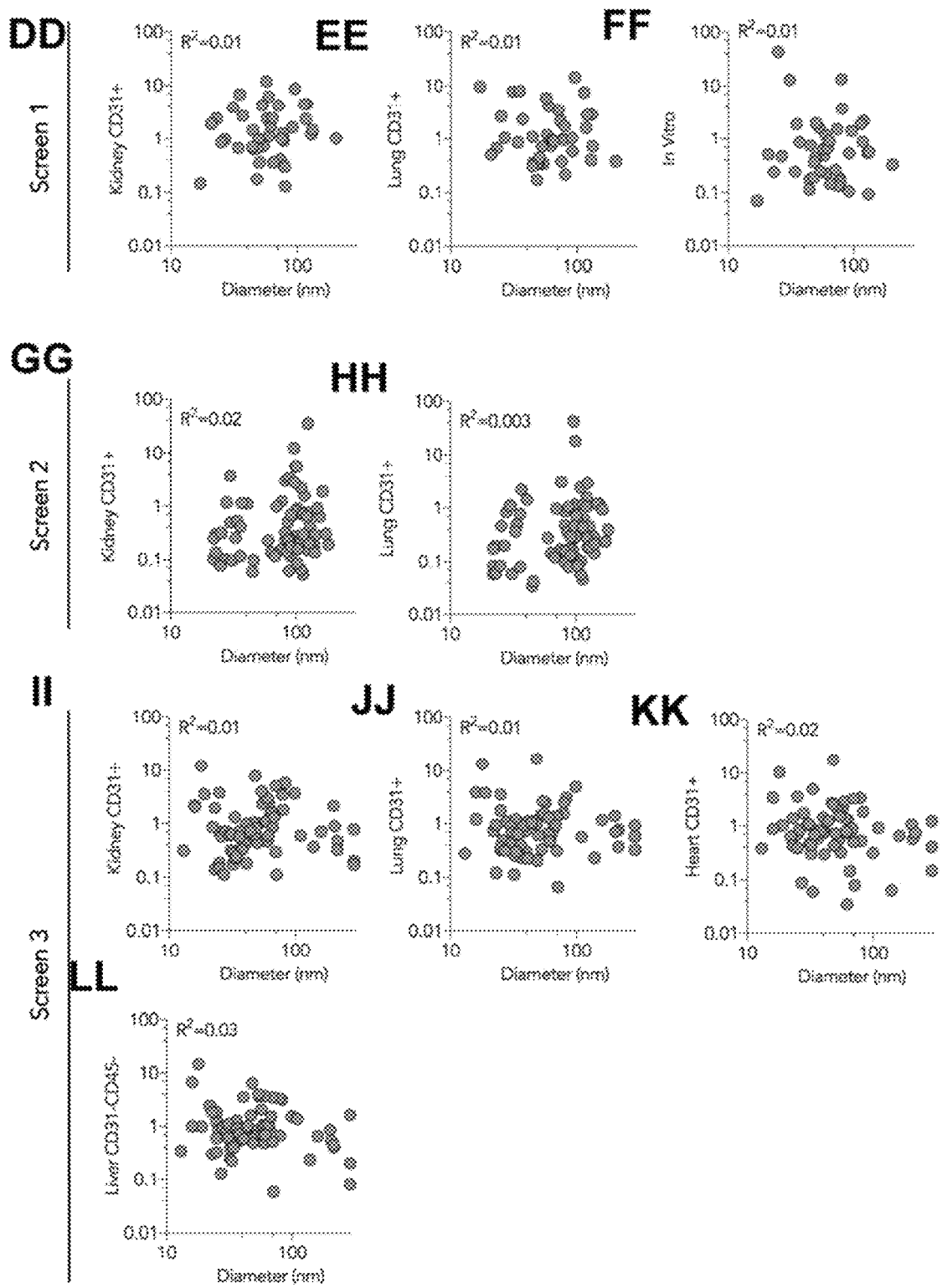

A second iterative LNP library was formulated, focusing on a key question: how do PEG, cholesterol, and helper lipids (e.g., DOPE) influence delivery to cells in vivo? Since 7C1-based LNPs were enriched in the $1^{st}$ screen, the focus was on LNPs made with this compound. 7C1 mole %, PEG mole %, as well as the alkyl length on the PEG were varied (FIGS. 5P-5V and Table 7). 78 out of 108 LNPs were stable, and administered to mice intravenously at a total mRNA dose of 1.5 mg/kg. 72 hrs later, $tdTomato^+$ lung and kidney endothelial cells were isolated, and barcodes were sequenced. LNPs had slightly different affinities for lung and kidney endothelial cells. $C_{14}$ alkyl PEG was enriched in lung LNPs compared to $C_{18}$ PEG (FIG. 2F-2G). A $3^{rd}$ LNP library designed to improve lung delivery relative to kidney delivery was formulated by only using $C_{14}$ alkyl tail PEG (FIGS. 5w-5cc and Table 8). 3.75× more lung endothelial cells were $tdTomato^+$ than kidney endothelial cells (FIG. 2H). These data support previous research suggesting PEG alkyl tail length influences biodistribution (Mui, Tam et al. 2013, Dahlman, Kauffman et al. 2017). No strong relationship between LNP delivery and LNP diameter was observed (FIG. 5dd-5ll).

Figure 6A:
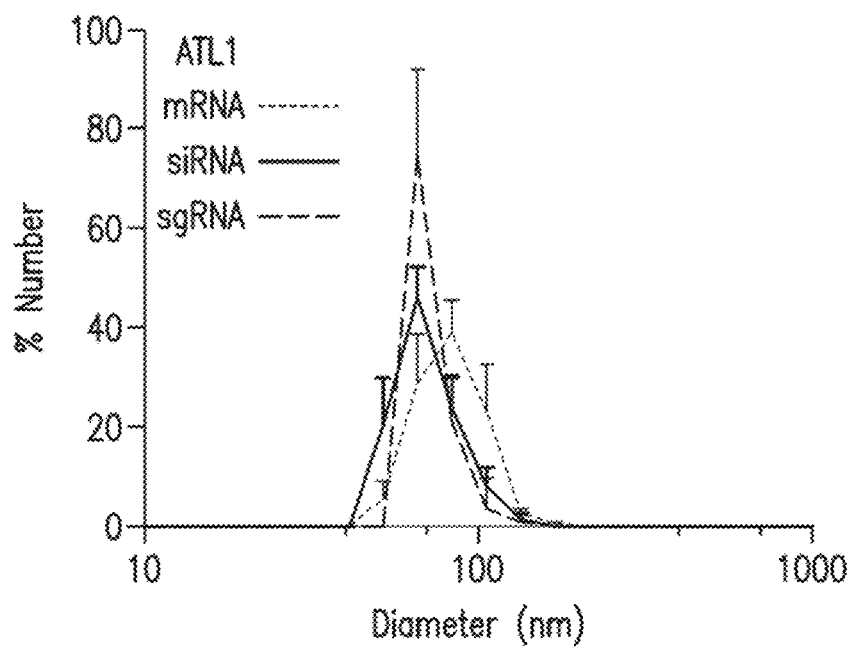
FIGS. 6A and 6B show DLS Spectra of ATL1 (FIG. 6A) and ATL2 (FIG. 6B) encapsulating mRNA, siRNA, and sgRNA.
Figure 6B:
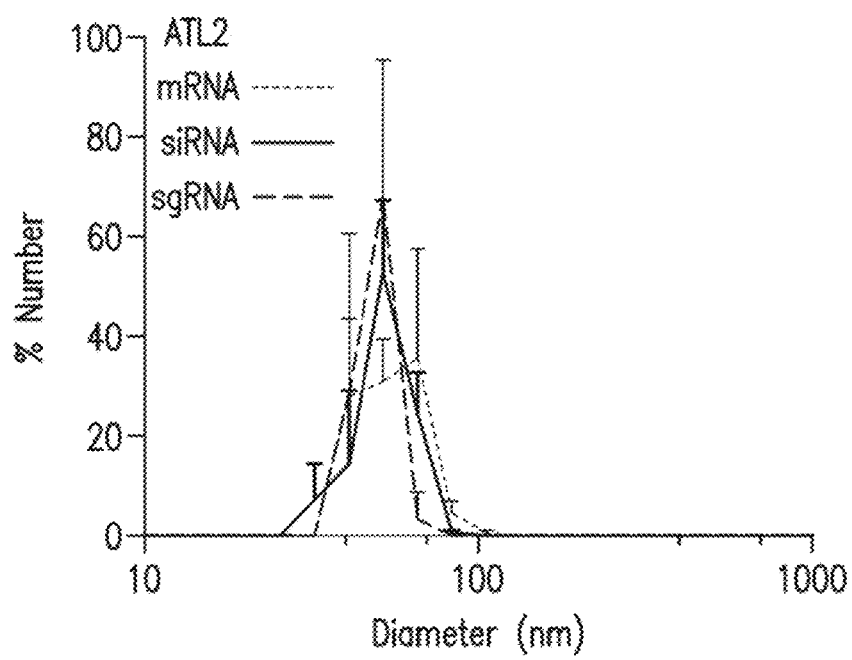
Figure 6C:
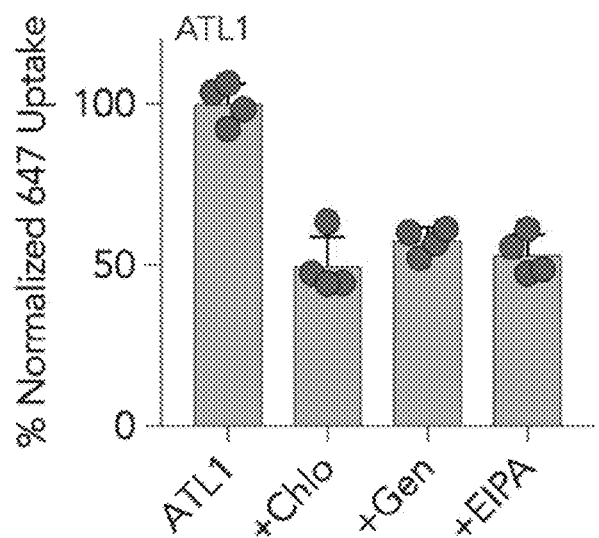
FIGS. 6C and 6D show endocytosis of AlexaFluor-647 barcode uptake encapsulated by ATL1 (FIG. 6C) and ATL2 (FIG. 6D) in the presence of chlorpromazine, genistein, and EIPA.
Figure 6D:
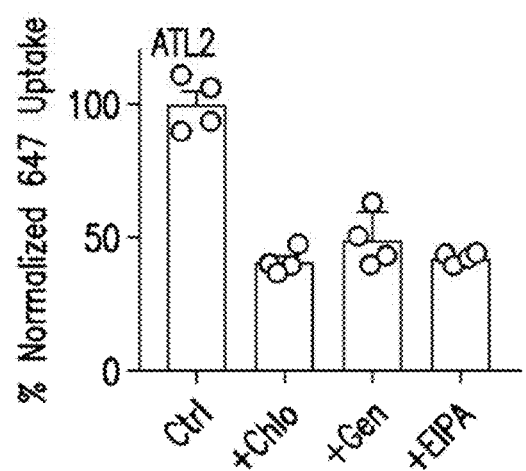
Figure 6E:
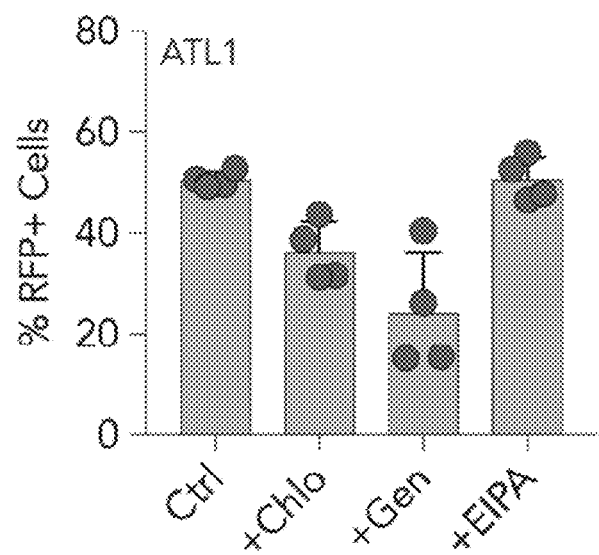
FIGS. 6E and 6F show delivery of Cre mRNA for ATL1 (FIG. 6E) and ATL2 (FIG. 6F) in the presence of chlorpromazine, genistein, and EIPA.
Figure 6F:
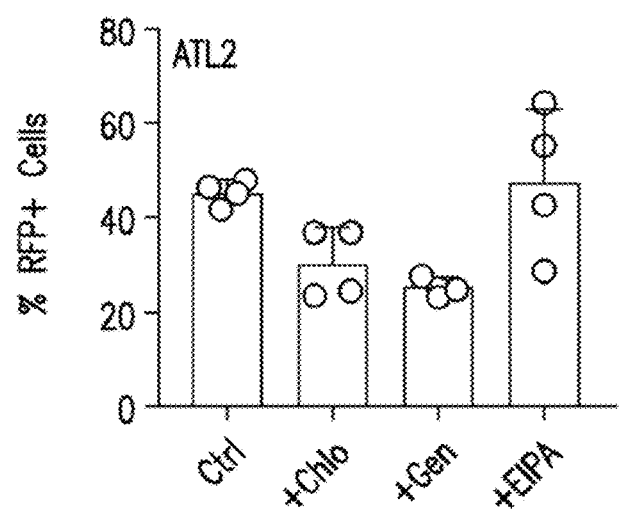

Like all high throughput screens, LNPs identified by FIND need to be validated. ATL1 and ATL2 (FIG. 3A, 3B-3E) were selected. ATL1 and ATL2 formed small, stable LNPs (FIG. 6A-6B). The in vitro endocytosis and functional Cre mRNA delivery of both LNPs in LGSL-RFP cells was inhibited by chlorpromazine and Genistein, whereas EIPA only impacted LNP uptake. (FIG. 6C-6F).

Figure 6G:
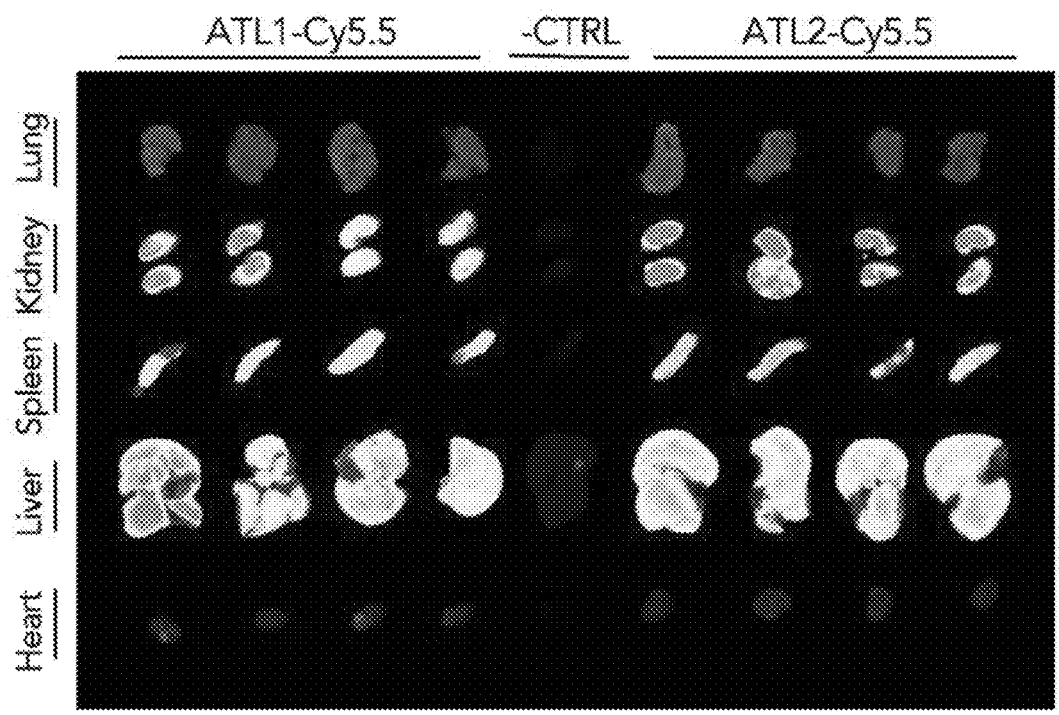
FIG. 6G shows barcode-Cy5.5 biodistribution of ATL1 and ATL2 measured in lung, kidney, spleen, liver, and heart by whole tissue ex vivo imaging.
Figure 6H:
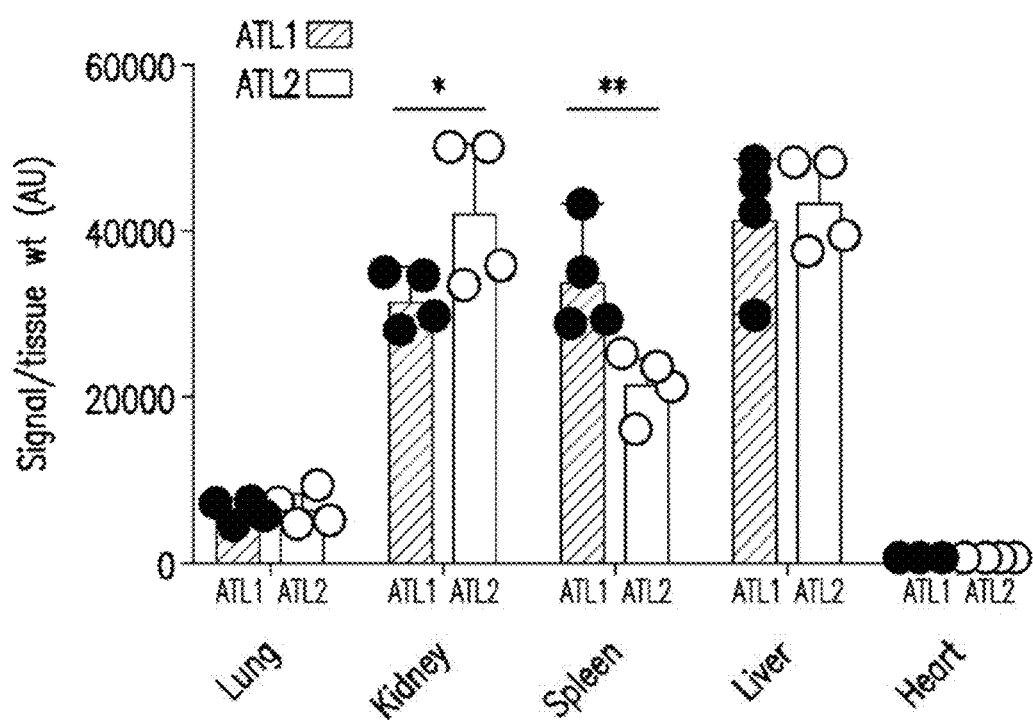
FIG. 6H shows ATL1 and ATL2 biodistribution normalized to tissue mass.

Biodistribution, tolerability, and ability to deliver siRNA, sgRNA, and mRNA to endothelial cells were measured in vivo. First, ATL1 and ATL2 were formulated with a Cy5.5 conjugated DNA barcode, and 0.75 mg/kg DNA was intravenously injected mice. Cy5.5 ex vivo fluorescence was highest in the spleen, kidney, and liver, suggesting that, like most LNPs, ATL1 and ATL2 distribute to, and/or are partially cleared by these tissues (FIG. 6G-6H).

Figure 6I:
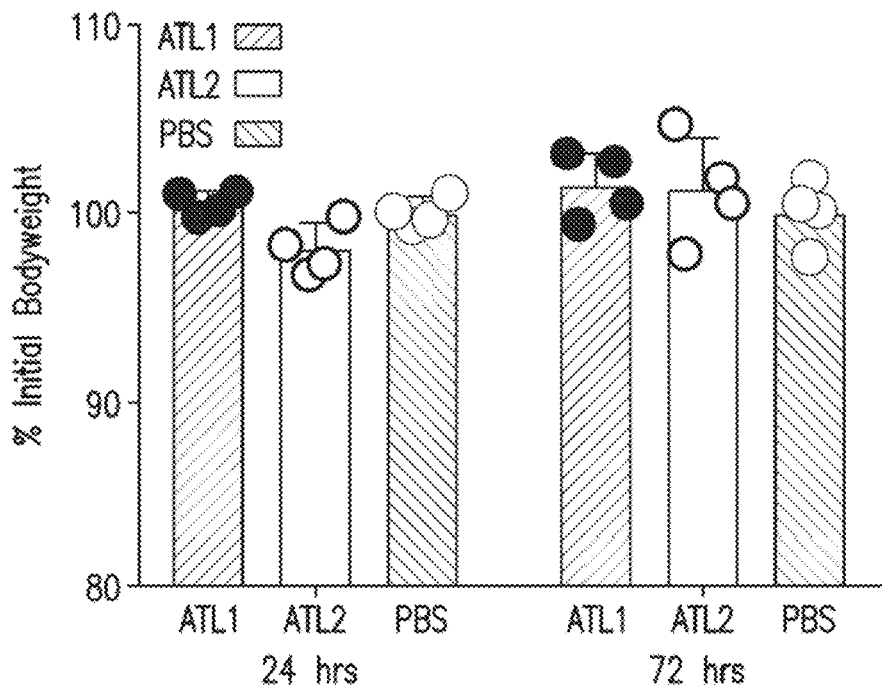
FIG. 6I shows changes in mouse bodyweight 24 and 72 hrs after administration of PBS or 2 mg/kg siGFP in ATL1 and ATL2.
Figure 6J:
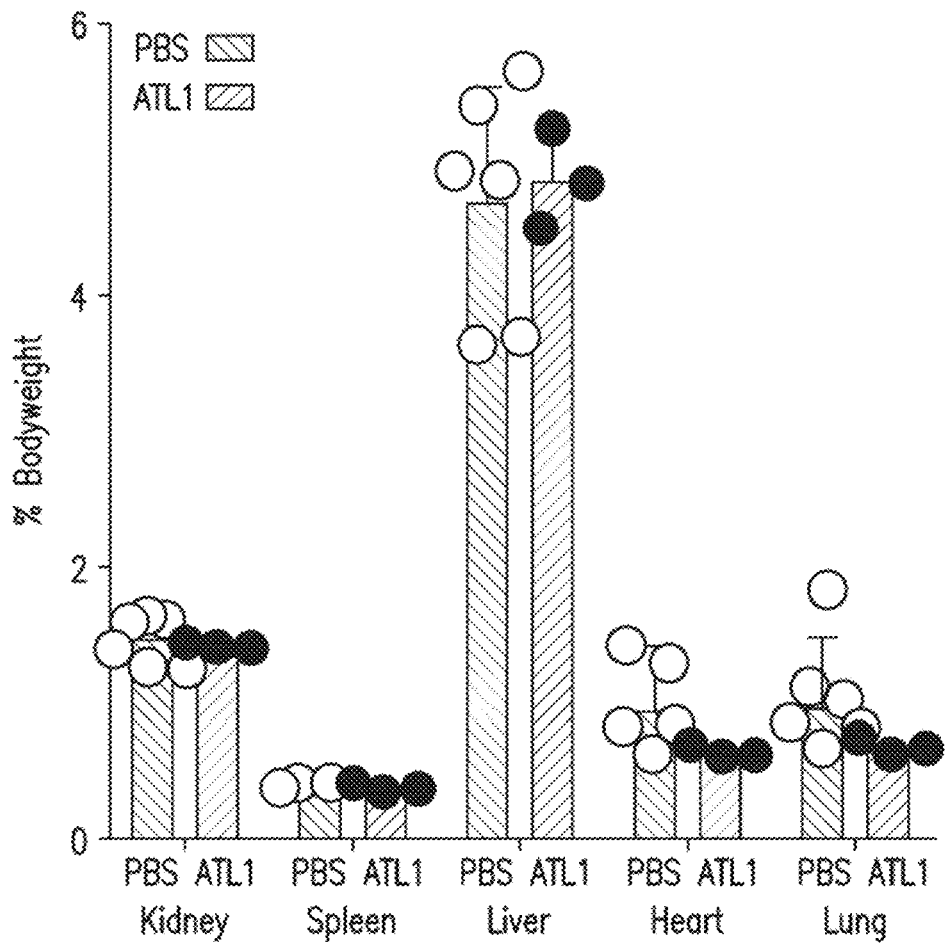
FIGS. 6J and 6K show organ weight as a percentage of bodyweight in mice 72 hrs after a 2 mg/kg injection of either PBS, ATL1 (FIG. 6J) or ATL2 (FIG. 6K).
Figures 6K, 6L:
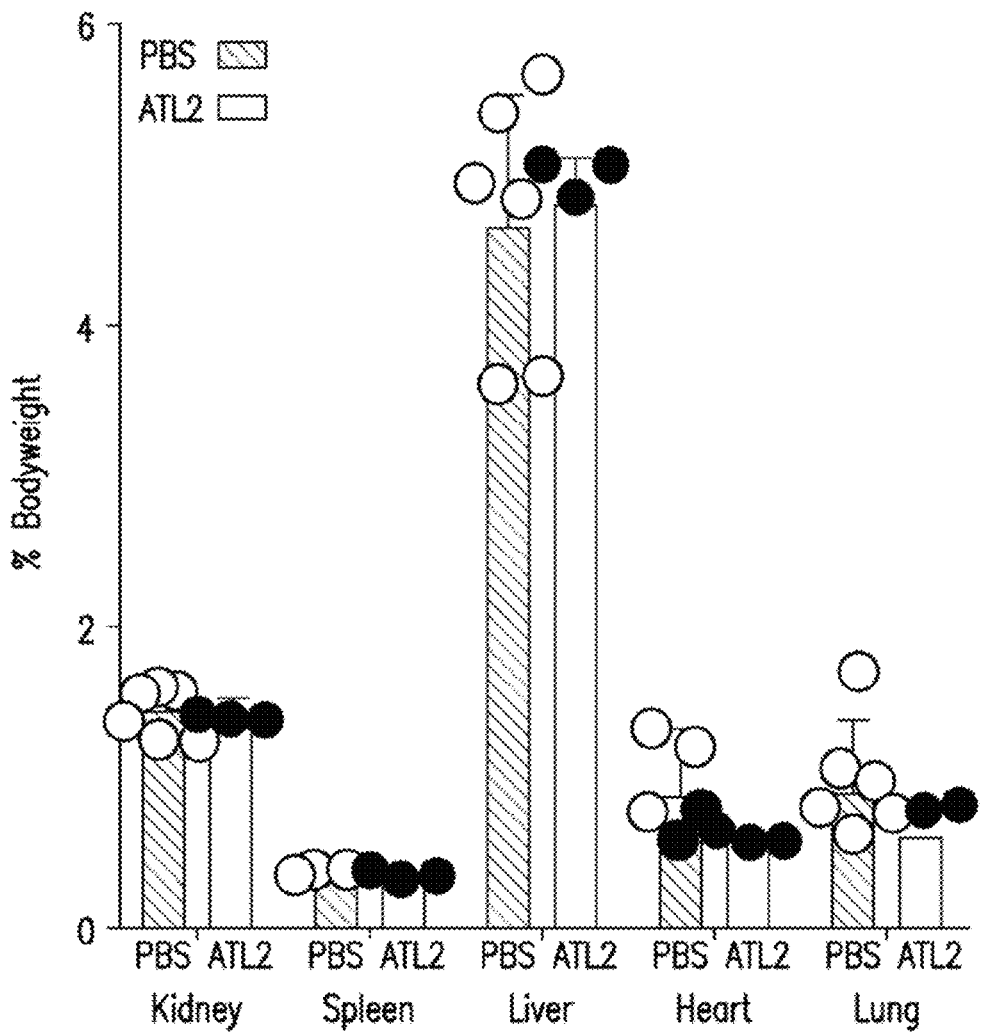
FIG. 6L shows sequences of siICAM2 (SEQ ID NO:2 and SEQ ID NO:3) and siGFP (SEQ ID NO:4 and SEQ ID NO:5) used.
Figure 6P:
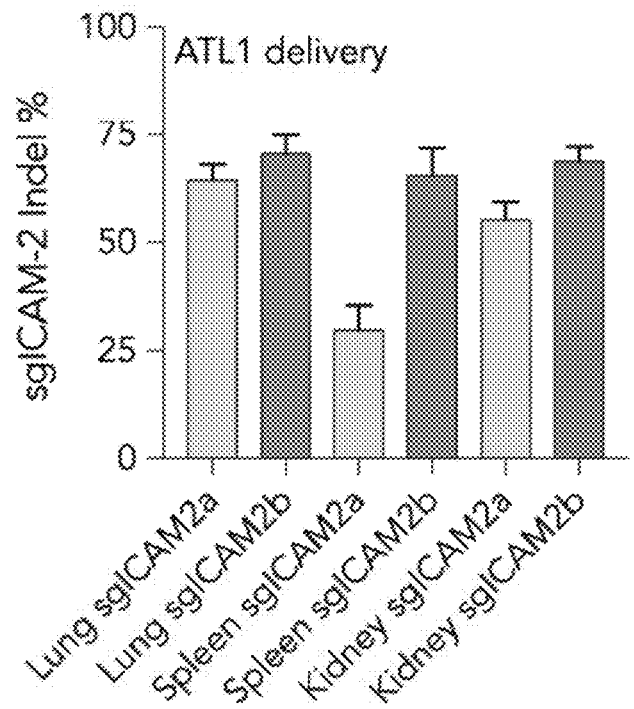
FIGS. 6P and 6Q show indel formation at each ICAM2 loci after three 1.5 mg/kg injections of ATL1- or ATL2-sgICAM2ab.
Figure 6Q:
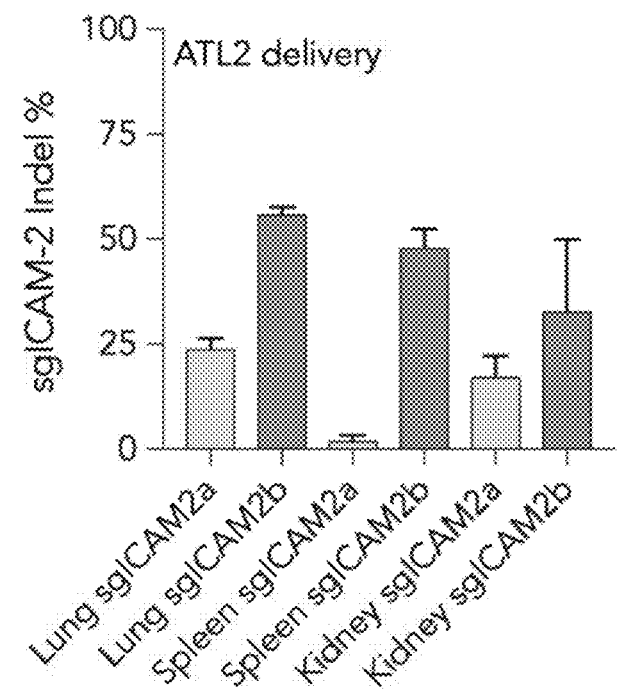

ATL1 and ATL2 were then formulated with siRNA targeting the endothelial specific gene ICAM-2. Three days after intravenously injecting mice with PBS, 2.0 mg/kg siGFP (higher dose to test tolerability), or 1.0 mg/kg siICAM-2, ICAM-2 protein median fluorescent intensity (MFI) was quantified on lung, kidney, and splenetic endothelial cells using FACS as previously described (Dahlman, Barnes et al. 2014, Sager, Dutta et al. 2016, Sager, Hulsmans et al. 2016). ICAM-2 MFI was constant in PBS- and siGFP-treated mice, but decreased by up to 60% in endothelial cells isolated from mice injected with siICAM-2. ATL1-mediated siRNA delivery was more robust than ATL2-mediated siRNA delivery in lung endothelial cells, and interestingly, ATL2 delivered siRNA to spleen endothelial cells more than lung endothelial cells (FIG. 3F. Mice injected with 2.0 mg/kg siGFP did not lose weight compared to mice injected with PBS (FIG. 6I-6K). Both previously validated (Dahlman, Barnes et al. 2014, Sager, Dutta et al. 2016, Sager, Hulsmans et al. 2016) siRNAs were synthesized using chemically modified RNA (FIG. 6L).

Figure 3G:
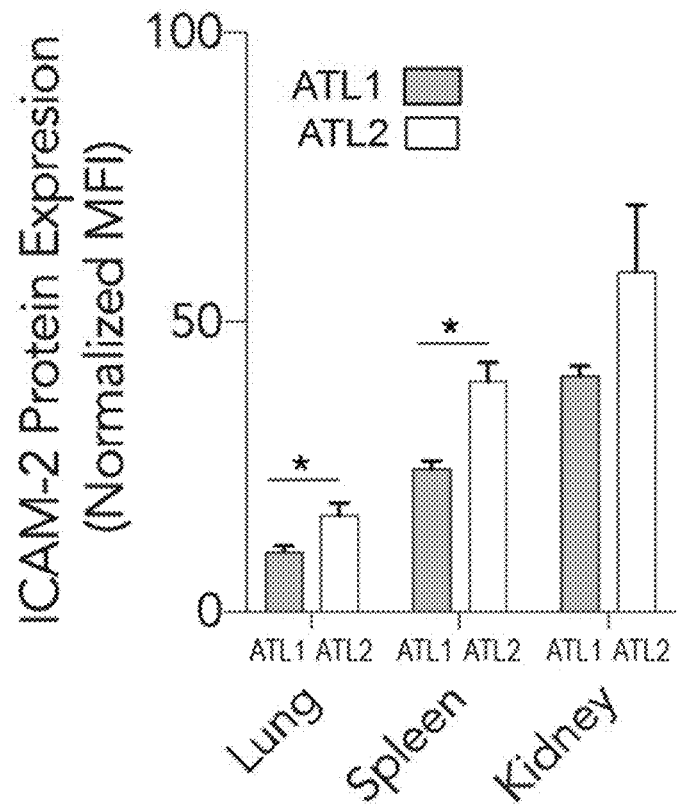
Figure 3H:
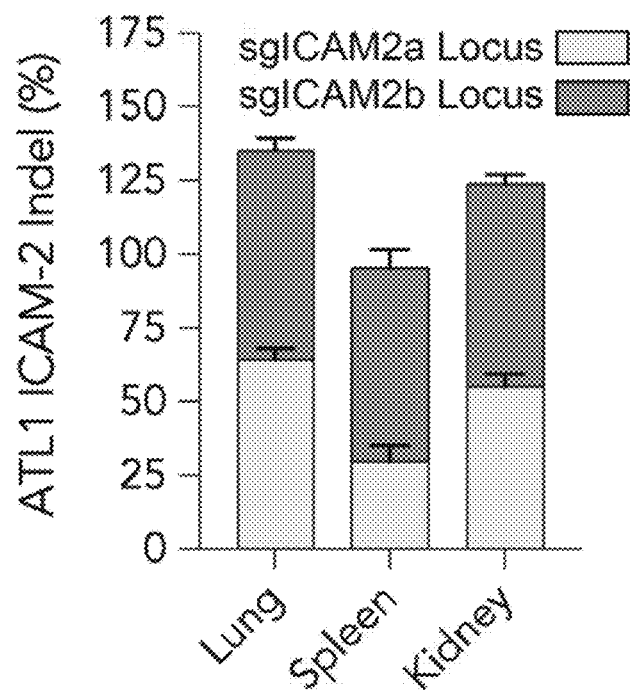
Figure 3I:
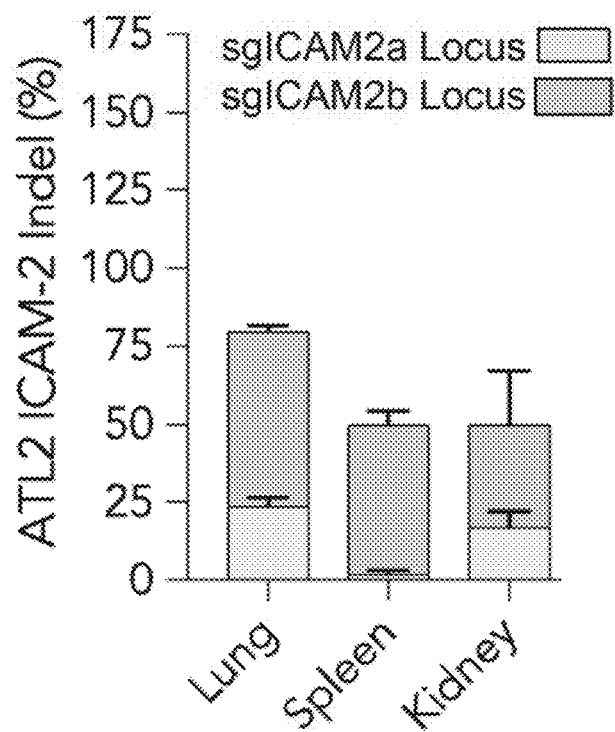

To determine whether ATL1 and ATL2 delivered sgRNAs to endothelial cells, 2 chemically modified (Hendel, Bak et al. 2015) sgRNAs targeting ICAM-2 were injected each at a dose of 0.75 mg/kg into mice that constitutively express SpCas9 (Platt, Chen et al. 2014) (FIG. 6M). No changes in weight gain compared to mice injected with PBS was observed (FIG. 6N-6O). After 3 injections, ICAM-2 MFI decreased by up to 90%, 75%, and 59% in lung, spleen, and kidney endothelial cells (FIG. 3G). To confirm protein silencing was mediated by gene editing, ICAM-2 insertions and deletions were measured in lung, spleen, and kidney endothelial cells isolated by FACS, and found between 30 and 70% editing per sgRNA, leading to 1.35, 0.95, and 1.23 ICAM-2 insertions and deletions per cell, respectively (FIG. 3H-3I, FIG. 6P-6Q. The siRNA and sgRNA data demonstrate that ATL1 and ATL2 deliver small RNA to endothelial cells in vivo, and suggest that formulation can alter the vascular beds LNPs target.

Figure 3J:
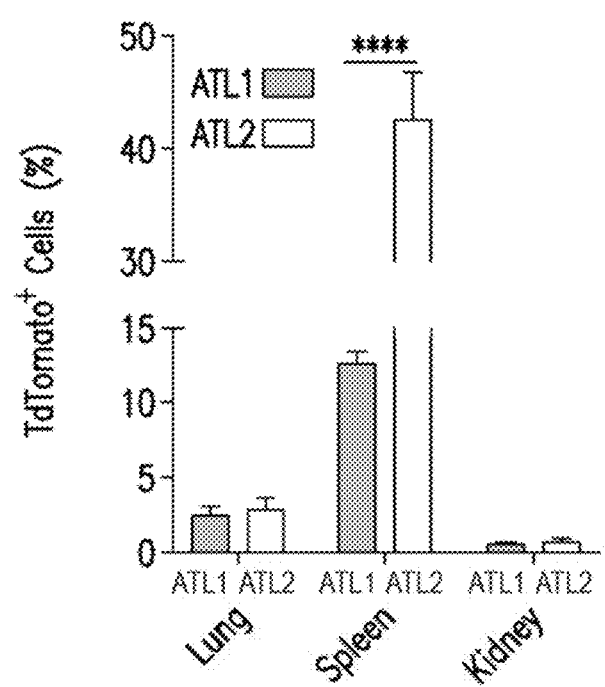
FIG. 3J shows percentage of tdTomato+ endothelial cells in various organs in LSL-Tom mice following a single, 1.5 mg/kg injection of Cre mRNA delivered by ATL1 or ATL2.
Figure 3O:
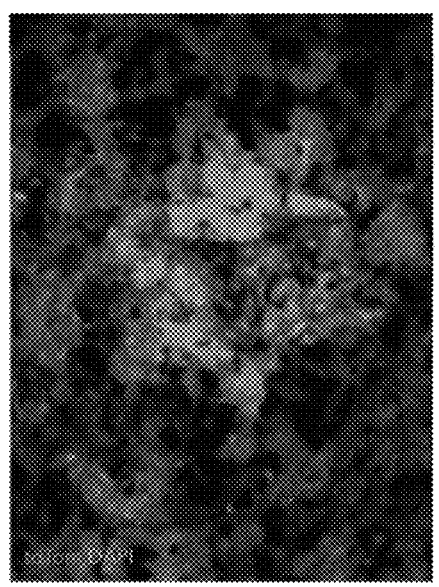
FIG. 3O shows a representative image of tdTomato+ cells in LSL-Tom liver following three 1.5 mg/kg ATL2-Cre injections.
Figure 6R:
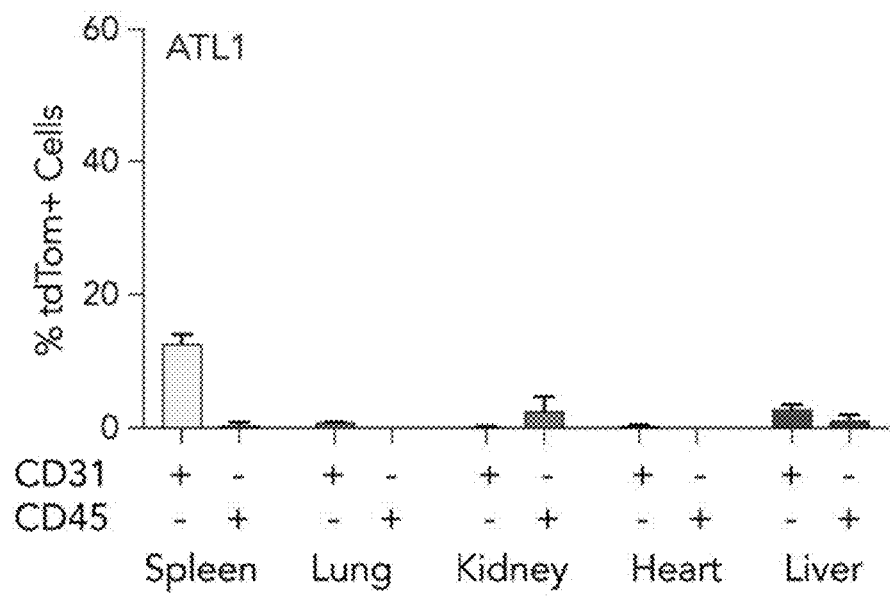
FIGS. 6R and 6S show tdTom+ cells in CD31+ and CD45+ cells in various organs after a single, 1.5 mg/kg injection of ATL1- or ATL2-Cre mRNA.
Figure 6S:
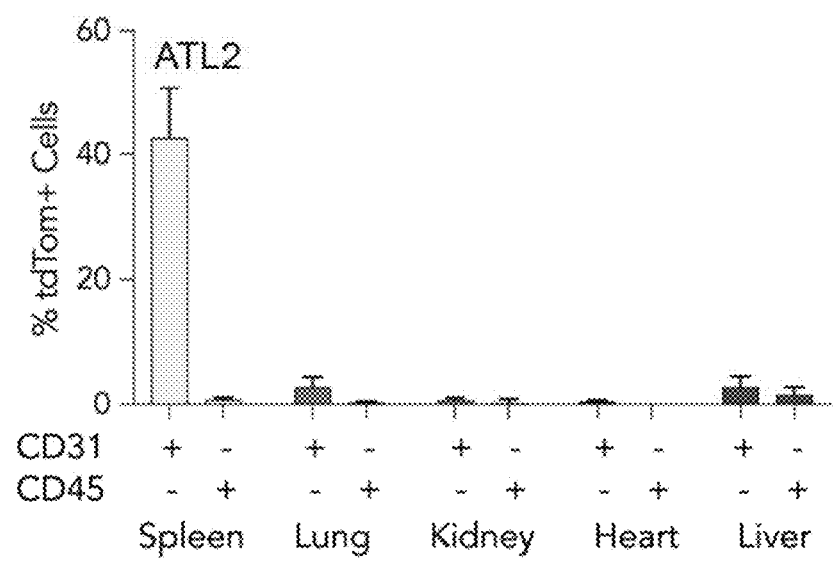
Figure 7A:
FIG. 7 is an illustration for conjugate based systems. These include peptide-based (FIG. 7A), lipid-based (FIG. 7B), ssRNA-based (FIG. 7C), dsRNA-based (FIG. 7D), ssDNA-based (FIG. 7E), dsDNA-based (FIG. 7F), and polymer based systems (FIG. 7G) containing a barcode and a reporter.
Figure 7B:
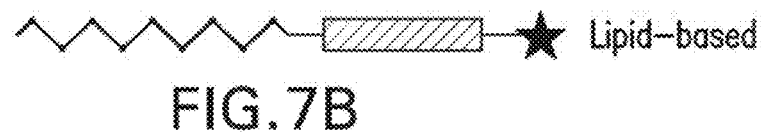
Figure 7C:
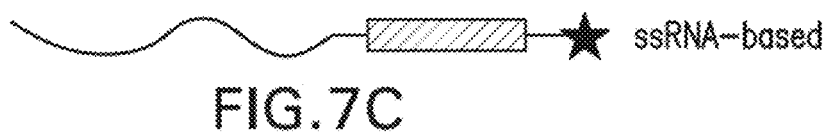
Figure 7D:
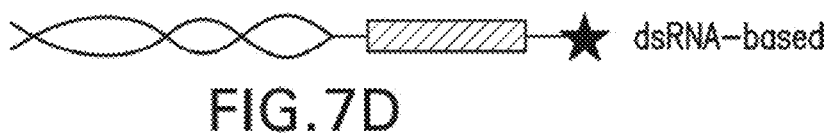
Figure 7E:
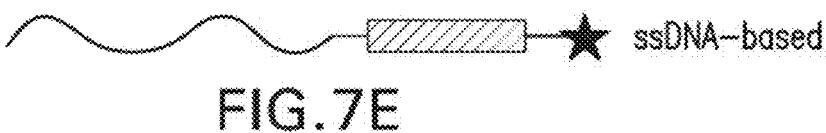
Figure 7F:
Figure 7G:
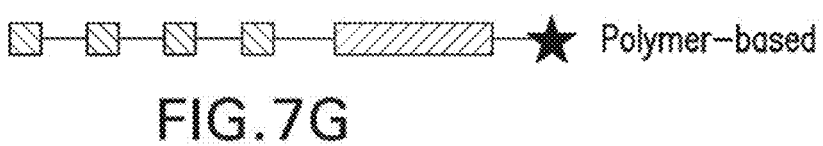

To determine whether ATL1 and ATL2 delivered mRNA to endothelial cells in vivo, 1.5 mg/kg Cre mRNA was intravenously injected into LSL-Tom reporter mice. After a single injection of ATL1 or ATL2, 12.6% and 40% of the splenetic endothelial cells were tdTomato$^+$, respectively (FIG. 3J). This was interesting for 2 reasons. First, both ATL1 and ATL2 preferentially delivered mRNA to splenetic endothelial cells over other vascular beds. Second, ATL2 outperformed ATL1 in the spleen. In all cases, endothelial cells were preferentially targeted more than other cell types (FIG. 6R-6S) a result confirmed by fluorescent blood vessels located throughout the spleen (FIG. 3K-3N).

Discussion

It is still difficult to predict whether a given nanoparticle will deliver its RNA payload into the cytoplasm in vivo. JORDAN, as well as other nanoparticle barcoding platforms, may be used to study LNPs in vivo. FIND complements these assays by measuring cytoplasmic mRNA delivery.

FIND has several advantages. First, it is agnostic to cell type; any combination of cells can be isolated. Second, FIND enables scientists to systematically study how LNP structure dictates cytoplasmic delivery in vivo. By screening 255 LNPs in vivo, the length of the PEG alkyl tail can affect in vivo delivery, recapitulating previous work. Third, FIND can be used in many animal models, enabling scientists to evaluate how disease affects delivery. Fourth, multiplexed studies were easier to perform than traditional 1-by-1 screening. When LNPs were screened in vitro 1 by 1, it was challenging to maintain exactly the same cell density, all the while relying on kits and reagents to be perfectly consistent for months. Analyzing many nanoparticles at once may make experimental results easier to interpret. Relatedly, FIND may be used in hard-to-passage cells that are not amenable to large scale expansion.

FIND enabled identification of ATL1 and ATL2, which mediated gene silencing and gene editing in vivo. Future studies optimizing sgRNA structure, or Cas9 mRNA stability may improve editing efficiency. Data in endothelial cells, and data in hepatocytes demonstrate that LNPs can mediate gene editing after intravenous administration.

TABLE 1

Normalized Delivery Example Calculation

| LNP | Barcode | Raw Counts Lung Endothelial Cells | | | Raw Counts Kidney Endothelial Cells | | | Input |
| --- | --- | --- | --- | --- | --- | --- | --- | --- |
| | | Mouse 1 | Mouse 2 | Mouse 3 | Mouse 1 | Mouse 2 | Mouse 3 | |
| 1 | GACACAGT | 100 | 80 | 200 | 300 | 200 | 250 | 100 |
| 2 | GCATAACG | 50 | 45 | 110 | 100 | 60 | 70 | 120 |
| 3 | ACAGAGGT | 120 | 105 | 250 | 150 | 90 | 110 | 110 |
| Total Counts | | 270 | 230 | 560 | 550 | 350 | 430 | 330 |

| LNP | Barcode | Normalized Counts Lung ECs (%) | | | Normalized Counts Kidney ECs (%) | | | Input |
| --- | --- | --- | --- | --- | --- | --- | --- | --- |
| | | Mouse 1 | Mouse 2 | Mouse 3 | Mouse 1 | Mouse 2 | Mouse 3 | |
| 1 | GACACAGT | 37 | 35 | 36 | 55 | 57 | 58 | 30 |

TABLE 1-continued

Normalized Delivery Example Calculation

| | | | | | | | | |
|---|---|---|---|---|---|---|---|---|
| 2 | GCAT AACG | 19 | 20 | 20 | 18 | 17 | 16 | 36 |
| 3 | ACAG AGGT | 44 | 46 | 45 | 27 | 26 | 26 | 33 |
| Total (%) | | 100 | 100 | 100 | 100 | 100 | 100 | 100 |

| | | Normalized to input Counts Lung ECs (%) | | | Normalized to input Counts Kidney ECs (%) | | |
|---|---|---|---|---|---|---|---|
| LNP | Barcode | Mouse 1 | Mouse 2 | Mouse 3 | Mouse 1 | Mouse 2 | Mouse 3 |
| 1 | GACA CAGT | 40 | 38 | 39 | 58 | 60 | 61 |
| 2 | GCAT AACG | 17 | 18 | 18 | 16 | 15 | 14 |
| 3 | ACAG AGGT | 44 | 45 | 44 | 26 | 25 | 24 |
| Total (%) | | 100 | 100 | 100 | 100 | 100 | 100 |

TABLE 2

Barcode Sequences

| LNP | Barcode |
|---|---|
| 1 | GAC ACA GT |
| 2 | GCA TAA CG |
| 3 | ACA GAG GT |
| 4 | CCA CTA AG |
| 5 | TGT TCC GT |
| 6 | GAT ACC TG |
| 7 | AGC CGT AA |
| 8 | CTC CTG AA |
| 9 | ACG AAT CC |
| 10 | AAT GGT CG |
| 11 | CGC TAC AT |
| 12 | CCT AAG TC |
| 13 | TTG CTT GG |
| 14 | CCT GTC AA |
| 15 | AGC CTA TC |
| 16 | TGA TCA CG |
| 17 | CCA CAT TG |
| 18 | TCG AGA GT |
| 19 | GGT CGT AT |
| 20 | ACA GGC AT |
| 21 | GTG ATC CA |
| 22 | TTC GTA CG |
| 23 | ATG ACA GG |
| 24 | CGA CCT AA |
| 25 | TAT GGC AC |
| 26 | ATA ACG CC |
| 27 | GTA GTA CC |
| 28 | CGC GTA TT |
| 28 | ATC CAC GA |
| 30 | TAA CGT CG |
| 31 | CCT TCC AT |
| 32 | GAT CAA GG |
| 33 | AAG CAT CG |
| 34 | AGG ATA GC |
| 35 | GGC TCA AT |
| 36 | TTC ACG GA |
| 37 | GGC GAA TA |
| 38 | AAG TGC AG |
| 39 | GCA ATT CC |
| 40 | CTT CGC AA |
| 41 | CAT TGA CG |
| 42 | TCT GGA CA |
| 43 | GCT ACA AC |
| 44 | CCG ATG TA |

TABLE 2-continued

Barcode Sequences

| LNP | Barcode |
|---|---|
| 45 | TAG GAG CT |
| 46 | AAC AAG GC |
| 47 | CTC GGT AA |
| 48 | AGC TTC AG |
| 49 | TCA CCT AG |
| 50 | CAA GTC GT |
| 51 | CTG TAT GC |
| 52 | AGT TCG CA |
| 53 | ATC GGA GA |
| 54 | AAG TCC TC |
| 55 | TGG ATG GT |
| 56 | AGG TGT TG |
| 57 | GAC GAA CT |
| 58 | GTT CTT CG |
| 59 | TTC GCC AT |
| 60 | CAA CTC CA |
| 61 | AAC CGT GT |
| 62 | CGG TTG TT |
| 63 | CTA GCA GT |
| 64 | ACC TCT TC |
| 65 | TAC TAG CG |
| 66 | ACA ACA GC |
| 67 | CGC AAT GT |
| 68 | CAG TGC TT |
| 69 | TCT AGG AG |
| 70 | GAT TGT CC |
| 71 | GGT ACG AA |
| 72 | CTT CAC TG |
| 73 | ATA GGT CC |
| 74 | ACC GAC AA |
| 75 | AAC ACT GG |
| 76 | ACC ATA GG |
| 77 | TCG ATG AC |
| 78 | GAC TTG TG |
| 79 | CCG TTA TG |
| 80 | CAA CGA GT |
| 81 | TTA CCG AC |
| 82 | GAG AGT AC |
| 83 | CTG TAC CA |
| 84 | TGA GCT GT |
| 85 | AGT ATG CC |
| 86 | TAC TGC TC |
| 87 | TGC TTG CT |
| 88 | TCC ACG TT |
| 89 | AAC CAG AG |
| 90 | ACG AAC GA |
| 91 | ATA GTC GG |
| 92 | CCA TGA AC |
| 93 | GAG CAA TC |
| 94 | CAA CTT GG |
| 95 | CCA CAA CA |
| 96 | TGG TGA AG |
| 97 | AAC ACG CT |
| 98 | AAC AGG TG |
| 99 | AAC CTA CG |
| 100 | AAG ACA CC |
| 101 | AAG CGA CT |
| 102 | AAT CGC TG |
| 103 | AAT TCC GG |
| 104 | ACA CCT CA |
| 105 | ACA GTT CG |
| 106 | ACC ATG TC |
| 107 | ACC GGT TA |
| 108 | ACG AGA AC |
| 109 | ACG CTT CT |
| 110 | ACT CCT AC |
| 111 | ACT GCG AA |
| 112 | AGA ACC AG |
| 113 | AGA TAC GG |
| 114 | AGC GAG AT |
| 115 | AGG AGG TT |
| 116 | AGG TAG GA |
| 117 | AGT CAG GT |
| 118 | AGT GCA TC |
| 119 | ATA CGC AG |

TABLE 2-continued

Barcode Sequences

| LNP | Barcode |
|---|---|
| 120 | ATC CGT TG |
| 121 | ATC GTG GT |
| 122 | ATG CCT AG |
| 123 | ATT AGC CG |
| 124 | CAA GAA GC |
| 125 | CAA TCA GG |
| 126 | CAT ACT CG |
| 127 | CAT CTG CT |
| 128 | CCA ACG AA |
| 129 | CCA GTT GA |
| 130 | CCG GAA TA |
| 131 | CCT ACC TA |
| 132 | CCT ATT GG |
| 133 | CCT TGG AA |
| 134 | CGA ATT GC |
| 135 | CGA GTT AG |
| 136 | CGC TGA TA |
| 137 | CGG CAT TA |
| 138 | CGT CAA GA |
| 139 | CTA AGA CC |
| 140 | CTA GGT TG |
| 141 | CTC ACC AA |
| 142 | CTC GAC TT |
| 143 | CTC TCA GA |
| 144 | CTG ATG AG |
| 145 | TAC CTG CA |
| 146 | CTT ACA GC |
| 147 | CTT CGG TT |
| 148 | GAA CGA AG |
| 149 | GAA GAT CC |
| 150 | GAC CGA TA |
| 151 | GAG AAG GT |
| 152 | GAG GCA TT |
| 153 | GAT CAG AC |
| 154 | GAT GCT AC |
| 155 | AAC AAC CG |
| 156 | AAC AGT CC |
| 157 | AAC GCA CA |
| 158 | AAG ACC GT |
| 159 | AAG CGT TC |
| 160 | AAT GAC GC |
| 161 | ACA AGA CG |
| 162 | ACA CGA GA |
| 163 | ACA GCA AG |
| 164 | ACC GAA TG |
| 165 | ACC TAG AC |
| 166 | ACG ATC AG |
| 167 | ACG GAC TT |
| 168 | ACT CGA TC |
| 169 | ACT GCT TG |
| 170 | AGA AGC CT |
| 171 | AGA TCG TC |
| 172 | AGC GTG TA |
| 173 | AGG CAA TG |
| 174 | AGG TTC CT |
| 175 | AGT CGA AG |
| 176 | AGT GGC AA |
| 177 | ATA CTG GC |
| 178 | ATC CTT CC |
| 179 | ATC TCC TG |
| 180 | ATG CGC TT |
| 181 | ATT CCG CT |
| 182 | CAA GCC AA |
| 183 | CAA TGC GA |
| 184 | CAT CAA CC |
| 185 | CAT GAG CA |
| 186 | CCA ACT TC |
| 187 | CCG AAG AT |
| 188 | CCG TAA CT |
| 189 | CCT AGA GA |
| 190 | CCT CAT CT |
| 191 | CGA ACA AC |
| 192 | CGA CAC TT |
| 193 | CGA TCG AT |
| 194 | CGG AGT AT |

TABLE 2-continued

Barcode Sequences

| LNP | Barcode |
|---|---|
| 195 | CGG TAA TC |
| 196 | CGT CCA TT |
| 197 | CTA CAA GG |
| 198 | CTA TCC AC |
| 199 | CTC AGA AG |
| 200 | CTC GTT CT |
| 201 | CTC TGG AT |
| 202 | CTG CCA TA |
| 203 | CTG AAC GT |
| 204 | CTT AGG AC |
| 205 | CTT GCT AG |
| 206 | GAA CGG TT |
| 207 | GAA GTG CT |
| 208 | GAC GTC AT |
| 209 | GAG ACC AA |
| 210 | GAG TAG AG |
| 211 | GAT CCA CT |
| 212 | GAT GGA GT |
| 213 | GCA CAC AA |
| 214 | GCA TTG GT |
| 215 | GCC TTC TT |
| 216 | GCT AAG GA |
| 217 | GCT GAA TC |
| 218 | GGA AGA GA |
| 219 | GGA CTA CT |
| 220 | GGA TGT AG |
| 221 | GGA TTC AC |
| 222 | GGT ATA GG |
| 223 | GGT TAG CT |
| 224 | GTA AGC AC |
| 225 | GTA CGA TC |
| 226 | GTC AAC AG |
| 227 | GTC CTT GA |
| 228 | GTC TGA GT |
| 229 | GTG TGT TC |
| 230 | GTT CCA TG |
| 231 | TAA GCG CA |
| 232 | TAC AGA GC |
| 233 | TAG CAG GA |
| 234 | TAG CTT CC |
| 235 | TAG TGC CA |
| 236 | TAT GAC CG |
| 237 | TCA CTC GA |
| 238 | TCA GTA GG |
| 239 | TCC GAT CA |
| 240 | TCG AAC CT |

TABLE 3

Dual Indices Design for Multiplexed Illumina Sequencing

| Index Name | Index Sequence |
|---|---|
| N701 | TAAGGCCA |
| N702 | CGTACTAG |
| N703 | AGGCAGAA |
| N704 | TCCTGAGC |
| N705 | GGACTCCT |
| N706 | TAGGCATG |
| N707 | CTCTCTAC |
| N710 | CGAGGCTG |
| N711 | AAGAGGCA |
| N712 | GTAGAGGA |
| N714 | GCTCATGA |
| N715 | ATCTCAGG |
| N716 | ACTCGCTA |
| N718 | GGAGCTAC |
| N719 | GCGTAGTA |
| N720 | CGGAGCCT |
| N721 | TACGCTGC |
| N722 | ATGCGCAG |
| N723 | TAGCGCTC |
| N724 | ACTGAGCG |
| N726 | CCTAAGAC |
| N727 | CGATCAGT |
| N728 | TGCAGCTA |
| N729 | TCGACGTC |

TABLE 3-continued

Dual Indices Design for Multiplexed Illumina Sequencing

| Index Name | Index Sequence |
|---|---|
| S502 | ATAGAGAG |
| S503 | AGAGGATA |
| S505 | CTCCTTAC |
| S506 | TATGCAGT |
| S507 | TACTCCTT |
| S508 | AGGCTTAG |
| S510 | ATTAGACG |
| S511 | CGGAGAGA |
| S513 | CTAGTCGA |
| S515 | AGCTAGAA |
| S516 | ACTCTAGG |
| S517 | TCTTACGC |
| S518 | CTTAATAG |
| S520 | ATAGCCTT |
| S521 | TAAGGCTC |
| S522 | TCGCATAA |

TABLE 4

Primers

| | |
|---|---|
| Universal Reverse Primer (N7XX) | AATGATACGGCGACCACCGAGATCTACACT AAGGCCAACACTCTTTCCCTACACGACGCT<u>CTTCCGATCT</u> (SEQ ID NO: 9) |
| Base Forward Primer | TGACTGGAGTTC<u>AGACGTGTGCTCTTCCGATCT</u> (SEQ ID NO: 10) |
| Universal Forward Primer (S5XX) | CAAGCAGAAGACGGCATACGAGATATAGAG AGGTGACTGGAGTTCAGACGTGTG (SEQ ID NO: 11) |

<u>Binds to Forward Universal Site</u>
<u>Binds to Reverse Universal Site</u>

TABLE 5

LNP library used for in vitro assays

| LNP # | Compound | PEG Type | Mass Ratio | Compound Mole % | Cholesterol Mole % | PEG Mole % |
|---|---|---|---|---|---|---|
| 1 | 7C1 | C14PEG | 10 | 80 | 0 | 20 |
| 2 | 7C1 | C14PEG | 10 | 80 | 5 | 15 |
| 3 | 7C1 | C14PEG | 10 | 80 | 10 | 10 |
| 4 | 7C1 | C14PEG | 10 | 80 | 15 | 5 |
| 5 | 7C1 | C14PEG | 10 | 80 | 17.5 | 2.5 |
| 6 | 7C1 | C14PEG | 10 | 80 | 19 | 1 |

TABLE 5-continued

LNP library used for in vitro assays

| LNP # | Compound | PEG Type | Mass Ratio | Compound Mole % | Cholesterol Mole % | PEG Mole % |
|---|---|---|---|---|---|---|
| 7 | 7C1 | C16PEG | 10 | 80 | 0 | 20 |
| 8 | 7C1 | C16PEG | 10 | 80 | 5 | 15 |
| 9 | 7C1 | C16PEG | 10 | 80 | 10 | 10 |
| 10 | 7C1 | C16PEG | 10 | 80 | 15 | 5 |
| 11 | 7C1 | C16PEG | 10 | 80 | 17.5 | 2.5 |
| 12 | 7C1 | C16PEG | 10 | 80 | 19 | 1 |
| 13 | 7C1 | C18PEG | 10 | 80 | 0 | 20 |
| 14 | 7C1 | C18PEG | 10 | 80 | 5 | 15 |
| 15 | 7C1 | C18PEG | 10 | 80 | 10 | 10 |
| 16 | 7C1 | C18PEG | 10 | 80 | 15 | 5 |
| 17 | 7C1 | C18PEG | 10 | 80 | 17.5 | 2.5 |
| 18 | 7C1 | C18PEG | 10 | 80 | 19 | 1 |
| 19 | 92 | C14PEG | 10 | 80 | 0 | 20 |
| 20 | 92 | C14PEG | 10 | 80 | 5 | 15 |
| 21 | 92 | C14PEG | 10 | 80 | 10 | 10 |
| 22 | 92 | C14PEG | 10 | 80 | 15 | 5 |
| 23 | 92 | C14PEG | 10 | 80 | 17.5 | 2.5 |
| 24 | 92 | C14PEG | 10 | 80 | 19 | 1 |
| 25 | 92 | C16PEG | 10 | 80 | 0 | 20 |
| 26 | 92 | C16PEG | 10 | 80 | 5 | 15 |
| 27 | 92 | C16PEG | 10 | 80 | 10 | 10 |
| 28 | 92 | C16PEG | 10 | 80 | 15 | 5 |
| 29 | 92 | C16PEG | 10 | 80 | 17.5 | 2.5 |
| 30 | 92 | C16PEG | 10 | 80 | 19 | 1 |
| 31 | 92 | C18PEG | 10 | 80 | 0 | 20 |
| 32 | 92 | C18PEG | 10 | 80 | 5 | 15 |
| 33 | 92 | C18PEG | 10 | 80 | 10 | 10 |
| 34 | 92 | C18PEG | 10 | 80 | 15 | 5 |
| 35 | 92 | C18PEG | 10 | 80 | 17.5 | 2.5 |
| 36 | 92 | C18PEG | 10 | 80 | 19 | 1 |
| 37 | 78 | C14PEG | 10 | 80 | 0 | 20 |
| 38 | 78 | C14PEG | 10 | 80 | 5 | 15 |
| 39 | 78 | C14PEG | 10 | 80 | 10 | 10 |
| 40 | 78 | C14PEG | 10 | 80 | 15 | 5 |
| 41 | 78 | C14PEG | 10 | 80 | 17.5 | 2.5 |
| 42 | 78 | C14PEG | 10 | 80 | 19 | 1 |
| 43 | 78 | C16PEG | 10 | 80 | 0 | 20 |
| 44 | 78 | C16PEG | 10 | 80 | 5 | 15 |
| 45 | 78 | C16PEG | 10 | 80 | 10 | 10 |
| 46 | 78 | C16PEG | 10 | 80 | 15 | 5 |
| 47 | 78 | C16PEG | 10 | 80 | 17.5 | 2.5 |
| 48 | 78 | C16PEG | 10 | 80 | 19 | 1 |
| 49 | 78 | C18PEG | 10 | 80 | 0 | 20 |
| 50 | 78 | C18PEG | 10 | 80 | 5 | 15 |
| 51 | 78 | C18PEG | 10 | 80 | 10 | 10 |
| 52 | 78 | C18PEG | 10 | 80 | 15 | 5 |
| 53 | 78 | C18PEG | 10 | 80 | 17.5 | 2.5 |
| 54 | 78 | C18PEG | 10 | 80 | 19 | 1 |

TABLE 6

LNP library used for in vivo screen 1

| LNP # | Compound | PEG Type | Mass Ratio | Compound Mole % | PEG Mole % | Cholesterol Mole % | DOPE Mole % |
|---|---|---|---|---|---|---|---|
| 1 | 7C1 | C14PEG | 10 | 80 | 20 | 0 | 0 |
| 2 | 7C1 | C14PEG | 10 | 80 | 15 | 5 | 0 |
| 3 | 7C1 | C14PEG | 10 | 80 | 10 | 10 | 0 |
| 4 | 7C1 | C14PEG | 10 | 80 | 5 | 15 | 0 |
| 5 | 7C1 | C14PEG | 10 | 80 | 2 | 18 | 0 |
| 6 | 7C1 | C14PEG | 10 | 62 | 26 | 12 | 0 |
| 7 | 7C1 | C14PEG | 10 | 62 | 16 | 22 | 0 |
| 8 | 7C1 | C14PEG | 10 | 62 | 6 | 32 | 0 |
| 9 | 7C1 | C14PEG | 10 | 62 | 2 | 36 | 0 |
| 10 | 7C1 | C14PEG | 10 | 50 | 1.5 | 38.5 | 10 |
| 11 | 7C1 | C14PEG | 10 | 50 | 11.5 | 28.5 | 10 |
| 12 | 7C1 | C14PEG | 10 | 50 | 21.5 | 18.5 | 10 |
| 13 | 7C1 | C14PEG | 10 | 50 | 26.5 | 13.5 | 10 |
| 14 | 7C1 | C14PEG | 10 | 35 | 25 | 25 | 15 |
| 15 | 7C1 | C14PEG | 10 | 35 | 15 | 35 | 15 |
| 16 | 7C1 | C14PEG | 10 | 35 | 5 | 45 | 15 |

TABLE 6-continued

LNP library used for in vivo screen 1

| LNP # | Compound | PEG Type | Mass Ratio | Compound Mole % | PEG Mole % | Cholesterol Mole % | DOPE Mole % |
|---|---|---|---|---|---|---|---|
| 17 | 90 | C14PEG | 10 | 80 | 20 | 0 | 0 |
| 18 | 90 | C14PEG | 10 | 80 | 15 | 5 | 0 |
| 19 | 90 | C14PEG | 10 | 80 | 10 | 10 | 0 |
| 20 | 90 | C14PEG | 10 | 80 | 5 | 15 | 0 |
| 21 | 90 | C14PEG | 10 | 80 | 2 | 18 | 0 |
| 22 | 90 | C14PEG | 10 | 62 | 26 | 12 | 0 |
| 23 | 90 | C14PEG | 10 | 62 | 16 | 22 | 0 |
| 24 | 90 | C14PEG | 10 | 62 | 6 | 32 | 0 |
| 25 | 90 | C14PEG | 10 | 62 | 2 | 36 | 0 |
| 26 | 90 | C14PEG | 10 | 50 | 1.5 | 38.5 | 10 |
| 27 | 90 | C14PEG | 10 | 50 | 11.5 | 28.5 | 10 |
| 28 | 90 | C14PEG | 10 | 50 | 21.5 | 18.5 | 10 |
| 29 | 88 | C14PEG | 10 | 50 | 26.5 | 13.5 | 10 |
| 30 | 88 | C14PEG | 10 | 35 | 25 | 25 | 15 |
| 31 | 88 | C14PEG | 10 | 35 | 15 | 35 | 15 |
| 32 | 88 | C14PEG | 10 | 35 | 5 | 45 | 15 |
| 33 | 88 | C14PEG | 10 | 80 | 20 | 0 | 0 |
| 34 | 88 | C14PEG | 10 | 80 | 15 | 5 | 0 |
| 35 | 88 | C14PEG | 10 | 80 | 10 | 10 | 0 |
| 36 | 88 | C14PEG | 10 | 80 | 5 | 15 | 0 |
| 37 | 88 | C14PEG | 10 | 80 | 2 | 18 | 0 |
| 38 | 88 | C14PEG | 10 | 62 | 26 | 12 | 0 |
| 39 | 88 | C14PEG | 10 | 62 | 16 | 22 | 0 |
| 40 | 88 | C14PEG | 10 | 62 | 6 | 32 | 0 |
| 41 | 88 | C14PEG | 10 | 62 | 2 | 36 | 0 |
| 42 | 88 | C14PEG | 10 | 50 | 1.5 | 38.5 | 10 |
| 43 | 88 | C14PEG | 10 | 50 | 11.5 | 28.5 | 10 |
| 44 | 88 | C14PEG | 10 | 50 | 21.5 | 18.5 | 10 |
| 45 | 88 | C14PEG | 10 | 50 | 26.5 | 13.5 | 10 |
| 46 | 88 | C14PEG | 10 | 35 | 25 | 25 | 15 |
| 47 | 88 | C14PEG | 10 | 35 | 15 | 35 | 15 |
| 48 | 88 | C14PEG | 10 | 35 | 5 | 45 | 15 |
| 49 | 83 | C14PEG | 10 | 80 | 20 | 0 | 0 |
| 50 | 83 | C14PEG | 10 | 80 | 15 | 5 | 0 |
| 51 | 83 | C14PEG | 10 | 80 | 10 | 10 | 0 |
| 52 | 83 | C14PEG | 10 | 80 | 5 | 15 | 0 |
| 53 | 83 | C14PEG | 10 | 80 | 2 | 18 | 0 |
| 54 | 83 | C14PEG | 10 | 62 | 26 | 12 | 0 |
| 55 | 83 | C14PEG | 10 | 62 | 16 | 22 | 0 |
| 56 | 83 | C14PEG | 10 | 62 | 6 | 32 | 0 |
| 57 | 83 | C14PEG | 10 | 62 | 2 | 36 | 0 |
| 58 | 83 | C14PEG | 10 | 50 | 1.5 | 38.5 | 10 |
| 59 | 83 | C14PEG | 10 | 50 | 11.5 | 28.5 | 10 |
| 60 | 83 | C14PEG | 10 | 50 | 21.5 | 18.5 | 10 |
| 61 | 83 | C14PEG | 10 | 50 | 26.5 | 13.5 | 10 |
| 62 | 83 | C14PEG | 10 | 35 | 25 | 25 | 15 |
| 63 | 83 | C14PEG | 10 | 35 | 15 | 35 | 15 |
| 64 | 83 | C14PEG | 10 | 35 | 5 | 45 | 15 |
| 65 | 80 | C14PEG | 10 | 80 | 20 | 0 | 0 |
| 66 | 83 | C14PEG | 10 | 80 | 15 | 5 | 0 |
| 67 | 83 | C14PEG | 10 | 80 | 10 | 10 | 0 |
| 68 | 83 | C14PEG | 10 | 80 | 5 | 15 | 0 |
| 69 | 83 | C14PEG | 10 | 80 | 2 | 18 | 0 |
| 70 | 83 | C14PEG | 10 | 62 | 26 | 12 | 0 |
| 71 | 83 | C14PEG | 10 | 62 | 16 | 22 | 0 |
| 72 | 83 | C14PEG | 10 | 62 | 6 | 32 | 0 |
| 73 | 83 | C14PEG | 10 | 62 | 2 | 36 | 0 |
| 74 | 83 | C14PEG | 10 | 50 | 1.5 | 38.5 | 10 |
| 75 | 83 | C14PEG | 10 | 50 | 11.5 | 28.5 | 10 |
| 76 | 83 | C14PEG | 10 | 50 | 21.5 | 18.5 | 10 |
| 77 | 83 | C14PEG | 10 | 50 | 26.5 | 13.5 | 10 |
| 78 | 83 | C14PEG | 10 | 35 | 25 | 25 | 15 |
| 79 | 83 | C14PEG | 10 | 35 | 15 | 35 | 15 |
| 80 | 83 | C14PEG | 10 | 35 | 5 | 45 | 15 |
| 81 | 78 | C14PEG | 10 | 80 | 20 | 0 | 0 |
| 82 | 78 | C14PEG | 10 | 80 | 15 | 5 | 0 |
| 83 | 78 | C14PEG | 10 | 80 | 10 | 10 | 0 |
| 84 | 78 | C14PEG | 10 | 80 | 5 | 15 | 0 |
| 85 | 78 | C14PEG | 10 | 80 | 2 | 18 | 0 |
| 86 | 78 | C14PEG | 10 | 62 | 26 | 12 | 0 |
| 87 | 78 | C14PEG | 10 | 62 | 16 | 22 | 0 |
| 88 | 78 | C14PEG | 10 | 62 | 6 | 32 | 0 |
| 89 | 78 | C14PEG | 10 | 62 | 2 | 36 | 0 |
| 90 | 78 | C14PEG | 10 | 50 | 1.5 | 38.5 | 10 |
| 91 | 78 | C14PEG | 10 | 50 | 11.5 | 28.5 | 10 |
| 92 | 78 | C14PEG | 10 | 50 | 21.5 | 18.5 | 10 |
| 93 | 78 | C14PEG | 10 | 50 | 26.5 | 13.5 | 10 |
| 94 | 78 | C14PEG | 10 | 35 | 25 | 25 | 15 |
| 95 | 78 | C14PEG | 10 | 35 | 15 | 35 | 15 |
| 96 | 78 | C14PEG | 10 | 35 | 5 | 45 | 15 |
| 97 | 73 | C14PEG | 10 | 80 | 20 | 0 | 0 |
| 98 | 73 | C14PEG | 10 | 80 | 15 | 5 | 0 |
| 99 | 73 | C14PEG | 10 | 80 | 10 | 10 | 0 |
| 100 | 73 | C14PEG | 10 | 80 | 5 | 15 | 0 |
| 101 | 73 | C14PEG | 10 | 80 | 2 | 18 | 0 |
| 102 | 73 | C14PEG | 10 | 62 | 26 | 12 | 0 |
| 103 | 73 | C14PEG | 10 | 62 | 16 | 22 | 0 |
| 104 | 73 | C14PEG | 10 | 62 | 6 | 32 | 0 |
| 105 | 73 | C14PEG | 10 | 62 | 2 | 36 | 0 |
| 106 | 73 | C14PEG | 10 | 50 | 1.5 | 38.5 | 10 |
| 107 | 73 | C14PEG | 10 | 50 | 11.5 | 28.5 | 10 |
| 108 | 73 | C14PEG | 10 | 50 | 21.5 | 18.5 | 10 |
| 109 | 73 | C14PEG | 10 | 50 | 26.5 | 13.5 | 10 |
| 110 | 73 | C14PEG | 10 | 35 | 25 | 25 | 15 |
| 111 | 73 | C14PEG | 10 | 35 | 15 | 35 | 15 |
| 112 | 73 | C14PEG | 10 | 35 | 5 | 45 | 15 |
| 113 | n | n | n | n | n | n | n |

TABLE 7

LNP library used for in vivo screen 3

| LNP # | Compound | PEG Type | Mass Ratio | Compound Mole % | Cholesterol Mole % | PEG Mole % | DOPE Mole % |
|---|---|---|---|---|---|---|---|
| 1 | 7C1 | C14PEG | 10 | 50 | 38.5 | 1.5 | 10 |
| 2 | 7C1 | C14PEG | 10 | 50 | 36.5 | 3.5 | 10 |
| 3 | 7C1 | C14PEG | 10 | 50 | 33.5 | 6.5 | 10 |
| 4 | 7C1 | C14PEG | 10 | 50 | 29.5 | 10.5 | 10 |
| 5 | 7C1 | C14PEG | 10 | 50 | 25 | 15 | 10 |
| 6 | 7C1 | C14PEG | 10 | 50 | 20 | 20 | 10 |
| 7 | 7C1 | C14PEG | 10 | 50 | 15 | 25 | 10 |
| 8 | 7C1 | C14PEG | 10 | 50 | 10 | 30 | 10 |
| 9 | 7C1 | C14PEG | 10 | 60 | 38.5 | 1.5 | 0 |
| 10 | 7C1 | C14PEG | 10 | 60 | 36.5 | 3.5 | 0 |
| 11 | 7C1 | C14PEG | 10 | 60 | 33.5 | 6.5 | 0 |
| 12 | 7C1 | C14PEG | 10 | 60 | 29.5 | 10.5 | 0 |
| 13 | 7C1 | C14PEG | 10 | 60 | 25 | 15 | 0 |
| 14 | 7C1 | C14PEG | 10 | 60 | 20 | 20 | 0 |
| 15 | 7C1 | C14PEG | 10 | 60 | 15 | 25 | 0 |
| 16 | 7C1 | C14PEG | 10 | 60 | 10 | 30 | 0 |
| 17 | 7C1 | C14PEG | 10 | 60 | 5 | 35 | 0 |
| 18 | 7C1 | C14PEG | 10 | 60 | 1.5 | 38.5 | 0 |
| 19 | 7C1 | C14PEG | 10 | 70 | 28.5 | 1.5 | 0 |
| 20 | 7C1 | C14PEG | 10 | 70 | 26.5 | 3.5 | 0 |
| 21 | 7C1 | C14PEG | 10 | 70 | 23.5 | 6.5 | 0 |
| 22 | 7C1 | C14PEG | 10 | 70 | 19.5 | 10.5 | 0 |
| 23 | 7C1 | C14PEG | 10 | 70 | 15 | 15 | 0 |
| 24 | 7C1 | C14PEG | 10 | 70 | 10 | 20 | 0 |
| 25 | 7C1 | C14PEG | 10 | 70 | 5 | 25 | 0 |
| 26 | 7C1 | C14PEG | 10 | 70 | 0 | 30 | 0 |
| 27 | 7C1 | C14PEG | 10 | 75 | 23.5 | 1.5 | 0 |
| 28 | 7C1 | C14PEG | 10 | 75 | 21.5 | 3.5 | 0 |
| 29 | 7C1 | C14PEG | 10 | 75 | 18.5 | 6.5 | 0 |
| 30 | 7C1 | C14PEG | 10 | 75 | 14.5 | 10.5 | 0 |
| 31 | 7C1 | C14PEG | 10 | 75 | 10 | 15 | 0 |
| 32 | 7C1 | C14PEG | 10 | 75 | 5 | 20 | 0 |
| 33 | 7C1 | C14PEG | 10 | 75 | 0 | 25 | 0 |
| 34 | 7C1 | C14PEG | 10 | 80 | 18.5 | 1.5 | 0 |
| 35 | 7C1 | C14PEG | 10 | 80 | 16.5 | 3.5 | 0 |
| 36 | 7C1 | C14PEG | 10 | 80 | 13.5 | 6.5 | 0 |
| 37 | 7C1 | C14PEG | 10 | 80 | 9.5 | 10.5 | 0 |
| 38 | 7C1 | C14PEG | 10 | 80 | 5 | 15 | 0 |
| 39 | 7C1 | C14PEG | 10 | 80 | 2.5 | 17.5 | 0 |
| 40 | 7C1 | C14PEG | 10 | 80 | 0 | 20 | 0 |
| 41 | 7C1 | C14PEG | 10 | 85 | 13.5 | 1.5 | 0 |
| 42 | 7C1 | C14PEG | 10 | 85 | 11.5 | 3.5 | 0 |

TABLE 7-continued

LNP library used for in vivo screen 3

| LNP # | Compound | PEG Type | Mass Ratio | Compound Mole % | Cholesterol Mole % | PEG Mole % | DOPE Mole % |
|---|---|---|---|---|---|---|---|
| 43 | 7C1 | C14PEG | 10 | 85 | 8.5 | 6.5 | 0 |
| 44 | 7C1 | C14PEG | 10 | 85 | 4.5 | 10.5 | 0 |
| 45 | 7C1 | C14PEG | 10 | 85 | 0 | 15 | 0 |
| 46 | 7C1 | C14PEG | 5 | 80 | 0 | 20 | 0 |
| 47 | 7C1 | C14PEG | 7 | 80 | 0 | 20 | 0 |
| 48 | 7C1 | C14PEG | 12 | 80 | 0 | 20 | 0 |
| 49 | 7C1 | C14PEG | 10 | 90 | 8.5 | 1.5 | 0 |
| 50 | 7C1 | C14PEG | 10 | 90 | 6.5 | 3.5 | 0 |
| 51 | 7C1 | C14PEG | 10 | 90 | 3.5 | 6.5 | 0 |
| 52 | 7C1 | C14PEG | 10 | 90 | 0 | 10 | 0 |
| 53 | 7C1 | C14PEG | 12 | 50 | 28.5 | 11.5 | 10 |
| 54 | 7C1 | C14PEG | 10 | 50 | 28.5 | 11.5 | 10 |
| 55 | 7C1 | C14PEG | 8 | 50 | 28.5 | 11.5 | 10 |
| 56 | 7C1 | C14PEG | 5 | 50 | 28.5 | 11.5 | 10 |
| 57 | 7C1 | C14PEG | 10 | 50 | 38.5 | 1.5 | 10 |
| 58 | 7C1 | C14PEG | 10 | 50 | 36.5 | 3.5 | 10 |
| 59 | 7C1 | C14PEG | 10 | 50 | 33.5 | 6.5 | 10 |
| 60 | 7C1 | C14PEG | 10 | 50 | 29.5 | 10.5 | 10 |
| 61 | 7C1 | C14PEG | 10 | 50 | 25 | 15 | 10 |
| 62 | 7C1 | C14PEG | 10 | 50 | 20 | 20 | 10 |
| 63 | 7C1 | C14PEG | 10 | 50 | 15 | 25 | 10 |
| 64 | 7C1 | C14PEG | 10 | 50 | 10 | 30 | 10 |
| 65 | 7C1 | C14PEG | 10 | 80 | 18.5 | 1.5 | 0 |
| 66 | 7C1 | C14PEG | 10 | 80 | 16.5 | 3.5 | 0 |
| 67 | 7C1 | C14PEG | 10 | 80 | 13.5 | 6.5 | 0 |
| 68 | 7C1 | C14PEG | 10 | 80 | 9.5 | 10.5 | 0 |
| 69 | 7C1 | C14PEG | 10 | 80 | 5 | 15 | 0 |
| 70 | 7C1 | C14PEG | 10 | 80 | 2.5 | 17.5 | 0 |
| 71 | 7C1 | C14PEG | 10 | 80 | 0 | 20 | 0 |
| 72 | 7C1 | C14PEG | 10 | 60 | 38.5 | 1.5 | 0 |
| 73 | 7C1 | C14PEG | 10 | 60 | 36.5 | 3.5 | 0 |
| 74 | 7C1 | C14PEG | 10 | 60 | 33.5 | 6.5 | 0 |
| 75 | 7C1 | C14PEG | 10 | 60 | 29.5 | 10.5 | 0 |
| 76 | 7C1 | C14PEG | 10 | 60 | 25 | 15 | 0 |
| 77 | 7C1 | C14PEG | 10 | 60 | 20 | 20 | 0 |
| 78 | 7C1 | C14PEG | 10 | 60 | 15 | 25 | 0 |
| 79 | 7C1 | C14PEG | 10 | 60 | 10 | 30 | 0 |
| 80 | 7C1 | C14PEG | 10 | 50 | 38.5 | 1.5 | 10 |
| 81 | 7C1 | C14PEG | 10 | 50 | 36.5 | 3.5 | 10 |
| 82 | 7C1 | C14PEG | 10 | 50 | 33.5 | 6.5 | 10 |
| 83 | 7C1 | C14PEG | 10 | 50 | 29.5 | 10.5 | 10 |
| 84 | 7C1 | C14PEG | 10 | 50 | 25 | 15 | 10 |
| 85 | 7C1 | C14PEG | 10 | 50 | 20 | 20 | 10 |
| 86 | 7C1 | C14PEG | 10 | 50 | 15 | 25 | 10 |
| 87 | 7C1 | C14PEG | 10 | 50 | 10 | 30 | 10 |
| 88 | 7C1 | C14PEG | 10 | 80 | 18.5 | 1.5 | 0 |
| 89 | 7C1 | C14PEG | 10 | 80 | 16.5 | 3.5 | 0 |
| 90 | 7C1 | C14PEG | 10 | 80 | 13.5 | 6.5 | 0 |
| 91 | 7C1 | C14PEG | 10 | 80 | 9.5 | 10.5 | 0 |
| 92 | 7C1 | C14PEG | 10 | 80 | 5 | 15 | 0 |
| 93 | 7C1 | C14PEG | 10 | 80 | 2.5 | 17.5 | 0 |
| 94 | 7C1 | C14PEG | 10 | 80 | 0 | 20 | 0 |
| 95 | 7C1 | C14PEG | 10 | 60 | 38.5 | 1.5 | 0 |
| 96 | 7C1 | C14PEG | 10 | 60 | 36.5 | 3.5 | 0 |
| 97 | 7C1 | C14PEG | 10 | 60 | 33.5 | 6.5 | 0 |
| 98 | 7C1 | C14PEG | 10 | 60 | 29.5 | 10.5 | 0 |
| 99 | 7C1 | C14PEG | 10 | 60 | 25 | 15 | 0 |
| 100 | 7C1 | C14PEG | 10 | 60 | 20 | 20 | 0 |
| 101 | 7C1 | C14PEG | 10 | 60 | 15 | 25 | 0 |
| 102 | 7C1 | C14PEG | 10 | 60 | 10 | 30 | 0 |
| 103 | n | n | n | n | n | n | n |

TABLE 8

LNP library used for in vivo screen 4

| LNP # | Compound | PEG Type | Mass Ratio | Helper Lipid Type | Compound Mole % | Cholesterol Mole % | PEG Mole % | Helper Lipid Mole % |
|---|---|---|---|---|---|---|---|---|
| 1 | 7C1 | C14PEG | 10 | DOPE | 50 | 38.5 | 1.5 | 10 |
| 2 | 7C1 | C14PEG | 10 | DOPE | 50 | 28.5 | 1.5 | 20 |
| 3 | 7C1 | C14PEG | 10 | DOPE | 50 | 48.5 | 1.5 | 0 |
| 4 | 7C1 | C14PEG | 10 | DOPE | 50 | 36.5 | 3.5 | 10 |
| 5 | 7C1 | C14PEG | 10 | DOPE | 50 | 26.5 | 3.5 | 20 |
| 6 | 7C1 | C14PEG | 10 | DOPE | 50 | 46.5 | 3.5 | 0 |
| 7 | 7C1 | C14PEG | 10 | DOPE | 50 | 33.5 | 6.5 | 10 |
| 8 | 7C1 | C14PEG | 10 | DOPE | 50 | 23.5 | 6.5 | 20 |
| 9 | 7C1 | C14PEG | 10 | DOPE | 50 | 43.5 | 6.5 | 0 |
| 10 | 7C1 | C14PEG | 10 | DOPE | 50 | 29.5 | 10.5 | 10 |
| 11 | 7C1 | C14PEG | 10 | DOPE | 50 | 19.5 | 10.5 | 20 |
| 12 | 7C1 | C14PEG | 10 | DOPE | 50 | 39.5 | 10.5 | 0 |
| 13 | 7C1 | C14PEG | 10 | DOPE | 50 | 15 | 25 | 10 |
| 14 | 7C1 | C14PEG | 10 | DOPE | 50 | 5 | 25 | 20 |
| 15 | 7C1 | C14PEG | 10 | DOPE | 50 | 25 | 25 | 0 |
| 16 | 7C1 | C14PEG | 10 | DOPC | 50 | 38.5 | 1.5 | 10 |
| 17 | 7C1 | C14PEG | 10 | DOPC | 50 | 28.5 | 1.5 | 20 |
| 18 | 7C1 | C14PEG | 10 | DOPC | 50 | 48.5 | 1.5 | 0 |
| 19 | 7C1 | C14PEG | 10 | DOPC | 50 | 36.5 | 3.5 | 10 |
| 20 | 7C1 | C14PEG | 10 | DOPC | 50 | 26.5 | 3.5 | 20 |
| 21 | 7C1 | C14PEG | 10 | DOPC | 50 | 46.5 | 3.5 | 0 |
| 22 | 7C1 | C14PEG | 10 | DOPC | 50 | 33.5 | 6.5 | 10 |
| 23 | 7C1 | C14PEG | 10 | DOPC | 50 | 23.5 | 6.5 | 20 |
| 24 | 7C1 | C14PEG | 10 | DOPC | 50 | 43.5 | 6.5 | 0 |
| 25 | 7C1 | C14PEG | 10 | DOPC | 50 | 29.5 | 10.5 | 10 |
| 26 | 7C1 | C14PEG | 10 | DOPC | 50 | 19.5 | 10.5 | 20 |
| 27 | 7C1 | C14PEG | 10 | DOPC | 50 | 39.5 | 10.5 | 0 |
| 28 | 7C1 | C14PEG | 10 | DOPC | 50 | 15 | 25 | 10 |
| 29 | 7C1 | C14PEG | 10 | DOPC | 50 | 5 | 25 | 20 |
| 30 | 7C1 | C14PEG | 10 | DOPC | 50 | 25 | 25 | 0 |
| 31 | 7C1 | C14PEG | 10 | DSPC | 50 | 38.5 | 1.5 | 10 |
| 32 | 7C1 | C14PEG | 10 | DSPC | 50 | 28.5 | 1.5 | 20 |
| 33 | 7C1 | C14PEG | 10 | DSPC | 50 | 48.5 | 1.5 | 0 |
| 34 | 7C1 | C14PEG | 10 | DSPC | 50 | 36.5 | 3.5 | 10 |

TABLE 8-continued

LNP library used for in vivo screen 4

| LNP # | Compound | PEG Type | Mass Ratio | Helper Lipid Type | Compound Mole % | Cholesterol Mole % | PEG Mole % | Helper Lipid Mole % |
|---|---|---|---|---|---|---|---|---|
| 35 | 7C1 | C14PEG | 10 | DSPC | 50 | 26.5 | 3.5 | 20 |
| 36 | 7C1 | C14PEG | 10 | DSPC | 50 | 46.5 | 3.5 | 0 |
| 37 | 7C1 | C14PEG | 10 | DSPC | 50 | 33.5 | 6.5 | 10 |
| 38 | 7C1 | C14PEG | 10 | DSPC | 50 | 23.5 | 6.5 | 20 |
| 39 | 7C1 | C14PEG | 10 | DSPC | 50 | 43.5 | 6.5 | 0 |
| 40 | 7C1 | C14PEG | 10 | DSPC | 50 | 29.5 | 10.5 | 10 |
| 41 | 7C1 | C14PEG | 10 | DSPC | 50 | 19.5 | 10.5 | 20 |
| 42 | 7C1 | C14PEG | 10 | DSPC | 50 | 39.5 | 10.5 | 0 |
| 43 | 7C1 | C14PEG | 10 | DSPC | 50 | 15 | 25 | 10 |
| 44 | 7C1 | C14PEG | 10 | DSPC | 50 | 5 | 25 | 20 |
| 45 | 7C1 | C14PEG | 10 | DSPC | 50 | 25 | 25 | 0 |
| 46 | 7C1 | C14PEG | 10 | 18:1 Lyso PC | 50 | 38.5 | 1.5 | 10 |
| 47 | 7C1 | C14PEG | 10 | 18:1 Lyso PC | 50 | 28.5 | 1.5 | 20 |
| 48 | 7C1 | C14PEG | 10 | 18:1 Lyso PC | 50 | 48.5 | 1.5 | 0 |
| 49 | 7C1 | C14PEG | 10 | 18:1 Lyso PC | 50 | 36.5 | 3.5 | 10 |
| 50 | 7C1 | C14PEG | 10 | 18:1 Lyso PC | 50 | 26.5 | 3.5 | 20 |
| 51 | 7C1 | C14PEG | 10 | 18:1 Lyso PC | 50 | 46.5 | 3.5 | 0 |
| 52 | 7C1 | C14PEG | 10 | 18:1 Lyso PC | 50 | 33.5 | 6.5 | 10 |
| 53 | 7C1 | C14PEG | 10 | 18:1 Lyso PC | 50 | 23.5 | 6.5 | 20 |
| 54 | 7C1 | C14PEG | 10 | 18:1 Lyso PC | 50 | 43.5 | 6.5 | 0 |
| 55 | 7C1 | C14PEG | 10 | 18:1 Lyso PC | 50 | 29.5 | 10.5 | 10 |
| 56 | 7C1 | C14PEG | 10 | 18:1 Lyso PC | 50 | 19.5 | 10.5 | 20 |
| 57 | 7C1 | C14PEG | 10 | 18:1 Lyso PC | 50 | 39.5 | 10.5 | 0 |
| 58 | 7C1 | C14PEG | 10 | 18:1 Lyso PC | 50 | 15 | 25 | 10 |
| 59 | 7C1 | C14PEG | 10 | 18:1 Lyso PC | 50 | 5 | 25 | 20 |
| 60 | 7C1 | C14PEG | 10 | 18:1 Lyso PC | 50 | 25 | 25 | 0 |
| 61 | 7C1 | C14PEG | 10 | DOPE | 50 | 5 | 35 | 10 |
| 62 | 7C1 | C14PEG | 10 | DOPE | 50 | 0 | 35 | 15 |
| 63 | 7C1 | C14PEG | 10 | DOPE | 50 | 15 | 35 | 0 |
| 64 | 7C1 | C14PEG | 10 | DOPE | 60 | 33.5 | 1.5 | 5 |
| 65 | 7C1 | C14PEG | 10 | DOPE | 60 | 23.5 | 2.5 | 15 |
| 66 | 7C1 | C14PEG | 10 | DOPE | 60 | 38.5 | 1.5 | 0 |
| 67 | 7C1 | C14PEG | 10 | DOPE | 60 | 31.5 | 3.5 | 5 |
| 68 | 7C1 | C14PEG | 10 | DOPE | 60 | 21.5 | 3.5 | 15 |
| 69 | 7C1 | C14PEG | 10 | DOPE | 60 | 36.5 | 3.5 | 0 |
| 70 | 7C1 | C14PEG | 10 | DOPE | 60 | 24.5 | 10.5 | 5 |
| 71 | 7C1 | C14PEG | 10 | DOPE | 60 | 14.5 | 10.5 | 15 |
| 72 | 7C1 | C14PEG | 10 | DOPE | 60 | 29.5 | 10.5 | 0 |
| 73 | 7C1 | C14PEG | 10 | DOPE | 60 | 10 | 25 | 5 |
| 74 | 7C1 | C14PEG | 10 | DOPE | 60 | 0 | 25 | 15 |
| 75 | 7C1 | C14PEG | 10 | DOPE | 60 | 15 | 25 | 0 |
| 76 | 7C1 | C14PEG | 10 | DOPE | 60 | 0 | 35 | 5 |
| 77 | 7C1 | C14PEG | 10 | DOPC | 50 | 5 | 35 | 10 |
| 78 | 7C1 | C14PEG | 10 | DOPC | 50 | 0 | 35 | 15 |
| 79 | 7C1 | C14PEG | 10 | DOPC | 50 | 15 | 35 | 0 |
| 80 | 7C1 | C14PEG | 10 | DOPC | 60 | 33.5 | 1.5 | 5 |
| 81 | 7C1 | C14PEG | 10 | DOPC | 60 | 23.5 | 2.5 | 15 |
| 82 | 7C1 | C14PEG | 10 | DOPC | 60 | 38.5 | 1.5 | 0 |
| 83 | 7C1 | C14PEG | 10 | DOPC | 60 | 31.5 | 3.5 | 5 |
| 84 | 7C1 | C14PEG | 10 | DOPC | 60 | 21.5 | 3.5 | 15 |
| 85 | 7C1 | C14PEG | 10 | DOPC | 60 | 36.5 | 3.5 | 0 |
| 86 | 7C1 | C14PEG | 10 | DOPC | 60 | 24.5 | 10.5 | 5 |
| 87 | 7C1 | C14PEG | 10 | DOPC | 60 | 14.5 | 10.5 | 15 |
| 88 | 7C1 | C14PEG | 10 | DOPC | 60 | 29.5 | 10.5 | 0 |
| 89 | 7C1 | C14PEG | 10 | DOPC | 60 | 10 | 25 | 5 |
| 90 | 7C1 | C14PEG | 10 | DOPC | 60 | 0 | 25 | 15 |
| 91 | 7C1 | C14PEG | 10 | DOPC | 60 | 15 | 25 | 0 |
| 92 | 7C1 | C14PEG | 10 | DOPC | 60 | 0 | 35 | 5 |
| 93 | 7C1 | C14PEG | 10 | DSPC | 50 | 5 | 35 | 10 |
| 94 | 7C1 | C14PEG | 10 | DSPC | 50 | 0 | 35 | 15 |
| 95 | 7C1 | C14PEG | 10 | DSPC | 50 | 15 | 35 | 0 |
| 96 | 7C1 | C14PEG | 10 | DSPC | 60 | 33.5 | 1.5 | 5 |
| 97 | 7C1 | C14PEG | 10 | DSPC | 60 | 23.5 | 2.5 | 15 |
| 98 | 7C1 | C14PEG | 10 | DSPC | 60 | 38.5 | 1.5 | 0 |
| 99 | 7C1 | C14PEG | 10 | DSPC | 60 | 31.5 | 3.5 | 5 |
| 100 | 7C1 | C14PEG | 10 | DSPC | 60 | 21.5 | 3.5 | 15 |
| 101 | 7C1 | C14PEG | 10 | DSPC | 60 | 36.5 | 3.5 | 0 |
| 102 | 7C1 | C14PEG | 10 | DSPC | 60 | 24.5 | 10.5 | 5 |
| 103 | 7C1 | C14PEG | 10 | DSPC | 60 | 14.5 | 10.5 | 15 |
| 104 | 7C1 | C14PEG | 10 | DSPC | 60 | 29.5 | 10.5 | 0 |
| 105 | 7C1 | C14PEG | 10 | DSPC | 60 | 10 | 25 | 5 |
| 106 | 7C1 | C14PEG | 10 | DSPC | 60 | 0 | 25 | 15 |
| 107 | 7C1 | C14PEG | 10 | DSPC | 60 | 15 | 25 | 0 |
| 108 | 7C1 | C14PEG | 10 | DSPC | 60 | 0 | 35 | 5 |
| 109 | 7C1 | C14PEG | 10 | 18:1 Lyso PC | 50 | 5 | 35 | 10 |

TABLE 8-continued

LNP library used for in vivo screen 4

| LNP # | Compound | PEG Type | Mass Ratio | Helper Lipid Type | Compound Mole % | Cholesterol Mole % | PEG Mole % | Helper Lipid Mole % |
|---|---|---|---|---|---|---|---|---|
| 110 | 7C1 | C14PEG | 10 | 18:1 Lyso PC | 50 | 0 | 35 | 15 |
| 111 | 7C1 | C14PEG | 10 | 18:1 Lyso PC | 50 | 15 | 35 | 0 |
| 112 | 7C1 | C14PEG | 10 | 18:1 Lyso PC | 60 | 33.5 | 1.5 | 5 |
| 113 | 7C1 | C14PEG | 10 | 18:1 Lyso PC | 60 | 23.5 | 2.5 | 15 |
| 114 | 7C1 | C14PEG | 10 | 18:1 Lyso PC | 60 | 38.5 | 1.5 | 0 |
| 115 | 7C1 | C14PEG | 10 | 18:1 Lyso PC | 60 | 31.5 | 3.5 | 5 |
| 116 | 7C1 | C14PEG | 10 | 18:1 Lyso PC | 60 | 21.5 | 3.5 | 15 |
| 117 | 7C1 | C14PEG | 10 | 18:1 Lyso PC | 60 | 36.5 | 3.5 | 0 |
| 118 | 7C1 | C14PEG | 10 | 18:1 Lyso PC | 60 | 24.5 | 10.5 | 5 |
| 119 | 7C1 | C14PEG | 10 | 18:1 Lyso PC | 60 | 14.5 | 10.5 | 15 |
| 120 | 7C1 | C14PEG | 10 | 18:1 Lyso PC | 60 | 29.5 | 10.5 | 0 |
| 121 | 7C1 | C14PEG | 10 | 18:1 Lyso PC | 60 | 10 | 25 | 5 |
| 122 | 7C1 | C14PEG | 10 | 18:1 Lyso PC | 60 | 0 | 25 | 15 |
| 123 | 7C1 | C14PEG | 10 | 18:1 Lyso PC | 60 | 15 | 25 | 0 |
| 124 | 7C1 | C14PEG | 10 | 18:1 Lyso PC | 60 | 0 | 35 | 5 |
| 125 | 7C1 | C14PEG | 10 | DOPE | 80 | 0 | 20 | 0 |
| 126 | 7C1 | C14PEG | 10 | DOPE | 90 | 3.5 | 1.5 | 5 |
| 127 | 7C1 | C14PEG | 10 | DOPE | 90 | 8.5 | 1.5 | 0 |
| 128 | 7C1 | C14PEG | 10 | DOPE | 90 | 1.5 | 3.5 | 5 |
| 129 | 7C1 | C14PEG | 10 | DOPE | 90 | 6.5 | 3.5 | 0 |
| 130 | 7C1 | C14PEG | 10 | DOPE | 90 | 0 | 10 | 0 |
| 131 | 7C1 | C14PEG | 10 | DOPC | 80 | 0 | 20 | 0 |
| 132 | 7C1 | C14PEG | 10 | DOPC | 90 | 3.5 | 1.5 | 5 |
| 133 | 7C1 | C14PEG | 10 | DOPC | 90 | 8.5 | 1.5 | 0 |
| 134 | 7C1 | C14PEG | 10 | DOPC | 90 | 1.5 | 3.5 | 5 |
| 135 | 7C1 | C14PEG | 10 | DOPC | 90 | 6.5 | 3.5 | 0 |
| 136 | 7C1 | C14PEG | 10 | DOPC | 90 | 0 | 10 | 0 |
| 137 | 7C1 | C14PEG | 10 | DOPE | 60 | 38.5 | 1.5 | 0 |
| 138 | 7C1 | C14PEG | 10 | DOPE | 50 | 36.5 | 3.5 | 10 |
| 139 | 7C1 | C14PEG | 10 | DOPE | 50 | 38.5 | 1.5 | 10 |
| 140 | 7C1 | C14PEG | 10 | DOPE | 75 | 0 | 25 | 0 |
| 141 | 7C1 | C14PEG | 10 | DOPE | 70 | 15 | 15 | 0 |
| 142 | 7C1 | C14PEG | 10 | DOPE | 90 | 0 | 10 | 0 |
| 143 | 7C1 | C14PEG | 10 | DOPE | 90 | 0.5 | 3.5 | 5 |
| 144 | 7C1 | C14PEG | 10 | DOPE | 90 | 8.5 | 1.5 | 0 |
| 145 | 7C1 | C14PEG | 10 | DOPE | 50 | 29.5 | 10.5 | 10 |
| 146 | 7C1 | C14PEG | 10 | DOPE | 60 | 5 | 35 | 0 |
| 147 | 7C1 | C14PEG | 10 | DOPE | 60 | 29.5 | 10.5 | 0 |
| 148 | 7C1 | C14PEG | 3 | DOPE | 80 | 0 | 20 | 0 |
| 149 | 7C1 | C14PEG | 5 | DOPE | 80 | 0 | 20 | 0 |
| 150 | 7C1 | C14PEG | 8 | DOPE | 80 | 0 | 20 | 0 |
| 151 | 7C1 | C14PEG | 10 | DOPE | 80 | 0 | 20 | 0 |
| 152 | 7C1 | C14PEG | 12 | DOPE | 80 | 0 | 20 | 0 |
| 153 | 7C1 | C14PEG | 3 | DOPE | 50 | 28.5 | 11.5 | 10 |
| 154 | 7C1 | C14PEG | 5 | DOPE | 50 | 28.5 | 11.5 | 10 |
| 155 | 7C1 | C14PEG | 8 | DOPE | 50 | 28.5 | 11.5 | 10 |
| 156 | 7C1 | C14PEG | 10 | DOPE | 50 | 28.5 | 11.5 | 10 |
| 157 | 7C1 | C14PEG | 12 | DOPE | 50 | 28.5 | 11.5 | 10 |
| 158 | n | n | n | n | n | n | n | n |

TABLE 9

ATLI siRNA Experiment

| Number | Strain | Experiment | Treatment | 0 hrs | 24 hrs | 48 hrs | 72 hrs |
|---|---|---|---|---|---|---|---|
| 353 | C57BL/6 | ATLI siRNA Experiment | PBS | 18.2 | 17.7 | 17.9 | 18.5 |
| 354 | C57BL/6 | ATLI siRNA Experiment | PBS | 16.2 | 15.8 | 16.1 | 16.9 |
| 355 | C57BL/6 | ATLI siRNA Experiment | PBS | 19.8 | 19.4 | 20 | 21 |
| 356 | C57BL/6 | ATLI siRNA Experiment | PBS | 20 | 19.8 | 19.9 | 20.9 |
| 357 | C57BL/6 | ATLI siRNA Experiment | ATLI - 2mpk siGFP | 17 | 16.6 | 17.2 | 18.2 |
| 358 | C57BL/6 | ATLI siRNA Experiment | ATLI - 2mpk siGFP | 18.8 | 18.6 | 18.9 | 20.2 |
| 359 | C57BL/6 | ATLI siRNA Experiment | ATLI - 2mpk siGFP | 19.6 | 19.4 | 19.6 | 20.3 |
| 360 | C57BL/6 | ATLI siRNA Experiment | ATLI - 2mpk siGFP | 20 | 19.6 | 19.8 | 20.9 |
| 361 | C57BL/6 | ATLI siRNA Experiment | ATLI - 1mpk siICAM2 | 19.4 | 19.4 | 20.15 | 21.3 |
| 362 | C57BL/6 | ATLI siRNA Experiment | ATLI - 1mpk siICAM2 | 21 | 19.7 | 21.2 | 19.7 |
| 363 | C57BL/6 | ATLI siRNA Experiment | ATLI - 1mpk siICAM2 | 18.2 | 17.7 | 18.6 | 21.8 |
| 364 | C57BL/6 | ATLI siRNA Experiment | ATLI - 1mpk siICAM2 | 19.3 | 19.5 | 19.9 | 20.5 |

TABLE 10

Organ Weight

|  | PBS.1 | PBS.2 | PBS.3 | ATL1-2mpk.1 | ATL1-2mpk.2 | ATL1-2mpk.3 |
|---|---|---|---|---|---|---|
| Kidney | 324 | 249 | 272 | 257 | 259 | 284 |
| Spleen | 84 | 72 | 81 | 62 | 65 | 81 |
| Liver | 1135 | 965 | 1170 | 966 | 821 | 982 |
| Heart | 284 | 257 | 129 | 109 | 110 | 136 |
| Lung | 364 | 168 | 139 | 134 | 118 | 116 |
| BW (mg @ sac) | 20100 | 20000 | 21700 | 18600 | 18300 | 20400 |

TABLE 11

Organ Weight/body weight

|  | PBS.1 | PBS.2 | PBS.3 | ATL1-2mpk.1 | ATL1-2mpk.2 | ATL1-2mpk.3 |
|---|---|---|---|---|---|---|
| Kidney | 0.0161 | 0.0125 | 0.0125 | 0.0138 | 0.0142 | 0.0139 |
| Spleen | 0.0042 | 0.0036 | 0.0037 | 0.0033 | 0.0036 | 0.0040 |
| Liver | 0.0565 | 0.0483 | 0.0539 | 0.0519 | 0.0449 | 0.0481 |
| Heart | 0.0141 | 0.0129 | 0.0059 | 0.0059 | 0.0060 | 0.0067 |
| Lung | 0.0181 | 0.0084 | 0.0064 | 0.0072 | 0.0064 | 0.0057 |

Example 2: Modifying a Commonly Expressed Endocytotic Receptor Retargets Nanoparticles In Vivo Materials and Methods Nanoparticle Formulation.

Nanoparticles were formulated using a microfluidic device as previously described (Chen D, et al., J Am Chem Soc 134:6948-6951 (2012)). Briefly, nucleic acids (DNA barcodes) were diluted in 10 mM citrate buffer (Teknova) while lipid-amine compounds, alkyl tailed PEG, cholesterol, and helper lipids were diluted in ethanol. All PEGs, cholesterol, and helper lipids were purchased from Avanti Lipids. Citrate and ethanol phases were combined in a microfluidic device by syringes (Hamilton Company) at a flow rate of 600 μL/min and 200 μL/min, respectively.

DNA Barcoding.

Figures 14A, 14B:
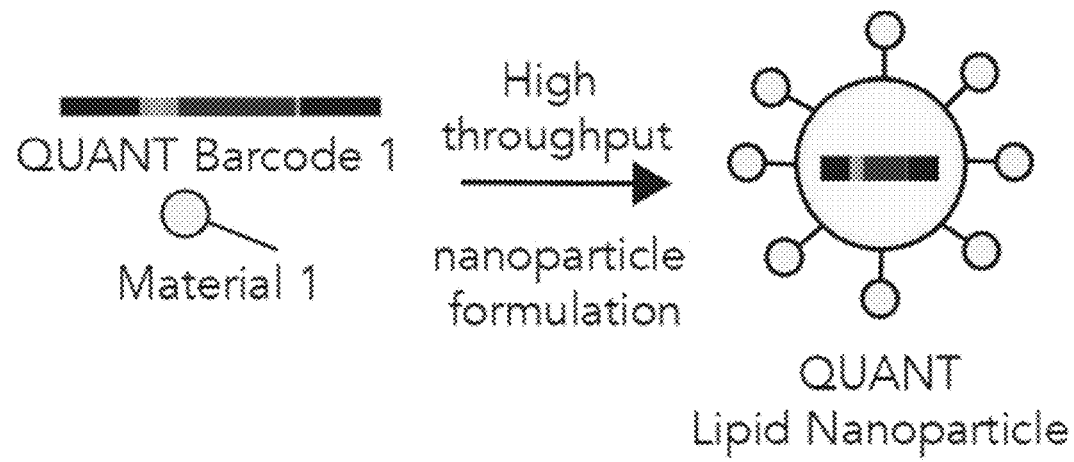
Figure 14C:
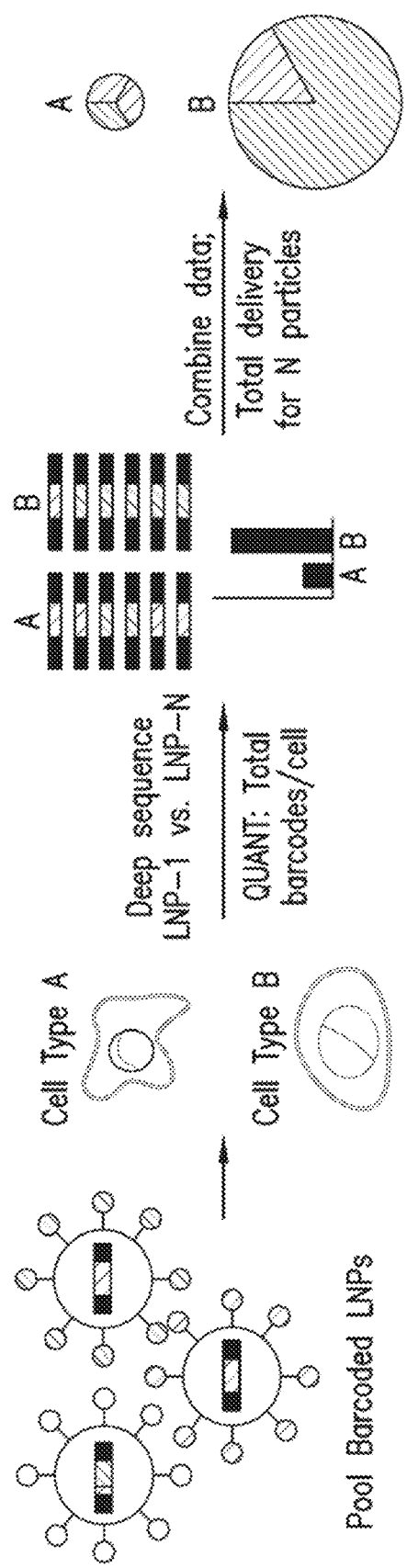

Each chemically distinct LNP was formulated to carry its own unique DNA barcode (FIG. 14A-B). For example, LNP1 carried DNA barcode 1, while the chemically distinct LNP2 carried DNA barcode 2. 91 nucleotide long single stranded DNA sequences were purchased as ultramers from Integrated DNA Technologies (IDT). Three nucleotides on the 5' and 3' ends were modified with phosphorothioates to reduce exonuclease degradation and improve DNA barcode stability. To ensure equal amplification of each sequence, universal forward and reverse primer regions were included on all barcodes. Each barcode was distinguished using a unique 8nt sequence. An 8nt sequence can generate over $4^8$ (65,536) distinct barcodes. 156 distinct 8nt sequences designed to prevent sequence bleaching on the Illumina MiniSeg™ sequencing machine were used. A 26nt probe was purchased from IDT with 5' FAM as the fluorophore, while internal Zen and 3' Iowa Black FQ were used as quenchers. Fluorescent barcode was purchased from IDT with AlexaFluor647 or AlexaFluor488 conjugated to the 5' end.

Nanoparticle Characterization.

LNP hydrodynamic diameter was measured using high throughput dynamic light scattering (DLS) (DynaPro Plate Reader II, Wyatt). LNPs were diluted in sterile 1xPBS to a concentration of ~0.06 μg/mL, and analyzed. To avoid using unstable LNPs, and to enable sterile purification using a 0.22 μm filter, LNPs were included only if they met the criteria of monodisperse population with diameter between 20 and 200 nm. Particles that met these criteria were dialyzed with 1x phosphate buffered saline (PBS, invitrogen), and were sterile filtered with a 0.22 μm filter.

Animal Experiments.

All animal experiments were performed in accordance with the Georgia Institute of Technology IACUC. C57BL/6J (#000664), SpCas9 (##026179) and Caveolin1$^{-/-}$ (#007083) mice were purchased from The Jackson Laboratory and used between 5-8 weeks of age. In all in vitro and in vivo experiments, we used N=3-5 group. Mice were injected intravenously via the lateral tail vein. The nanoparticle concentration was determined using NanoDrop (Thermo Scientific). For in vivo nanoparticle screens, mice were administered at a dose of 0.5 mg/kg.

Cell Isolation & Staining.

Cells were isolated 24 (for screens) or 96 (for in vivo gene editing) hours after injection with LNPs unless otherwise noted. Mice were perfused with 20 mL of 1xPBS through the right atrium. Tissues were finely cut, and then placed in a digestive enzyme solution with Collagenase Type I (Sigma Aldrich), Collagenase XI (Sigma Aldrich) and Hyaluronidase (Sigma Aldrich) at 37° C. at 550 rpm for 45 minutes. The digestive enzyme for heart and spleen included Collagenase IV (Dahlman J E, et al. (2014) Nat Nano 9(8):648-655; Sager H B, et al. (2016) Sci Transl Med. 8(342): 342ra380-342ra380; Sager H B, et al. (2016) Circ Res 119(7):853-864). Cell suspension was filtered through 70 μm mesh and red blood cells were lysed. Cells were stained to identify specific cell populations and sorted using the BD FacsFusion and BD Facs Aria Illu cell sorters in the Georgia Institute of Technology Cellular Analysis Core. For in vitro flow cytometry experiments, a BD Accuri C6 was used in the Georgia Institute of Technology Cellular Analysis Core. The antibody clones used were: anti-CD31 (390, BioLegend), anti-CD45.2 (104, BioLegend), anti-CD68 (FA-11, BioLegend), and anti-CD11b (M1/70, BioLegend). Representative flow gates are located in Supplementary FIG. 4.

ddPCR. The QX200™ Droplet Digital™ PCR System (Bio-Rad) was used to prep and analyze all ddPCR results. All FOR samples were prepared with 10 μL ddPCR with ddPCR™ Supermix for Probes (Bio-Rad), 1 μL of primer and probe mix (solution of 10 μM of target probe and 20 μM of Reverse/Forward Primers), 1 μL of template/TE buffer, and 8 μL water. 20 μL of each reaction and 70 μL of Droplet Generation Oil for Probes (Bio-Rad) were loaded into DG8™ Cartridges and covered with DG8™ Gaskets. Cartridges were placed in the QX200™ Droplet Generator to create water-oil emulsion droplets. Cycle conditions for PCR were as follows: 1 cycle of 95° for 10 minutes, followed by 40 cycles of 94° C. for 30 seconds, 60° C. for 1 minute, and 1 cycle of 95° C. for 10 minutes. Plates were stored at 4° C. until ran on the GX200™ Droplet Digital™ PCR System. For each biological rep, 3 technical repetitions were completed. In all cases, technical reps were averaged. Technical reps were only excluded if they saturated the detection or showed inconsistent positive event amplitudes.

PCR Amplification for Illumina Sequencing.

Figure 19D:
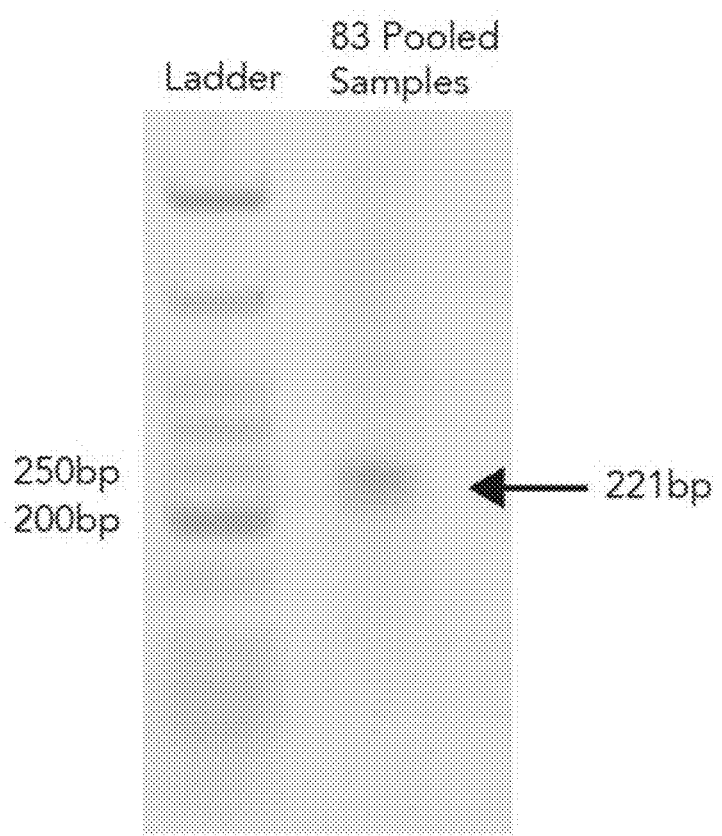

All samples were amplified and prepared for sequencing using a two-step, nested PCR protocol (FIG. 19D). More specifically, 2 μL of primers (10 uM for Base Reverse/Forward) were added to 5 μL of Kapa HiFi 2x master mix, and 3 μL template DNA/water. This first PCR reaction was ran for 20-30 cycles. The second PCR, to add Nextera XT chemistry, indices, and i5/i7 adapter regions was ran for 5-10 cycles and used the product from 'PCR 1' as template. Dual-indexed samples were ran on a 2% agarose gel to ensure that PCR reaction occurred before being pooled and purified using BluePippin (Sage Science).

Deep Sequencing.

Illumina sequencing was conducted in Georgia Institute of Technology's Molecular Evolution core. Runs were performed on an Illumina Miniseq. Primers were designed based on Nextera XT adapter sequences.

Barcode Sequencing Normalization.

Counts for each particle, per cell type, were normalized to the barcoded LNP mixture applied to cells or injected into the mouse.

Data Analysis & Statistics.

Sequencing results were processed using a custom R script to extract raw barcode counts for each tissue. These raw counts were then normalized with an R script prior for further analysis. Statistical analysis was done using GraphPad Prism 7; more specifically, 1-tail T-test, Paired 2-tail T-test, or One-way ANOVAs were used where appropriate. Data is plotted as mean±standard error mean unless otherwise stated.

Figure 19E:
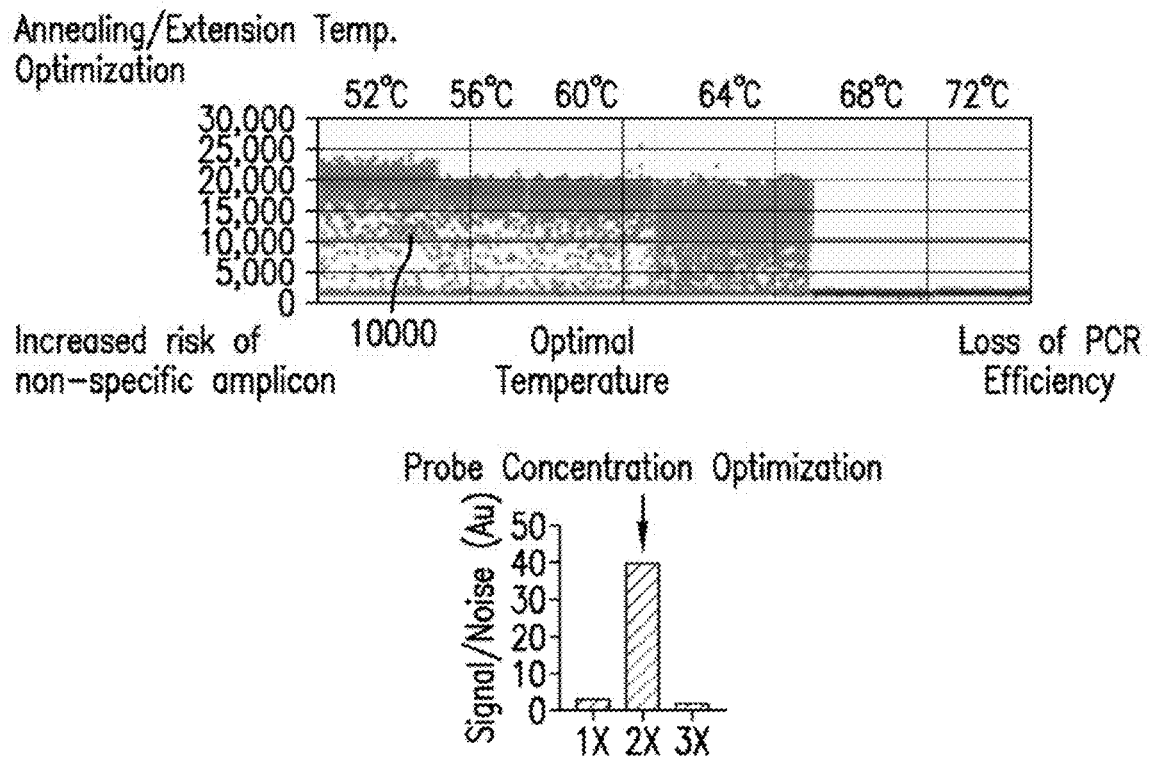
Figure 19F:
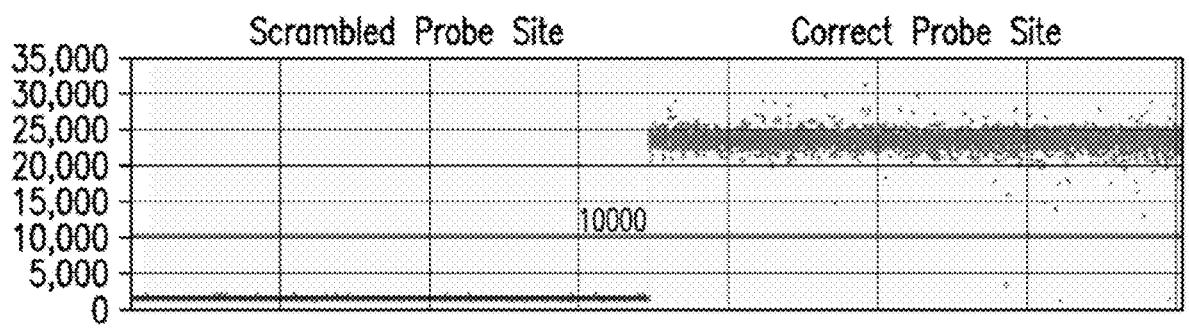

Results ddPCR requires efficient DNA amplification, and as a result, QUANT DNA barcodes were rationally designed to increase DNA polymerase access. DNA secondary structure on the forward and reverse primer sites were minimized and G-quadruplex formation was minimized by separating the fully randomized 7 nucleotide region (Dahlman J E, et al. (2017) Proc Natl Acad Sci USA. 114(8):2060-2065; Paunovska K, et al. (2018) Nano Lett 18(3):2148-2157) into NWNH and NWH sites. The primer sites were also flanked with 3 phosphorothioate-modified nucleotides to reduce exonuclease degradation. Finally, universal primer binding sites were identified that would not amplify any mouse or human genomic DNA (gDNA). Specifically, a library of primers with similar melting temperatures (within 1° C.) were designed and added to human and mouse gDNA without barcode template; 40 cycle PCRs (FIG. 19A-19B) were then run. Primers were identified that did not amplify gDNA after 40 cycles (Table X) but amplified barcode templates with as few as 20 cycles. After adding these 'no background' universal primer sites to our barcodes, the ddPCR protocol (FIG. 19C-E) was optimized. Annealing temperatures, primer concentrations, and probe concentrations were varied, increasing the signal: noise ratio 14-fold compared to current gold standard protocols (Hindson C M, et al. (2013) Nat Methods 10(10):1003-1005). To confirm ddPCR readouts were specific, the ddPCR probe site was scrambled; no signal was generated in this control condition, demonstrating that the signal required specific barcode-probe interactions (FIG. 19F).

Figure 14D:
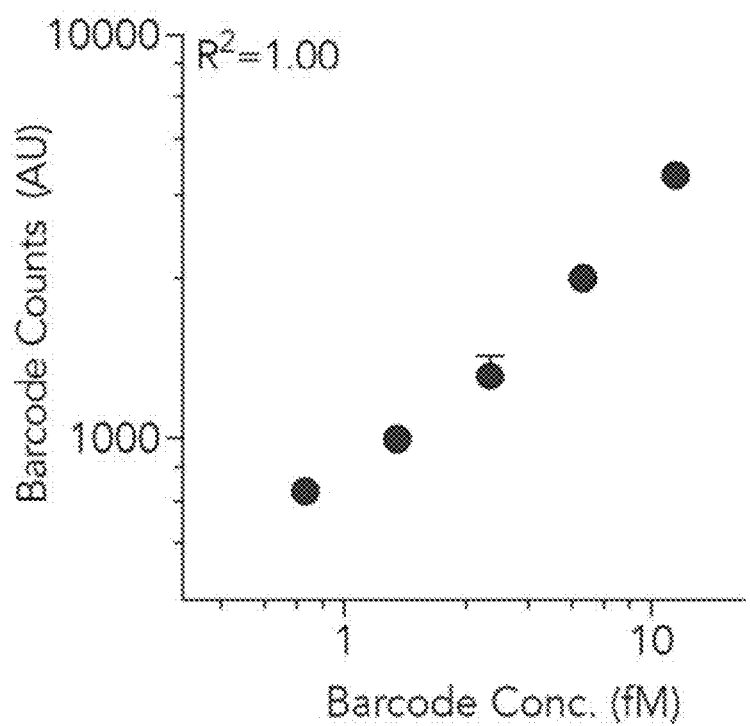
Figure 14E:
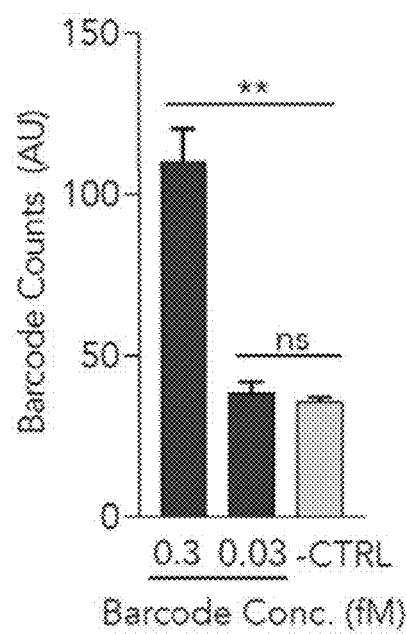
Figure 14F:
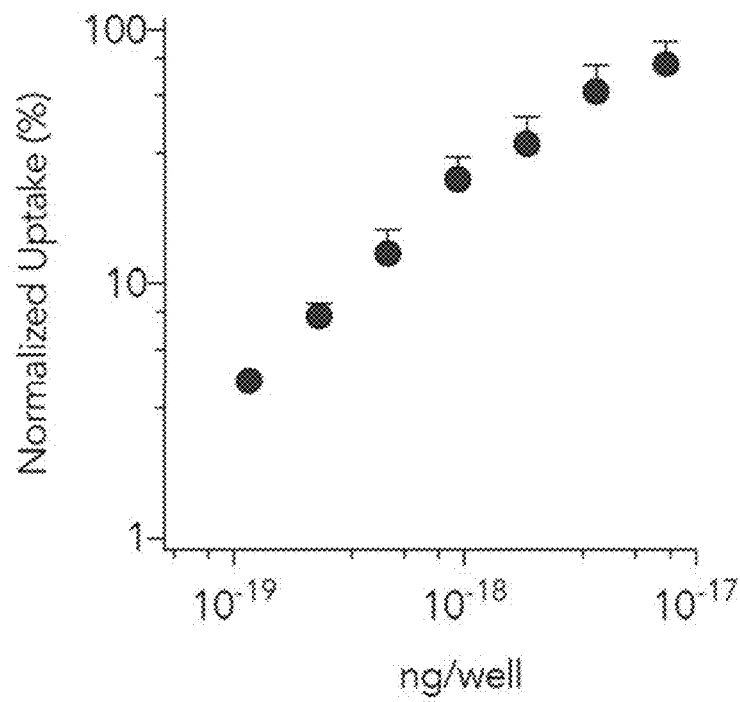
Figure 14G:
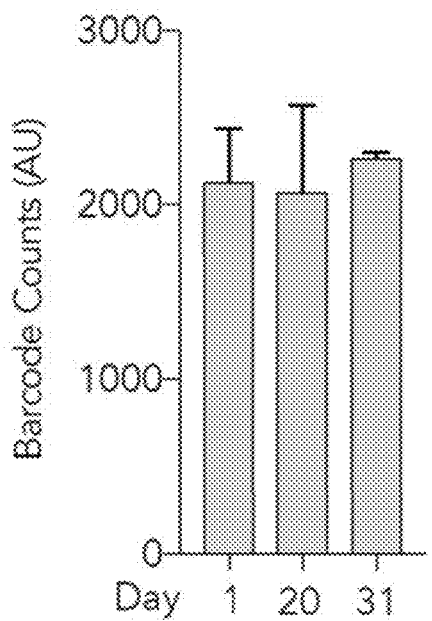
Figure 19G:
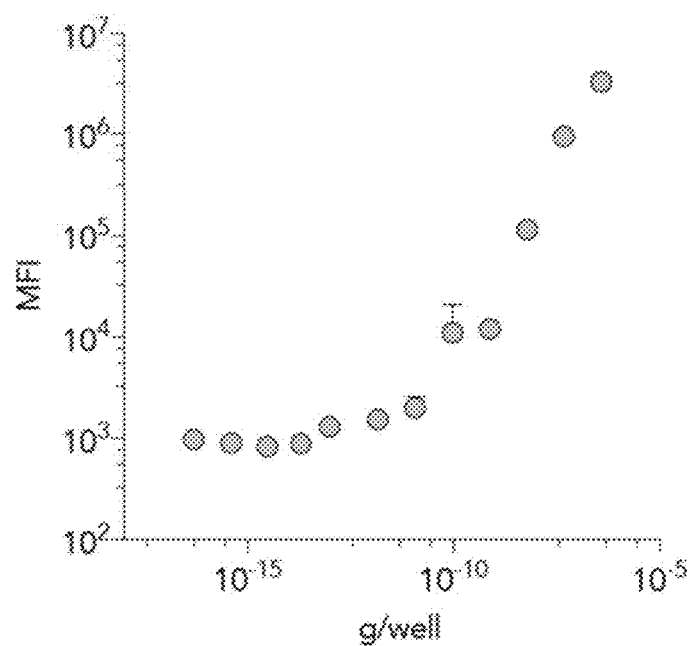

Standard curve control experiments were then performed to measure QUANT sensitivity. The QUANT ddPCR signal was linear when barcodes were diluted in Tris-EDTA buffer to a concentration between 750 aM and 12 fM ($R^2$=1.00) and was detected at 300 aM (FIG. 14D-14E). As a control, the concentration was reduced to 30 aM, and there were no readouts above untreated baseline. The sensitivity of QUANT was then analyzed in vitro. QUANT barcodes were fluorescently tagged and administered to immortalized aortic endothelial cells (iMAECs) (Ni C W, et al. (2014) Vascular cell 6(1):7) in 96 well plates with Lipofectamine 2000 (L2K) at doses between 1 pg and 400 ng/well. Twenty-four hours later, biodistribution was analyzed using flow cytometry, demonstrating measurable, but non-linear, increases in mean fluorescence intensity at doses above 10 pg/well (FIG. 19G). Separately, QUANT barcodes were administered without a fluorophore at doses between 60 and 10,000 zg/well. ddPCR readouts were linear ($R^2$=0.91) between 15 and 1000 zg/well, doses that were $10^9$× lower than fluorescence (FIG. 14F). Lastly, QUANT barcodes were formulated into validated LNPs (Dahlman J E, et al. (2014) Nat Nano 9(8):648-655); LNPs carrying barcodes formed nanoparticles with an average hydrodynamic diameter of 53 nm. These were intravenously administered at the clinically relevant (Coelho T, et al. (2013) N Engl J Med 369(9):819-829) barcode dose of 0.5 mg/kg, isolated lung endothelial ($CD31^+CD45^-$) cells using fluorescence activated cell sorting (FACS) (Dahlman J E, et al. (2014) Nat Nano 9(8):648-655; Paunovska K, et al. (2018) Nano Letters) 24 hours later, and barcode delivery was quantified using ddPCR. To evaluate the robustness of QUANT, samples were compared immediately after completing this experiment, and the measurements repeated after storing samples at −20° C. for 20 or 31 days. Readouts were consistent when performed by different individuals using different reagent stocks (FIG. 14G).

Figure 15B:
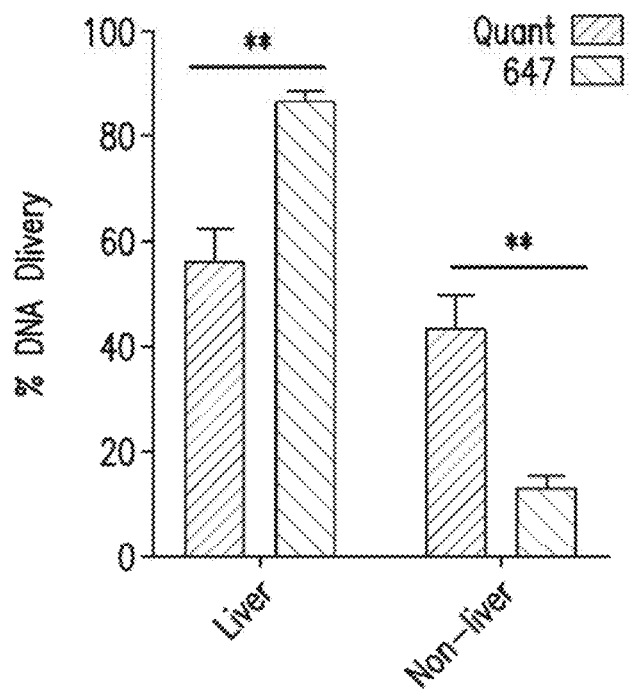
Figure 15C:
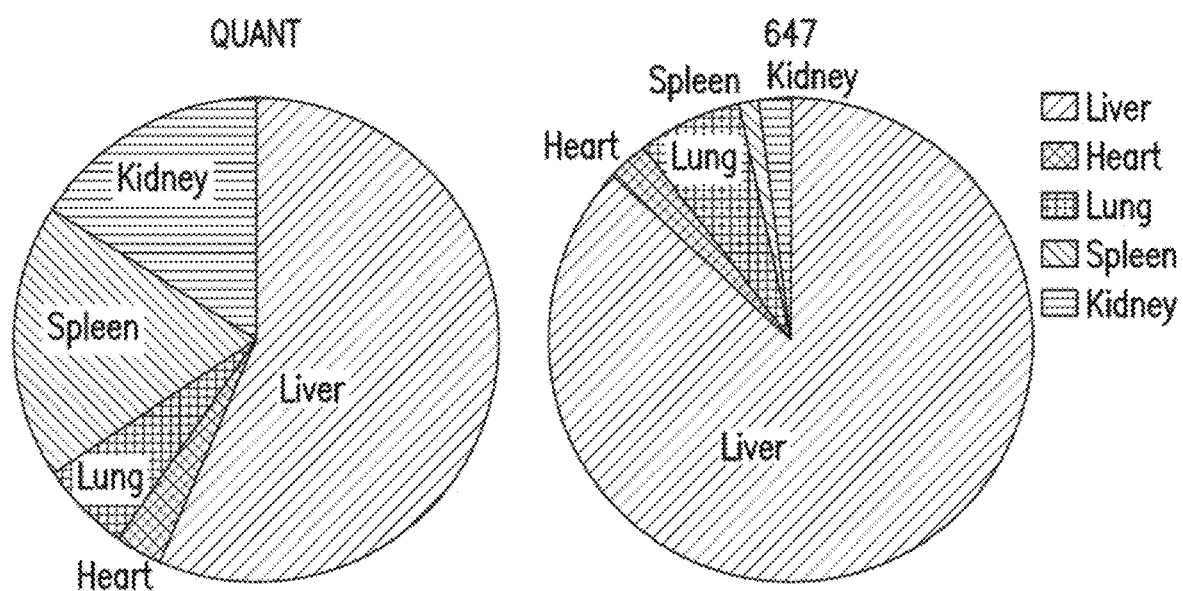
Figure 15D:
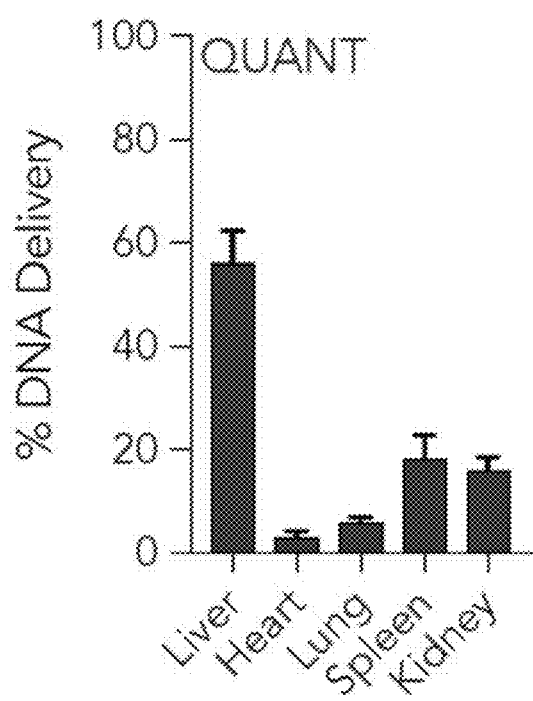
Figure 15E:
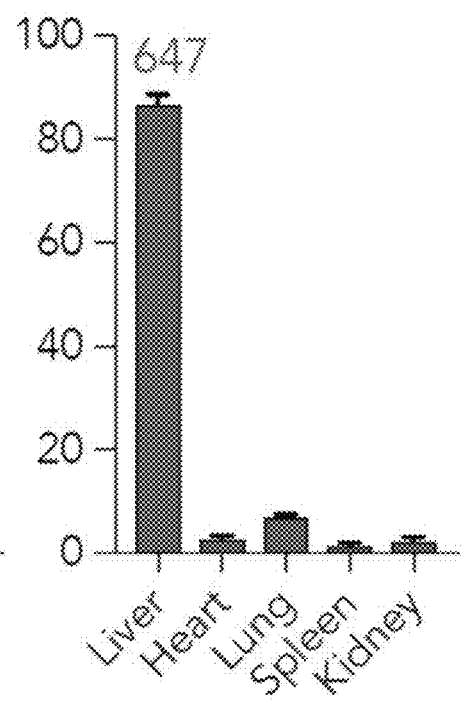
Figure 15F:
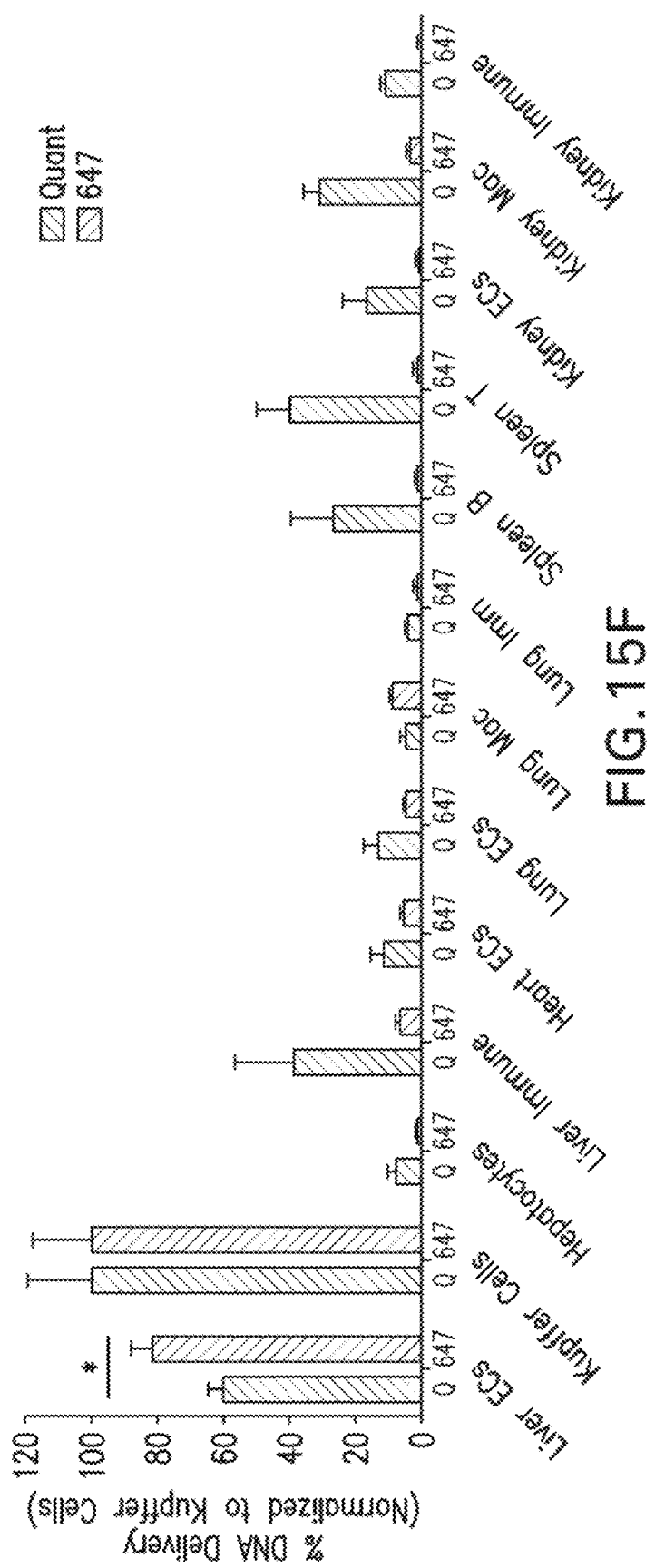
FIG. 15F shows comparison of biodistribution in the 13 cell types examined by QUANT and fluorescence. *$p<0.05$, $p<0.01$, *$p<0.001$, 2 tailed t-test.
Figure 20:
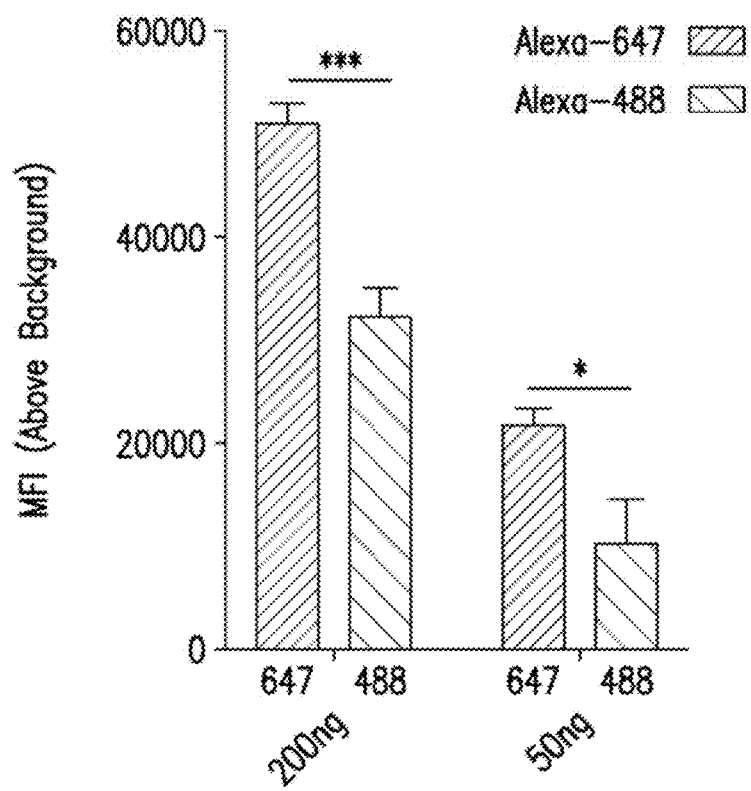
FIG. 20 shows comparison of Mean Fluorescent Intensity (MFI) of barcodes conjugated with Alexa-488 and Alexa-647 at 200ng and 50ng per well. *p<0.05, ***p<0.001, 2 tailed t-test.

Nucleic acids are degraded by nucleases that cleave phosphodiester bonds (Yang W (2011) Quarterly reviews of biophysics 44(1):1-93); fluorophores are not. Given that fluorophores and nucleic acids degrade via different mechanisms, it was hypothesized that in vivo readouts of biodistribution based on fluorescent tags attached to the DNA might yield different results than QUANT, which directly measures the nucleic acid. To test this hypothesis, a validated LNP (Dahlman J E, et al. (2014) Nat Nano 9(8):648-655) was formulated with QUANT barcodes that were, or were not, fluorescently tagged with Alexa-647. Alexa-647 was chosen after finding it had minimal cellular autofluorescence, compared to Alexa-488 (FIG. 20). One hour after administering the clinically relevant dose (Coelho T, et al. (2013) N Engl J Med 369(9):819-829) of 0.5 mg/kg intravenously, 13 cell types were isolated from 5 tissues using FACS and quantified LNP delivery using Alexa-647 mean fluorescent intensity (MFI) or ddPCR (FIG. 15A). Recapitulating commonly observed results, nearly all the fluorescent signal (87%) was found in liver cells (FIG. 15B-15E). The remaining 10 cell types only generated 13% of the total fluorescent signal. By contrast, QUANT biodistribution was more evenly distributed; 56% of the ddPCR signal derived from liver cells, whereas 44% of the signal derived from the other cell types. Based on these results, delivery was compared in all 13 cell types (in both cases, normalized to Kupffer cells—a resident liver macrophage known to readily clear nanoparticles), demonstrating statistically significant differences in 7 of them (FIG. 15F). In all cases, these data suggested that fluorescence overestimated liver biodistribution.

Figure 16G:
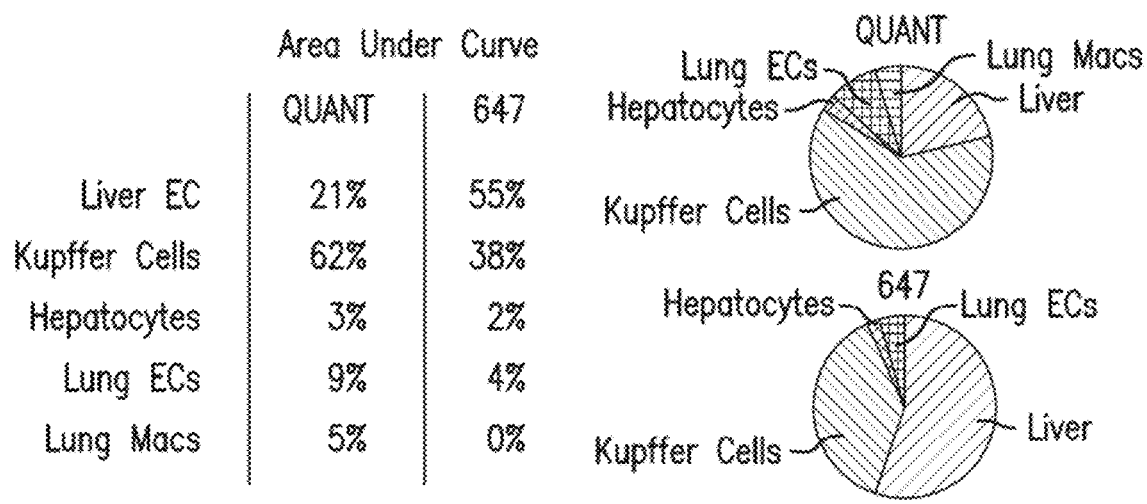
FIG. 16G shows comparisons of area under the curve as measured by QUANT or fluorescence. Delivery to the lungs was underestimated by >3 fold by fluorescence.
Figure 16H:
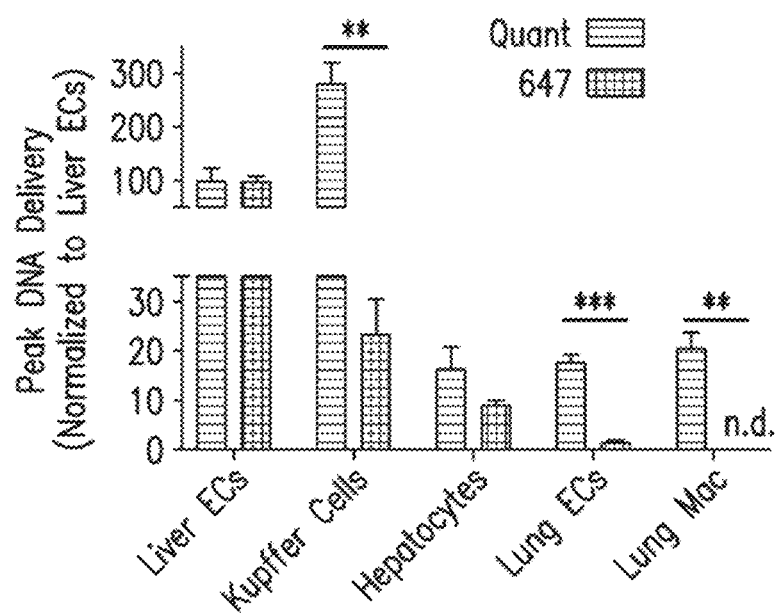
FIG. 16H shows peak DNA delivery (normalized to liver ECs) as measured by QUANT and fluorescence. No fluorescent signal was detected in lung macrophages. p<0.01, *p<0.001 2 tailed t-test.

To exclude the possibility that these results were due to a specific timepoint, nanoparticle pharmacokinetics, a key parameter used to characterize nanoparticle behavior in vivo, were analyzed. Biodistribution was quantified in 5 cell types: liver endothelial cells, Kupffer cells, hepatocytes, lung endothelial cells, and lung macrophages 0.4, 0.75, 1.25, 12, 24, and 36 hours after intravenously injecting mice with 0.5 mg/kg of QUANT barcodes or fluorescently tagged QUANT barcodes (FIG. 16A) encapsulated in the same validated LNP (Dahlman J E, et al. (2014) Nat Nano 9(8):648-655). Once again, at the earlier timepoints, fluorescent biodistribution was localized to liver cells (FIG. 16B). At later timepoints, fluorescent biodistribution was not significantly above PBS-treated mice (FIG. 16B). By contrast, ddPCR-based biodistribution was observed in all 5 cell types at all 6 timepoints (FIG. 16C-16F). All analyses performed—including area under the curve and maximum DNA delivery—suggested that fluorescence overestimated delivery to the liver (FIG. 16G-16H).

Figure 17:
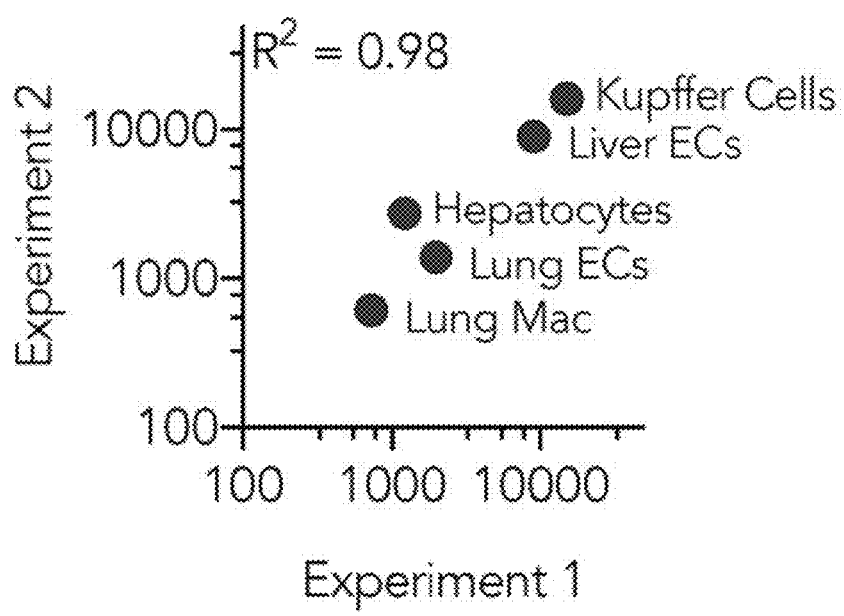
FIG. 17 shows QUANT readouts are highly repeatable across in vivo experiments. R2 analysis of QUANT absolute counts from the 1 hour timepoint and the 1.25 hour timepoint across two experiments performed on separate days.

Finally, the robustness of QUANT readouts across experiments was investigated. First, the R-squared correlation between QUANT mice were calculated at each timepoint. The absolute ddPCR values from all 5 cell types in the first biodistribution experiment (FIG. 15) and the pharmacokinetic experiment (FIG. 16) at similar timepoints (1 and 1.25 hours, respectively) were calculated. These absolute values were plotted, demonstrating a highly linear relationship ($R^2=0.98$) between experiments and that QUANT experiments were repeatable (FIG. 17). The data in FIGS. 2 to 4 suggest that the biodistribution of the fluorophore may not accurately represent the biodistribution of the nucleic acid itself. If recapitulated by other laboratories, this has significant implications for many pre-clinical nanoparticle studies. More generally, the data in FIGS. 1 to 4 demonstrate that QUANT is a sensitive, robust, and repeatable method of quantifying nanoparticle biodistribution.

In addition to its increased sensitivity, QUANT barcodes can be multiplexed. This is the first DNA nanoparticle barcoding method that enables the concurrent measurement of absolute delivery mediated by >100 nanoparticles. This new capability was used to study the biological factors that influence nanoparticle delivery in vivo. The focus was on Caveolin-1 (Cav1), an endocytosis gene involved in fibrotic (Gvaramia D, et al. (2013) Matrix Biol. 32(6):307-315) neurological (Gaudreault S B, et al. (2004) Neurobiol Aging. 25(6):753-759) disease, as well as cancer (Yang G, et al. (1999) Cancer Res 59(22):5719-5723; Wtkiewicz A K, et al. (2009) Am J Pathol 174(6):2023-2034). Cav1 is also a canonical endocytosis gene that influences nanoparticle uptake in vitro (Sahay G, et al. (2010) J Control Release 145(3):182-195). However, whether it affects nanoparticles in vivo—and to what extent its effect is cell-type dependent—is unclear. More broadly, although a small number of studies have investigated the role genes play in nanoparticle targeting in vivo (Akinc A, et al. (2010) Mol Ther 18(7): 1357-1364; Bertrand N, et al. (2017) Nat Commun. 8(1): 777), it was unknown whether a given expressed by multiple cell types can affect nanoparticle delivery in a cell type-specific manner. It was reasoned that Cav1 would exhibit cell type-specific behavior since its expression can be governed by the tissue microenvironment (Sotgia F, et al. (2011) Breast Cancer Res. 13(4):213).

Figure 18A:
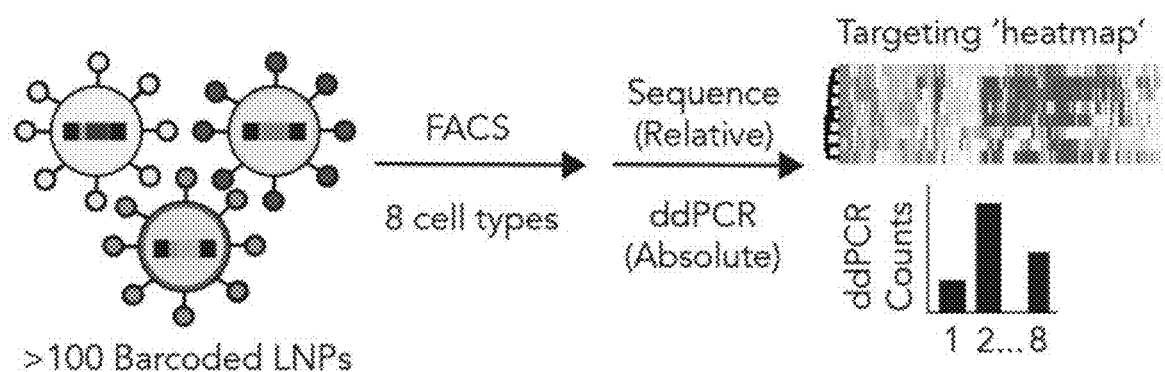
Figure 18B:
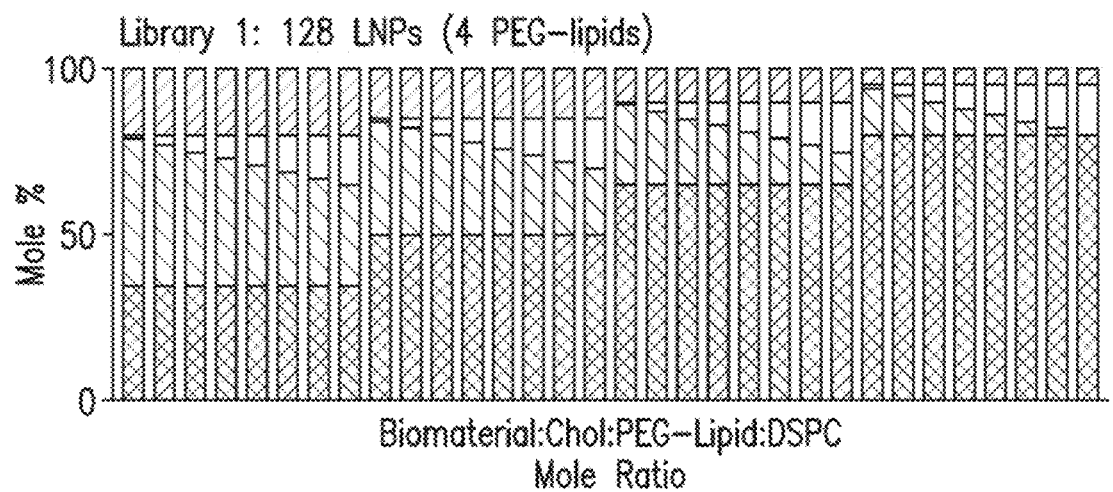

To test the hypothesis that Cav1 knockout affects LNP delivery in a cell type-specific manner, 2 high throughput in vivo LNP screens were performed. LNP-1, with chemical structure 1, carried QUANT barcode 1; LNP-N, with chemical structure N, carried QUANT barcode N (FIG. 18A). The 8 nucleotide barcode region on QUANT barcodes can generate 65,536 unique barcodes; 156 were selected that were compatible with one another on Illumina sequencing machines (Paunovska K, et al. (2018) Nano Lett 18(3):2148-2157). The hydrodynamic diameter of each LNP individually was analyzed using dynamic light scattering, and small LNPs (<200 nm diameters) were pooled together in 1×PBS. In the first LNP library, 128 LNPs were formulated; 111 were stable and pooled together. A total DNA dose of 0.5 mg/kg (roughly 0.004 mg/kg per particle on average) as intravenously administered to wildtype and $Cav1^{-/-}$ mice. In separate mice, a second library of 120 LNPs (of which 115 were stable) were formulated, pooled, and injected (FIG. 18B, Tables 13 and 14). In both experiments, cells from the liver, lung, heart and kidney were isolated using FACS 24 hours after administration. Relative delivery was then measured using deep sequencing, and absolute delivery using ddPCR. Normalized delivery measures how well a specific barcode was delivered, relative to other barcodes (Dahlman J E, et al. (2017) Proc Natl Acad Sci USA. 114(8):2060-2065; Paunovska K, et al. (2018) Nano Lett 18(3):2148-2157).

Figure 18C:
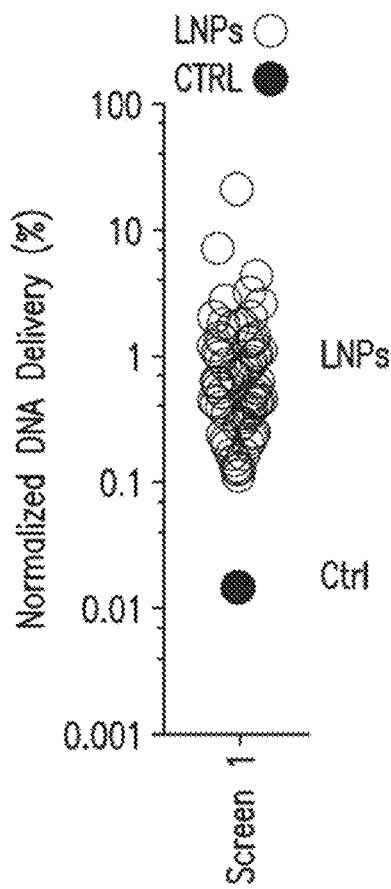
Figure 18D:
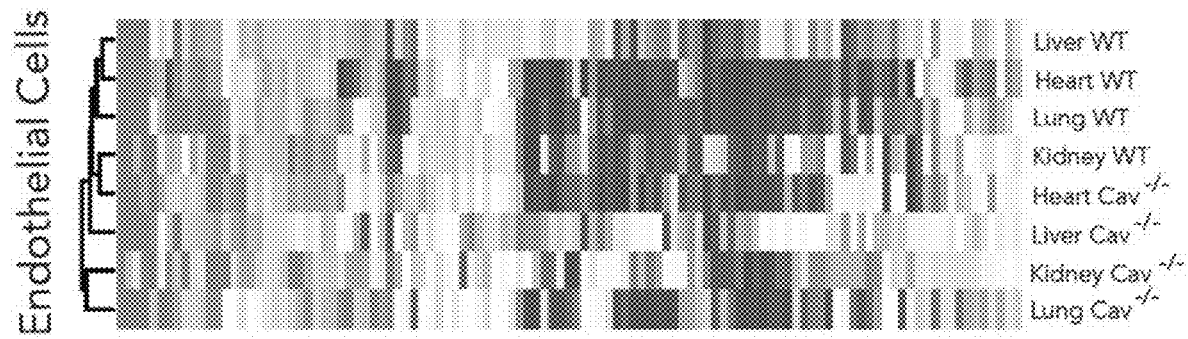
Figure 18E:
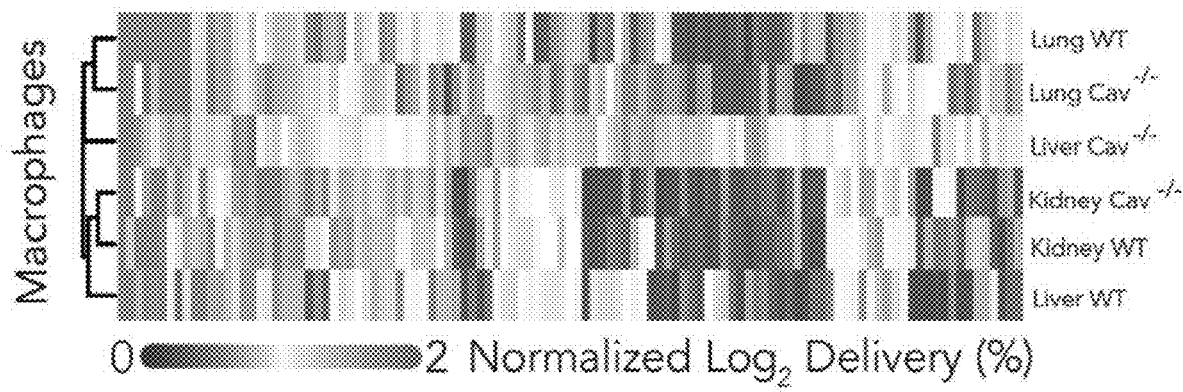
Figure 18F:
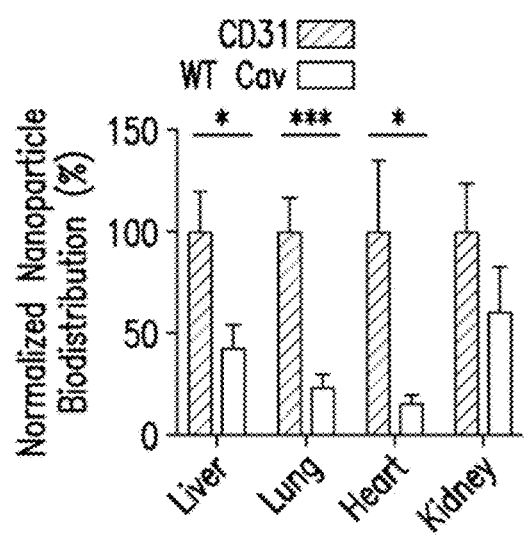
Figure 18G:
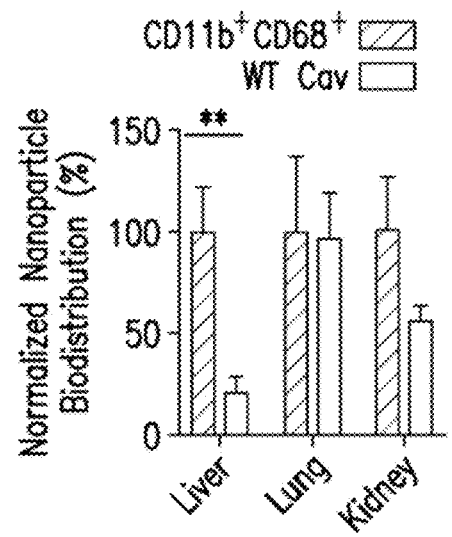
Figure 21A:
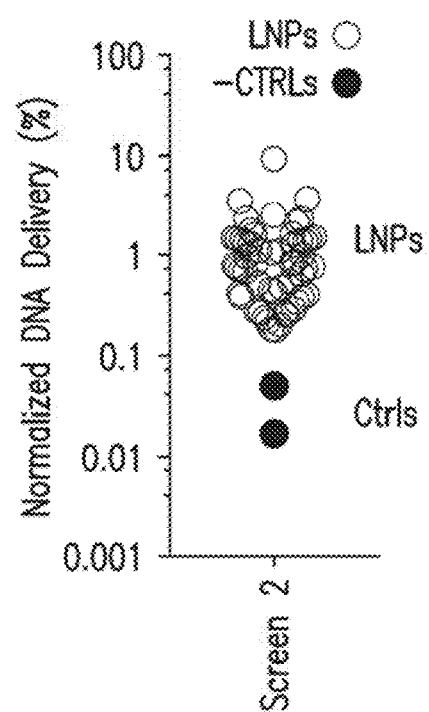
FIG. 21A shows average normalized delivery of each LNP from screen 2. Naked barcode—the negative control—was delivered less efficiently than barcodes carried by LNPs, as expected.
Figure 21B:
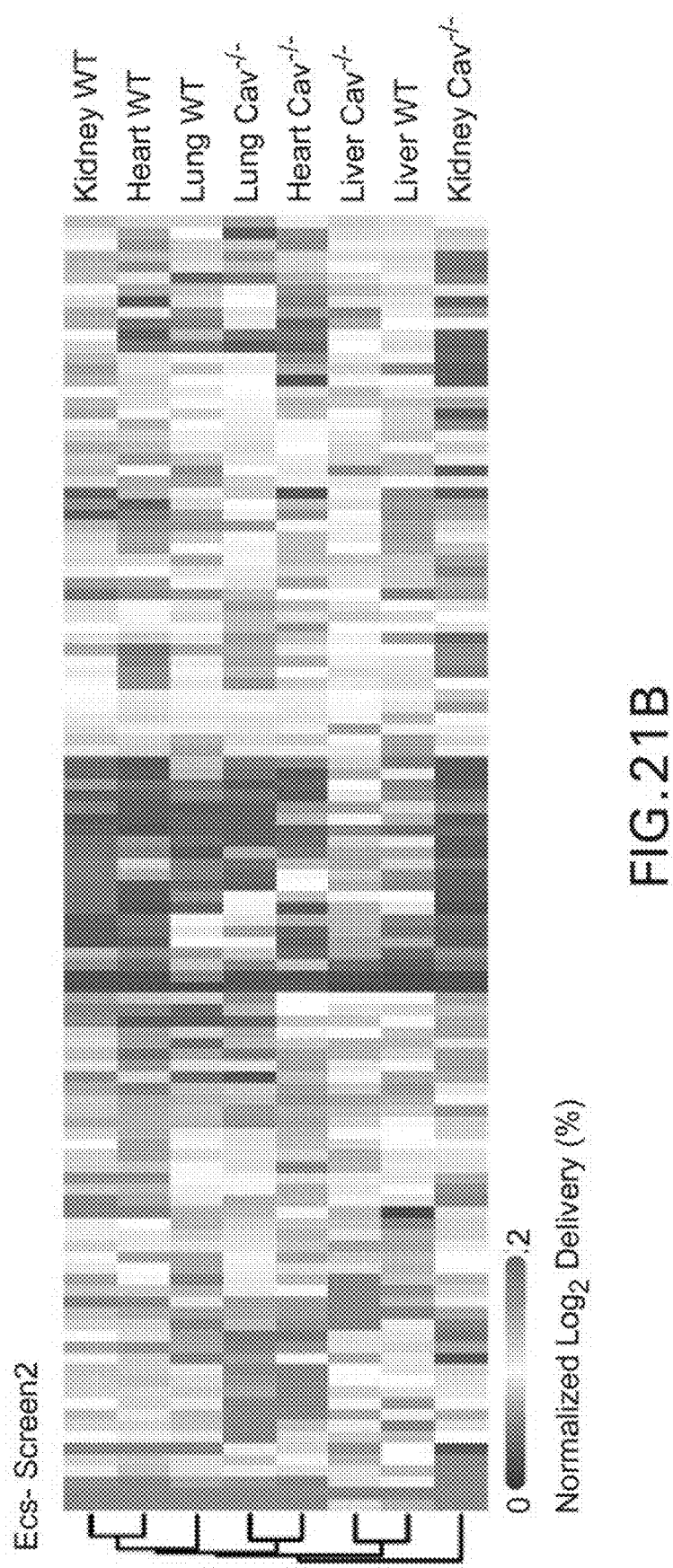
FIGS. 21B and 21C show heatmaps of relative nanoparticle delivery in wild-type and Cav1−/− mice from screen 2. Euclidean clustering was performed on cell-types to generate the dendrogram.
Figure 21C:
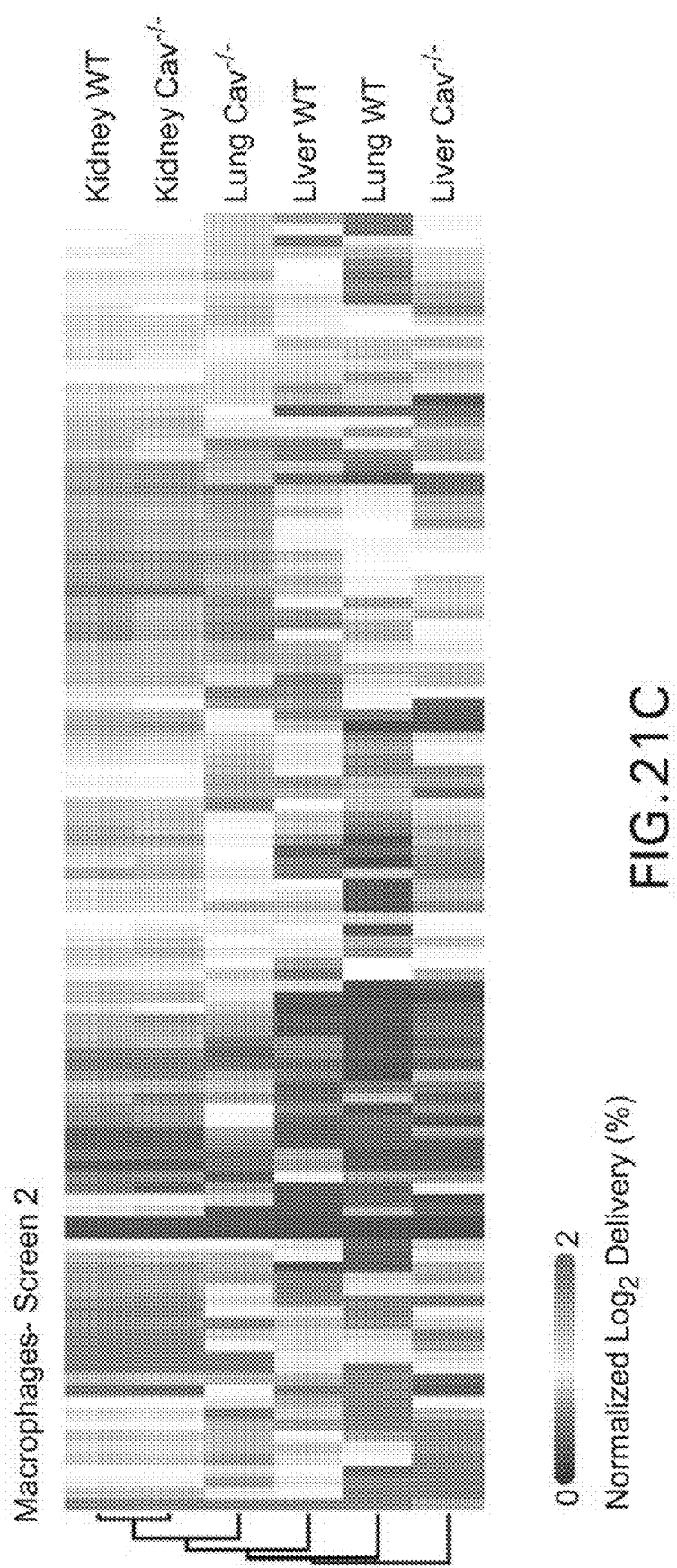
Figures 21D, 21E:
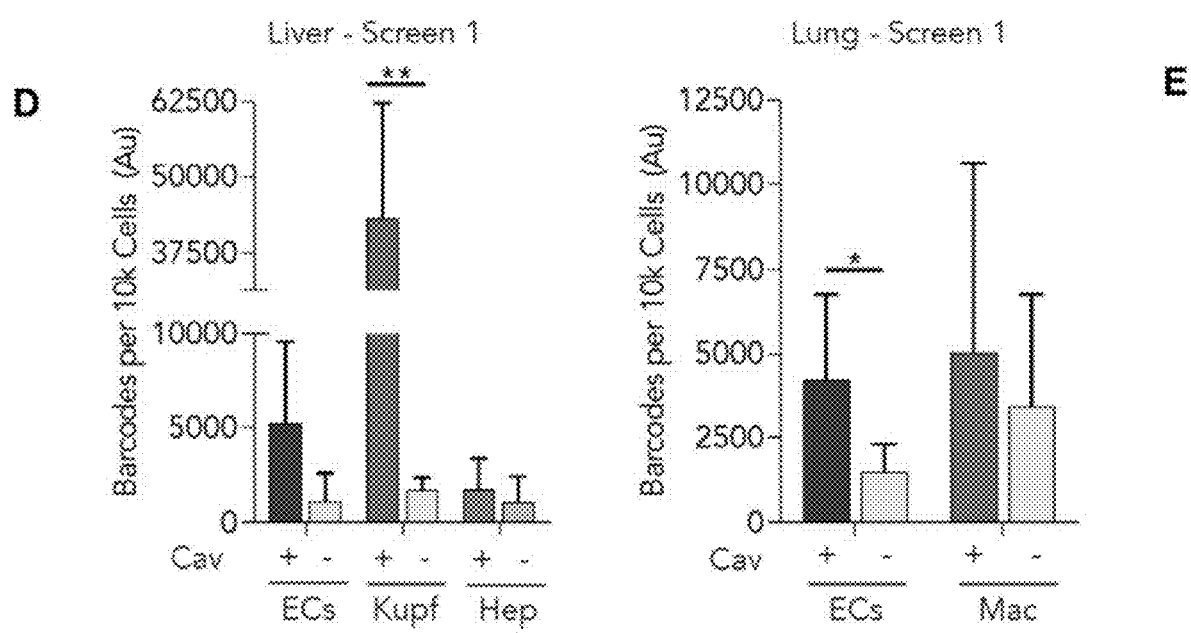
FIGS. 21D to 21K show nanoparticle distribution across screen 1 (FIGS. 21D-21G) and screen 2 (FIGS. 21H-21K) from multiple organs and cells types from wild-type and Cav1−/− mice.
Figures 21F, 21G:
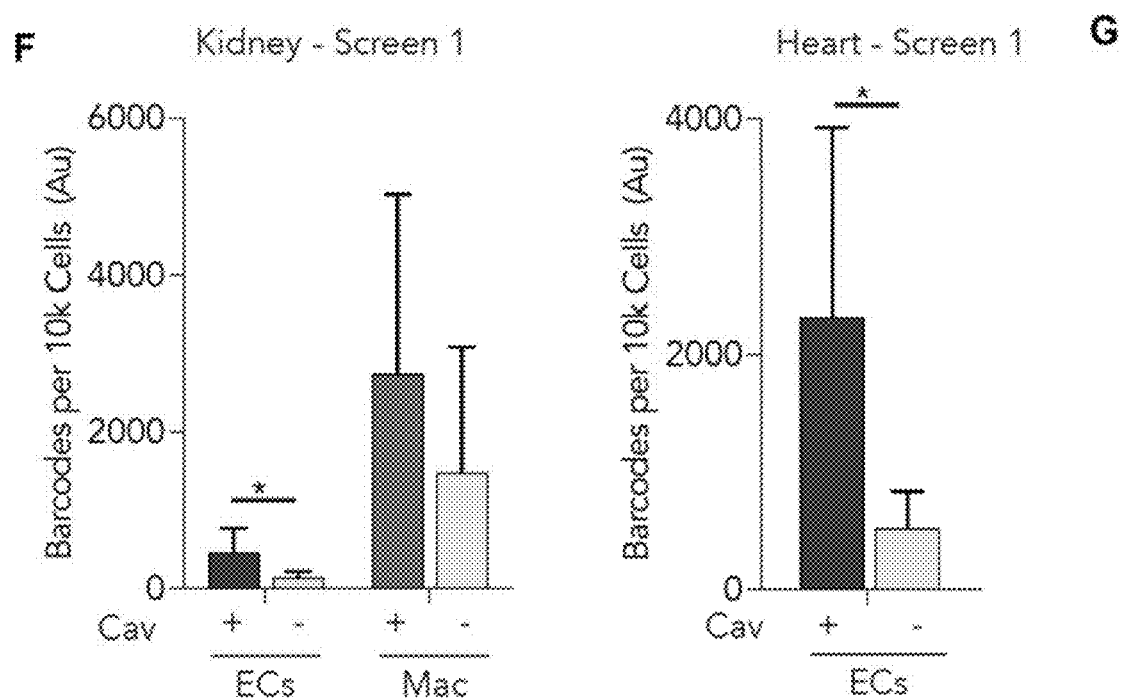
Figures 21H, 21I:
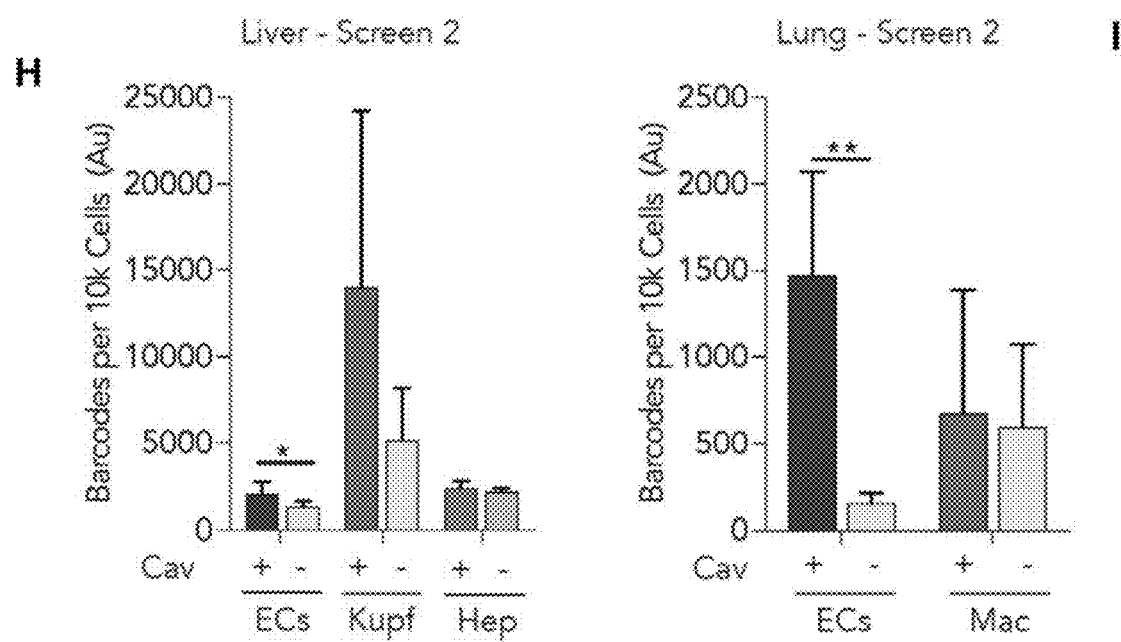
Figures 21J, 21K:
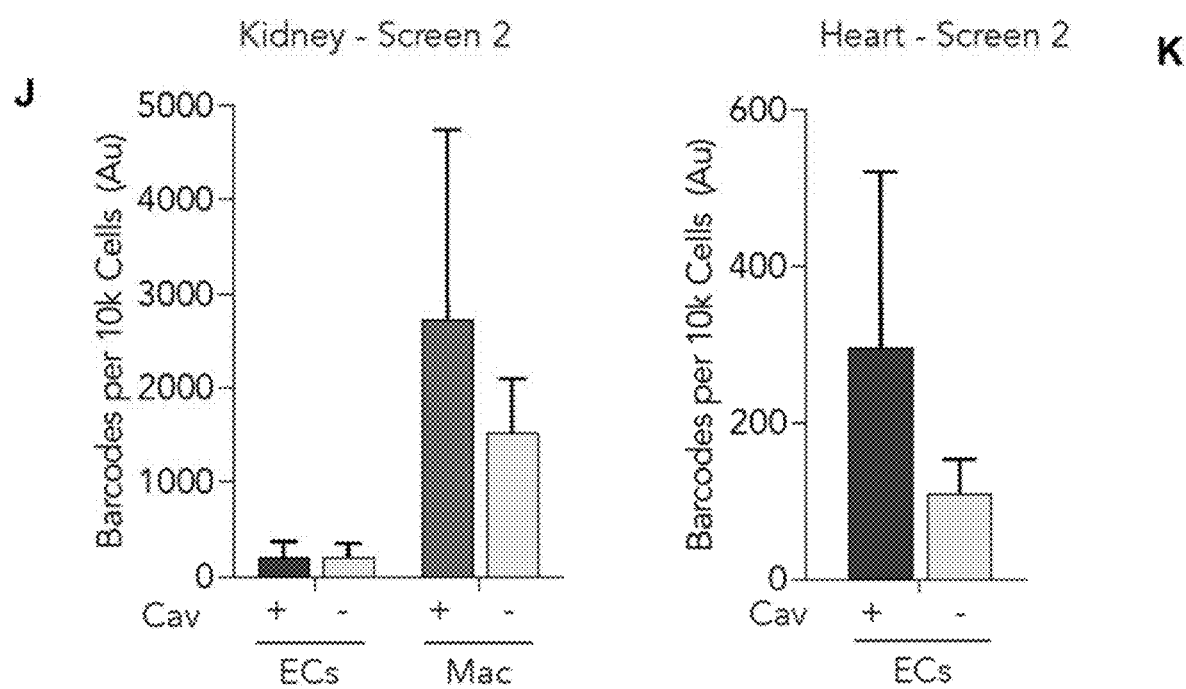
Figure 21L:
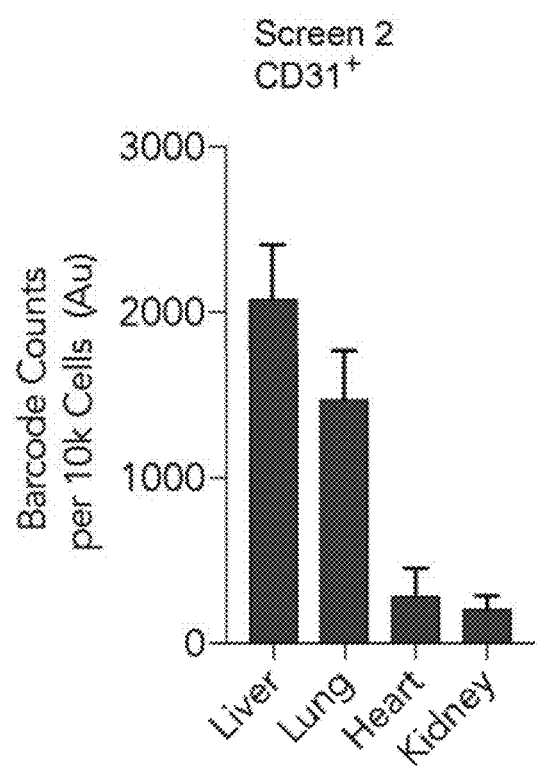
FIGS. 21L and 21M show screen 2 nanoparticle biodistribution from wild-type and Cav1−/− mice in endothelial cells (FIG. 21L), macrophages and Kupffer cells (FIG. 21M). **p<0.01, 1 tailed t-test.
Figure 21M:
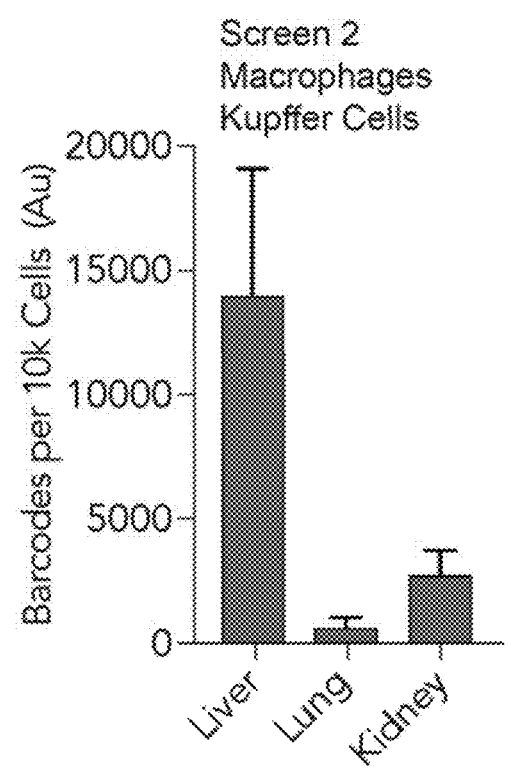

As expected, the normalized delivery of naked DNA barcode (the negative control) was much lower than the normalized delivery for barcodes carried by LNPs (FIG. 18C, 21A). Barcodes were deep sequenced from each cell type and delivery analyzed with Euclidean clustering, a common bioinformatics framework that compares how similar/dissimilar many samples are (Ronan T, et al. (2016) Sci Signal. 9(432):re6). Multiple lines of evidence suggested that Cav1 expression influenced delivery to endothelial cells more so than delivery to macrophages. First, endothelial cell Euclidean clustering was affected by whether the mouse was WT or $Cav1^{-/-}$ more than macrophage clustering (FIG. 18D-18E, 21B-21C). Second, compared to WT mice, nanoparticle delivery to liver, pulmonary and heart endothelial cells decreased substantially in $Cav1^{-/-}$ mice. Interestingly, renal endothelial cell delivery was affected less (FIG. 18F, 21D-21K). Less change was observed in macrophages. Delivery to lung macrophages did not change, whereas delivery to renal macrophages changed slightly. Interestingly, delivery to Kupffer cells was reduced significantly in $Cav1^{-/-}$ mice (FIG. 18H). These results are important given that Kupffer cells sequester nanoparticles after systemic administration; they suggest that inhibiting Cav1 expression may prevent Kupffer cell-mediated nanoparticle clearance.

Figure 22A:
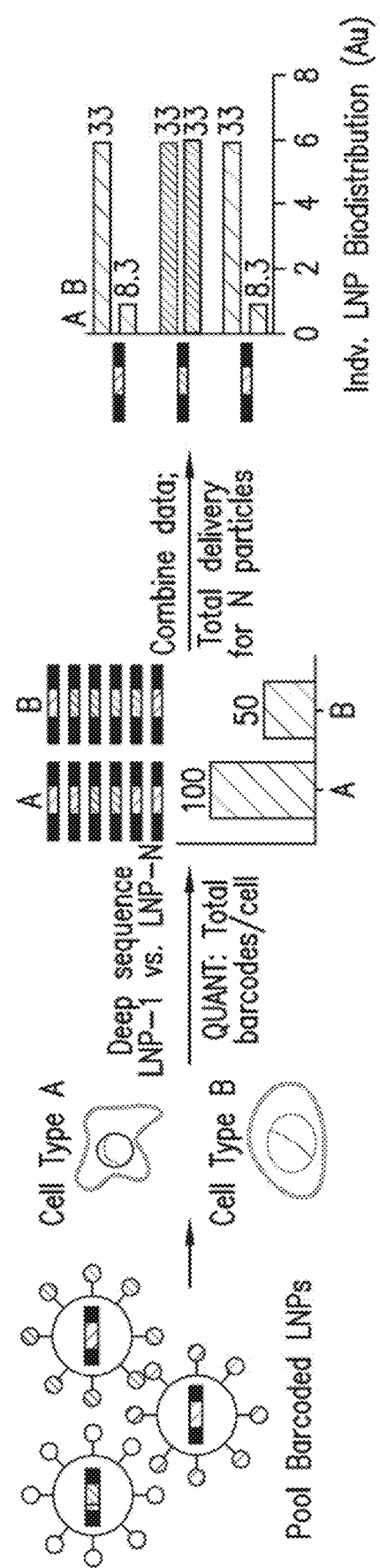
FIG. 22A shows a schematic workflow describing how ddPCR and deep sequencing data can be combined to calculate absolute delivery of >100 LNPs in the same experiment.
Figure 22B:
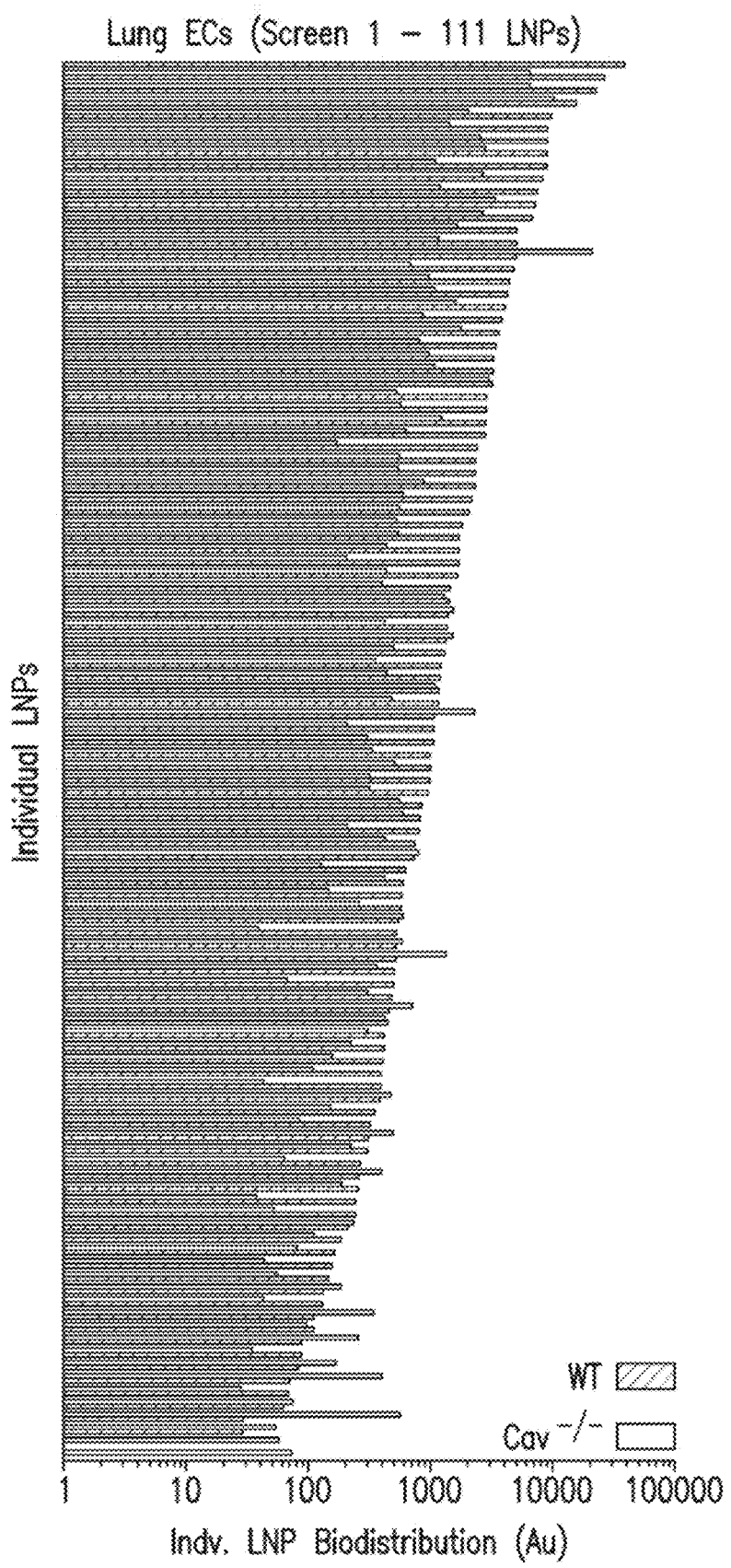
FIGS. 22B and 22C show combined sequencing data and ddPCR results for each LNP in lung endothelial cells in wild type and Cav1−/− mice from screen 1 (FIG. 22B) and screen 2 (FIG. 22C).
Figure 22C:
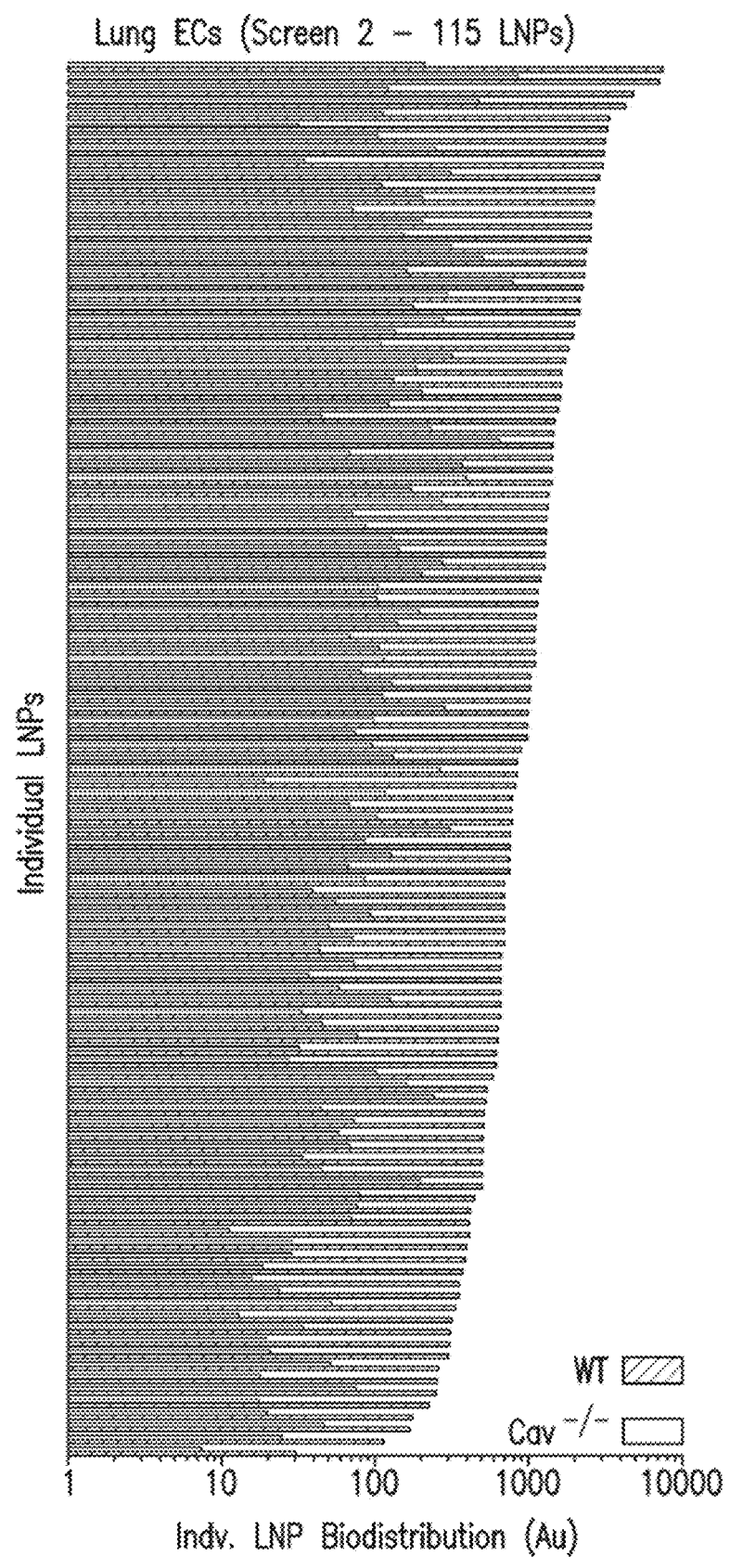
Figure 22D:
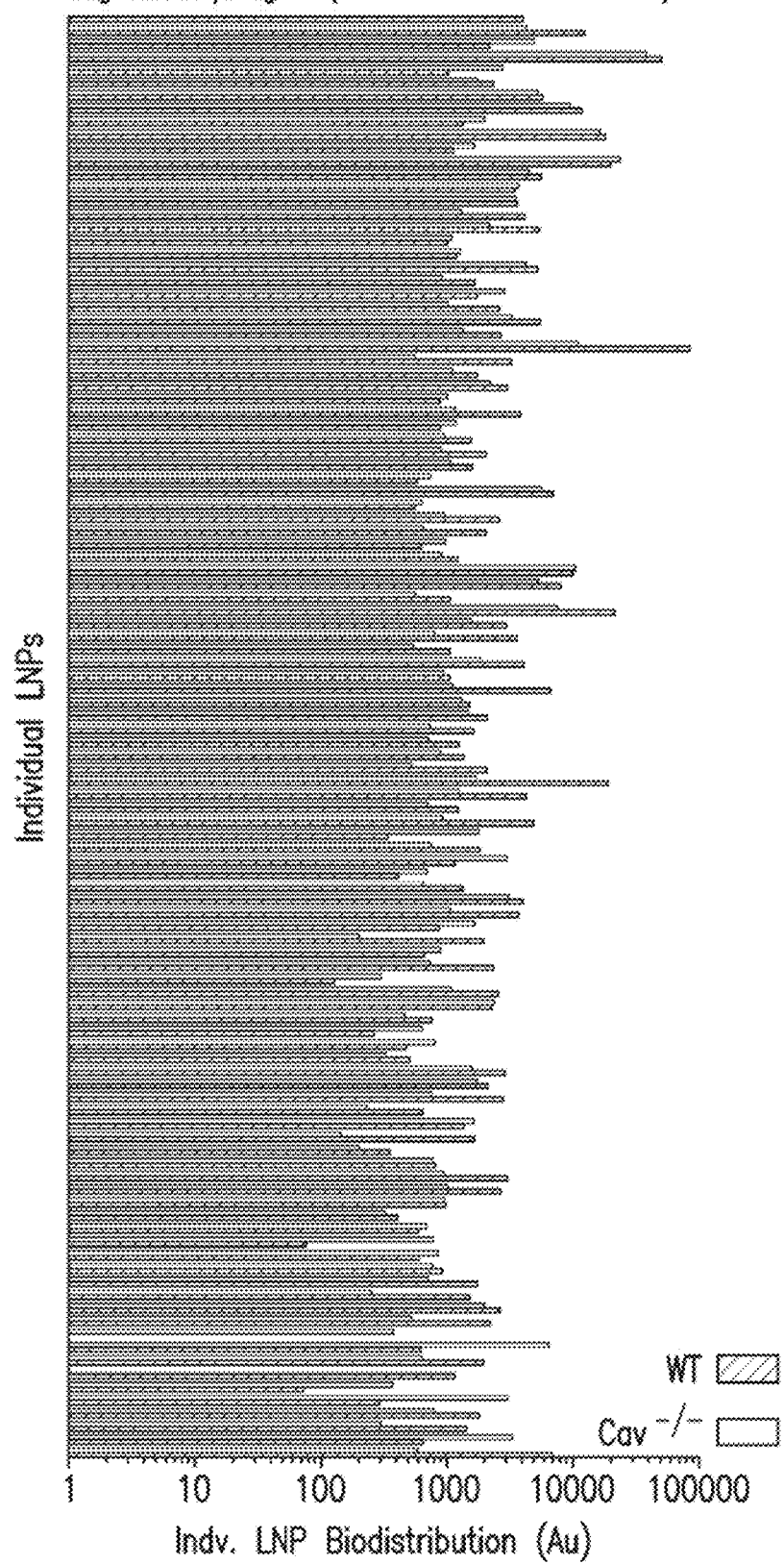
FIGS. 22D and 22E show combined sequencing data and ddPCR results for each LNP in lung macrophages in wild type and Cav1−/− mice from screen 1 (FIG. 22D) and screen 2 (FIG. 22E).
Figure 22E:
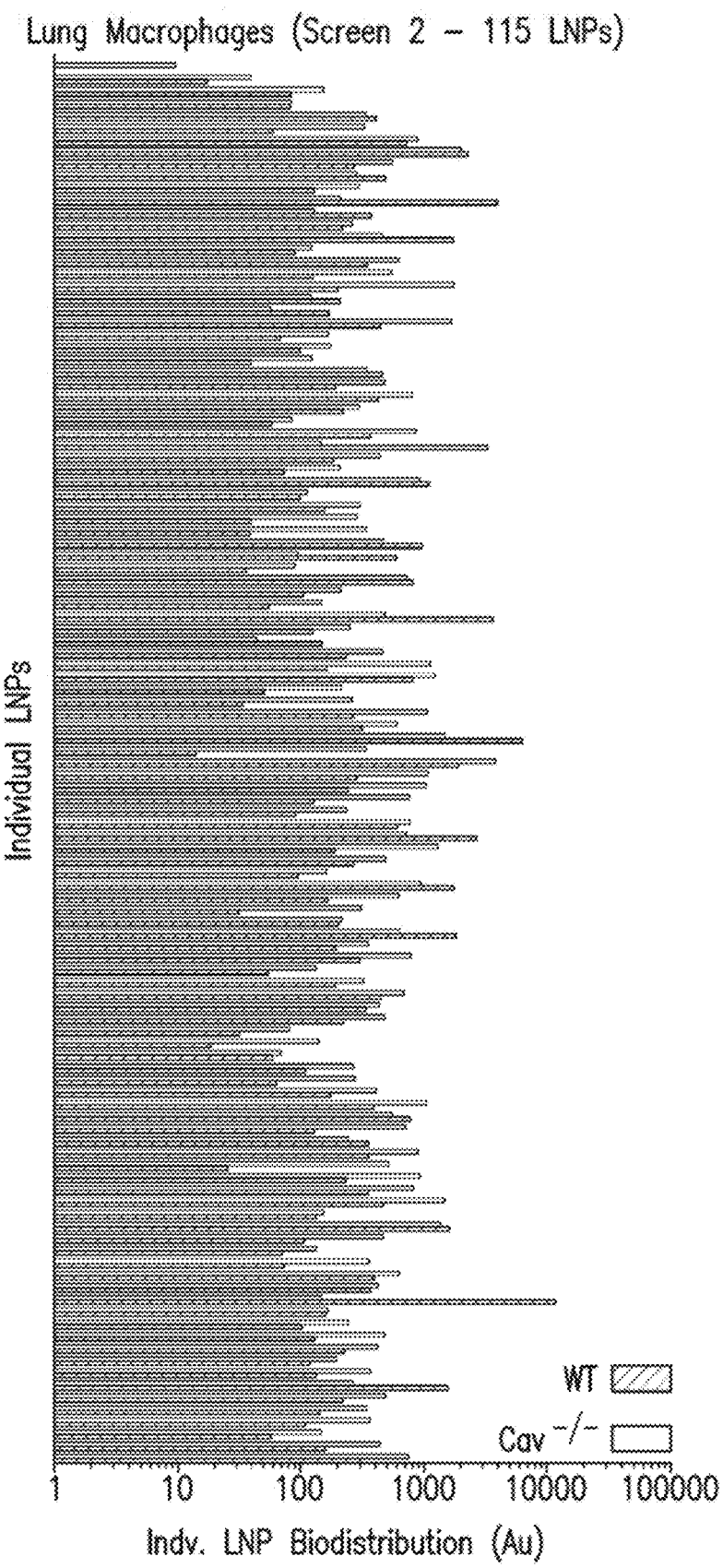
Figure 24A:
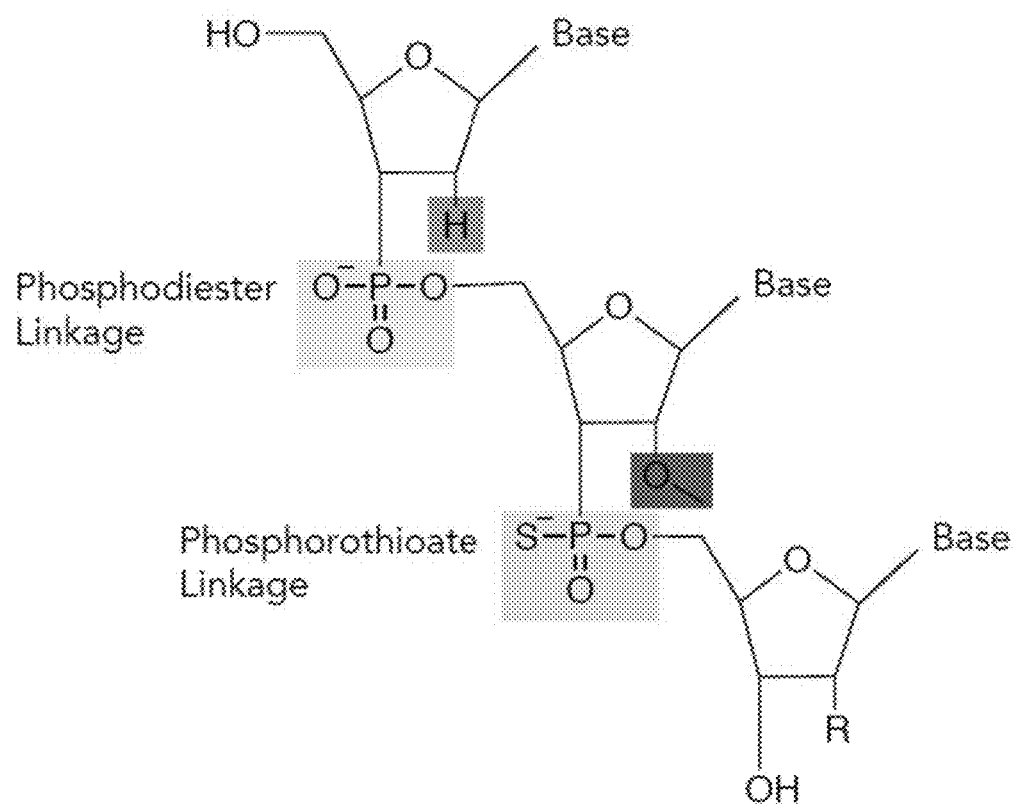
FIG. 24A illustrates phosphodiester and phosphorothioate (PS) linkages and a 2'O-methyl ribonucleotide (Ome).
Figure 24B:
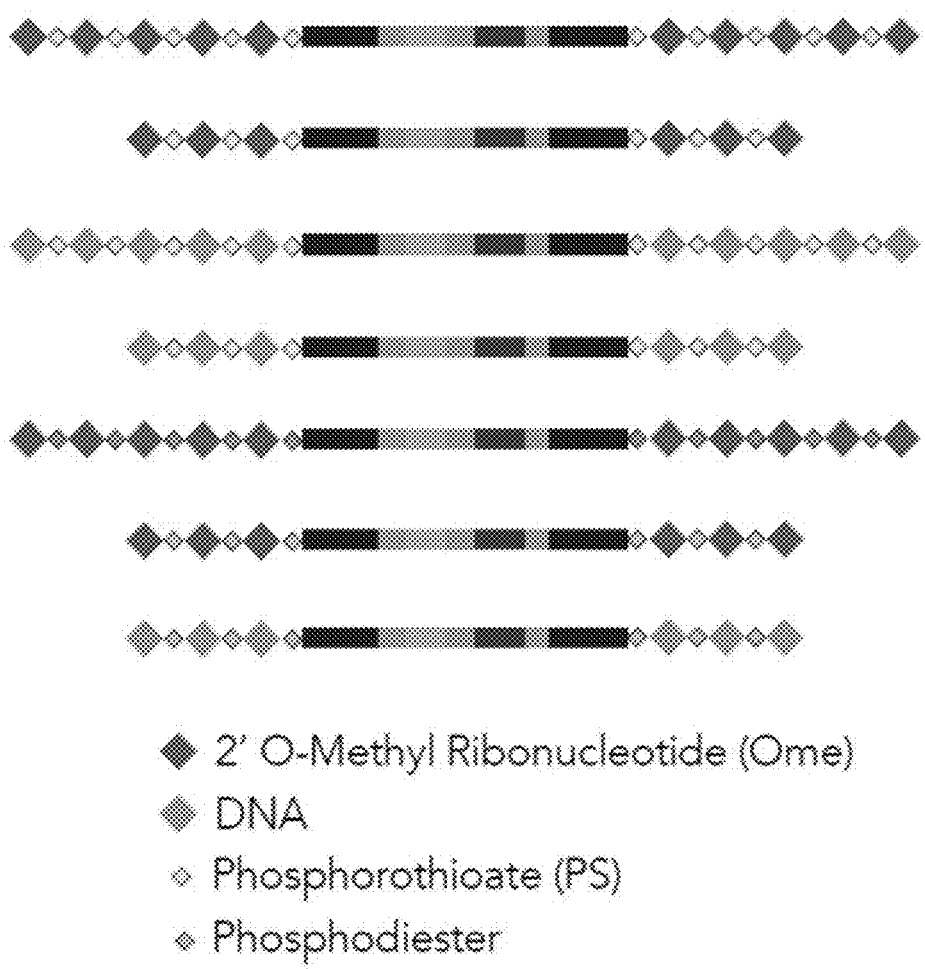
FIG. 24B illustrates various barcode approaches including combinations of DNA, Ome, with phosphodiester and phosphorothioate linkages.
Figure 24C:
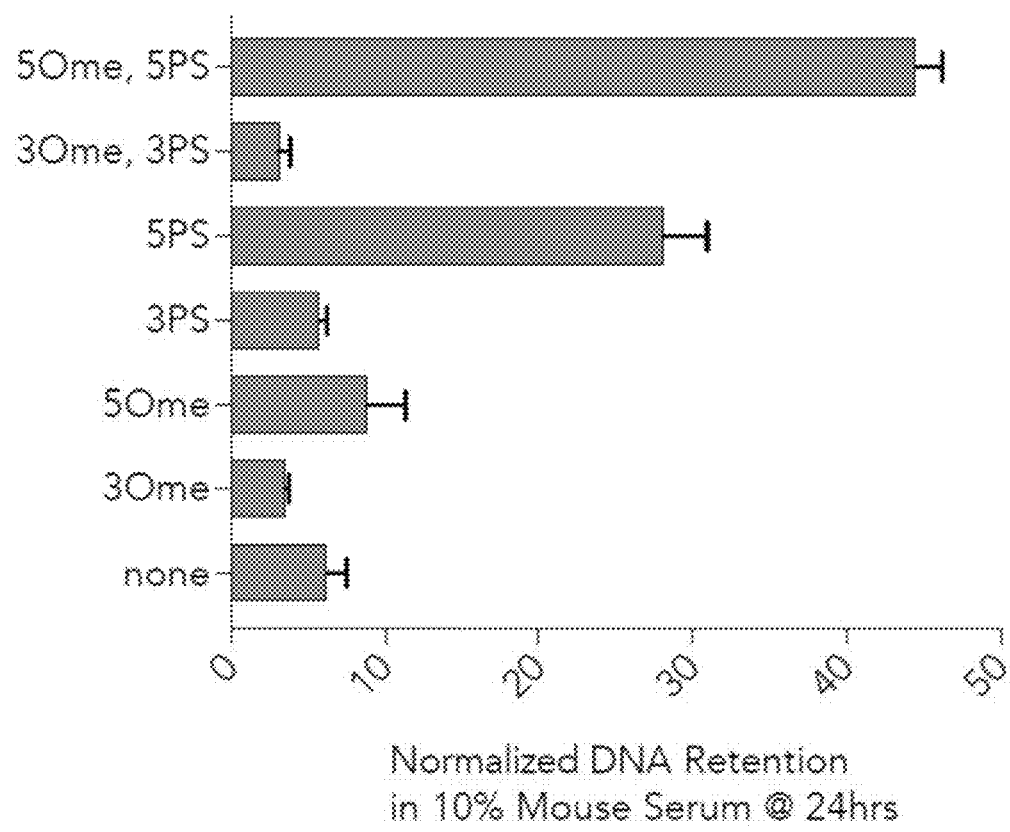
FIG. 24C is a bar graph showing stability of barcodes 5 Ome and 5 PS, 3 Ome and 3 PS, 5PS, 3 PS, 5Ome, 3Ome, or no modifications.

To further validate these data, sequencing data (relative delivery by many LNPs) and ddPCR (absolute delivery) were combined to calculate how all >200 LNPs were affected by Caveolin 1 in all cell types (FIG. 22A). Once again, delivery to endothelial cells (FIG. 22B-22C) was more affected than delivery to macrophages (FIG. 22D-22E). The ease with which QUANT can be multiplexed enabled analysis of >2,000 data points generated over 2 in vivo experiments; this would have taken nearly 10,000 mice using traditional methods.

Taken together, QUANT enabled 3 new scientific observations pertaining to the biology of in vivo drug delivery that would not be made with traditional experiments. First, Caveolin 1 expression affects delivery to endothelial cells more than macrophages in vivo. Second, delivery to Kupffer cells—a major clearance cell type—may be reduced by manipulating Caveolin 1. Third, endothelial cells from different tissues are differentially targeted by LNPs; the same is true for macrophages. These lines of evidence coalesce to suggest that cell type-specific changes in nanoparticle delivery can be driven by a single genetic change.

DISCUSSION

Despite being a universal problem for nucleic acid therapeutics, on- and off-target biodistribution is difficult to study in vivo. As disclosed herein, ddPCR, a technique that quantifies rare genomic events, can be used in concert with rationally designed DNA barcodes to measure nanoparticle delivery. Although this work is distinct, ddPCR has also sensitively counted nanoparticles in an environmental toxicology study (Paunescu D, et al. (2015) ACS nano 9(10): 9564-9572).

The increased sensitivity of QUANT was used to ask new questions in drug delivery. It is anticipated that QUANT will enable scientists to evaluate how thousands of nanoparticles target rare or hard to isolate cell types. As an example, it has been difficult to predict and design nanoparticles that target stem cells and rare tumor cells in vivo; QUANT may help identify how nanoparticle structure promotes targeting to these cell types. Relatedly, over the course of 2 experiments and multiple time points, it was found that fluorescent biodistribution tended to overestimate delivery to the liver relative to other cell types. This raises the exciting possibility that nanoparticles which target non-liver cell types may have already been reported, and simply mislabeled as 'liver specific' during preliminary biodistribution assays. This is important, given the clinical success of liver-targeted RNA therapies, and the current inability to deliver nucleic acid drugs to other organs. These data also suggest that on- and off-target delivery should be measured in many cell types independently isolated with FACS.

QUANT can be multiplexed; this was exploited to analyze delivery mediated by >200 LNPs in WT and Cav1$^{-/-}$ mice. This approach revealed that Cav1 affects LNP delivery in a cell type-specific manner. This is the first demonstration that a commonly expressed gene can affect nanoparticle delivery in a cell type-specific manner in vivo. These data also suggest that inhibiting Cav1 expression globally may be used to shift delivery away from specific cell types. More broadly, QUANT may be used to study the 'biology of in vivo drug delivery'.

(SEQ ID NO: 8)
G*A*T*GCTCTCATACGAACTCGTCCNHNW*CCTGCTAGTCCAC GTCCATGTCCACC*NWNH-8nt Barcode Seq-NWHGTGGTT AGTCGAGCAGAGAC\*T\*A\*G

TABLE 12

| Barcode Sequences | |
|---|---|
| BC# | SEQ |
| 1 | TGATATTG |
| 2 | GACGCAAT |
| 3 | GCGAGTAT |
| 4 | ACCTAATC |
| 5 | AGGCGCTA |
| 6 | GATCTACC |
| 7 | CTACTGAT |
| 8 | TGATCTAT |
| 9 | ATGAGATG |
| 10 | GCGAATTC |
| 11 | GATTCCGG |
| 12 | ATAATATA |
| 13 | AGCATGCG |
| 14 | GATTCAAC |

TABLE 12-continued

| Barcode Sequences | |
|---|---|
| BC# | SEQ |
| 15 | TACCTGCT |
| 16 | GCTAATCG |
| 17 | CTCCTTCG |
| 18 | ACGCTAGC |
| 19 | GCAGGACT |
| 20 | ATTGCTCT |
| 21 | TACGCTCG |
| 22 | ACGCTCCA |
| 23 | CGGTCAAT |
| 24 | CGCCTATT |
| 25 | TTGCGTTG |
| 26 | TCCTAAGA |
| 27 | CAAGAAGG |
| 28 | TAGAATTA |
| 29 | GGCGCCAA |
| 30 | TAGATCCG |
| 31 | CGAGCAGC |
| 32 | TAAGATGA |
| 33 | AGCTCGGA |
| 34 | TAACCGAA |
| 35 | TATATCTA |
| 36 | AAGAGGAT |
| 37 | ACGTCGAA |
| 38 | CATCATTA |
| 39 | TTGCAACT |
| 40 | TCTAACTG |
| 41 | TATGCCTT |
| 42 | GTAATTGC |
| 43 | GTCTCCGT |
| 44 | TGCATGGT |
| 45 | AGTCCGGT |
| 46 | TCCTGATG |
| 47 | ATCGTCTA |
| 48 | GGACGTCC |
| 49 | CTACGAGG |
| 50 | CAATCCGT |
| 51 | GGCGCTTG |
| 52 | GTCCGTTA |

TABLE 12-continued

Barcode Sequences

| BC# | SEQ |
|---|---|
| 53 | GCCTCTCG |
| 54 | GAGAGTTG |
| 55 | CATAATAG |
| 56 | TCTAGAGT |
| 57 | AAGTCTAG |
| 58 | ATTCGAGA |
| 59 | CTACCATT |
| 60 | GTTAGTCA |
| 61 | ATAGAATC |
| 62 | CTCAACTA |
| 63 | CTTACGTC |
| 64 | TGAGTTCG |
| 65 | ATGGTAGA |
| 66 | TCCAGGCG |
| 67 | CTCAGCAT |
| 68 | TGCGTATA |
| 69 | AATGCTAC |
| 70 | CGCGAGGC |
| 71 | GTCGAAGT |
| 72 | ACTATCTC |
| 73 | GTCGCCTC |
| 74 | AGTTACCG |
| 75 | GAGTATAC |
| 76 | GGCAGTAG |
| 77 | TGGAGACG |
| 78 | ATTAGGAC |
| 79 | ATCAATTG |
| 80 | GGTCGGTC |
| 81 | TTGGATCC |
| 82 | ATTGGTTC |
| 83 | GATGGCCT |
| 84 | TTATAGCA |
| 85 | GTCAATCT |
| 86 | CGCTCCGG |
| 87 | ACTCAAGT |
| 88 | CCGTTCGG |
| 89 | CCGCAGAG |
| 90 | CGGTATCT |
| 91 | TTATTAAT |
| 92 | AGGCTCAT |
| 93 | TAGTACGT |
| 94 | AATATACG |
| 95 | CGATGCTT |
| 96 | CCAAGATT |
| 97 | TCCATTAT |
| 98 | AATACCAT |
| 99 | CTGCGACC |
| 100 | GACTTGAG |
| 101 | CAGAAGCA |
| 102 | TCTCCTAA |
| 103 | CTGAGCCA |
| 104 | TCCTGCGC |
| 105 | CGAACGCC |
| 106 | CTGCTCTA |
| 107 | GCCTACCA |
| 108 | GGATGAAG |
| 109 | CTATATAC |
| 110 | CGAATATG |
| 111 | ACGCATTA |
| 112 | GGTAGACC |
| 113 | CGTTATGC |
| 114 | TCTGCGGA |
| 115 | CCTTGCAT |
| 116 | ATTATAGT |
| 117 | CTCGTAAT |
| 118 | CGCTTAAC |
| 119 | CTGACCGC |
| 120 | TGACCAGG |
| 121 | CTCATAGG |
| 122 | CCGTAAGC |
| 123 | CGAGACGT |
| 124 | GACGATAA |
| 125 | CCGCTGCT |
| 126 | GGTTAGAA |

TABLE 12-continued

Barcode Sequences

| BC# | SEQ |
|---|---|
| 127 | TTATCCGG |
| 128 | AGTAGGTA |
| 129 | CGTACTAC |
| 130 | AACTAGCG |
| 131 | TGCTCCTT |
| 132 | TCGCCAAC |
| 133 | CGCGGCTC |
| 134 | AAGGCGGT |
| 135 | GTAATGAG |
| 136 | AGATACTA |
| 137 | GAATCGTC |
| 138 | AGGAAGAG |
| 139 | CAGGTACC |
| 140 | TAGATAGC |
| 141 | AGAGTAAG |
| 142 | TCATTCCG |
| 143 | CGGCGTCG |
| 144 | ATCAAGCA |
| 145 | TTGGCGTA |
| 146 | CGTCCGCA |
| 147 | AGGACCGA |
| 148 | CCTCGATC |
| 149 | TATCTGAG |
| 150 | CGGAGTAA |
| 151 | AGAATGAA |
| 152 | AATCGGTT |
| 153 | CATCGCCA |
| 154 | TATTGACT |
| 155 | GTAGGCGG |
| 156 | GTTCGTAT |

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. An in vivo method for characterizing delivery vehicles for in vivo delivery of an agent comprising:
   (a) formulating multiple delivery vehicles having different chemical compositions, wherein each different delivery vehicle comprises a molecule that can generate a detectable signal by performing a biological activity when delivered to the cytoplasm of cells of the subject, and a chemical composition identifier that identifies the chemical composition of the delivery vehicle;
   (b) administering the multiple delivery vehicles to a non-human mammal;
   (c) sorting cells from multiple tissues of the non-human mammal that generate the detectable signal from cells that do not generate the detectable signal, wherein the cells that generate the detectable signal are also sorted based on the presence or absence of a cell surface protein that is indicative of tissue type or cell type; and
   (d) identifying the composition identifier in the sorted cells that generate the detectable signal and have a cell surface protein present to determine the chemical composition of the delivery vehicle in the sorted cells to correlate the chemical composition of the delivery vehicle with the tissue or cell type containing the delivery vehicle.

2. The method of claim 1, wherein the delivery vehicles are optionally loaded with the agent to be delivered.

3. The method of claim 1, wherein the delivery vehicles are lipid nanoparticles.

4. The method of claim 1, wherein the agent is a nucleic acid.

5. The method of claim 4, wherein the nucleic acid comprises RNA, DNA, or both.

6. The method of claim 1, wherein the molecule that can generate a detectable signal is a nucleic acid that encodes a protein that is capable of generating a detectable signal in the cytoplasm of a cell.

7. The method of claim 1, wherein the detectable signal is fluorescence.

8. The method of claim 1, wherein the detectable signal is the down regulation of a gene typically expressed in the cells.

9. The method of claim 1, wherein the chemical composition identifier is a nucleic acid barcode.

10. The method of claim 9, wherein the nucleic acid barcode is sequenced to identify the chemical composition of the delivery vehicle.

11. The method of claim 1, wherein the non-human mammal is a transgenic mouse engineered to have a stop codon in a gene that encodes a fluorescent protein, and wherein the molecule that can generate a detectable signal is a nucleic acid that encodes a nuclease or recombinase that removes the stop codon in the gene.

12. The method of claim 1, wherein the method is a high-throughput method.

13. The method claim 1, wherein the delivery vehicle comprises at least one lipid-amine compound, alkyl tailed PEG, and cholesterol, and wherein lipid-amine compound, molar amount of PEG, structure of PEG, and molar amount of cholesterol in the delivery vehicle is varied among the delivery vehicles.

14. The method of claim 1, further comprising the step of identifying tropism of the delivery vehicles that cause a detectable signal to be generated in the cells.

15. The method of claim 1, wherein greater than 100 different delivery vehicle formulations are assayed.

16. The method of claim 1, wherein greater than 250 different delivery vehicle formulations are assayed.

17. The method of claim 1, wherein the delivery vehicle comprises a conjugate.

18. The method of claim 1, wherein the molecule that can generate a detectable signal when delivered to the cytoplasm is selected from the group consisting of siRNA, mRNA, sgRNA, a nuclease, a recombinase, a small molecule, an epigenetic modifier, and a combination thereof.

* * * * *

SEQUENCE LISTING

<160> NUMBER OF SEQ ID NOS: 11

<210> SEQ ID NO 1
<211> LENGTH: 58
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (32)..(38)
<223> OTHER INFORMATION: n is A, C, G, or T

<400> SEQUENCE: 1
agacgtgtgc tcttccgatc tgagggtact tnnnnnnnag atcggaagag cgtcgtgt        58

<210> SEQ ID NO 2
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: n is 2'-O-Methyl cytosine
<220> FEATURE:
<221> NAME/KEY: misc_feature
<222> LOCATION: (8)..(8)

```
<223> OTHER INFORMATION: n is 2'-O-Methyl uracil
<220> FEATURE:
<221> NAME/KEY: misc_feature
<222> LOCATION: (9)..(9)
<223> OTHER INFORMATION: n is 2'-O-Methyl cytosine
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (11)..(11)
<223> OTHER INFORMATION: n is 2'-O-Methyl cytosine
<220> FEATURE:
<221> NAME/KEY: misc_feature
<222> LOCATION: (14)..(14)
<223> OTHER INFORMATION: n is 2'-O-Methyl cytosine
<220> FEATURE:
<221> NAME/KEY: misc_feature
<222> LOCATION: (15)..(18)
<223> OTHER INFORMATION: n is 2'-O-Methyl uracil
<220> FEATURE:
<221> NAME/KEY: misc_feature
<222> LOCATION: (19)..(19)
<223> OTHER INFORMATION: n is 2'-O-Methyl cytosine
<220> FEATURE:
<221> NAME/KEY: misc_feature
<222> LOCATION: (20)..(20)
<223> OTHER INFORMATION: n is deoxy-T
<220> FEATURE:
<221> NAME/KEY: misc_feature
<222> LOCATION: (21)..(21)
<223> OTHER INFORMATION: n is phosphorothioate deoxy-T

<400> SEQUENCE: 2
agganggnnn naannnnnnn n                                              21

<210> SEQ ID NO 3
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (8)..(8)
<223> OTHER INFORMATION: n is 2'-O-Methly uracil
<220> FEATURE:
<221> NAME/KEY: misc_feature
<222> LOCATION: (20)..(20)
<223> OTHER INFORMATION: n is deoxy-T
<220> FEATURE:
<221> NAME/KEY: misc_feature
<222> LOCATION: (21)..(21)
<223> OTHER INFORMATION: n is phosphorothioate deoxy-T

<400> SEQUENCE: 3
gaaaagunga gaccguccun n                                              21

<210> SEQ ID NO 4
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: n is 2'-O-Methly cytosine
<220> FEATURE:
<221> NAME/KEY: misc_feature
<222> LOCATION: (4)..(4)
<223> OTHER INFORMATION: n is 2'-O-Methly uracil
<220> FEATURE:
<221> NAME/KEY: misc_feature
```

<222> LOCATION: (9)..(9)
<223> OTHER INFORMATION: n is 2'-O-Methly cytosine
<220> FEATURE:
<221> NAME/KEY: misc_feature
<222> LOCATION: (12)..(12)
<223> OTHER INFORMATION: n is 2'-O-Methly cytosine
<220> FEATURE:
<221> NAME/KEY: misc_feature
<222> LOCATION: (18)..(18)
<223> OTHER INFORMATION: n is 2'-O-Methly uracil
<220> FEATURE:
<221> NAME/KEY: misc_feature
<222> LOCATION: (20)..(20)
<223> OTHER INFORMATION: n is deoxy-T
<220> FEATURE:
<221> NAME/KEY: misc_feature
<222> LOCATION: (21)..(21)
<223> OTHER INFORMATION: n is phosphorothioate deoxy-T

<400> SEQUENCE: 4
anangaagna gnacgacnun n                                              21

<210> SEQ ID NO 5
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(20)
<223> OTHER INFORMATION: n is deoxy-T
<220> FEATURE:
<221> NAME/KEY: misc_feature
<222> LOCATION: (21)..(21)
<223> OTHER INFORMATION: n is phosphorothioate deoxy-T

<400> SEQUENCE: 5
aagucgugcu gcuucaugun n                                              21

<210> SEQ ID NO 6
<211> LENGTH: 106
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: n is 2'-O-Methly guanine
<220> FEATURE:
<221> NAME/KEY: misc_feature
<222> LOCATION: (2)..(2)
<223> OTHER INFORMATION: n is phosphorothioate
<220> FEATURE:
<221> NAME/KEY: misc_feature
<222> LOCATION: (3)..(3)
<223> OTHER INFORMATION: n is 2'-O-Methly cytosine
<220> FEATURE:
<221> NAME/KEY: misc_feature
<222> LOCATION: (4)..(4)
<223> OTHER INFORMATION: n is phosphorothioate
<220> FEATURE:
<221> NAME/KEY: misc_feature
<222> LOCATION: (5)..(5)
<223> OTHER INFORMATION: n is 2'-O-Methly uracil
<220> FEATURE:
<221> NAME/KEY: misc_feature
<222> LOCATION: (6)..(6)
<223> OTHER INFORMATION: n is phosphorothioate
<220> FEATURE:
<221> NAME/KEY: misc_feature
<222> LOCATION: (100)..(100)
<223> OTHER INFORMATION: n is 2'-O-Methly uracil
<220> FEATURE:

```
<221> NAME/KEY: misc_feature
<222> LOCATION: (101)..(101)
<223> OTHER INFORMATION: n is phosphorothioate
<220> FEATURE:
<221> NAME/KEY: misc_feature
<222> LOCATION: (102)..(102)
<223> OTHER INFORMATION: n is 2'-O-Methly uracil
<220> FEATURE:
<221> NAME/KEY: misc_feature
<222> LOCATION: (103)..(103)
<223> OTHER INFORMATION: n is phosphorothioate
<220> FEATURE:
<221> NAME/KEY: misc_feature
<222> LOCATION: (104)..(104)
<223> OTHER INFORMATION: n is 2'-O-Methly uracil
<220> FEATURE:
<221> NAME/KEY: misc_feature
<222> LOCATION: (105)..(105)
<223> OTHER INFORMATION: n is phosphorothioate

<400> SEQUENCE: 6
nnnnnnuacc ugggcuguag aacguuuuag agcuagaaau agcaaguuaa aauaaggcua      60
guccguuauc aacuugaaaa aguggcaccg agucggugcn nnnnu                    106

<210> SEQ ID NO 7
<211> LENGTH: 106
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: n is 2'-O-Methly adenine
<220> FEATURE:
<221> NAME/KEY: misc_feature
<222> LOCATION: (2)..(2)
<223> OTHER INFORMATION: n is phosphorothioate
<220> FEATURE:
<221> NAME/KEY: misc_feature
<222> LOCATION: (3)..(3)
<223> OTHER INFORMATION: n is 2'-O-Methly adenine
<220> FEATURE:
<221> NAME/KEY: misc_feature
<222> LOCATION: (4)..(4)
<223> OTHER INFORMATION: n is phosphorothioate
<220> FEATURE:
<221> NAME/KEY: misc_feature
<222> LOCATION: (5)..(5)
<223> OTHER INFORMATION: n is 2'-O-Methly guanine
<220> FEATURE:
<221> NAME/KEY: misc_feature
<222> LOCATION: (6)..(6)
<223> OTHER INFORMATION: n is phosphorothioate
<220> FEATURE:
<221> NAME/KEY: misc_feature
<222> LOCATION: (100)..(100)
<223> OTHER INFORMATION: n is 2'-O-Methly uracil
<220> FEATURE:
<221> NAME/KEY: misc_feature
<222> LOCATION: (101)..(101)
<223> OTHER INFORMATION: n is phosphorothioate
<220> FEATURE:
<221> NAME/KEY: misc_feature
<222> LOCATION: (102)..(102)
<223> OTHER INFORMATION: n is 2'-O-Methly uracil
<220> FEATURE:
<221> NAME/KEY: misc_feature
<222> LOCATION: (103)..(103)
<223> OTHER INFORMATION: n is phosphorothioate
<220> FEATURE:
<221> NAME/KEY: misc_feature
<222> LOCATION: (104)..(104)
<223> OTHER INFORMATION: n is 2'-O-Methly uracil
<220> FEATURE:
<221> NAME/KEY: misc_feature
```

<222> LOCATION: (105)..(105)
<223> OTHER INFORMATION: n is phosphorothioate

<400> SEQUENCE: 7
nnnnnnacgg acaggcaccu acgguuuuag agcuagaaau agcaaguuaa aauaaggcua    60
guccguuauc aacuugaaaa aguggcaccg agucggugcn nnnnu                  106

<210> SEQ ID NO 8
<211> LENGTH: 91
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (24)..(24)
<223> OTHER INFORMATION: n is A, T, G, or C
<220> FEATURE:
<221> NAME/KEY: misc_feature
<222> LOCATION: (25)..(25)
<223> OTHER INFORMATION: n is A, T, or C
<220> FEATURE:
<221> NAME/KEY: misc_feature
<222> LOCATION: (26)..(26)
<223> OTHER INFORMATION: n is A, T, G, or C
<220> FEATURE:
<221> NAME/KEY: misc_feature
<222> LOCATION: (27)..(27)
<223> OTHER INFORMATION: n is A or T
<220> FEATURE:
<221> NAME/KEY: misc_feature
<222> LOCATION: (54)..(54)
<223> OTHER INFORMATION: n is A, T, G, or C
<220> FEATURE:
<221> NAME/KEY: misc_feature
<222> LOCATION: (55)..(55)
<223> OTHER INFORMATION: n is A or T
<220> FEATURE:
<221> NAME/KEY: misc_feature
<222> LOCATION: (56)..(56)
<223> OTHER INFORMATION: n is A, T, G, or C
<220> FEATURE:
<221> NAME/KEY: misc_feature
<222> LOCATION: (57)..(57)
<223> OTHER INFORMATION: n is A, T, or C
<220> FEATURE:
<221> NAME/KEY: misc_feature
<222> LOCATION: (66)..(66)
<223> OTHER INFORMATION: n is A, T, G, or C
<220> FEATURE:
<221> NAME/KEY: misc_feature
<222> LOCATION: (67)..(67)
<223> OTHER INFORMATION: n is A or T
<220> FEATURE:
<221> NAME/KEY: misc_feature
<222> LOCATION: (68)..(68)
<223> OTHER INFORMATION: n is A, T, or C

<400> SEQUENCE: 8
gatgctctca tacgaactcg tccnnnncct gctagtccac gtccatgtcc accnnnntga    60
tattgnnngt ggttagtcga gcagagacta g                                  91

<210> SEQ ID NO 9
<211> LENGTH: 70
<212> TYPE: DNA
<213> ORGANISM: Artificial Sequence
<220> FEATURE:
<223> OTHER INFORMATION: Synthetic

<400> SEQUENCE: 9
aatgatacgg cgaccaccga gatctacact aaggccaaca ctctttccct acacgacgct    60

```
cttccgatct                                                                70

<210> SEQ ID NO 10
<211> LENGTH: 33
<212> TYPE: DNA
<213> ORGANISM: Artificial Sequence
<220> FEATURE:
<223> OTHER INFORMATION: Synthetic

<400> SEQUENCE: 10
tgactggagt tcagacgtgt gctcttccga tct                                      33

<210> SEQ ID NO 11
<211> LENGTH: 54
<212> TYPE: DNA
<213> ORGANISM: Artificial Sequence
<220> FEATURE:
<223> OTHER INFORMATION: Synthetic

<400> SEQUENCE: 11
caagcagaag acggcatacg agatatagag aggtgactgg agttcagacg tgtg               54
```